(12) United States Patent
Jennewein et al.

(10) Patent No.: US 12,037,622 B2
(45) Date of Patent: *Jul. 16, 2024

(54) PRODUCTION OF HUMAN MILK OLIGOSACCHARIDES IN MICROBIAL HOSTS WITH ENGINEERED IMPORT / EXPORT

(71) Applicant: Chr. Hansen HMO GmbH, Rheinbreitbach (DE)

(72) Inventors: Stefan Jennewein, Bad Honnef (DE); Dirk Wartenberg, Bonn (DE)

(73) Assignee: Chr. Hansen HMO GmbH, Rheinbreitbach (DE)

(*) Notice: Subject to any disclaimer, the term of this patent is extended or adjusted under 35 U.S.C. 154(b) by 358 days.

This patent is subject to a terminal disclaimer.

(21) Appl. No.: 17/323,737

(22) Filed: May 18, 2021

(65) Prior Publication Data
US 2021/0277435 A1 Sep. 9, 2021

Related U.S. Application Data

(62) Division of application No. 15/758,653, filed as application No. PCT/EP2016/071420 on Sep. 12, 2016, now Pat. No. 11,046,985.

(30) Foreign Application Priority Data

Sep. 12, 2015 (EP) .................................. 15184968

(51) Int. Cl.
| C12P 19/18 | (2006.01) |
| C12N 1/20 | (2006.01) |
| C12N 9/10 | (2006.01) |
| C12N 15/70 | (2006.01) |

(52) U.S. Cl.
CPC ............ *C12P 19/18* (2013.01); *C12N 9/1051* (2013.01); *C12N 15/70* (2013.01); *C12Y 204/01146* (2013.01)

(58) Field of Classification Search
CPC .. C12N 15/70; C12N 9/10; C12N 1/20; C12P 19/18; C07H 3/06; C12Y 204/01146
See application file for complete search history.

(56) References Cited

U.S. PATENT DOCUMENTS

| 8,652,808 | B2 | 2/2014 | Jennewein et al. |
| 9,512,433 | B2 | 12/2016 | Jennewein et al. |
| 11,046,985 | B2 | 6/2021 | Jennewein et al. |
| 2011/0236934 | A1 | 9/2011 | Samain et al. |
| 2012/0135467 | A1 | 5/2012 | Jennewein et al. |
| 2014/0120611 | A1 | 5/2014 | Jennewein et al. |

FOREIGN PATENT DOCUMENTS

| CN | 103060252 B | 4/2015 |
| EP | 2722394 A1 | 4/2014 |
| JP | 2003504072 A | 2/2003 |
| JP | 2007525186 A | 9/2007 |
| JP | 2012529274 A | 11/2012 |
| RU | 2473695 C2 | 1/2013 |
| WO | 2007101862 A1 | 9/2007 |
| WO | 2010142305 A1 | 6/2010 |
| WO | 2014122328 A1 | 8/2014 |
| WO | 2015032413 A1 | 3/2015 |
| WO | 2015106943 A1 | 7/2015 |
| WO | 2015117812 A1 | 8/2015 |
| WO | 2015150328 A1 | 10/2015 |

OTHER PUBLICATIONS

Smilovitz et al.; Breast milk oligosaccharides: structure-function relationships in the neonate; Annu. Rev. Nutr. (2014) 34: 143-169.
PCT International Search Report for PCT/EP2016/071420, dated Oct. 28, 2016.
Weichert, et al., "Bioengineered 2'-fucosyllactose and 3-fucosyllactose inhibit the adhesion of Pseudomonas aeruginosa and enteric pathogens to human intestinal and respiratory cell lines," Nutrition Research, (2013), vol. 33: 831-838.
Jennewein: "Abschlussbericht zum Forderprojekt Entwicklung eines innovativen Produktionsverfahrens fur Fucosyllctosen Mit dem," Jennewein Biotechnologie GmbH, Project Report, 2012, pp. 1-31.
Khushnuma Koita, "Optimizing Pentose Sugar Utilization in *Escherichia coli* for the Production of Biofuels," University of Illinois at Urbana-Champaign Dissertation, 2012.
Koita, et al., "Identification and Analysis of the Putative Pentose Sugar Efflux Transporters in *Escherichia coli*," PLOS One, (2012), vol. 7, No. 8: pp. 1-10.
Baumgärtner, et al., "Construction of *Escherichia coli* strains with chromosomally integrated expression cassettes for the synthesis of 2'-fucosyllactose," Microbial Cell Factories, (2013), vol. 12: 1-13.
Petschacher, et al., "Biotechnological production of fucosylated human milk oligosaccharides: Prokaryotic fucosyltransferases and their use in biocatalytic cascades or whole cell conversion systems," Journal of Biotechnology, (2016), vol. 235: 61-83.
Baumgärtner, et al., "Synthesis of fucosylated lacto-N-tetraose using whole-cell biotransformation," Bioorganic & Medicinal Chemistry, (2015), vol. 23: 6799-6806.
Saumonneau et al.,"Design of an alpha-L-transfucosidase for the synthesis of fucosylated HMOs," Glycobiology, (2016), vol. 26, No. 3: 261-269.
Bernard Priem, et al., "A new fermentation process allows large-scale production of human milk oligosaccharides by metabolically engineered bacteria," Glycobiology, (2002), vol. 12, No. 4: 235-240.
Florian Baumgartner, "Synthesis of the Human Milk Oligosaccharide Lacto-N-Tetraose in Metabolically Engineered, Plasmid-Free *E. coli*," ChemBioChem Communications, (201), vol. 15, 1896-1900.
Baumgartner, et al., "Synthesis of the Human Milk Oligosaccharide Lacto-N-Tetraose in Metabolically Engineered, Plasmid-Free *E. coli*," ChemBioChem (2014), 15(13): 1896-1900.

(Continued)

*Primary Examiner* — Maryam Monshipouri

(57) ABSTRACT

The present invention relates to methods for the production of oligosaccharides in genetically modified bacterial host cells, as well as to the genetically modified host cells used in the methods. The genetically modified host cell comprises at least one recombinant glycosyltransferase, and at least one nucleic acid sequence coding for a protein enabling the export of the oligosaccharide.

2 Claims, 6 Drawing Sheets

Specification includes a Sequence Listing.

(56) References Cited

OTHER PUBLICATIONS

Baumgartner, et al., "Galactose-limited fed-batch cultivation of *Escherichia coli* for the production of lacto-N-tetraose," Enzyme and Microbial Technology (2015), 75-76: 37-43.

Han, et al., "Biotechnological production of human milk oligosaccharides," Biotechnology Advances (2012), 30(6): 1268-1278.

Koita, Dissertation, University of Illinois at Urbana Champaign (2012), pp. 1-121.

Pao, et al., "Major Facilitator Superfamily," Microbiology and Molecular Biology Reviews (1998), 62(1): 1-34.

Mncent, et al., "Structure and Kinetics of a Monomeric Glucosamine 6-Phosphate Deaminase," JBC (2005), 280(20): 19649-19655.

PRODUCTION OF HUMAN MILK OLIGOSACCHARIDES IN MICROBIAL HOSTS WITH ENGINEERED IMPORT / EXPORT

CROSS-REFERENCE TO RELATED APPLICATIONS

This application is a Divisional of U.S. application Ser. No. 15/758,653, filed on Mar. 8, 2018, which is a National Stage entry of International Application No. PCT/EP2016/071420, filed Sep. 12, 2016, which claims priority to European Patent Application No. 15184968.4, filed Sep. 12, 2015.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "3000045-002002_Sequence_Listing_ST25.txt" created on 18 May 2021, and 291,413 bytes in size) is submitted concurrently with the instant application, and the entire contents of the Sequence Listing are incorporated herein by reference.

BACKGROUND

Field

Human milk is regarded as the best diet for the development of infants. It is composed of fats, proteins, vitamins, minerals, trace elements and a complex carbohydrate mixture which comprises lactose and approximately 150 structurally diverse oligosaccharides (Human milk oligosaccharides, HMO).

Description of Related Art

Efforts to produce HMO chemically or by biotechnological approaches mainly attracted common attention due to their beneficial impact on the development of the gastrointestinal flora of infants, thus, advocating their use as nutritional additives. Besides these prebiotic properties, many other positive effects of HMO could be observed so far, expanding their field of application.

However, extensive scientific studies demand pure single compounds which are hardly achievable. This is especially true for complex free neutral and acidic oligosaccharides for which competitive large-scale production processes are still lacking. (e.g. lacto-N-tetraose (Gal(β1-3)GlcNAc(β1-3)Gal (β1-4)Gluc), lacto-N-neotetraose (Gal(β1-4)GlcNAc(β1-3) Gal(β1-4)Gluc), lacto-N-fucopentaose I (Fuc(α1-2) Gal(β1-3)GlcNAc(β1-3)Gal(β1-4)Gluc) lacto-N-neofucopenaose I (Fuc(α1-2) Gal(β1-4)GlcNAc(β1-3)Gal(β1-4)Gluc) (Lacto-N-sialylpentaose a (LST-a; Neu5Ac(α2-3)Gal(β1-3) GlcNAc(β1-3)Gal(β1-4)Gluc)) The metabolic engineering of a microorganism to produce these compounds represents the most promising approach since chemical methods are rather inefficient to produce these molecules at multi-ton scale.

Several fermentative approaches were already developed for the structural simpler HMOs such as 2'-fucosyllactose, 3-fucosyllactose or 3'-sialyllactose, using mainly metabolically engineered *Escherichia coli* strains.

However, large-scale quantities are only achievable through boosting the oligosaccharide export out of the bacterial cell, thus, (i) enhancing the productivity and (ii) allowing the recovering of the desired oligosaccharide from the culture broth. The need for solving the export problem seems to enlarge with the size of the produced sugar. Also, with the currently available fermentation processes, upon production of more complex oligosaccharides, the problem of an unwanted export of oligosaccharide precursors from the producing cell occurs, leading to an undesirable mix of product and precursor oligosaccharides in the fermentation medium. Whereas multiple transporter proteins are known to transfer mono- or disaccharides across the membrane, hardly any knowledge exists on the transport of larger oligosaccharides (e.g., trisaccharides and larger oligosaccharides).

For example, the genome of the often used fermentation model organism *E. coli* encodes more than 500 distinct transporter proteins (Busch and Saier, Crit Rev Biochem Mol Biol. 2002; 37(5):287-337). The classification of those membrane transport proteins is quite diverse and subgroups may vary in translocation mechanisms, protein structures or evolutionary origins.

Classically energy-driven active transporters perform substrate movement against its concentration or electrochemical gradient, while kinetics and direction of the substrate flow through channels primarily follows such gradients. Depending on the source of energy used for the translocation, pumps can be principally divided into primary active and secondary active transporters, exploiting metabolic energy like ATP or the electrochemical potential, respectively (Davidson and Maloney, Trends Microbiol. 2007 October; 15(10):448-55; Forrest et al, Biochim Biophys Acta. 2011 February; 1807(2):167-88). Although in-depth knowledge was achieved for several membrane proteins permitting energy generation, the import of carbohydrates and the efflux of proteins and antibacterial substances, however, keen insights into mechanistic processes or information on natural or probable substrates were gained only for a minor portion of annotated bacterial transporters so far.

The *E. coli* lactose permease LacY probably represents the most intensively characterized solute transporter (Guan and Kaback, Annu Rev Biophys Biomol Struct. 2006; 35:67-91) and is a member of the large and exceptionally diverse major facilitator superfamily (MFS)—that belongs to the secondary active transporter class-transporting sugars, drugs, hydrophobic molecules, peptides, organic ions, etc. by uniport, symport or antiport (Saier et al., J Mol Microbiol Biotechnol. 1999 November; 1(2):257-79). Apart from a few exceptions a common structural feature of MFS transporters are two six-helical subdomains that transverse the cytoplasmic membrane. The existence of functionally homologous amino acid positions between related $H^+$-coupled MFS symporters further suggests a similar kinetic mechanism as determined for the lactose permease (Madej and Kaback, Proc Natl Acad Sci USA. 2013 Dec. 10; 110(50):E4831-8).

Since decades, enormous knowledge about the import of carbohydrates into bacteria could be acquired. But regarding the export of carbohydrates, especially about molecules that are non-surface-associated, only little information is available. This is not unexpected since sugars actually depict a favourable carbon- and energy source, thus, once in the cell they shouldn't be released to a competitive environment.

However, the natural function of sugar exporters probably involve the reduction of osmotic or sugar-phosphate stress which might point to a flexible substrate spectrum. Interestingly, the export of a variety of galactosides like IPTG, TMG and lactose was shown for members of the so called sugar efflux transporter family (SET), which belong to the group of MFS transporters (Liu et al., J Biol Chem. 1999 Aug. 13; 274(33):22977-84; Liu et al., Mol Microbiol. 1999 March; 31(6):1845-51).

The *E. coli* transport protein SetA was even described to transfer the human milk oligosaccharide 3-fucosyllactose resulting in an improved production of said compound during fermentation of a recombinant *E. coli* strain overexpressing setA (see applicant's international patent application WO 2010/142305). Similarly, the expression of a sugar efflux transporter from *Yersinia* was shown to enable the export of the human milk oligosaccharide 2'-fucosyllactose out of an engineered *E. coli* production strain.

Apart from this, from a mechanistic and energetic point of view, only the ion-gradient-driven transport systems have the potential to translocate solutes in both directions across the membrane. This is exemplarily true for the above mentioned LacY, a galactoside/$H^+$ symporter, which is part of the bacterial lac operon that allows the metabolism of lactose in *E. coli*. This permease primarily imports lactose into the cell but it is also capable to transfer its substrate in the opposite direction.

Besides the major facilitator superfamily, which represents the largest group of transporters, bacteria possess further mechanisms to excrete solutes—often summarized in the classes of multidrug efflux pumps. Alike for the MFS, the activities of the small multidrug resistance superfamily (SMR), the multidrug and toxic compound extrusion superfamily (MATE) and the resistance-nodulation-cell division superfamily (RND) rely on the electrochemical gradient. The fifth class is the adenosine triphosphate (ATP)-binding cassette superfamily (ABC) which uses ATP as energy source to drive molecules from the cell. As for the MFS, members of SMR, MATE, RND and ABC transport structurally diverse molecules. Further, most of their so far identified substrates are not naturally occurring, and, thus, their preferences are hardly predictable.

Although chemical synthesizing processes are known for human milk oligosaccharides, these processes are very cost-intensive and do not lead to satisfying amounts. On the other hand, fermentation processes using genetically modified microorganisms still have the drawback that the export of larger oligosaccharides (tetra-, penta-, hexasaccharides) represents a major limitation for the establishment of cost effective production processes. As a consequence, there still is the need for improved processes for the production of large-scale human oligosaccharides.

SUMMARY

According to the invention, this and other objects are solved by the methods and microbial host cell(s) as claimed in the attached claims.

With the methods and host cells according to the invention it is possible to produce a desired oligosaccharide, preferably an oligosaccharide that is not produced in an unmodified host cell, and also preferably an oligosaccharide belonging to the human milk oligosaccharides, in large amounts obtainable from the medium. As such, the oligosaccharide is, so to say, obtainable in free from in the medium; it is not bound to a surface protein or membrane protein or other protein of the surface of the host cell.

According to the invention, a method for the production of a desired oligosaccharide by a genetically modified microbial host cell, comprising the steps of a) providing a genetically modified microbial host cell that comprises at least one recombinant glycosyltransferase, and that has the expression or activity of at least one endogenous sugar export protein modified such, that the expression or activity of the sugar export protein is either (i) increased or (ii) decreased or inactivated as compared to an genetically unmodified host cell, so that (i) the export of a oligosaccharide into the medium is either decreased or abolished, or (ii) the transport of a desired oligosaccharide is increased, respectively, as compared to an genetically unmodified host cell, b) cultivating the host cell in a medium under conditions permissive for the production of the desired oligosaccharide, whereby the desired oligosaccharide is transported into the medium. The method may further comprise the step of c) obtaining the desired oligosaccharide from the medium.

DETAILED DESCRIPTION OF A PREFERRED EMBODIMENT

Figure 1:
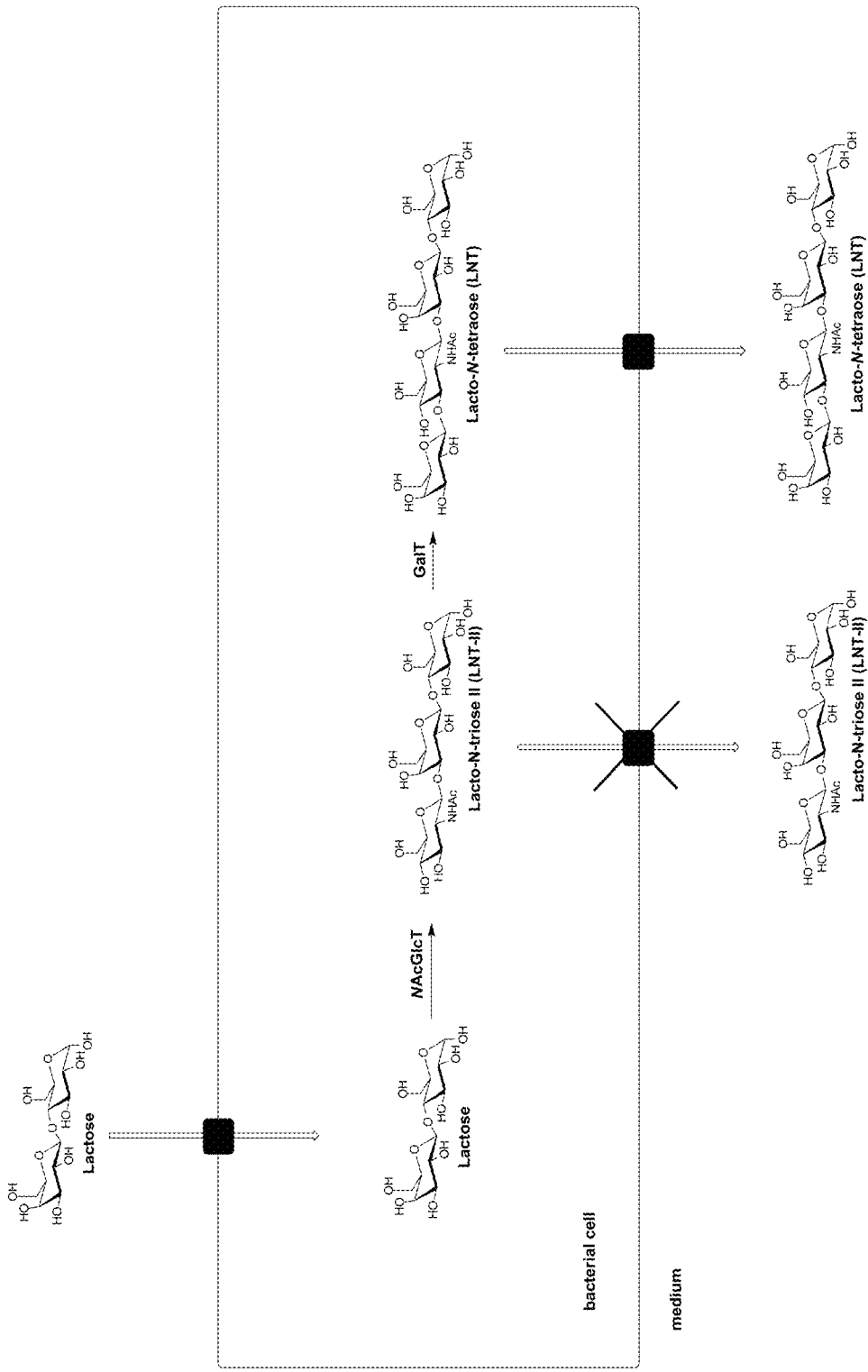
FIG. 1 shows a schematic illustration for the production of either lac-to-N-triose II or lacto-N-tetraose in a host cell cultivated in a medium.

In the method according to the invention, it is preferred if the desired oligosaccharide is a human milk oligosaccharide comprising a lacto-N-triose II (LNT-II; GlcNAc(β1-3)Gal (β1-4)Gluc) as a core trisaccharide. In this connection, an oligosaccharide having a "core trisaccharide" is meant to comprise the specific trisaccharide representing the reducing end of a desired oligosaccharide, and comprising, as the case may be, additional saccharide moieties, with the specific trisaccharide representing the major moiety.

Accordingly, in an embodiment of the method and the host cell according to the invention, the desired oligosaccharide is selected from the group consisting of: lacto-N-triose II, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexaose II, lacto-N-sialylpentaose LSTa, LSTb, LSTc, disialyllacto-N-tetraose, disialyllacto-N-neotetraose.

In order to overcome the above mentioned drawbacks of limited oligosaccharide export the object is further solved by a method according to the invention, wherein the host cell comprises: at least one homologous or heterologous nucleic acid sequence coding for a protein enabling the export of a desired oligosaccharide into the culture medium, wherein said host cell has been modified such, that the expression of the homologous or heterologous nucleic acid sequence is overexpressed or under control of a promoter enabling the overexpression of the nucleic acid sequence; and/or the deletion, disruption, diminishment or inactivation of at least one endogenous nucleic acid sequence coding for an exporter protein that exports precursors of the desired oligosaccharide outside the host cell; and/or at least one homologous or heterologous nuclei acid sequence coding for a protein mediating the import of a precursor of a desired oligosaccharide into said host cell, wherein preferably the nucleic acid sequence is overexpressed, and wherein preferably the precursor is larger than a disaccharide.

The genetically modified microbial host cell comprising the characteristics as set forth herein are cultured in the presence of glucose, sucrose, glycerin or a combination thereof—using these substrates as carbon- and energy sources—as well as in the presence of lactose or oligosaccharides larger than disaccharides, e.g., LNT-II.

In a preferred embodiment of this method and host cell, said protein enabling the export of a desired oligosaccharide belongs to the class of secondary active transporters, and more preferably effects the export of an oligosaccharide comprising at least three moieties.

According to preferred embodiments, for the export of desired oligosaccharides a suitable exporter is expressed in addition to the genes that are responsible for intracellular oligosaccharide biosynthesis.

According to one aspect of the method and host cell of the invention, the at least one nucleic acid sequence coding for a protein enabling the export of a desired oligosaccharide is an endogenous or a recombinant nucleic acid.

In a preferred embodiment of the method and the host cell of the invention, the nucleic acid sequence coding for a protein enabling the export of a desired oligosaccharide is of bacterial, archeal, plant, yeast or animal origin; preferably, the at least one nucleic acid sequence coding for a protein enabling the export of a desired oligosaccharide is a gene selected from the group consisting of yebQ and yjhB from *Escherichia coli*, proP from *Mannheimia succiniciproducens* and setA from *Cedecea neteri* or functional fragments thereof.

Preferably, the oligosaccharide exporter is a protein selected from at least one of the following: SetA, SetB, SetC, YdeA, Cmr, YnfM, MdtD, YfcJ, YhhS, EmrD, YdhC, YbdA, YdeE, MhpT, YebQ, YjhB, Bcr and YdeA of *E. coli*, or ProP from *Mannheimia succiniciproducens* and SetA from *Cedecea neterior* variants or homologs thereof.

In yet another preferred embodiment, the recombinant glycosyltransferase is selected from at least one of the following: a galactosyltransferase, a sialyltransferase, an N-acetylglucosaminyltransferase and a fucosyltransferase, and is preferably selected from at least one of the following: β-1,3-N-acetylglucosaminyltransferase, β-1,3-galactosyltransferase, β-1,4-galactosyltransferase, β-1,6-galactosyltransferase, α-2,3-sialyltransferase, α-2,6-sialyltansferase, α-1,2-fucosyltransferase, or α-1,3-fucosyltransferase.

A preferred embodiment of the method and the host cell of the invention, concerns the a host cell or its provision, wherein the host cell comprises (i) a β-1,3-N-acetylglucosaminyltransferase, and (ii) a β-1,3-galactosyltransferase or a β-1,4-galactosyltransferase as glycosyltransferases. In this connection it is preferred, if said β-1,3-N-acetylglucosaminyltransferase has the activity of ligating N-acetylglucosamine to lactose generating lacto-N-triose II, and if said β-1,3-galactosyltransferase or said β-1,4-galactosyltransferase, respectively, have the activity to galactosylate lacto-N-triose II thus generating lacto-N-tetraose or lacto-N-neotetraose, respectively. The here developed system is easily adaptable to even more complex oligosaccharides by the expression of further glycosyltransferases.

With the microbial cell and the method according to the invention, it is possible to ferment a desired oligosaccharide in large quantities, especially an oligosaccharide comprising LNT-II as core structure, and to recover it from the culture broth.

In a preferred embodiment, said β-1,3-N-acetylglucosaminyltransferase belongs to the class of lgtA of *Neisseria meningitides* or PmnagT of *Pasteurella multocida*, or variants thereof.

Preferably, the glycosyltransferase is selected from a galactosyltransferase, a sialyltransferase, an N-acetylglucosaminyltransferase and a fucosyltransferase.

In yet another preferred embodiment, the lacto-N-tetraose generating β-1,3-galactosyltransferase is WbdO or a functional variant thereof. According to an aspect of the invention, the β-1,3-galactosyltransferase is a β-1,3-galactosyltransferase derived from *Salmonella enterica* (wbdO, acc. no. AY730594), and is preferably encoded by a gene selected from the group consisting of wbgO from *Escherichia coli* 055:H7 or furA from *Lutiella nitroferrum*, or a functional fragments thereof.

The invention also concerns a genetically modified microbial host cell, preferably a bacterial host cell, as described above in which the endogenous β-galactosidase gene is inactivated or deleted and in which a functional lactose permease gene is present.

Accordingly, in a preferred embodiment of the method and the host cell of the invention, a genetically modified host cell is provided, in which, where applicable, an endogenous β-galactosidase gene and a glucosamine-6-phosphate deaminase gene are inactivated or deleted, and wherein said genetically modified host cell comprises a nucleic acid sequence coding for a functional lactose permease protein, preferably LacY.

In a preferred embodiment, the genetically modified host cell comprises an increased UDP-N-acetylglucosamine and UDP-galactose, GDP-fucose or CMP-N-acetylneuraminic acid production capability as compared to a genetically unmodified host cell.

In a refinement of this embodiment of the method of and of the host cell of the invention, said increased UDP-N-acetylglucosamine and UDP-galactose production capability comprises the overexpression of one or more genes encoding for proteins comprising the following activities for a: L-glutamine: D-fructose-6-phosphate aminotransferase, N-acetyl glucosamine-1-phosphate uridyltransferase/glucosamine-1-phosphate acetyl transferase, phosphoglucosamine mutase, UDP-galactose-4-epimerase, phosphoglucomutase, glucose-1-phosphate uridylyltransferase.

For the synthesis of, e.g. LNT, UDP-galactose and UDP-N-acetylglucosamine are required. UDP-galactose can be obtained by feeding galactose to the HMO producing bacterial host cell via the fermentation medium. The galactose is then taken up by the cell, phosphorylated to galactose-1-phosphate and then converted to UDP-galactose. Genes encoding these enzymatic activities are well known in the literature (Grossiord et al., J. Bacteriol 2003185(3) 870-878). The supply for UDP-galactose can be also obtained from the cells own metabolism, and the metabolism can be improved by further genetic modification, such as the overexpression of the UDP-galactose-4'-epimerase, or the UDP-galactose-4'-epimerase in combination with the glucose-1-phosphate-1-uridinyltransferase. UDP-N-acetlyglucosamine can be also obtained from the bacterial host cell's own UDP-N-acetylglucosamine metabolism. The provision of UDP-N-acetylglucosamine for the synthesis of N-aectylglucosamine containing oligosaccharides can be improved by the inactivation of the N-acetylglucosamine catabolism within the producing cell.

According to one aspect of the invention, the genetically modified host cell is cultivated in the presence of glucose, sucrose, glycerol or a combination thereof, but neither by addition or in the presence of N-acetylglucosamine or galactose nor in a combination thereof.

In a preferred embodiment of the method and of the host cell of the invention, the desired oligosaccharide is lacto-N-triose II, which is produced by total fermentation from a simple carbon source in the host cell by the action of the heterologous expressed glycosyltransferases β-1,4-galactosyltransferase and β-1,3-N-acetylglucosaminyltransferase.

The present invention, as already mentioned above, also concerns a genetically modified host cell for the production of a desired oligosaccharide, the oligosaccharide comprising a lacto-N-triose II (LNT-II; GlcNAc(β1-3)Gal(β1-4)Gluc) as a core trisaccharide, wherein the host cell comprises at least one recombinant glycosyltransferase, the glycosyltransferase being preferably selected from a galactosyltransferase, a sialyltransferase, and an N-acetylglucosaminyltransferase, and has the expression or activity of at least endogenous sugar transport protein modified such, that the expression or activity of the endogenous sugar transport protein is functionally inactivated for the export of a precursor of the desired oligosaccharide.

A preferred embodiment concerns a host cell as described above, comprising (i) a heterologous expressed β-1,3-N-acetylglucosaminyltransferase, and (ii) a heterologous expressed β-1,3-galactosyltransferase or a heterologous expressed β-1,4-galactosyltransferase as glycosyltransferases, wherein the host cell further preferably comprises at least one homologous or heterologous nucleic acid sequence coding for a protein enabling the export of the oligosaccharide into a culture medium the host cell is cultivated in, wherein said protein enabling the export of the desired oligosaccharide belongs to the class of secondary active transporters, wherein said host cell has been modified such, that the expression of the homologous or heterologous nucleic acid sequence is overexpressed or under control of a promoter enabling the overexpression of the nucleic acid sequence. In preferred embodiments of the host cell, said at least one nucleic acid sequence coding for a protein enabling the export of the desired oligosaccharide is an endogenous or a recombinant nucleic acid sequence.

As already outlined for the method according to the invention, it is also preferred in the host cell of the invention, if said nucleic acid sequence coding for a protein enabling the export of a desired oligosaccharide is of bacterial, archeal, plant, yeast or animal origin.

According to another aspect of the invention, the host cell as described above further comprises: the deletion, disruption, diminishment or inactivation of at least one endogenous nucleic acid sequence coding for an exporter protein that exports precursors of the desired oligosaccharide outside the host cell; and/or at least one homologous or heterologous nucleic acid sequence coding for a protein enabling the import of a precursor of a desired oligosaccharide into said host cell, wherein preferably the nucleic acid sequence is overexpressed, and wherein preferably the precursor is larger than a disaccharide.

With the overexpression of at least one homologous or heterologous nucleic acid sequence coding for a protein enabling the import of a precursor of a desired oligosaccharide into said host cell, it is possible to feed precursors of a desired oligosaccharide to the culture medium, which get imported into the host cell, such as, e.g., LNT-II.

According to one aspect of the invention, in the host cell said at least one nucleic acid sequence coding for a protein enabling the export of a desired oligosaccharide is a gene selected from the group consisting of yebQ and yjhB from *Escherichia coli*, proP from *Mannheimia succiniciproducens* and setA from *Cedecea neteri* or functional fragments thereof.

According to yet another preferred embodiment, the desired oligosaccharide is lacto-N-triose II, and the protein enabling the export of the oligosaccharide into a culture medium the host cell is cultivated in, is YjhB from *Escherichia coli*, ProP from *Mannheimia succiniciproducens* and SetA from *Cedecea neteri* or functional fragments thereof.

According to a preferred embodiment, the microbial host according to the invention is further modified not to express proteins exporting precursors of a desired oligosaccharide.

In a preferred embodiment of the host cell, the desired oligosaccharide is lacto-N-tetraose, the precursor is lacto-N-triose II, and the host cell has deleted, disrupted or inactivated at least one nucleic acid sequence coding for an exporter protein that is able to export lacto-N-triose II outside the host cell.

In this connection it is preferred, if the protein enabling the export of lacto-N-tetraose is selected from YebQ from *Escherichia coli* BL21(DE3), SpoVB of *Bacillus amyloliquefaciens*, YabM of *Erwinia pyrilfolia*, Bcr of *E. coli* MG1655, YdeA of *E. coli* MG1655, ProP2 of *Haemophilus parainfluenzae*, SetA of *Pectobacterium carotovorum*, FucP of *E. coli* MG1655, MdeA of *Staphylococcus aureus* Bmb9393, ImrA of *Lactococcus lactis*, SetA of *Pseudomonas* sp. MT-1 and SetA of *Beauveria bassiana* D1-5.

Preferably, the oligosaccharide exporter is a protein selected from at least one of the following: SetA, SetB, SetC, YdeA, Cmr, YnfM, MdtD, YfcJ, YhhS, EmrD, YdhC, YbdA, YdeE, MhpT, YebQ, YjhB, Bcr and YdeA of *E. coli*, or ProP from *Mannheimia succiniciproducens* and SetA from *Cedecea neterior* variants or homologs thereof.

Presently, the term "nucleic acid" refers to a single- or double-stranded deoxyribonucleotide or ribonucleotide macromolecule and encompasses known analogues or natural or synthetically produced nucleotides that hybridize with the desired nucleic acid and that encode a certain polypeptide.

The term "recombinant" or "genetically modified", as used herein with reference to a microbial host cell indicates that the microbial host cell replicates a heterologous nucleic acid, or expresses a peptide or protein encoded by a heterologous nucleic acid (i.e., a sequence "foreign to said cell"). Recombinant cells can contain genes that are not found within the native (non-recombinant) form of the cell. Recombinant cells can also contain genes found in the native form of the cell wherein the genes are modified and reintroduced into the cell by artificial means. The term also encompasses cells that contain a nucleic acid endogenous to the cell that has been modified without removing the nucleic acid from the cell; such modifications include those obtained by gene replacement, site-specific mutation, and related techniques. Accordingly, a "recombinant polypeptide" is one which has been produced by a recombinant cell. A "heterologous sequence" or a "heterologous nucleic acid", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microbial host cell, thus representing a genetically modified host cell. Techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989).

Accordingly, a "microbial host cell" is presently understood as a microbial, preferably bacterial, cell which has been transformed or transfected, or is capable of transformation or transfection by an exogenous polynucleotide sequence.

Thus, the nucleic acid sequences as used in the present invention, may, e.g., be comprised in a vector which is to be stably transformed/transfected or otherwise introduced into host microorganism cells.

Presently, the term "operably linked" as used herein, shall mean a functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. Accordingly, the term "Promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesize a polypeptide in a host may be used for expression in this regard. The appropriate DNA sequence may be inserted into the expression system by any of a variety of well-known and routine techniques, such as, for example, those set forth in Sambrook et al., supra.

The art is rich in patent and literature publications relating to "recombinant DNA" methodologies for the isolation, synthesis, purification and amplification of genetic materials for use in the transformation of selected host organisms. Thus, it is common knowledge to transform host organisms with "hybrid" viral or circular plasmid DNA which includes selected exogenous (i.e. foreign or "heterologous") DNA sequences. The procedures known in the art first involve generation of a transformation vector by enzymatically cleaving circular viral or plasmid DNA to form linear DNA strands. Selected foreign DNA strands usually including sequences coding for desired protein product are prepared in linear form through use of the same/similar enzymes. The linear viral or plasmid DNA is incubated with the foreign DNA in the presence of ligating enzymes capable of effecting a restoration process and "hybrid" vectors are formed which include the selected exogenous DNA segment "spliced" into the viral or circular DNA plasmid.

As used herein, the term "cultivating" means growing a bacterial cell in a medium and under conditions permissive and suitable for the production of the desired oligosaccharide(s). A couple of suitable bacterial host cells as well as mediums and conditions for their cultivation will be readily available for one skilled in the art upon reading the disclosure of this invention in connection with the skilled person's technical and expert background.

As used herein, the term "recovering" or "obtaining" means isolating, harvesting, purifying, collecting or otherwise separating from the host cell culture the oligosaccharide produced by the host cell according to the invention.

A "microbial" host cell according to the invention, and as generally understood, means any microorganism, including bacteria, fungi and archaea, which is generally suitable for cultivation in large amounts, and which can be genetically modified according to the invention in order to produce a desired oligosaccharide. Preferred microorganisms are bacteria, e.g. *Escherichia coli, Corynebacterium glutamicum* and the yeast *Saccharomyces* sp., which have the advantage that these microorganisms can be grown easily and inexpensively in laboratory settings, and the bacteria and yeast have been intensively investigated for over many years.

Generally, and throughout the present invention, the term "glycosyltransferase activity" or "glycosyltransferase" designates and encompasses enzymes that are responsible for the biosynthesis of disaccharides, oligosaccharides and polysaccharides, and they catalyze the transfer of monosaccharide moieties from an activated nucleotide monosaccharide/sugar (the "glycosyl donor") to a glycosyl acceptor molecule.

Generally, and throughout the present invention, the terms "exporter" or "exporter protein" or "protein enabling the export of a desired oligosaccharide", which terms are presently being used synonymously, designates one or more polypeptides that solely or as part of a multi-protein complex transfers an oligosaccharide from the intracellular milieu of a bacterial cell into the periplasm of said cell or the culture supernatant, thus, enabling the oligosaccharide to pass the cellular membrane and/or the cell wall of said cell.

Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a wild type glycosyltransferase activity or oligosaccharide export displaying protein.

"Variant(s)" as the term is used herein, is a polynucleotide or polypeptide that differs from a reference polynucleotide or polypeptide, respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

Accordingly, a "functional fragment" of any of the genes/proteins disclosed therein, is meant to designate sequence variants of the genes/proteins still retaining the same or somewhat lesser activity of the gene or protein the respective fragment is derived from.

In this connection, the term "nucleic acid sequence encoding . . . " generally refers to any polyribonucleotide or polydeoxyribonucleotide, which may be unmodified RNA or DNA or modified RNA or DNA, and generally represents a gene which encodes a certain polypeptide or protein.

In this context, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as "proteins". Polypeptides may contain amino acids other than the 20 gene encoded amino acids. "Polypeptide(s)" include those modified either by natural processes, such as processing and other post-translational modifications, but also by chemical modification techniques. It will be appreciated that the same type of modification may be present in the same or varying degree at several sites in a given polypeptide, without essentially altering the activity of the polypeptide. Also, a given polypeptide may contain many types of modifications. Modifications can occur anywhere in a polypeptide, including the peptide backbone, the amino acid side-chains, and the amino or carboxyl termini.

Further, with the expression "precursor" compounds are encompassed which are involved in the biosynthetic pathway of the oligosaccharide according to the invention or which are produced and naturally present in the host cell.

A "precursor that is larger than a disaccharide" is presently understood as a sugar moiety that comprises more than two monosaccharide residues.

The term "desired oligosaccharide" refers to a sugar polymer consisting of at least three moieties, thus, comprising trisaccharides, tetrasaccharides, pentasaccharides etc., preferably an oligosaccharide selected from at least one of the following: lacto-N-triose II, lacto-N-tetraose, lacto-N-neotetraose, lacto-N-fucopentaose I, lacto-N-fucopentaose II, lacto-N-fucopentaose III, lacto-N-fucopentaose V, lacto-N-difucosylhexose I, lacto-N-difucosylhexaose II, lacto-N-sialylpentaose LSTa, LSTb, LSTc, disialyllacto-N-tetraose, disialyllacto-N-neotetraose.

Presently, and as generally understood in the relevant field, the expression "homologous" refers to a nucleic acid sequence that encodes for a specific product or products and is derived from the same species, in which said nucleic acid sequence is inserted. Accordingly, the term "heterologous" refers to a nucleic acid sequence encoding for a specific product or products and being derived from a species other than those in which said nucleic acid sequence is inserted.

The term "endogenous" herein and generally within the field means that the nucleic acid encoding for an enzyme of interest is originating from the bacterial host cell and has not been introduced into said host cell, whereas a "recombinant" nucleic acid has been introduced into said host cell and does not originates from said host cell.

The expression "overexpressed", or "overexpressing" or "under control of a promoter sequence enabling the overexpression of said nucleic acid sequence" presently, and generally in the art, means the expression of a gene in greater-than-normal amounts, i.e. in increased quantity thus leading to an increased amount of the protein the nucleic acid sequence is coding for.

In some embodiments, the nucleic acid sequence is placed under the control of an inducible promoter, which is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the proteins used in the present invention. For E. coli, and other microbial host cells, inducible promoters are known to those of skill in the art.

Further advantages are evident from the description and the drawings.

It is understood that the features mentioned above and those yet to be explained below can be used not only in the respective combinations indicated, but also in other combinations or in isolation, without leaving the context of the present invention.

Figure 2:
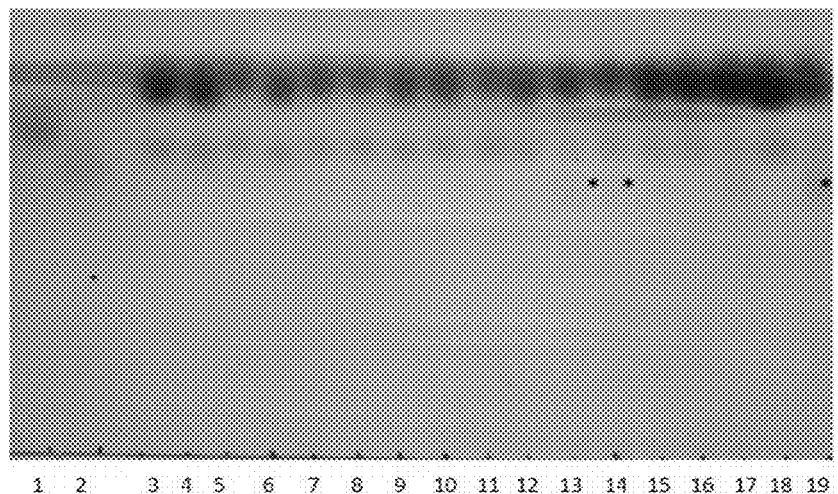
FIG. 2 shows the results of the TLC analysis of culture extracts of lacto-N-triose II (LNT II) producing *E. coli* BL21(DE3) strains overexpressing the β-1,3-N-acetyl glucosaminyltransferase gene PmnagT(13, 14)
Figure 3:
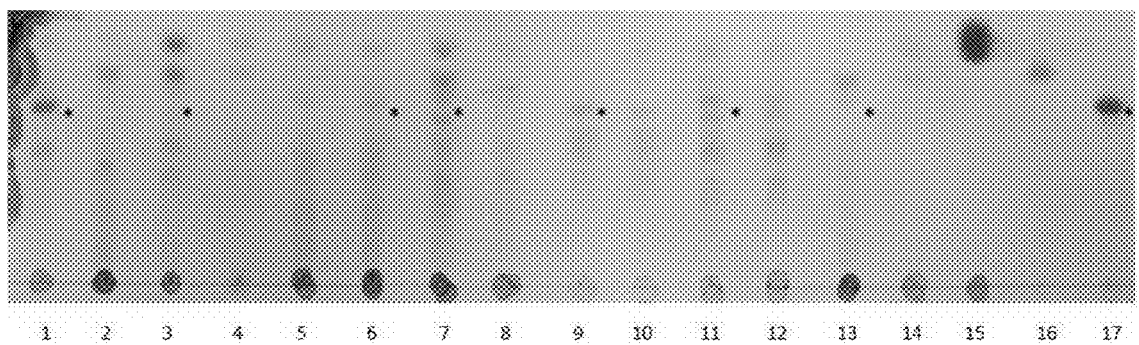
FIG. 3 shows the results of the TLC analysis of culture extracts of lacto-N-tetraose (LNT) producing *E. coli* BL21 (DE3) strains overexpressing the β-1,4-galactosyltransferase encoding genes BfgalT2 (1), PmgalT7 (3), MsgalT8 (6), gatD (7), lex1 (9), lgtB (11) or lsgD (13)
Figure 4:
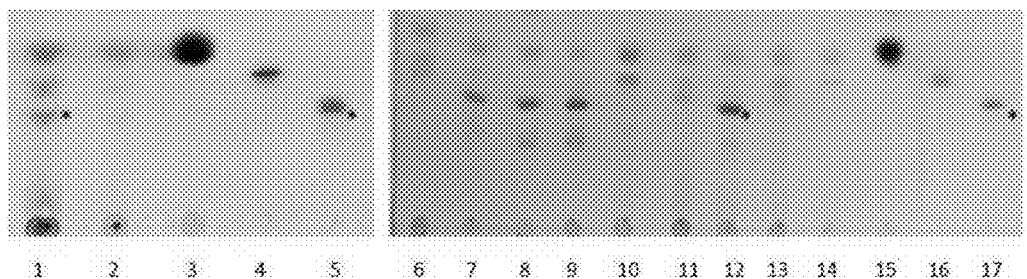
FIG. 4 shows the results of the TLC analysis of culture extracts of lacto-N-tetraose (LNT) producing *E. coli* BL21 (DE3) strains overexpressing the β-1,4-galactosyltransferase encoding genes KdgalT10 (1), cpsl14J (7), cpslaJ (8, 9), HpgalT (12)
Figure 5:
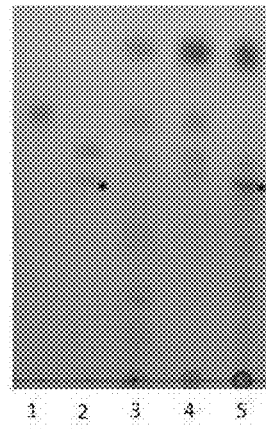
FIG. 5 shows the results of the TLC analysis of culture extracts of lacto-N-tetraose producing *E. coli* BL21(DE3) strains overexpressing the β-1,4-galactosyltransferase encoding gene waaX (5)
Figure 6:
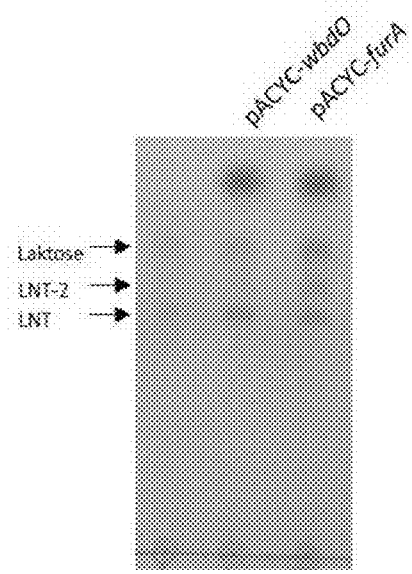
FIG. 6 shows the results of the TLC analysis of culture extracts of lacto-N-tetraose producing *E. coli* BL21(DE3) strains overexpressing the β-1,3-galactosyltransferase encoding genes wbdO or furA.
Figure 7:
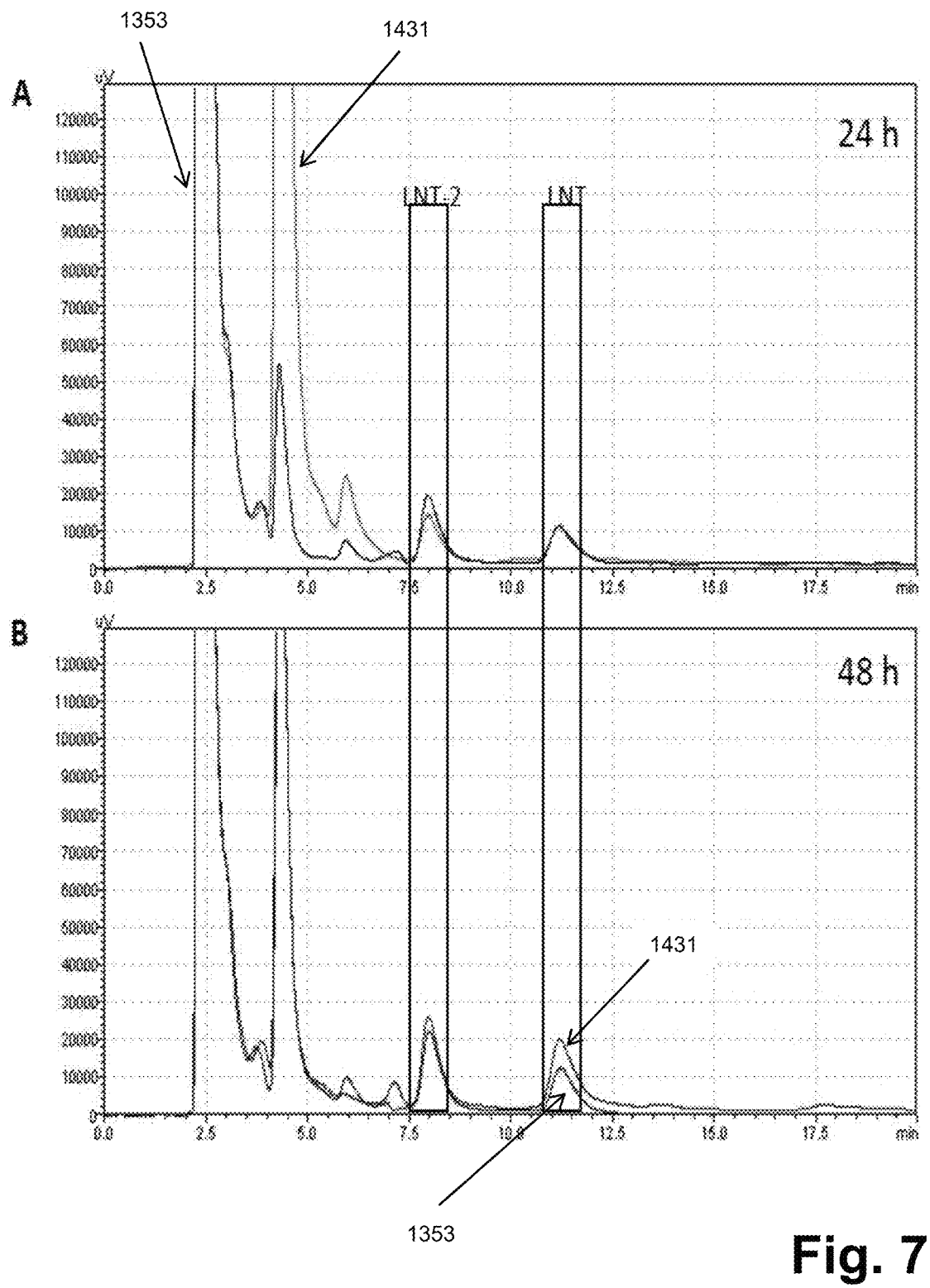
FIG. 7 shows the results of HPLC analyses of the culture superna-tant of lacto-N-tetraose producing *E. coli* BL21 (DE3) strain. (A) Supernatant of *E. coli* BL21(DE3) 1353 and 1431 grown in the presence of glucose and lactose after 24 h of incubation. (B) Supernatant of *E. coli* BL21(DE3) 1353 and 1431 grown in the presence of glucose and lactose after 48 h of incubation.
Figure 8:
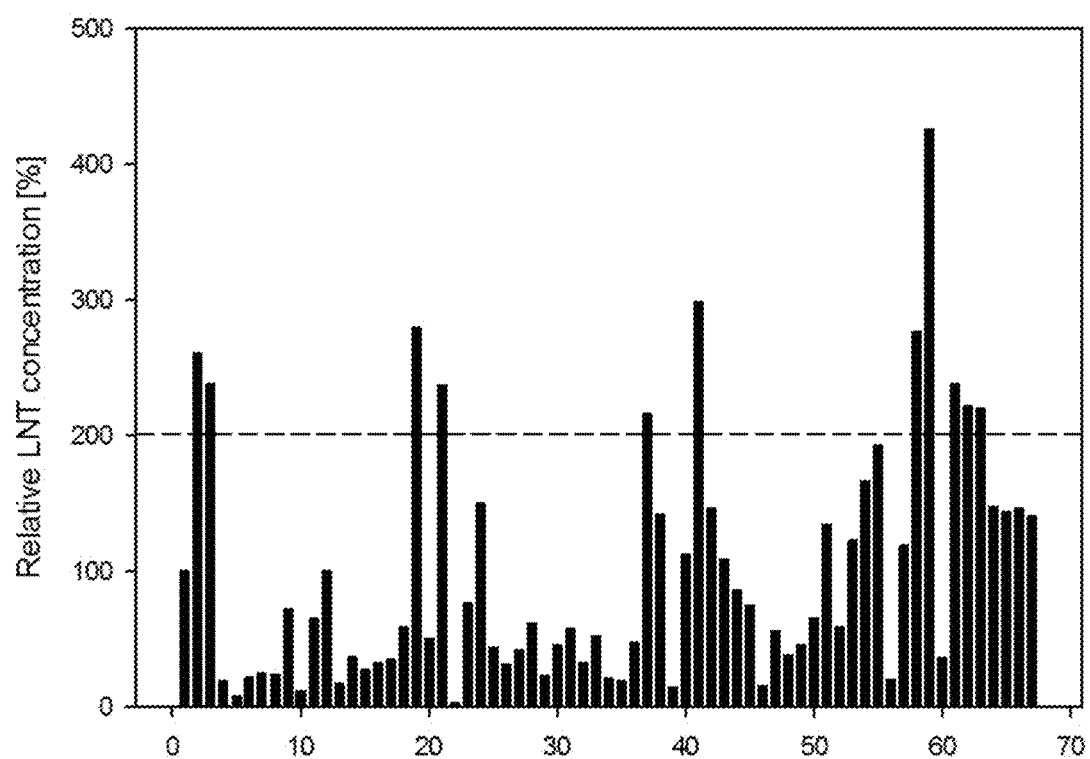
FIG. 8 shows a diagram depicting the relative concentration of lacto-N-tetraose in the supernatant of *E. coli* BL21 (DE3) strains overexpressing sugar efflux transporters compared to the control strain 1353.
Figure 9:
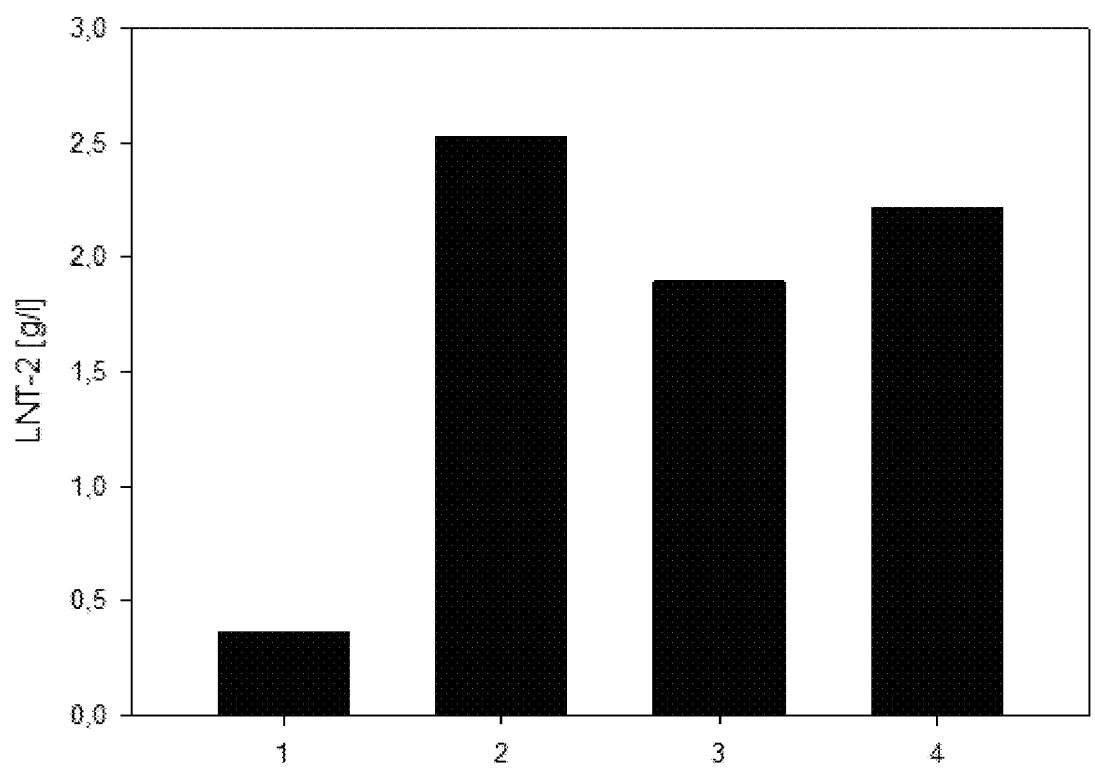
FIG. 9 shows a diagram depicting concentrations of lacto-N-triose II in the supernatant of *E. coli* BL21 (DE3) strains overexpressing the sugar efflux transport-ers TP11 (2), YjhB (3) or TP70 (4).

The invention will be described in more detail in the examples and the attached figures, in which FIG. 1 shows a schematic illustration for the production of either lacto-N-triose II or lacto-N-tetraose in a host cell cultivated in a medium;

FIG. 2 shows the results of the TLC analysis of culture extracts of lacto-N-triose II (LNT II) producing *E. coli* BL21(DE3) strains overexpressing the β-1,3-N-acetyl glucosaminyltransferase gene PmnagT(13, 14);

FIG. 3 shows the results of the TLC analysis of culture extracts of lacto-N-tetraose (LNT) producing *E. coli* BL21 (DE3) strains overexpressing the β-1,4-galactosyltransferase encoding genes BfgalT2 (1), PmgalT7(3), MsgalT8 (6), gatD (7), lex1 (9), lgtB (11) or IsgD (13);

FIG. 4 shows the results of the TLC analysis of culture extracts of lacto-N-tetraose (LNT) producing *E. coli* BL21 (DE3) strains overexpressing the β-1,4-galactosyltransferase encoding genes KdgalT10 (1), cpsl14J (7), cpslaJ (8, 9), HpgalT (12);

FIG. 5 shows the results of the TLC analysis of culture extracts of lacto-N-tetraose producing *E. coli* BL21(DE3) strains overexpressing the β-1,4-galactosyltransferase encoding gene waaX (5);

FIG. 6 shows the results of the TLC analysis of culture extracts of lacto-N-tetraose producing *E. coli* BL21(DE3) strains overexpressing the β-1,3-galactosyltransferase encoding genes wbdO or furA;

FIG. 7 shows the results of HPLC analyses of the culture supernatant of lacto-N-tetraose producing *E. coli* BL21 (DE3) strain. (A) Supernatant of *E. coli* BL21(DE3) 1353 and 1431 grown in the presence of glucose and lactose after 24 h of incubation. (B) Supernatant of *E. coli* BL21(DE3) 1353 and 1431 grown in the presence of glucose and lactose after 48 h of incubation;

FIG. 8 shows a diagram depicting the relative concentration of lacto-N-tetraose in the supernatant of *E. coli* BL21 (DE3) strains overexpressing sugar efflux transporters compared to the control strain 1353; and FIG. 9 shows a diagram depicting concentrations of lacto-N-triose II in the supernatant of *E. coli* BL21 (DE3) strains overexpressing the sugar efflux transporters TP11 (2), YjhB (3) or TP70 (4).

EXAMPLES

FIG. 1 shows a schematic drawing of an exemplary host cell 10 according to the invention, importing lactose and synthesizing lacto-N-triose II (LNT II) and lacto-N-tetraose (LNT). Lactose is imported from the medium the host cell is cultivated in into the cell via transporter 1. The enzyme N-acetylglucosaminyltransferase NacGlcT ligates N-acetylglucosamine to the acceptor substrate lactose, thus generating LNT-II. LNT-II is exported from the cell via exporter protein 20. Since LNT-II is a precursor of LNT or LNnT, the exporter exporting LNT-II represents an exporter protein exporting precursors of the latter oligosaccharides. As can further be seen from FIG. 1, the cell comprises a protein having β-1,3-galactosyltransferase activity enabling the galactosylation of LNT-II to intracellularly generate LNT; the cell may also and/or alternatively comprise or β-1,4-galactosyltransferase activity enabling the galactosylation of LNT-II to intracellularly generate lacto-N-neotetraose LNnt. LNT—or as the case may be LNnt—is then exported, via a oligosaccharide exporter from the cell into the culture medium the cell is cultivated in.

The exporters are membrane-bound, and their expression can be either overexpressed, which—in case of overexpression of the LNT-II exporter leads to an increased LNT-II export and to a decreased LNT export, whereas when the LNT-II exporting exporter protein is deleted or otherwise inactivated, this leads to an improved LNT-export. The LNT-II exporter preferably is an endogenous exporter protein, whereas the LNT-exporter protein preferably is a heterologous exporter protein.

Example 1

Development of an *E. coli* Lacto-N-Triose II Production Strain

*Escherichia coli* BL21(DE3) was used to construct a lacto-N-triose II (LNT-2) producing strain. Metabolic engineering included mutagenesis and deletions of specific genes, respectively, and genomic integrations of heterologous genes. The genes lacZ and araA were inactivated by mutagenesis using mismatch-oligonucleotides as described by Ellis et al., "High efficiency mutagenesis, repair, and engineering of chromosomal DNA using single-stranded oligonucleotides", Proc. Natl. Acad. Sci. USA 98: 6742-6746 (2001).

Genomic deletions were performed according to the method of Datsenko and Warner (Proc. Natl. Acad. Sci. USA 97:6640-6645 (2000)). To prevent intracellular degradation of N-acetylglucosamine, genes encoding N-acetylglucosamine-6-phosphate deacetylase (nagA) and glucosamine-6-phosphate deaminase (nagB) were deleted from the genome of the *E. coli* strain BL21 (DE3) strain. Also genes wzxC-wcaJ were deleted. WcaJ encodes an UDP-glucose:undecaprenyl phosphate glucose-1-phosphate transferase catalysing the first step in colanic acid synthesis (Stevenson et al., J. Bacteriol. 1996, 178:4885-4893). In addition the genes fucI and fucK, coding for L-fucose isomerase and L-fuculose kinase, respectively, were removed.

Genomic integration of heterologous genes was performed by transposition. Either the EZ-Tn5™ transposase (Epicentre, USA) was used to integrate linear DNA-fragments or the hyperactive C9-mutant of the mariner transposase Himar1 (Lampe et al., Proc. Natl. Acad. Sci. 1999, USA 96:11428-11433) was employed for transposition. To produce EZ-Tn5 transposomes the gene of interest together with a FRT-site flanked antibiotic resistance marker was amplified with primer 1119 and 1120 (all primer used are listed in table 3 below); the resulting PCR-product carried on both sites the 19-bp Mosaic End recognition sites for the EZ-Tn5 transposase. For integration using Himar1 transposase expression constructs (operons) of interest were similarly cloned together with a FRT-site flanked antibiotic resistance marker into the pEcomar vector. The pEcomar vector encodes the hyperactive C9-mutant of the mariner transposase Himar1 under the control of the arabinose inducible promoter $P_{araB}$. The expression fragment <$P_{tet}$-lacY-FRT-aadA-FRT>(SeqID1) was integrated by using the EZ-Tn5 transposase. After successful integration of the gene for the lactose importer LacY from *E. coli* K12 TG1 (acc. no. ABN72583) the resistance gene was eliminated from streptomycin resistant clones by the FLP recombinase encoded on plasmid pCP20 (Datsenko and Warner, Proc. Natl. Acad. Sci. 2000, USA 97:6640-6645). The N-acetylglucosaminyltransferase gene lgtA from *Neisseria meningitidis* MC58 (acc. no. NP_274923) was codon-optimized for expression in *E. coli* and prepared synthetically by gene synthesis. Together with the gene galT, encoding a galactose-1-phosphate uridylyltransferase from *E. coli* K-12 substr. MG1655 (acc. no. NP_415279) that was similarly obtained by gene synthesis, lgtA was inserted by transposition (SeqID2) using plasmid pEcomar-lgtA-galT. To enhance de novo synthesis of UDP-N-acetylglucosamine, genes encoding L-glutamine:D-fuctose-6-phosphate aminotransferase (glmS), phosphoglucosamine mutase from *E. coli* K-12 substr. MG1655 (glmM) and N-acetylglucosamine-1-phosphate uridyltransferase/glucosamine-1-phosphate acetyltransferase (glmU) from *E. coli* K-12 substr. MG1655 (acc. no. NP_418185, NP_417643, NP_418186, respectively) were codon-optimized and obtained by gene synthesis. The operon glmUM was cloned under the control of constitutive tetracyclin promoter $P_{tet}$ while glmS was cloned under the constitutive $P_{T5}$ promoter. The transposon cassette <$P_t$et-glmUM-$P_{T5}$-glmS-FRT-dhfr-FRT>(SeqID3), flanked by the inverted terminal repeats specifically recognized by the mariner-like element Himar1 transposase was inserted from pEcomar-glmUM-glmS revealing a lacto-N-triose II production strain. Additionally, the expression fragment <$P_{tet}$-lacY(6H/S)-FRT-aadA-FRT>(SeqID4) was integrated by using the EZ-Tn5 transposase.

The gal-operon (galETKM) was amplified from *E. coli* K12 TG1 (SeqID6) using primer 605 and 606 and inserted into the galM ybhJ locus of *E. coli* BL21 (DE3) strain by homologous recombination facilitated by using the red recombinase helper plasmid pKD46 (Datsenko and Warner, Proc. Natl. Acad. Sci. 2000, USA 97:6640-6645). Sequences of the heterologous genes and gene clusters are deposit in appendix 1.

Example 2

Batch Fermentation of *E. coli* BL21 (DE3) 707 Screening Various β-1,3-N-acetyl-glycosaminyl Transferases The gene for the β-1,3-N-acetyl-glucosaminyltransferase PmnagT from *Pasteurella multocida* subsp. *multocida* str. HN06 (acc. no. PMCN06_0022) was codon-optimized and synthetically synthesized by GenScript Cooperation (Piscataway, USA). Cloning of the gene occurred by sequence and ligation-independent cloning into the plasmid pET-DUET (Merck KGaA, Darmstadt, Germany). All primer used for cloning are listed in table 3 below.

*E. coli* BL21(DE3) 707 (table 2 below) harbouring plasmid pET-PmnagT coding for a β-1,3-N-acetyl glucosaminyltransferase was grown at 30° C. in mineral salts medium (Samain et al., J. Biotech. 1999, 72:33-47) supplemented with 2% (wt/vol) glucose and ampicillin 100 μg ml$^{-1}$. When the cultures reached an OD660 nm of 0.1, gene expression was induced by addition of 0.3 mM IPTG. After four hours of incubation 1.5 mM lactose was added. After an additional incubation for 24 hours at 30'C in shaking flasks cells were harvested. LNT-2 was detected by thin layer chromatography. Therefore, cells were mechanically disrupted in a defined volume using glass beads. Subsequently, samples were applied on TLC Silica Gel 60 $F_{254}$ (Merck KGaA, Darmstadt, Germany). The mobile phase was composed of acetone:butanol:acetic acid:water (35:35:7:23).

The result of the TLC analysis is shown in FIG. 2. The formation of a compound showing the same migration rate as the trisaccharide standard LNT-II could be observed when the gene PmnagT was overexpressed. The LNT-II production strain 724 served as a control (19). Standards for lactose (1) and LNT-II (2) are depicted. LNT-II product formation in the samples is marked by asterisks.

Example 3

Generation of an *E. coli* Lacto-N-Triose II Production Strain Overexpressing a Homologous Sugar Efflux Transporter The export of oligosaccharides produced in *E. coli* was proven to be a limiting factor during the fermentation process. However, trisaccharides like 2'-fucosyllactose and LNT-2 are translocated into the culture supernatant to some extent, thus probably encoding a working sugar efflux transporter. In order to improve the efflux of lacto-N-triose II (LNT-II; GluNAc(1-3)Gal(β1-4)Glc), the *E. coli* BL21 (DE3) strain 1326 (table 2 below) was used for the screening of a library of sugar efflux transporters (SET). Putative SET proteins from *E. coli* were amplified from genomic DNA of *E. coli* BL21 (DE3) and integrated into vector pINT by sequence and ligation-independent cloning. Using the example of the gene yjhB, the primer 2567, 2568, 2526 and 2443 were used, generating the plasmid pINT-yjhB. The primer sequences used for cloning are listed in table 3 below.

*E. coli* BL21(DE3) 1326 harbouring plasmids encoding for 20 different *E. coli* transporters were grown at 30° C. in mineral salts medium (Samain et al., J. Biotech. 1999, 72:33-47) supplemented with 2% (wt/vol) glucose, ampicillin 100 μg ml$^{-1}$ and zeocin 40 μg ml$^{-1}$. When the cultures reached an OD660 nm of 0.1, gene expression of the genes was induced by addition of 200 ng/ml anhydrotetracycline. After four hours of incubation 2.5 mM lactose was added. After an additional incubation for 24 and 48 hours at 30° C. in shaking flasks the LNT-II concentration in the supernatant was determined by LC-MS.

Mass analysis was performed by characteristic fragment ion detection using an LC Triple-Quadrupole MS detection system. Precursor ions are selected and analyzed in quadrupole 1, fragmentation takes place in the collision cell using nitrogen as CID gas, selection of fragment ions is performed in quadrupole 3.

Lacto-N-tetraose (LNT (Gal(β1-3)GlcNAc(β1-3)Gal(β1-4)Glc)), LNT-II and Maltotriose (internal standard for quantification) were analyzed in ESI positive ionization mode. LNT forms an ion of m/z 708.3 [M+H$^+$], LNT-II an ion of m/z 546.1 [M+H$^+$] and Maltotriose an ion of m/z 522.0 [M+NH$_4^+$]. Adduct formation of this carbohydrate [m/z 504.0] takes place with an ammonium ion (NH4$^+$), resulting in mass shift of +18. Thus for Maltotriose a precursor ion of m/z 522.0 was selected. The precursor ion was further fragmented in the collision cell into the characteristic fragment ions m/z 487.1, m/z 325.0 and m/z 163.2. The molecular ion of LNT (m/z 708.3) was fragmented into m/z 546.3, m/z 528.3, m/z 366.2 and m/z 204.0. LNT-II (m/z 546.1) was fragmented into m/z 204.2, 186.0, 138.0 and 126.0 (see method description).

Chromatographic separation of LNT and LNT-II was performed on a Luna NH$_2$ HPLC column (Phenomenex, Aschaffenburg, Germany). This was necessary due to partial fragmentation of LNT during ionization resulting in LNT-II signals affecting quantification results of the individual carbohydrates.

Only for the strain expressing the gene yjhB, an increased amount of LNT-2 in the culture supernatant was observed (see table 1 below).

TABLE 1

Calculated concentrations of LNT-II in the culture supernatant of an E. coli BL21 (DE3) strain overexpressing yjhB and the reference strain.

| Sample | Calc. conc. after 24 h of incubation [μM] | Calc. conc. after 48 h of incubation [μM] | Analyte RT |
|---|---|---|---|
| 1326 | 751 | 1265 | 0.616 |
| 1326 pINT-yjhB | 413 | 1975 | 0.609 |

Example 4

Batch Fermentations of E. coli BL21(DE3) 724 Screening Various β-1,4-Galactosyltransferases The genes for the β-1,4-galactosyltransferases lex1 from *Aggregatibacter aphrophilus* NJ8700 (acc. no. YP_003008647), PmgalT7 from *Pasteurella multocida* subsp. *multocida* str. HN06 (acc. No. PMCN06_0021), MsgalT8 from *Myxococcus stipitatus* DSM14675 (acc. no. MYSTI_04346), KdgalT10 from *Kingella denitrificans* ATCC 33394 (acc. no. HMPREF9098_2407), gatD from *Pasteurella multocida* M1404 (acc. no. GQ444331), BfgalT2 from *Bacterioidis fragilis* NCTC9343 (acc. no. BF9343_0585), IsgD from *Haemophilus influenza* (acc. no. AAA24981) and HpgalT from *Helicobacter pylori* (acc. no. AB035971) were codon-optimized and synthetically synthesized by GenScript Cooperation (Piscataway, USA). Cloning of the genes occurred by sequence and ligation-independent cloning (Li and Elledge, Nat Methods. 2007 March; 4(3):251-6.). Therefore, the plasmid pINT, harbouring the malE gene under control of an anhydrotetracyline-inducible promoter, was used, enabling the generation of a N-terminal fusion of the β-1,4-galactosyltransferase genes with malE. Solely, the β-1,4-galactosyltransferase encoding gene waaX from *Pectobacterium atrosepticum* JG10-08 (acc. no. ECA0154) was cloned into plasmid pACYC-Duet (Merck KGaA, Darmstadt, Germany). All primer used for cloning are listed in table 3 below.

*E. coli* BL21(DE3) 724 (table 2 below) harbouring plasmid pCDF-galE and a plasmid coding for the gene fusion of malE with a β-1,4-galactosyltransferase was grown at 30° C. in mineral salts medium (Samain et al., J. Biotech. 1999, 72:33-47) supplemented with 2% (wt/vol) glucose, ampicillin 100 μg ml$^{-1}$ and zeocin 40 μg ml$^{-1}$. When the cultures reached an OD660 nm of 0.1, gene expression of the galE gene and the β-1,4-galactosyltransferase was induced by addition of 0.3 mM IPTG and 200 ng/ml anhydrotetracycline. *E. coli* BL21(DE3) 534 (table 2 below) harbouring plasmids pET-lgtA, pCOLA-glmUM-glmS, pCDF-galT-galE and pACYC-waaX was grown at 30° C. in mineral salts medium supplemented with 2% (wt/vol) glucose, ampicillin 100 μg ml$^{-1}$, chloramphenicol 34 μg ml$^{-1}$, streptomycin 50 μg ml$^{-1}$ and kanamycin 30 μg ml$^{-1}$. When the cultures reached an OD660 nm of 0.1, gene expression was induced by addition of 0.3 mM IPTG. Four hours after induction of gene expression 2 mM lactose were added. After an additional incubation for 48 hours at 30° C. in shaking flasks, cells were harvested and mechanically disrupted. Lacto-N-neotetraose (LNnT (Gal(β1-4)GlcNAc(β1-3)Gal(β1-4)Glc)) was detected by thin layer chromatography. Therefore, cells were mechanically disrupted using glass beads. Subsequently, samples were applied on TLC Silica Gel 60 F$_{254}$ (Merck KGaA, Darmstadt, Germany). The mobile phase was composed of acetone:butanol:acetic acid:water (35:35:7:23).

The results of the TLC analyses are shown in FIGS. 3-5.

FIG. 3 shows the TLC analysis of culture extracts of lacto-N-tetraose (LNT) producing *E. coli* BL21(DE3) strains overexpressing the β-1,4-galactosyltransferase encoding genes BfgalT2 (1), PmgalT7 (3), MsgalT8 (6), gatD (7), lex1 (9), IgtB (11) or IsgD (13). Standards for lactose (15), LNT-II (16) and LNnT (17) are depicted. LNnT product formation in the samples is marked by asterisks.

FIG. 4 shows the TLC analysis of culture extracts of lacto-N-tetraose (LNT) producing *E. coli* BL21(DE3) strains overexpressing the β-1,4-galactosyltransferase encoding genes KdgalT10 (1), cpsl14J (7), cpslaJ (8, 9), HpgalT (12). Standards for lactose (3, 15), LNT-II (4, 16) and LNnT (5, 17) are depicted. LNnT product formation in the samples is marked by asterisks.

FIG. 5 shows the TLC analysis of culture extracts of lacto-N-tetraose producing *E. coli* BL21(DE3) strains overexpressing the β-1,4-galactosyltransferase encoding gene waaX (5). Standards for lactose (1), LNT-II and LNnT (2) are depicted. Again, LNnT product formation in the samples is marked by asterisks.

The formation of a compound showing the same migration rate as the tetrasaccharide standard LNnT could be observed when the following genes were overexpressed: lex1, PmgalT7, MsgalT8, BfgalT2, gatD, IsgD, KdgalT10, HpgalT, wax.

The β-1,4-galactosyltransferases cpslaJ and cpsl14J, known from literature to produce LNnT (Watanabe et al., J Biochem. 2002 February; 131(2):183-91; Kolkman et al., J Bacteriol. 1996 July; 178(13):3736-41), were also included in the activity screening and served as positive control. Using the described expression system, the formation of LNnT could be observed by CpslaJ and Cpsl14J (FIG. 3). In total, 11 out of 30 tested genes were observed to produce LNnT from LNT-II and UDP-galactose.

Example 5

Batch Fermentations of E. coli BL21(DE3) 534 Screening Different β-1,3-Galactosyltransferases Using genomic DNA of *E. coli* K12 DH5α as template, galE was amplified using primer 1163 and 1162. The PCR product was purified, restricted with restriction endonucleases NdeI and XhoI and ligated into the second multiple cloning site of vector pCDFDuet (Merck KGaA, Darmstadt, Germany), which was cut with the same enzymes. GalE is expressed from the IPTG inducible T7 promoter. The *E. coli* K12 gene galT was amplified from genomic DNA and integrated into plasmid pCDF-galE by sequence and ligation-independent cloning using primer 991-994, producing the plasmid pCDF-galT-galE.

Using the codon-optimized gene of lgtA as template, amplification occurred using primer 688 and 689. The PCR product was purified, restricted with restriction endonucleases NdeI and AatII and ligated into the multiple cloning site of vector pETDuet (Merck KGaA, Darmstadt, Germany), which was cut with the same enzymes, producing the plasmid pET-lgtA.

Cloning of the codon-optimized gene construct of glmUM occurred by sequence and ligation-independent cloning into the plasmid pCOLA-Duet (Merck KGaA, Darmstadt, Germany) using primer 848-851. The codon-optimized form of glmS was amplified using primer 852 and 853. The PCR product was purified, restricted with restriction endonucleases NdeI and AatII and ligated into the second multiple cloning site of vector pCOLA-glmUM, which was cut with the same enzymes, producing the plasmid pCOLA-glmUM-glmS.

The genes for the β-1,3-galactosyltransferases wbdO from *Salmonella enterica* subsp. *salamae* serovar Greenside (acc. no. AY730594) and furA from *Lutiella nitroferrum* 2002 (FuraDRAFT_0419) were also codon-optimized and synthetically synthesized by GenScript Cooperation (Piscataway, USA). Cloning of the genes occurred by sequence and ligation-independent cloning into the plasmid pACYC-Duet (Merck KGaA, Darmstadt, Germany). All primer used for cloning are listed in table 3 below.

*E. coli* BL21(DE3) 534 harbouring plasmids pET-lgtA, pCOLA-glmUM-glmS, pCDF-galT-galE and a plasmid coding for a β-1,3-galactosyltransferase pACYC-furA or pACYC-wbdO was grown at 30° C. in mineral salts medium (Samain et al., J. Biotech. 1999, 72:33-47) supplemented with 2% (w/v) glucose, ampicillin 100 µg ml-1, chloramphenicol 34 µg ml$^{-1}$, streptomycin 50 µg ml$^{-1}$ and kanamycin 30 µg ml$^{-1}$. When the cultures reached an OD660 nm of 0.1, gene expression was induced by addition of 0.3 mM IPTG. After four hours of incubation 2 mM lactose was added. After an additional incubation for 48 hours at 30° C. in shaking flasks, cells were harvested. LNT was detected by thin layer chromatography. Therefore, cells were mechanically disrupted using glass beads. Subsequently, samples were applied on TLC Silica Gel 60 $F_{254}$ (Merck KGaA, Darmstadt, Germany). The mobile phase was composed of acetone:butanol:acetic acid:water (35:35:7:23).

The results of the TLC analyses are shown in FIG. 6, showing TLC analysis of culture extracts of lacto-N-tetraose producing *E. coli* BL21(DE3) strains overexpressing the β-1,3-galactosyltransferase encoding genes wbdO or furA. LNT product formation in the samples is marked. Out of 12 tested putative β-1,3-galactosyltransferases, the formation of a compound showing the same migration rate as the tetrasaccharide standard LNT could only be observed when genes wbdO and furA were overexpressed.

Example 6

Development of an Improved Plasmid-Free *E. coli* Lacto-N-Tetraose Production Strain

*Escherichia coli* BL21(DE3) strain 724 was used to construct a lacto-N-tetraose (LNT) producing strain. Metabolic engineering included the genomic integration of the transposon cassettes <$P_{tet}$-wbdO-$P_{T5}$-galE-FRT-cat-FRT> (SeqID5), flanked by the inverted terminal repeats specifically recognized by the mariner-like element Himar1 transposase, which was inserted from pEcomar-wbdO-galE. The resulting strain 1353 was further metabolically engineered to exhibit an increased intracellular LNT-II pool resulting in the elevated production of LNT. Therefore, the mayor facilitator superfamily transporter yjhB (acc. no. YP_003001824) was deleted from the genome of the *E. coli* strain, generating strain 1431 (table 2 below).

Batch fermentation of the *E. coli* BL21(DE3) strains 1353 and 1431 was conducted for 48 hours at 30° C. in mineral salts medium (Samain et al., J. Biotech. 1999, 72:33-47) containing 2% (wt/vol) glucose as sole carbon and energy source. When the cultures reached an OD660 nm of 0.5, 2.5 mM lactose was added. The presence of LNT-II and LNT in the culture supernatant was detected by high performance liquid chromatography (HPLC).

Analysis by HPLC was performed using a refractive index detector (RID-10A) (Shimadzu, Duisburg, Germany) and a ReproSil Carbohydrate, 5 µm (250 mm×4.6 mm) (Dr. Maisch GmbH, Germany) connected to an HPLC system (Shimadzu, Duisburg, Germany). Elution was performed isocratically with acetonitril:$H_2O$ (68/32 (v/v)) as eluent at 35° C. and a flow rate of 1.4 ml/min. 40 µl of the sample were applied to the column. Samples were filtered (0.22 µm pore size) and cleared by solid phase extraction on an ion exchange matrix (Strata ABW, Phenomenex, Aschaffenburg, Germany).

The results of the HPLC analyses are shown in FIG. 7, showing HPLC analyses of the culture supernatant of lacto-N-tetraose producing *E. coli* BL21 (DE3) strain. (A) Supernatant of *E. coli* BL21(DE3) 1353 (black graph) and 1431 (pink graph) grown in the presence of glucose and lactose after 24 h of incubation. (B) Supernatant of *E. coli* BL21 (DE3) 1353 (blue graph) and 1431 (brown graph) grown in the presence of glucose and lactose after 48 h of incubation. As can be seen from the HPLC analyses, the deletion of yjhB in a LNT producing strain resulted in an elevated accumulation of LNT in the culture supernatant.

Example 7

Generation of an *E. coli* Lacto-N-Tetraose Production Strain Overexpressing a Sugar Efflux Transporter Since an export of lacto-N-tetraose into the medium is only moderate for production strains, a screening of a sugar efflux transporter library was conducted. In accordance to example 3 putative SET proteins were either amplified from *E. coli* genomic DNA or were codon-optimized and synthetically synthesized by GenScript Cooperation (Piscataway, USA). Following amplification genes were integrated into vector pINT by sequence and ligation-independent cloning. The primer design for the cloning of *E. coli* genes was in accordance to example 3. Synthetic genes were synthesized with standardized nucleotide overhangs and likewise integrated into the expression vector using the primer 2527, 2444, 2526 and 2443. The primer sequences used for cloning are listed in table 3 below.

*E. coli* BL21(DE3) 1353 (table 2 below) harbouring plasmids encoding for 66 different transporters were grown at 30° C. in mineral salts medium (Samain et al., J. Biotech. 1999, 72:33-47) supplemented with 3% (w/v) glucose, 5 gl$^{-1}$ $NH_4Cl_2$, ampicillin 100 µg ml$^{-1}$ and kanamycin 15 µg ml$^{-1}$. Precultivation appeared in 96-well plates harbouring a total volume of 200 µl. After 24 h of incubation at 30° C. by continuous shaking, 50 µl per well was transferred into 96-well deep well plates harbouring a total volume of 400 µl mineral salts medium additionally supplemented with 200 ng ml$^{-1}$ anhydrotetracycline and 10 mM lactose. After a sustained incubation for 24 to 48 hours the LNT concentrations in the supernatant were determined by LC-MS. Mass analysis was performed as described in example 3.

FIG. 8 shows the relative concentration of lacto-N-tetraose in the supernatant of *E. coli* BL21 (DE3) strains overexpressing sugar efflux transporters compared to the control strain 1353. The LNT titer of strain 1353 was set to 100%. As shown in FIG. 8, the overexpression of 11 out of 66 genes resulted in a doubled LNT production. Among these, also a protein encoded in the genome of *E. coli* BL21 (DE3) proved to enhance the LNT export (TP37, yebQ, acc. no. NC_012971). YebQ is a predicted MFS transporter, putatively involved in multi drug efflux, which might represent a responsible transporter protein that realizes the observed basal efflux of LNT during fermentation of strain 1353.

Furthermore, the exporters encoded by the genes spoVB of *Bacillus amyloliquefaciens* (TP1, acc. no. AFJ60154), yabM of *Erwinia pyrifoliae* (TP2, acc. no. CAY73138), bcr of *E. coli* MG1655 (TP18, acc. no. AAC75243), ydeA of *E. coli* MG1655 (TP20, acc. no. AAC74601), proP2 of *Haemophilus parainfluenzae* (TP54, acc. no. EGC72107), setA of *Pectobacterium carotovorum* (TP55, acc. no. ZP_03829909), fucP of *E. coli* MG1655 (TP59, acc. no. AIZ90162), mdeA of *Staphylococcus aureus* Bmb9393 (TP61, acc. no. SABB_01261), ImrA of *Lactococcus lactis* (TP62, acc. no. L116532), setA of *Pseudomonas* sp. MT-1 (TP72, acc. no. BAP78849) and setA of *Beauveria bassiana* D1-5 (TP73, acc. no. KGQ13398) resulted in an increased LNT production when overexpressed in the *E. coli* production strain 1353.

Example 8

Generation of an *E. coli* Lacto-N-Triose II Production Strain by Overexpression of Heterologous Sugar Efflux Transporters The LNT exporter screening described in example 6 interestingly disclosed two proteins—TP11 from *Mannheimia succiniciproducens* MBEL55E (proP, acc. no. AAU37785) and TP70 from *Cedecea neteri* M006 (setA, acc. no. WP_039290253)—whose overexpression resulted in a significantly increased production of LNT-II and consequently in a decreased LNT production (data not shown). This observation was confirmed in an experimental setup as described in example 3. The overexpression of the sugar efflux transporter YjhB served as a positive control. The overexpression of TP11 as well as TP70 resulted in an approximately 4-fold increase in LNT-II production which was even slightly more than for YjhB: FIG. 9 shows a diagram displaying the concentrations of lacto-N-triose II in the supernatant of *E. coli* BL21 (DE3) strains overexpressing the sugar efflux transporters TP11 (2), YjhB (3) or TP70 (4). Strain 1326 harbouring an empty control plasmid served as a control (1). Thus, 3 sugar efflux transporters were identified which target LNT-II for export and whose overexpression might be useful to engineer a LNT-II production strain.

TABLE 2

Strains and plasmids

| Strain | Genotype | Ref. |
|---|---|---|
| *E. coli* BL21(DE3) | F-ompT hsdSB(rB-, mB-) gal dcm (DE3) | Merck KGaA, Darmstadt, Germany |
| *E. coli* BL21(DE3) 534 | *E. coli* BL21(DE3) ΔlacZ Δara ΔwcaJ ΔfucIK ΔnagAB harbouring genomic integrations of: galETKM, lacy | This study |
| *E. coli* BL21(DE3) 724 | *E. coli* BL21(DE3) ΔlacZ Δara ΔwcaJ ΔfucIK ΔnagAB harbouring genomic integrations of: galETKM, lacY, IgtA-galT-kanR, glmUM-glmS-dhfr | This study |
| *E. coli* BL21(DE3) 1326 | *E. coli* BL21(DE3) ΔlacZ Δara ΔwcaJ ΔfucIK ΔnagAB harbouring genomic integrations of: galETKM, lacY, IgtA-galT-kanR, glmUM-glmS-dhfr, lacy(6HIS)-aadA | This study |
| *E. coli* BL21(DE3) 707 | *E. coli* BL21(DE3) ΔlacZ Δara ΔwcaJ ΔfucIK ΔnagAB harbouring genomic integrations of: galETKM, lacY, glmUM-glmS-dhfr | This study |
| *E. coli* BL21(DE3) 1353 | *E. coli* BL21(DE3) ΔlacZ Δara ΔwcaJ ΔfucIK ΔnagAB harbouring genomic integrations of: galETKM, lacY, IgtA-galT-kanR, glmUM-glmS-dhfr, wbdO-galE-cat | This study |
| *E. coli* BL21(DE3) 1431 | *E. coli* BL21(DE3) ΔlacZ Δara ΔwcaJ ΔfucIK ΔnagAB harbouring genomic integrations of: galETKM, lacY, IgtA-galT-kanR, glmUM-glmS-dhfr, wbdO-galE-cat, ΔyjhB-aacC1 | This study |
| pCDF-galE | galE of *E. coli* K12 integrated into vector pCDFDuet | EP 14 162 869.3 |
| pET-IgtA (SeqID7) | IgtA of *Neisseria meningitidis* integrated into vector pETDuet | This study |
| pCDF-galT-galE (SeqID8) | galT and galE of *Escherichia coli* K12 integrated into vector pCDFDuet | This study |

TABLE 2-continued

Strains and plasmids

| Strain | Genotype | Ref. |
|---|---|---|
| pCOLA-glmUM-glmS (SeqID9) | glmU, glmM and glmS of *Escherichia coli* K12 integrated into vector pCOLADuet | This study |
| pINT-malE-lex1 | Gene fusion of malE with lex-1 of *Aggregatibacter aphrophilus* NJ8700 integrated into vector pINT | EP 14 162 869.3 |
| pINT-malE-PmgalT7 (SeqID10) | Gene fusion of PmgalT7 of *Pasteurella multocida* subsp. *multocida* str. HN06 integrated into vector pINT | This study |
| pINT-malE-MsgalT8 SeqID11) | Gene fusion of MsgalT8 of *Myxococcus stipitatus* DSM14675 integrated into vector pINT | This study |
| pINT-malE-KdgalT10 (SeqID12) | Gene fusion of KdgalT10 of *Kingella denitrificans* ATCC 33394 integrated into vector pINT | This study |
| pINT-malE-gatD (SeqID13) | Gene fusion of gatD of *Pasteurella multocida* M1404 integrated into vector pINT | This study |
| pINT-malE-BFgalT2 (SeqID14) | Gene fusion of BfgalT2 of *Bacterioidis fragilis* NCTC9343 integrated into vector pINT | This study |
| pINT-malE-IsgD (SeqID15) | Gene fusion of IsgD of *Haemophilus influenza* integrated into vector pINT | This study |
| pINT-malE-HPgalT (SeqID16) | Gene fusion of HpgalT of *Helicobacter pylori* integrated into vector pINT | This study |
| pACYC-waaX (SeqID17) | waaX of *Pectobacterium atrosepticum* JG10-08 integrated into vector pACYCDuet | This study |
| pACYC-wbdO (SeqID18) | wbdO of *Salmonella enterica* subsp. *salamae* serovar Greenside integrated into vector pACYCDuet | This study |
| pACYC-furA (SeqID19) | furA of *Lutiella nitroferrum* 2002 integrated into vector pACYCDuet | This study |
| pET-PmnagT (SeqID20) | PmnagT of *Pasteurella multocida* subsp. *multocida* str. HN06 integrated into vector pETDuet | This study |
| pINT-yjhB (SeqID21) | yjhB of *E. coli* BL21 DE3 integrated into vector pINT | This study |
| pINT-yebQ (SeqID22) | yebQ of *E. coli* BL21 DE3 integrated into vector pINT | This study |
| pINT-proP (SeqID23) | proP of *Mannheimia succiniciproducens* MBEL55E integrated into vector pINT | This study |
| pINT-Cn-setA (SeqID24) | setA of *Cedecea neteri* M006 integrated into vector pINT | This study |
| pINT-spoVB (SeqID25) | spoVB of *Bacillus amyloliquefaciens* integrated into vector pINT | This study |
| pINT-yabM (SeqID26) | yabM of *Erwinia pyrifoliae* integrated into vector pINT | This study |
| pINT-ydeA (SeqID27) | ydeA of *E. coli* MG1655 integrated into vector pINT | This study |
| pINT-proP2 (SeqID28) | proP2 of *Haemophilus parainfluenzae* integrated into vector pINT | This study |
| pINT-Pc-setA (SeqID29) | setA of *Pectobacterium carotovorum* integrated into vector pINT | This study |
| pINT-fucP (SeqID30) | fucP of *Escherichia coli* BL21 (DE3) integrated into vector pINT | This study |
| pINT-mdeA (SeqID31) | mdeA of *Staphylococcus aureus* Bmb9393 integrated into vector pINT | This study |
| pINT-lmrA (SeqID32) | lmrA of *Lactococcus lactis* integrated into vector pINT | This study |
| pINT-Ps-setA (SeqID33) | setA of *Pseudomonas* sp. MT-1 integrated into vector pINT | This study |
| pINT-Bb-setA (SeqID34) | setA of *Beauveria bassiana* D1-5 integrated into vector pINT | This study |

TABLE 3

Oligonucleotides used for PCR

| Primer | Sequence 5'-3' |
|---|---|
| 605 KI gal fwd | TTACTCAGCAATAAACTGATATTCCGTCAGGCTGG (SeqID35) |
| 606 KI gal rev | TTGTAATCTCGCGCTCTTCACATCAGACTTTCCATATAGAGCGTAATTTC CGTTAACGTCGGTAGTGCTGACCTTGCCGGAGG (SeqID36) |

TABLE 3-continued

Oligonucleotides used for PCR

| Primer | Sequence 5'-3' |
|---|---|
| 1119 ME-for | CTGTCTCTTATCACATCTCCTGAAATGGCCAGATGTAATTCCTAATTTTT GTTG (SeqID37) |
| 1120 ME rev | CTGTCTCTTATCACATCTCACATTACATCTGAGCGATTGTTAGG (SeqID38) |
| 1163 galE_NdeI-for | GATCACATATGAGAGTTCTGGTTACCGGTG (SeqID39) |
| 1164 galE_XhoI-rev | GATCACTCGAGTCATTAATCGGGATATCCCTGTGGATGGC (SeqID40) |
| 5176 lex1 pINT-f | GTCGATGAAGCCCTGAAAGACGCGCAGACTATGCACTTCATTGAAAAC AAAAACTTCGTC (SeqID41) |
| 5177 lex1 pINT-r | GATGGCCTTTTTGCGTGTCGACGCGGCCGCCTAGATAAACAGGATGAT ATTTTTGCCTIG (SeqID42) |
| 5178 pINT lex1-f | CAAGGCAAAAATATCATCCTGTTTATCTAGGCGGCCGCGTCGACACGC AAAAAGGCCATC (SeqID43) |
| 5179 pINT lex1-r | GACGAAGTTTTTGTTTTCAATGAAGTGCATAGTCTGCGCGTCTTTCAGG GCTTCATCGAC (SeqID44) |
| 5192 waaX pINT for | GTCGATGAAGCCCTGAAAGACGCGCAGACTATGATTGATAACCTGATTA AGCGTACCCCG (SeqID45) |
| 5193 waaX pINT rev | ATGGCCTTTTTGCGTGTCGACGCGGCCGCTTAATTCGAGCGGGTAAAG ATCTTCATCAGG (SeqID46) |
| 5194 pINT waaX for | CTGATGAAGATCTTTACCCGCTCGAATTAAGCGGCCGCGTCGACACGC AAAAAGGCCATC (SeqID47) |
| 5195 pINT waaX rev | CGGGGTACGCTTAATCAGGTTATCAATCATAGTCTGCGCGTCTTTCAGG GCTTCATCGAC (SeqID48) |
| 5164 PmgalT7 pINT for | GTCGATGAAGCCCTGAAAGACGCGCAGACTATGAGCGGTGAACACTAT GTCATTAGCCTG (SeqID49) |
| 5165 PmgalT7 pINT rev | GATGGCCTTTTTGCGTGTCGACGCGGCCGCTCATTTAAATTCGATGATC ATCTTGTCGTT (SeqID50) |
| 5166 pINT PmgalT7 for | AACGACAAGATGATCATCGAATTTAAATGAGCGGCCGCGTCGACACGC AAAAAGGCCATC (SeqID51) |
| 5167 pINT PmgalT7 rev | CAGGCTAATGACATAGTGTTCACCGCTCATAGTCTGCGCGTCTTTCAGG GCTTCATCGAC (SeqID52) |
| 5168 MsgalT8 pINT for | GTCGATGAAGCCCTGAAAGACGCGCAGACTATGGATGAAATCAAACTG TCGGTGGTTATG (SeqID53) |
| 5169 MsgalT8 pINT rev | GATGGCCTTTTTGCGTGTCGACGCGGCCGCTCATTGGCGACGCCAATC GAACGCAACGCG (SeqID54) |
| 5170 pINT MsgalT8 for | CGCGTTGCGTTCGATTGGCGTCGCCAATGAGCGGCCGCGTCGACACG CAAAAAGGCCATC (SeqID55) |
| 5171 pINT MsgalT8 rev | CATAACCACCGACAGTTTGATTTCATCCATAGTCTGCGCGTCTTTCAGG GCTTCATCGAC (SeqID56) |
| 5561 KdgalT10 pINT for | GTCGATGAAGCCCTGAAAGACGCGCAGACTATGGAAAACTATGTCGTC TCTATCCGCACC (SeqID57) |
| 5562 KdgalT10 pINT-rev | GATGGCCTTTTTGCGTGTCGACGCGGCCGCTCATTTGAACGGAACAAT CTTTTTGTCATC (SeqID58) |
| 5563 pINT-KdgalT10 for | GATGACAAAAAGATTGTTCCGTTCAAATGAGCGGCCGCGTCGACACGC AAAAAGGCCATC (SeqID59) |
| 5564 pINT-KdgalT10 rev | GGTGCGGATAGAGACGACATAGTTTTCCATAGTCTGCGCGTCTTTCAG GGCTTCATCGAC (SeqID60) |
| 5172 gatD pINT for | GTCGATGAAGCCCTGAAAGACGCGCAGACTATGTCCTCAGCTTTCCATT ACGTCATTAGC (SeqID61) |
| 5173 gatD pINT rev | GATGGCCTTTTTGCGTGTCGACGCGGCCGCTCATTCAAATTCGATAATC ATGGTGATTTT (SeqID62) |

TABLE 3-continued

Oligonucleotides used for PCR

| Primer | Sequence 5'-3' |
|---|---|
| 5174 pINT gatD for | AAAATCACCATGATTATCGAATTTGAATGAGCGGCCGCGTCGACACGCA AAAAGGCCATC (SeqID63) |
| 5175 pINT gatD rev | GCTAATGACGTAATGGAAAGCTGAGGACATAGTCTGCGCGTCTTTCAG GGCTTCATCGAC (SeqID64) |
| 5160 BfglaT2 pINT for | GTCGATGAAGCCCTGAAAGACGCGCAGACTATGAACGTGAATAAGCCG ACCACCGAAAAG (SeqID65) |
| 5161 BfgalT2 pINT rev | GATGGCCTTTTTGCGTGTCGACGCGGCCGCTCAGTATTCTTCAATTTTG TCCAGTTGATA (SeqID66) |
| 5162 pINT BfgalT2 for | TATCAACTGGACAAAATTGAAGAATACTGAGCGGCCGCGTCGACACGC AAAAAGGCCATC (SeqID67) |
| 5163 pINT BfgalT2 rev | CTTTTCGGTGGTCGGCTTATTCACGTTCATAGTCTGCGCGTCTTTCAGG GCTTCATCGAC (SeqID68) |
| 5746 | GTGATCAACGCCGCCAGCGGTCGTCAGACTGTCGATGAAGCCCTGAAA GACGCGCAGACT (SeqID69) |
| 5747 | GCGGCCGCGTCGACACGCAAAAAGGCCATCCATCCGTCAGGATGGCC TTCTGCTTAATTT (SeqID70) |
| 5748 | AAATTAAGCAGAAGGCCATCCTGACGGATGGATGGCCTTTTTGCGTGT CGACGCGGCCGC (SeqID71) |
| 5749 | AGTCTGCGCGTCTTTCAGGGCTTCATCGACAGTCTGACGACCGCTGGC GGCGTTGATCAC (SeqID72) |
| 1886 SLIC wbdO pACYC for | GTTTAACTTTAATAAGGAGATATACCATGCTGACGGAAGTGCGCCCGGT CTCTACGACGAAACCGC (SeqID73) |
| 1887 SLIC wbdO pACYC rev | CGACCTGCAGGCGCGCCGAGCTCGAATTCATTTGATGTATTTGCAATA GAACACAGAAAAGACCGT (SeqID74) |
| 1888 SLIC pACYC wbdo rev | GTGTTCTATTGCAAATACATCAAATGAATTCGAGCTCGGCGCGCCTGCA GGTCGACAAGCTTGCGG (SeqID75) |
| 1889 SLIC pACYC WbdO For | GAGACCGGGCGCACTTCCGTCAGCATGGTATATCTCCTTATTAAAGTTA AACAAAATTATTTCTACAGG (SeqID76) |
| 1890 SLIC pACYC furA rev | GTATGGTGACCCTGTGGCGCAAATGAGAATTCGAGCTCGGCGCGCCTG CAGGTCGACAAGCT (SeqID77) |
| 1891 SLIC pACYC furA for | GCGCTGCCCTGTTTGATTTTATCCATGGTATATCTCCTTATTAAAGTTAA ACAAAATTATTTCT (SeqID78) |
| 1892 SLIC furA pACYC rev | CCTGCAGGCGCGCCGAGCTCGAATTCTCATTTGCGCCACAGGGTCACC ATACGTGCCGGCAGG (SeqID79) |
| 1893 SLIC furA pACYC for | GlTTAACTTTAATAAGGAGATATACCATGGATAAAATCAAACAGGGCAG CGCCTCTCTGGTTGTCG (SeqID80) |
| 3055 SLIC PmnagT pET rev | CAGACTCGAGGGTACCGACGTCCTAATAAGTAGATGAATATTTATCAGG ACGAAGAT (SeqID81) |
| 3056 SLIC pET PmnagT for | AACTAAAGGTTTATTTTCCATATGTATATCTCCTTCTTATACTTAACTAAT ATAC (SeqID82) |
| 3057 SLIC pET PmnagT rev | TAAATATTCATCTACTTATTAGGACGTCGGTACCCTCGAGTCTGGTAAA GAAACCGCTGCTGCG (SeqID83) |
| 3058 SLIC PmnagT pET for | GTATAAGAAGGAGATATACATATGGAAAATAAACCTTTAGTTTCAGTTTT GATTTGTGC (SeqID84) |
| 2567_SLIC_yjhB-for | TAACTTTAAGAAGGAGATATACAAGAGCTCGAGTCGAAGGAGATAGAAC CATGGCAACAGCATGGTATAAACAAG (SeqID85) |
| 2568_SLIC_yjhB-rev | GCGTGTCGACGCGTTTAGAGGCCCCAAGGGGTTATGCTAGTATCGATT TATCATTTAGCCACGGATAGTTTATAAATTTTAC (SeqID86) |
| 2526_SLIC_pINT_TP-rev | GGTTCTATCTCCTTCGACTCGAGCTCTTGTATATCTCCTTCTTAAAGTTA AACAAAATTATTTCTAGATTTTTGTCGAAC (SeqID87) |

TABLE 3-continued

Oligonucleotides used for PCR

| Primer | Sequence 5'-3' |
|---|---|
| 2443_SLIC_pINT_TP-forw | TAAATCGATACTAGCATAACCCCTTGGGGCCTCTAAACGCGTCGACAC GCAAAAAGGCCATCC (SeqID88) |
| 2527_SLIC_TP_pINT-forw | GTTCGACAAAAATCTAGAAATAATTTTGTTTAACTTTAAGAAGGAGATAT ACAAGAGCTCGAGTCGAAGGAGATAGAACC (SeqID89) |
| 2444_SLIC_TP_pINT-rev | GGATGGCCTTTTTGCGTGTCGACGCGTTTAGAGGCCCCAAGGGGTTAT GCTAGTATCGATTTA (SeqID90) |
| 688 IgtA AatII rev | ATATGACGTCTCATTAGCGGTTTTTCAGGAGACG (SeqID91) |
| 689 IgtA NdeI for | ATATCATATGCCGTCCGAAGCATTCCGTCGTCACC (SeqID92) |
| 991 galT-pCDF for | TAACTTTAATAAGGAGATATACCATGACGCAATTTAATCCCGTTGATCAT CCACATCGCCGC (SeqID93) |
| 992 pCDF-galT for | ATTTTCGCGAATCCGGAGTGTAAAAGCTTGCGGCCGCATAATGCTTAAG TCGAACAGAAAGTAATCG (SeqID94) |
| 993 galT-pCDF rev | AAGCATTATGCGGCCGCAAGCTTTTACACTCCGGATTCGCGAAAATGG ATATCGCTGACTGCGCGCAAACGC (SeqID95) |
| 994 pCDF-galT rev | TCAACGGGATTAAATTGCGTCATGGTATATCTCCTTATTAAAGTTAAACA AAATTATTTCTACAGGGG (SeqID96) |
| 848 glmM pCOLA SLIC rev | ATGGTGATGGCTGCTGCCCATTTAAACCGCTTTGACTGCGTCGGCAATA CGGTGCGC (SeqID97) |
| 849 glmU pCOLA SLIC for | GTTTAACTTTAATAAGGAGATATACCATGCTGAACAACGCGATGTCTGTT GTTATCCTGG (SeqID98) |
| 850 pCOLA glmM SLIC rev | CGCAGTCAAAGCGGTTTAAATGGGCAGCAGCCATCACCATCATCACCA CAGCC (SeqID99) |
| 851 pCOLA glmU SLIC for | TCGCGTTGTTCAGCATGGTATATCTCCTTATTAAAGTTAAACAAAATTAT TTCTACAGG (SeqID100) |
| 852 glmSco pCOLA for NdeI | ATATATCATATGTGCGGTATCGTTGGTGCTATCGC (SeqID101) |
| 853 glmSco pCOLA rev AatII | ATATATGACGTCTTATTCCACGGTCACGGATTTCGC (SeqID102) |

The invention claimed is:

1. A method for the production of lacto-N-triose II by a genetically modified microbial host cell, comprising
providing a genetically modified microbial host cell that comprises:
at least one recombinant β-1,3-N-acetylglucosaminyltransferase, wherein the at least one recombinant β-1,3-N-acetylglucosaminyltransferase belongs to the class of lgtA of *Neisseria meningitidis*, and
increased expression of at least one sugar export protein capable of exporting the lacto-N-triose II, wherein the at least one sugar export protein is SetA from *Cedecea neteri*;
cultivating the microbial host cell in a medium under conditions permissive for the production of the lacto-N-triose II, whereby the lacto-N-triose II is exported into the medium at an increased level compared to the unmodified microbial host cell, and
obtaining the lacto-N-triose II from the medium.

2. A genetically modified microbial host cell for the production of lacto-N-triose II, wherein the microbial host cell comprises:
at least one recombinant β-1,3-N-acetylglucosaminyltransferase, wherein the at least one recombinant β-1,3-N-acetylglucosaminyltransferase belongs to the class of lgtA of *Neisseria meningitidis*, and
increased expression of at least one sugar export protein capable of exporting the lacto-N-triose II, wherein the at least one sugar export protein is SetA from *Cedecea neteri*.

* * * * *

SEQUENCE LISTING

<160> NUMBER OF SEQ ID NOS: 102

<210> SEQ ID NO 1
<211> LENGTH: 2851
<212> TYPE: DNA
<213> ORGANISM: Artificial Sequence
<220> FEATURE:
<223> OTHER INFORMATION: construct Ptet-lacY-FRT-add1-FRT

<400> SEQUENCE: 1

```
tggccagatg attaattcct aattttttgtt gacactctat cattgataga gttatttttac      60 cactccctat cagtgataga gaaaagtgaa atgaatagtt cgacaaaaat ctagaaataa     120
ttttgtttaa ctttaagaag gagatataca aatgtactat ttaaaaaaca caaacttttg     180
gatgttcggt ttattctttt tcttttactt ttttatcatg ggagcctact tcccgttttt     240
cccgatttgg ctacatgaca tcaaccatat cagcaaaagt gatacgggta ttattttgc      300 cgctatttct ctgttctcgc tattattcca accgctgttt ggtctgcttt ctgacaaact     360
cgggctgcgc aaatacctgc tgtggattat taccggcatg ttagtgatgt ttgcgccgtt     420 ctttatttttt atcttcgggc cactgttaca atacaacatt ttagtaggat cgattgttgg     480
```

```
tggtatttat ctaggctttt gttttaacgc cggtgcgcca gcagtagagg catttattga    540
gaaagtcagc cgtcgcagta atttcgaatt tggtcgcgcg cggatgtttg gctgtgttgg    600
ctgggcgctg tgtgcctcga ttgtcggcat catgttcacc atcaataatc agtttgtttt    660
ctggctgggc tctggctgtg cactcatcct cgccgtttta ctcttttcg ccaaaacgga    720 tgcgccctct tctgccacgg ttgccaatgc ggtaggtgcc aaccattcgg catttagcct    780
taagctggca ctgaactgt tcagacagcc aaaactgtgg tttttgtcac tgtatgttat    840
tggcgtttcc tgcacctacg atgtttttga ccaacagttt gctaatttct ttacttcgtt    900
ctttgctacc ggtgaacagg gtacgcgggt atttggctac gtaacgacaa tgggcgaatt    960
acttaacgcc tcgattatgt tctttgcgcc actgatcatt aatcgcatcg gtgggaaaaa   1020
cgccctgctg ctggctggca ctattatgtc tgtacgtatt attggctcat cgttcgccac   1080
ctcagcgctg gaagtggtta ttctgaaaac gctgcatatg tttgaagtac cgttcctgct   1140
ggtgggctgc tttaaatata ttaccagcca gtttgaagtg cgttttttcag cgacgattta   1200 tctggtctgt ttctgcttct ttaagcaact ggcgatgatt tttatgtctg tactggcggg   1260
caatatgtat gaaagcatcg gtttccaggg cgcttatctg gtgctgggtc tggtggcgct   1320
gggcttcacc ttaatttccg tgttcacgct agcggcccc ggcccgcttt ccctgctgcg   1380
tcgtcaggtg aatgaagtcg ctgggagcta agcggccgcg tcgacacgca aaaaggccat   1440
ccgtcaggat ggccttctgc ttaatttgat gcctggcagt ttatggcggg cgtcctgccc   1500 gccacccctcc gggccgttgc ttcgcaacgt tcaaatccgc tcccggcgga tttgtcctac   1560
tcaggagagc gttcaccgac aaacaacaga taaaacgaaa ggcccagtct ttcgactgag   1620
cctttcgttt tatttgatgc ctggcagttc cctactctcg catggggaga ccccacacta   1680
ccatcatgta tgaatatcct ccttagttcc tattccgaag ttcctattct ctagaaagta   1740
taggaacttc ggcgcgtcct acctgtgaca cgcgtgccgc agtctcacgc ccggagcgta   1800
gcgaccgagt gagctagcta tttgtttatt tttctaaata cattcaaata tgtatccgct   1860
catgagacaa taaccctgat aaatgcttca ataatattga aaaggaaga gtatgaggga   1920 agcggtgatc gccgaagtat cgactcaact atcagaggta gttggcgtca tcgagcgcca   1980
tctcgaaccg acgttgctgg ccgtacattt gtacggctcc gcagtggatg gcggcctgaa   2040
gccacacagt gatattgatt tgctggttac ggtgaccgta aggcttgatg aaacaacgcg   2100
gcgagctttg atcaacgacc ttttggaaac ttcggcttcc cctggagaga gcgagattct   2160
ccgcgctgta gaagtcacca ttgttgtgca cgacgacatc attccgtggc gttatccagc   2220
taagcgcgaa ctgcaatttg gagaatggca gcgcaatgac attcttgcag gtatcttcga   2280
gccagccacg atcgacattg atctggctat cttgctgaca aaagcaagag aacatagcgt   2340
tgccttggta ggtccagcgg cggaggaact ctttgatccg gttcctgaac aggatctatt   2400
tgaggcgcta aatgaaacct aacgctatg gaactcgccg cccgactggg ctggcgatga   2460
gcgaaatgta gtgcttacgt tgtcccgcat ttggtacagc gcagtaaccg gcaaaatcgc   2520
gccgaaggat gtcgctgccg actgggcaat ggagcgcctg ccggcccagt atcagcccgt   2580
catacttgaa gctagacagg cttatcttgg acaagaagaa gatcgcttgg cctcgcgcgc   2640
agatcagttg gaagaatttg tccactacgt gaaaggcgag atcaccaagg tagtcggcaa   2700
ataatgtcta acaattcgtt caagccgagg ggccgcaaga tccggccacg atgacccggt   2760
cgtcgggtac cggcagggcg gggcgtaagg cgcgccattt aaatgaagtt cctattccga   2820
```
agttcctatt ctctagaaag tataggaact t            2851

<210> SEQ ID NO 2
<211> LENGTH: 4568
<212> TYPE: DNA
<213> ORGANISM: Artificial Sequence
<220> FEATURE:
<223> OTHER INFORMATION: construct Ptet-lgtA-PT5-galT-FRT-kanR-FRT

<400> SEQUENCE: 2

| | |
|---|---|
| acaggttggc tgataagtcc ccggtctagc ttgcatgcag attgcagcat tacacgtctt | 60 |
| gagcgattgt gtaggctgga gctgcttcga agttcctata cttcctagag aataggaact | 120 |
| tcggaatagg aacttcattt aaatggcgcg ccttacgccc cgccctgccg gtaccgagag | 180 |
| cgcttttgaa gctggggtgg gcgaagaact ccagcatgag atccccgcgc tggaggatca | 240 |
| tccagccggc gtcccggaaa acgattccga agcccaacct tcatagaag gcggcggtgg | 300 |
| aatcgaaatc tcgtgatggc aggttgggcg tcgcttggtc ggtcatttcg aaccccagag | 360 |
| tcccgctcag aagaactcgt caagaaggcg atagaaggcg atgcgctgcg aatcgggagc | 420 |
| ggcgataccg taaagcacga ggaagcggtc agcccattcg ccgccaagct cttcagcaat | 480 |
| atcacgggta gccaacgcta tgtcctgata gcggtccgcc acacccagcc ggccacagtc | 540 |
| gatgaatcca gaaaagcggc catttccac catgatattc ggcaagcagg catcgccatg | 600 |
| ggtcacgacg agatcctcgc cgtcgggcat gcgcgccttg agcctggcga acagttcggc | 660 |
| tggcgcgagc ccctgatgct cttcgtccag atcatcctga tcgacaagac cggcttccat | 720 |
| ccgagtacgt gctcgctcga tgcgatgttt cgcttggtgg tcgaatgggc aggtagccgg | 780 |
| atcaagcgta tgcagccgcc gcattgcatc agccatgatg gatactttct cggcaggagc | 840 |
| aaggtgagat gacaggagat cctgccccgg cacttcgccc aatagcagcc agtcccttcc | 900 |
| cgcttcagtg acaacgtcga gcacagctgc gcaaggaacg cccgtcgtgg ccagccacga | 960 |
| tagccgcgct gcctcgtcct gcagttcatt cagggcaccg gacaggtcgg tcttgacaaa | 1020 |
| aagaaccggg cgcccctgcg ctgacagccg gaacacggcg gcatcagagc agccgattgt | 1080 |
| ctgttgtgcc cagtcatagc cgaatagcct ctccacccaa gcggccggag aacctgcgtg | 1140 |
| caatccatct tgttcaatca tgcgaaacga tcctcatcct gtctcttgat cagatcttga | 1200 |
| tcccctgcgc catcagatcc ttggcggcaa gaaagccatc cagtttactt tgcagggctt | 1260 |
| cccaacctta ccagagggcg ccccagctgg caattccggt tcgcttgctg tccataaaac | 1320 |
| cgcccagtct agctatcgcc atgtaagccc actgcaagct acctgctttc tctttgcgct | 1380 |
| tgcgttttcc cttgtccaga tagcccagta gctgacattc atccggggtc agcaccgttt | 1440 |
| ctgcggactg gctttctacg tgttccgctt cctttagcag cccttgcgcc ctgagtgctt | 1500 |
| gcggcagcgt gaggggatct tgacgcgtgt cacaggtagg acgcgccgaa gttcctatac | 1560 |
| tttctagaga ataggaactt cggaatagga actaaggagg atattcatac atgatggtag | 1620 |
| tgttcgaaat taatacgact cactataggg gaattgattc tggtaccaaa tgagtcgacc | 1680 |
| ggccagatga ttaattccta atttttgttg acactctatc attgatagag ttattttacc | 1740 |
| actccctatc agtgatagag aaaagtgaaa tgaatagttc gacaaaaatc tagaaataat | 1800 |
| tttgtttaac tttaagaagg agatatacaa atgccgtccg aagcattccg tcgtcaccgt | 1860 |
| gcttatcgcg aaaacaaact gcagccactg gtctctgtcc tgatctgcgc atacaacgtt | 1920 |
| gagaaatact tcgcacagtc tctggcagct gtagttaacc agacctggcg taacctggat | 1980 |
| atcctgatcg tagatgacgg ctctacggat ggtacgctgg cgatcgcaca gcgtttccag | 2040 |

```
gaacaggacg gtcgtatccg cattctcgct cagccgcgta actctggtct gatcccgtct    2100
ctgaacatcg gtctggacga actggccaaa tctggtggtg gtggcgaata catcgcccgt    2160
actgacgccg acgacattgc ggccccggat tggatcgaaa aaatcgtagg tgaaatggag    2220
aaagaccgct ctatcatcgc gatgggtgct tggctgaagg ttctgtccga agagaaagac    2280
ggtaaccgtc tggcccgtca ccatgaacac ggcaaaatct ggaaaaaacc gacccgtcac    2340
gaagatatcg cggacttctt cccgttcggt aacccgatcc ataacaacac catgatcatg    2400
cgtcgtagcg taatcgacgg tggtctgcgt tacaacaccg aacgtgattg ggcagaagac    2460
taccagtttt ggtatgacgt gtctaaactg ggtcgtctgg cttactaccc agaagcgctg    2520
gttaaatacc gtctgcacgc caaccaggtt agctccaaat actccatccg tcagcacgaa    2580
atcgcacagg gtatccagaa aacggctcgt aacgacttcc tgcagtccat gggtttcaaa    2640
acccgtttcg actctctgga gtaccgtcag atcaaagcgg ttgcgtatga gctgctggag    2700
aaacacctgc cggaagagga ctttgaacgt gcgcgtcgtt tcctgtacca gtgcttcaaa    2760
cgtaccgaca ctctgccggc gggtgcatgg ctcgactttg cagcggatgg tcgtatgcgt    2820
cgtctgttta ccctgcgtca gtacttcggt atcctgcatc gtctcctgaa aaaccgctaa    2880
tgatttcgtc gacacacagg aaacatatta aaaattaaaa cctgcaggag tttaaacgcg    2940
gccgcgatat cgttgtaaaa cgacggccag tgcaagaatc ataaaaaatt tatttgcttt    3000
caggaaaatt tttctgtata atagattcat aaatttgaga gaggagtttt tgtgagcgga    3060
taacaattcc ccatcttagt atattagtta agtataaata cacaaggaga tataccatga    3120
cgcaatttaa tcccgttgat catccacatc gccgctacaa cccgctcacc gggcaatgga    3180
ttctggtttc accgcaccgc gctaagcgcc cctggcaggg ggcgcaggaa acgccagcca    3240
aacaggtgtt acctgcgcac gatccagatt gcttcctctg cgcaggtaat gtgcgggtga    3300
caggcgataa aaaccccgat tacaccggga cttacgtttt cactaatgac tttgcggctt    3360
tgatgtctga cacgccagat gcgccagaaa gtcacgatcc gctgatgcgt tgccagagcg    3420
cgcgcggcac cagccgggtg atctgctttt caccggatca cagtaaaacg ctgccagagc    3480
tcagcgttgc agcattgacg gaaatcgtca aaacctggca ggagcaaacc gcagaactgg    3540
ggaaaacgta cccatgggtg caggttttg aaaacaaagg cgcggcgatg gctgctcta    3600 acccgcatcc gcacggtcag atttgggcaa atagcttcct gcctaacgaa gctgagcgcg    3660
aagaccgcct gcaaaagaa tattttgccg aacagaaatc accaatgctg gtggattatg    3720
ttcagcgcga gctggcagac ggtagccgta ccgttgtcga aaccgaacac tggttagccg    3780
tcgtgcctta ctgggctgcc tggccgttcg aaacgctact gctgcccaaa gcccacgttt    3840
tacggatcac cgatttgacc gacgcccagc gcagcgatct ggcgctggcg ttgaaaaagc    3900
tgaccagtcg ttatgacaac ctcttccagt gctccttccc ctactctatg gctggcacg    3960 gcgcgccatt aatgcgaa gagaatcaac actggcagct gcacgcgcac ttttatccgc    4020
ctctgctgcg ctccgccacc gtacgtaaat ttatggttgg ttatgaaatg ctggcagaga    4080
cccagcgaga cctgaccgca gaacaggcag cagagcgttt gcgcgcagtc agcgatatcc    4140
attttcgcga atcggagtg taacgcggag gcgcgccatt taaatcaacc tcagcggtca    4200
tagctgtttc ctgtgactga gcaataacta gcataacccc ttgggccctc taaacgggtc    4260
ttgaggggtt ttttgctgaa accaatttgc ctggcggcag tagcgcggtg gtcccacctg    4320
accccatgcc gaactcagaa gtgaaacgcc gtagcgccga tggtagtgtg gggtctcccc    4380
```

```
atgcgagagt agggaactgc caggcatcaa ataaaacgaa aggctcagtc gaaagactgg    4440
gcctttcggg atccaggccg gcctgttaac gaattaatct tccgcggcaa caaaaattag    4500
gaattaatca tctggccaat ttcaggtggc acttttcggg cagaccgggg acttatcagc    4560
caacctgt                                                            4568

<210> SEQ ID NO 3
<211> LENGTH: 6521
<212> TYPE: DNA
<213> ORGANISM: Artificial Sequence
<220> FEATURE:
<223> OTHER INFORMATION: construct Ptet-glmUM-PT5-glmS-FRT-dhfr-FRT

<400> SEQUENCE: 3
acaggttggc tgataagtcc ccggtctagc ttgcatgcag attgcagcat tacacgtctt      60
gagcgattgt gtaggctgga gctgcttcga aattaatacg actcactata ggggaattga     120
ttctggtacc aaatgagtcg accggccaga tgattaattc ctaattttg ttgacactct      180 atcattgata gagtttatttt accactccct atcagtgata gagaaaagtg aaatgaatag    240
ttcgacaaaa atctagaaat aattttgttt aactttaaga aggagatata caaatgctga    300
acaacgcgat gtctgttgtt atcctggcgg cgggtaaagg tacccgtatg tactctgacc    360
tgccgaaagt tctgcacacc ctggcgggta agcgatggt tcagcacgtt atcgacgcgg     420
cgaacgaact gggtgcggcg cacgttcacc tggtttacgg tcacggtggt gacctgctga    480
aacaggcgct gaaagacgac aacctgaact gggttctgca ggcggaacag ctgggtaccg    540
gtcacgcgat gcagcaggcg cgccgttct tcgcggacga cgaagacatc ctgatgctgt     600
acggtgacgt tccgctgatc tctgttgaaa ccctgcagcg tctgcgtgac gcgaaaccgc    660
agggtggtat cggtctgctg accgttaaac tggacgaccc gaccggttac ggtcgtatca    720
cccgtgaaaa cggtaaagta accggtatcg ttgaacacaa agacgcgacc gacgaacagc    780
gtcagatcca ggagatcaac accggtatcc tgatcgcgaa cggtgcagac atgaaacgtt    840
ggctggcgaa actgaccaac aacaacgcgc agggtgaata ctacatcacc gacatcatcg    900
cgctggcgta ccaggaaggt cgtgaaatcg ttgcggttca cccgcagcgt ctgtctgaag    960
ttgaaggtgt taacaaccgt ctgcagctgt ctcgtctgga acgtgtttac cagtctgaac   1020
aggcggaaaa actgctgctg gcgggtgtta tgctgcgtga cccggcgcgt ttcgacctgc   1080 gtggtacccct gacccacggt cgtgacgttg aaatcgacac caacgttatc atcgaaggta   1140
acgttaccct gggtcaccgt gtaaaaatcg gcaccggttg cgttatcaaa aactctgtta   1200
tcggtgacga ctgcgaaatc tctccgtaca ccgttgttga agacgcgaac ctggcggcgg   1260
cgtgcaccat cggtccgttc gcgcgtctgc gtccgggtgc ggaactgctg gaaggtgcgc   1320
acgttggtaa cttcgttgaa atgaaaaaag cgcgtctggg taaggttct aaagcgggtc    1380 acctgacccta cctgggtgac gcggaaatcg gtgacaacgt taacatcggt gcgggtacca   1440
tcacctgcaa ctacgacggt gcgaacaaat tcaaaaccat catcggtgac gacgttttcg   1500
ttggttctga cacccagctg gttgcgccgg ttaccgttgg taaggtgcg accatcgcgg    1560 cgggtaccac cgttacccgt aacgttggtg aaaacgcgct ggcgatctct cgtgttccgc   1620
agacccagaa agaaggttgg cgtcgtccgg ttaaaaaaaa ataacgaagg agatagaacc   1680
atgtccaacc gtaaatactt cggtacggac ggtatccgtg gtcgtgtagg tgatgctccg   1740
attacgccgg atttcgtcct gaaactcggt tgggcagcgg gtaaagttct cgcacgtcac   1800
ggctctcgta aaatcatcat cggtaaagac accccgtatct ctggttacat gctcgaatct   1860
```

```
gcactggaag cgggtctggc tgcagctggt ctgtctgcac tgttcacggg tccgatgcca    1920 acccccagctg tagcgtacct gactcgcact ttccgtgcag aagcaggtat cgtgatctct   1980
gcctctcaca acccgttcta cgacaacggt atcaaattct tcagcatcga tggtaccaaa   2040
ctcccagacg cggttgaaga ggctatcgaa gcggaaatgg agaaagaaat ctcttgtgta   2100
gactctgccg aactcggtaa agcgtctcgt atcgttgatg cagcgggtcg ttacatcgag   2160
ttctgcaaag ccacctttcc gaacgaactg agcctgtctg agctgaaaat cgtcgtagac   2220
tgtgccaacg gtgcgactta ccacattgcc ccaaacgtac tgcgtgagct gggtgctaac   2280
gtcatcgcga tcggttgtga accgaacggt gtcaacatca cgcggaagt aggtgcgacc   2340 gatgttcgtg cactgcaggc tcgtgtactc gcggagaaag cggatctcgg tatcgccttt   2400
gacggtgatg gtgaccgtgt tatcatggtt gaccacgaag gtaacaaagt ggatggtgac   2460
cagatcatgt acatcattgc ccgtgaaggt ctgcgtcagg gtcagctgcg tggtggtgca   2520
gtaggtaccc tcatgagcaa catgggtctg gaactggccc tgaaacagct gggtatccca   2580
ttcgctcgtg ctaaagtagg cgaccgttac gttctggaga aaatgcagga gaaaggttgg   2640
cgtatcggtg ccgaaaactc tggtcacgtc atcctgctgg acaaaaccac taccggtgac   2700
ggtatcgtag caggtctgca ggtactcgcc gctatggccc gtaaccacat gtccctccat   2760
gacctctgct ctggtatgaa aatgttcccg cagatcctgg ttaacgttcg ttacaccgca   2820
ggttctggtg atccgctgga acacgagtct gtgaaagccg ttaccgcaga agtggaagcg   2880
gccctgggta accgtggtcg tgtactgctg cgtaaatccg gtactgagcc actgatccgt   2940
gttatggttg agggcgaaga tgaagcccag gtcaccgaat tgcgcaccg tattgccgac   3000 gcagtcaaag cggtttaatt tcgtcgacac acaggaaaca tattaaaaat taaaacctgc   3060
aggagtttaa acgcggccgc gatatcgttg taaaacgacg gccagtgcaa gaatcataaa   3120
aaatttattt gctttcagga aaattttct gtataataga ttcataaatt tgagagagga   3180 gttttttgtga gcggataaca attccccatc ttagtatatt agttaagtat aaatacacaa   3240
ggagatatac atatgtgcgg tatcgttggt gctatcgcac agcgtgatgt agcggagatc   3300
ctcctggaag gtctgcgtcg tctcgaatac cgtggttacg actctgccgg tctggcagta   3360
gtggatgcag aaggtcacat gactcgtctg cgtcgtctgg gtaaagtgca gatgctcgcg   3420
caggcggcgg aagaacaccc actccacggt ggtacgggta tcgcacacac tcgttgggca   3480
acccacggtg aaccgtctga ggtcaacgca cacccgcatg ttagcgagca catcgtagtc   3540
gttcacaacg gtatcatcga gaaccacgaa ccactccgtg aggaactcaa agcccgtggt   3600
tacaccttcg taagcgaaac cgacacggaa gttatcgccc acctcgttaa ctgggaactc   3660
aaacaggggt gtactctgcg tgaagcagtt ctgcgtgcca ttccacagct gcgtggtgca   3720
tacggtaccg tgatcatgga ctctcgtcat ccggataccc tgctcgccgc acgttctggt   3780
tctccactcg ttatcggtct gggtatgggt gagaacttca tcgcctctga tcagctggcc   3840
ctgctcccag ttacccgtcg cttcatcttc ctggaagagg gtgacatcgc cgaaatcacc   3900
cgtcgttccg ttaacatctt cgacaaaacg ggtgcggaag ttaaacgtca ggacatcgag   3960
tctaacctgc agtatgacgc tggtgacaaa ggcatctacc gtcactacat gcagaaagag   4020
atctacgaac agccgaacgc gatcaaaaac accctgaccg tcgtatctc tcacggtcag   4080 gttgacctgt ctgagctggg tccaaacgcg gacgaactcc tgtccaaagt cgagcacatc   4140
cagatcctgg cttgtggtac ctcttacaac tccggtatgg tttctcgtta ctggttcgaa   4200
```

```
tctctggcag gtatcccatg cgacgttgaa atcgcctccg aattccgtta tcgtaaatct    4260
gcggtacgtc gtaactccct catgatcacc ctgtctcagt ctggtgaaac cgctgatact    4320
ctggcaggtc tgcgtctcag caaagaactg ggttacctgg ttctctggc catctgcaac     4380
gttccgggtt ctagcctggt tcgtgagtct gacctggctc tgatgaccaa cgcgggtacg    4440
gagatcggtg ttgcctctac caaagcgttc actacccagc tcactgtcct gctgatgctg    4500
gttgccaaac tgtctcgtct caaaggcctc gacgctagca tcgaacacga catcgtacac    4560
ggtctgcagg ccctcccatc tcgtatcgag cagatgctgt ctcaggacaa acgtatcgaa    4620
gcactggcag aagacttcag cgacaaacac cacgcgctgt ttctgggtcg tggtgaccag    4680
tacccaattg cgctggaagg tgccctgaaa ctgaaagaga tcagctacat ccatgcagag    4740
gcatacgcag cgggtgagct gaaacatggt ccactggccc tgatcgacgc agatatgccg    4800
gttattgtgg ttgctccgaa caacgaactg ctggagaaac tgaaatccaa catcgaggaa    4860
gtacgtgcgc gtggtggtca gctgtacgtg tttgctgacc aggacgcggg tttcgtttcc    4920
agcgacaaca tgcacatcat cgaaatgccg catgttgaag aggtaatcgc gccaatcttc    4980
tacaccgtac cgctgcagct gctggcgtac catgtagccc tgatcaaagg tacggacgtt    5040
gaccagccgc gtaacctggc gaaatccgtg accgtgaat aacgcggagg cgcgccattt     5100
aaatcaaccc tcagcggtcat agctgttttcc tgtgactgag caataactag cataacccct    5160
tggggcctct aaacgggtct gaggggtttt tttgctgaaa ccaatttgcc tggcggcagt    5220
agcgcggtgg tcccacctga ccccatgccg aactcagaag tgaaacgccg tagcgccgat    5280
ggtagtgtgg ggtctcccca tgcgagagta gggaactgcc aggcatcaaa taaaacgaaa    5340
ggctcagtcg aaagactggg cctttcggga tccaggccgg cctgttaacg aattaatctt    5400
ccgcggcggt atcgataagc ttgatatcga attccgaagt tcctattctc tagaaagtat    5460
aggaacttca ggtctgaaga ggagtttacg tccagccaag ctagcttggc tgcaggtcgt    5520
cgaaattcta ccgggtaggg gaggcgcttt tcccaaggca gtctggagca tgcgctttag    5580
cagccccgct gggcacttgg cgctacacaa gtggcctctg gcctcgcaca cattccacat    5640
ccaccggtag cgccaaccg gctccgttct ttggtggccc cttcgcgcca ccttctactc     5700
ctcccctagt caggaagttc cccccgccc cgcagctcgc gtcgtgcagg acgtgacaaa     5760
tggaagtagc acgtctcact agtctcgtgc agatggacag caccgctgag caatggaagc    5820
gggtaggcct ttggggcagc ggccaatagc agctttgctc cttcgctttc tgggctcaga    5880
ggctgggaag gggtgggtcc gggggcgggc tcaggggcgg gctcagggc ggggcgggcg      5940
cccgaaggtc ctccggaggc ccggcattct gcacgcttca aaagcgcacg tctgccgcgc    6000
tgttctcctc ttcctcatct ccgggccttt cgacctgcag cctgttgaca attaatcatc    6060
ggcatagtat atcggcatag tataatacga caaggtgagg aactaaacca tgggtcaaag    6120
tagcgatgaa gccaacgctc ccgttgcagg gcagtttgcg cttcccctga gtgccacctt    6180
tggcttaggg gatcgcgtac gcaagaaatc tggtgccgct tggcagggtc aagtcgtcgg    6240
ttggtattgc acaaaactca ctcctgaagg ctatgcggtc gagtccgaat cccacccagg    6300
ctcagtgcaa atttatcctg tggctgcact tgaacgtgtg gcctaatgag gggatcaatt    6360
ctctagagct cgctgatcag aagttcctat tctctagaaa gtataggaac ttcgatggcg    6420
cctcatccct gaagccaata caacaaaaat taggaattaa tcatctggcc aatttcaggt    6480
ggcacttttc gggcagaccg gggacttatc agccaacctg t                       6521
```

<210> SEQ ID NO 4
<211> LENGTH: 2937
<212> TYPE: DNA
<213> ORGANISM: Artificial Sequence
<220> FEATURE:
<223> OTHER INFORMATION: construct <Ptet-lacY(6HIS)-FRT-aadA-FRT>

<400> SEQUENCE: 4

| | | | | | |
|---|---|---|---|---|---|
| ggccagatga | ttaattccta | attttttgttg | acactctatc | attgatagag | ttattttacc | 60 |
| actccctatc | agtgatagag | aaaagtgaaa | tgaatagttc | gacaaaaatc | tagaaataat | 120 |
| tttgtttaac | tttaagaagg | agatatacaa | atgggctact | atttaaaaaa | cacaaacttt | 180 |
| tggatgttcg | gtttattctt | tttctttttac | ttttttatca | tgggagccta | cttcccgttt | 240 |
| ttcccgattt | ggctacatga | catcaaccat | atcagcaaaa | gtgatacggg | tattattttt | 300 |
| gccgctattt | ctctgttctc | gctattattc | caaccgctgt | tggtctgct | ttctgacaaa | 360 |
| ctcgggctgc | gcaaatacct | gctgtggatt | attaccggca | tgttagtgat | gtttgcgccg | 420 |
| ttctttattt | ttatcttcgg | gccactgtta | caatacaaca | ttttagtagg | atcgattgtt | 480 |
| ggtggtattt | atctaggctt | tgttttaac | gccggtgcgc | cagcagtaga | ggcatttatt | 540 |
| gagaaagtca | gccgtcgcag | taatttcgaa | tttggtcgcg | cgcggatgtt | tggctgtgtt | 600 |
| ggctgggcgc | tgtgtgcctc | gattgtcggc | atcatgttca | ccatcaataa | tcagtttgtt | 660 |
| ttctggctgg | gctctggctg | tgcactcatc | ctcgccgttt | tactcttttt | cgccaaaacg | 720 |
| gatgcgccct | cttctcatca | ccatcaccat | cacgccacgg | ttgccaatgc | ggtaggtgcc | 780 |
| aaccattcgg | catttagcct | taagctggca | ctggaactgt | tcagacagcc | aaaactgtgg | 840 |
| ttttttgtcac | tgtatgttat | tggcgtttcc | tgcacctacg | atgtttttga | ccaacagttt | 900 |
| gctaatttct | ttacttcgtt | ctttgctacc | ggtgaacagg | gtacgcgggt | atttggctac | 960 |
| gtaacgacaa | tgggcgaatt | acttaacgcc | tcgattatgt | tctttgcgcc | actgatcatt | 1020 |
| aatcgcatcg | gtgggaaaaa | cgccctgctg | ctggctggca | ctattatgtc | tgtacgtatt | 1080 |
| attggctcat | cgttcgccac | tcagcgctg | gaagtggtta | ttctgaaaac | gctgcatatg | 1140 |
| tttgaagtac | cgttcctgct | ggtgggctgc | tttaaatata | ttaccagcca | gtttgaagtg | 1200 |
| cgttttttcag | cgacgattta | tctggtctgt | ttctgcttct | ttaagcaact | ggcgatgatt | 1260 |
| tttatgtctg | tactggcggg | caatatgtat | gaaagcatcg | gtttccaggg | cgcttatctg | 1320 |
| gtgctgggtc | tggtggcgct | gggcttcacc | ttaatttccg | tgttcacgct | agcggcccc | 1380 |
| ggcccgcttt | ccctgctgcg | tcgtcaggtg | aatgaagtcg | cttaagcggc | cgcgtcgaca | 1440 |
| cgcaaaaagg | ccatccgtca | ggatggcctt | ctgcttaatt | tgatgcctgg | cagttatatgg | 1500 |
| cgggcgtcct | gcccgccacc | ctccgggccg | ttgcttcgca | acgttcaaat | ccgctcccgg | 1560 |
| cggatttgtc | ctactcagga | gagcgttcac | cgacaaacaa | cagataaaac | gaaaggccca | 1620 |
| gtctttcgac | tgagcctttc | gttttatttg | atgcctggca | gttccctact | ctcgcatggg | 1680 |
| gagaccccac | actaccatca | tgtatgaata | tcctccttag | ttcctattcc | gaagttccta | 1740 |
| ttctctagaa | agtataggaa | cttcggcgcg | tcctacctgt | gacacgcgtg | ccgcagtctc | 1800 |
| acgcccggag | cgtagcgacc | gagtgagcta | gctatttgtt | tattttttcta | aatacattca | 1860 |
| aatatgtatc | cgctcatgag | acaataaccc | tgataaatgc | ttcaataata | ttgaaaaagg | 1920 |
| aagagtatga | gggaagcggt | gatcgccgaa | gtatcgactc | aactatcaga | ggtagttggc | 1980 |
| gtcatcgagc | gccatctcga | accgacgttg | ctggccgtac | atttgtacgg | ctccgcagtg | 2040 |
| gatggcggcc | tgaagccaca | cagtgatatt | gatttgctgg | ttacggtgac | cgtaaggctt | 2100 |

```
gatgaaacaa cgcggcgagc tttgatcaac gaccttttgg aaacttcggc ttcccctgga    2160
gagagcgaga ttctccgcgc tgtagaagtc accattgttg tgcacgacga catcattccg    2220
tggcgttatc cagctaagcg cgaactgcaa tttggagaat ggcagcgcaa tgacattctt    2280
gcaggtatct tcgagccagc cacgatcgac attgatctgg ctatcttgct gacaaaagca    2340
agagaacata gcgttgcctt ggtaggtcca gcggcggagg aactctttga tccggttcct    2400
gaacaggatc tatttgaggc gctaaatgaa accttaacgc tatggaactc gccgcccgac    2460
tgggctggcg atgagcgaaa tgtagtgctt acgttgtccc gcatttggta cagcgcagta    2520
accggcaaaa tcgcgccgaa ggatgtcgct gccgactggg caatggagcg cctgccggcc    2580
cagtatcagc ccgtcatact tgaagctaga caggcttatc ttggacaaga agaagatcgc    2640
ttggcctcgc gcgcagatca gttggaagaa tttgtccact acgtgaaagg cgagatcacc    2700
aaggtagtcg gcaaataatg tctaacaatt cgttcaagcc gaggggccgc aagatccggc    2760
cacgatgacc cggtcgtcgg gtaccggcag ggcggggcgt aaggcgcgcc atttaaatga    2820
agttcctatt ccgaagttcc tattctctag aaagtatagg aacttcgaag cagctccagc    2880
ctacacaatc gctcaagacg tgtaatgctg caatctgcat gcaagcttgg cactggc      2937
```

<210> SEQ ID NO 5
<211> LENGTH: 3856
<212> TYPE: DNA
<213> ORGANISM: Artificial Sequence
<220> FEATURE:
<223> OTHER INFORMATION: construct <Ptet-wbdO-PT5-galE-FRT-cat-FRT>

<400> SEQUENCE: 5

```
acaggttggc tgataagtcc ccggtctgcc cgaaaagtgc cacctgaaat tggccagatg      60
attaattcct aattttttgtt gattctggta ccaaatgagt cgaccggcca gatgattaat     120
tcctaatttt tgttgacact ctatcattga tagagttatt ttaccactcc ctatcagtga     180
tagagaaaag tgaaatgaat agttcgacaa aaatctagaa ataattttgt ttaacttttaa    240 gaaggagata tacaaatgct gacggaagtg cgcccggtct ctacgacgaa accgctggtg     300
tctgtgattc tgccggtgaa caaattcaac ccgtatctgg atcgtgcaat tcattcaatc     360
ctgagtcagt cctatccgtc gattgaactg attatcattg caaacaattg caccaatgac     420
tttttcgatg ctctgaaaaa acgtgaatgt gaaaccatta agtgctgcg cacgaacatc      480 gcgtatctgc cgtactgcct gaataaaggc ctggatctgt gtaacggtga ctttgttgcc     540
cgcatggatt cagatgacat ttcgcacccg gaacgtatcg atcgccaggt cgacttcctg     600
attaacaatc cggacatcga tgtggttggc accaatgcag tctatattga tgaagatgac     660
atcgaactgg aaaaaagcaa cctgccggtg aacaataacg ctattcgtaa aatgctgccg     720
tataaatgct gtctggtgca tccgtctgtt atgtttcgca aaaatgtcgt gatcaccagc     780
ggcggttaca tgttcgcgaa ttattctgaa gattacgaac tgtggaaccg tctgccgtt     840 gaaggccgca atttttataa cctgagcgaa tacctgctgt attaccgtct gcacaataac     900
caatcaacgt cgaaaaataa cctgtttatg gtgatggcga acgatgtcgc cattaaagtg     960
aaatatttcc tgctgaccaa gaaaattagc tacctgctgg gtatcattcg cacggtcttt    1020
tctgtgttct attgcaaata catcaaatga tttcgtcgac acacaggaaa catattaaaa    1080
attaaaacct gcaggagttt aaacgcggcc gcgatatcgt tgtaaaacga cggccagtgc    1140
aagaatcata aaaaatttat ttgctttcag gaaaattttt ctgtataata gattcataaa    1200
tttgagagag gagttttttgt gagcggataa caattcccca tcttagtata ttagttaagt    1260
```

```
ataaatacac cgcggaggcg tcgaaggaga tacaaccatg agagttctgg ttaccggtgg    1320
tagcggttac attggaagtc atacctgtgt gcaattactg caaaacggtc atgatgtcat    1380
cattcttgat aacctctgta acagtaagcg cagcgtactg cctgttatcg agcgtttagg    1440
cggcaaacat ccaacgtttg ttgaaggcga tattcgtaac gaagcgttga tgaccgagat    1500
cctgcacgat cacgctatcg acaccgtgat ccacttcgcc gggctgaaag ccgtgggcga    1560
atcggtacaa aaaccgctgg aatattacga caacaatgtc aacggcactc tgcgcctgat    1620
tagcgccatg cgcgccgcta acgtcaaaaa ctttattttt agctcctccg ccaccgttta    1680
tggcgatcag cccaaaattc catacgttga aagcttcccg accggcacac cgcaaagccc    1740
ttacggcaaa agcaagctga tggtggaaca gatcctcacc gatctgcaaa aagcccagcc    1800
ggactggagc attgccctgc tgcgctactt caacccggtt ggcgcgcatc cgtcgggcga    1860
tatgggcgaa gatccgcaag gcattccgaa taacctgatg ccatacatcg cccaggttgc    1920
tgtaggccgt cgcgactcgc tggcgatttt tggtaacgat tatccgaccg aagatggtac    1980
tggcgtacgc gattacatcc acgtaatgga tctggcggac ggtcacgtcg tggcgatgga    2040
aaaactggcg aacaagccag gcgtacacat ctacaacctc ggcgctggcg taggcaacag    2100
cgtgctggac gtggttaatg ccttcagcaa agcctgcggc aaaccggtta attatcattt    2160
tgcaccgcgt cgcgagggcg accttccggc ctactgggcg gacgcagca aagccgaccg    2220 tgaactgaac tggcgcgtaa cgcgcacact cgatgaaatg gcgcaggaca cctggcactg    2280
gcagtcacgc catccacagg gatatcccga ttaacgccat ttaaatcaac ctcagcggtc    2340
atagctgttt cctgtgactg agcaataact agcataaccc cttggggcct ctaaacgggt    2400
cttgaggggt tttttgctga aaccaatttg cctggcggca gtagcgcggt ggtcccacct    2460
gaccccatgc cgaactcaga agtgaaacgc cgtagcgccg atggtagtgt ggggtctccc    2520
catgcgagag tagggaactg ccaggcatca aataaaacga aaggctcagt cgaaagactg    2580
ggcctttcgg gatccaggcc ggcctgttaa cgaattaatc ttccgcggcg gtatcgataa    2640
gcttgatatc gaggctgaca tgggaattag ccatggtcca tatgaatatc ctccttagtt    2700
cctattccga agttcctatt ctctagaaag tataggaact tcggcgcgcc tacctgtgac    2760
ggaagatcac ttcgcagaat aaataaatcc tggtgtccct gttgataccg ggaagccctg    2820
ggccaacttt tggcgaaaat gagacgttga tcggcacgta agaggttcca actttcacca    2880
taatgaaata agatcactac cgggcgtatt ttttgagttg tcgagatttt caggagctaa    2940
ggaagctaaa atggagaaaa aaatcactgg atataccacc gttgatatat cccaatggca    3000
tcgtaaagaa catttgaggc atttcagtc agttgctcaa tgtacctata accagaccgt    3060
tcagctggat attacggcct ttttaaagac cgtaaagaaa aataagcaca gttttatcc    3120 ggcctttatt cacattcttg cccgcctgat gaatgctcat ccggaattac gtatggcaat    3180
gaaagacggg gagctggtga tatgggatag tgttcaccct tgttacaccg ttttccatga    3240
gcaaactgaa acgttttcat cgctctggag tgaataccac gacgatttcc ggcagtttct    3300
acacatatat tcgcaagatg tggcgtgtta cggtgaaaac ctggcctatt tccctaaagg    3360
gtttattgag aatatgtttt tcgtctcagc caatccctgg gtgagtttca ccagttttga    3420
tttaaacgtg gccaatatgg acaacttctt cgcccccgtt ttcaccatgg gcaaatatta    3480
tacgcaaggc gacaaggtgc tgatgccgct ggcgattcag gttcatcatg ccgtttgtga    3540
tggcttccat gtcggcagat gcttaatgaa tacaacagta ctgcgatgag tggcagggcg    3600
```

```
gggcgtaagg cgcgccattt aaatgaagtt cctattccga agttcctatt ctctagaaag   3660
tataggaact tcgaagcagc tccagcctac acaatcgctc aagacgtgta atgctgcaat   3720
ctgcatgcaa gcttggcact ggcgatggcg cctcatccct gaagccaata agcagctcca   3780
gcctacacaa tcgctcaaga cgtgtaatgc tgcaatctgc atgcaagcta gaccggggac   3840
ttatcagcca acctgt                                                  3856

<210> SEQ ID NO 6
<211> LENGTH: 4259
<212> TYPE: DNA
<213> ORGANISM: Artificial Sequence
<220> FEATURE:
<223> OTHER INFORMATION: construct galMKTE

<400> SEQUENCE: 6
ttactcagca ataaactgat attccgtcag gctggaatac tcttcgccag gacgcaggaa     60
gcagtccggt tgcggccatt cagggtggtt cgggctgtcc ggtagaaact cgctttccag    120
agccagccct tgccagtcgg cgtaaggttc ggttccccgc gacggtgtgc cgccgaggaa    180
gttgccggag tagaattgca gagccggagc ggtggtgtag accttcagct gcaattttc    240 atctgctgac cagacatgcg ccgccacttt cttgccatcg cctttggcct gtaacaagaa    300
tgcgtgatcg taacctttca ctttgcgctg atcgtcgtcg gcaagaaact cactggcgat    360
gattttggcg ctgcggaaat caaaagacgt tccggcgaca gatttcaggc cgtcgtgcgg    420
aatgccgcct tcatcaaccg gcagatattc gtccgccaga atctgcaact tgtgattgcg    480
cacgtcagac tgctcgccgt caagattgaa atagacgtga ttagtcatat tcaccgggca    540
aggtttatca actgtggcgc gataagtaat ggagatacgg ttatcgtcgg tcagacgata    600
ttgcaccgtc gcgccgagat tacccgggaa gccctgatca ccatcatctg aactcagggc    660
aaacagcacc tgacgatcgt tctggttcac aatctgccag cgacgtttgt cgaacccttc    720
cggcccgccg tgcagctggt taacgccctg acttggcgaa agcgtcacgg tttcaccgtc    780
aaaggtataa cggctattgg cgatacggtt ggcataacga ccaatagagg ccccagaaa    840 cgcggcctga tcctgatagc attccgggct ggcacagccg agcagcgcct cgcggacgct    900
gccatcggaa agcggaatac gggcggaaag taaagtcgca ccccagtcca tcagcgtgac    960
taccatccct gcgttgttac gcaaagttaa cagtcggtac ggctgaccat cgggtgccag   1020
tgcgggagtt tcgttcagca ctgtcctgct ccttgtgatg gtttacaaac gtaaaaagtc   1080
tctttaatac ctgttttgc ttcatattgt tcagcgacag cttgctgtac ggcaggcacc    1140
agctcttccg ggatcagcgc gacgatacag ccgccaaatc cgccgccggt catgcgtacg   1200
ccacctttgt cgccaatcac agctttgacg atttctacca gagtgtcaat ttgcggcacg   1260
gtgatttcga atcatcgcg catagaggca tgagactccg ccatcaactc gcccatacgt    1320
ttcaggtcgc cttgctccag cgcgctggca gcttcaacgg tgcgggcgtt ttcagtcagt   1380
atatgacgca cgcgttttgc cacgatcggg tccagttcat gcgcaacagc gttgaactct   1440
tcaatggtga catcacgcag ggctggctgc tggaagaaac gcgcaccggt ttcgcactgt   1500
tcacgacggg tgttgtattc gctgccaacc agggtacgtt tgaagttact gttgatgatg   1560
acgacagcca cacctttggg catggaaact gctttggtcc ccagtgagcg gcaatcgatc   1620
agcaaggcat gatctttctt gccgagcgcg gaaattagct gatccatgat cccgcagtta   1680
cagcctacaa actggttttc tgcttcctga ccgttaagcg cgatttgtgc gccgtccagc   1740
ggcagatgat aaagctgctg caatacggtt ccgaccgcga cttccagtga agcggaagaa   1800
```

```
cttaacccgg cacctgcgg cacattgccg ctgatcacca tgtccacgcc gccgaagctg    1860
ttgttacgca gttgcagatg tttcaccacg ccacgaacgt agttagccca ttgatagttt    1920
tcatgtgcga caatgggcgc atcgagggaa aactcgtcga gctgattttc ataatcggct    1980
gccatcacgc gaactttacg gtcatcgcgt ggtgcacaac tgatcacggt ttgataatca    2040
atcgcgcagg gcagaacgaa accgtcgttg tagtcggtgt gttcaccaat caaattcacg    2100
cggccaggcg cctgaatggt gtgagtggca gggtagccaa atgcgttggc aaacagagat    2160
tgtgtttttt ctttcagact catttcttac actccggatt cgcgaaaatg gatatcgctg    2220
actgcgcgca aacgctctgc tgcctgttct gcggtcaggt ctcgctgggt ctctgccagc    2280
atttcataac caaccataaa tttacgtacg gtggcggagc gcagcagagg cggataaaag    2340
tgcgcgtgca gctgccagtg ttgattctct tcgccattaa atggcgcgcc gtgccagccc    2400
atagagtagg ggaaggagca ctggaagagg ttgtcataac gactggtcag ctttttcaac    2460
gccagcgcca gatcgctgcg ctgggcgtcg gtcaaatcgg tgatccgtaa acgtgggct    2520 ttgggcagca gtagcgtttc gaacggccag gcagcccagt aaggcacgac ggctaaccag    2580
tgttcggttt cgacaacggt acggctaccg tctgccagct cgcgctgaac ataatccacc    2640
agcattggtg atttctgttc ggcaaaatat tcttttgca ggcggtcttc gcgctcagct    2700
tcgttaggca ggaagctatt tgcccaaatc tgaccgtgcg gatgcgggtt agagcagccc    2760
atcgccgcgc ctttgttttc aaaaacctgc acccatgggt acgttttccc cagttctgcg    2820
gtttgctcct gccaggtttt gacgatttcc gtcaatgctg caacgctgag ctctggcagc    2880
gttttactgt gatccggtga aaagcagatc acccggctgg tgccgcgcgc gctctggcaa    2940
cgcatcagcg gatcgtgact ttctggcgca tctggcgtgt cagacatcaa agccgcaaag    3000
tcattagtga aaacgtaagt cccggtgtaa tcggggtttt tatcgcctgt cacccgcaca    3060
ttacctgcgc agaggaagca atctggatcg tgcgcaggta acacctgttt ggctggcgtt    3120
tcctgcgccc cctgccaggg gcgcttagcg cggtgcggtg aaaccagaat ccattgcccg    3180
gtgagcgggt tgtagcggcg atgtggatga tcaacgggat taaattgcgt catggtcgtt    3240
ccttaatcgg gatatccctg tggatggcgt gactgccagt gccaggtgtc ctgcgccatt    3300
tcatcgagtg tgcgcgttac gcgccagttc agttcacggt cggctttgct ggcgtccgcc    3360
cagtaggcca gaaggtcgcc ctcgcgacgc ggtgcaaaat gataattaac cggtttgccg    3420
caggctttgc tgaaggcatt aaccacgtcc agcacgctgt tgcctacgcc agcgccgagg    3480
ttgtagatgt gtacgcctgg cttgttcgcc agttttccca tcgccacgac gtgaccgtcc    3540
gccagatcca ttacgtggat gtaatcgcgt acgccagtac catcttcggt cggataatcg    3600
ttaccaaaaa tcgccagcga gtcgcgacgg cctacagcaa cctgggcgat gtatggcatc    3660
aggttattcg gaatgccttg cggatcttcg cccatatcgc ccgacggatg cgcgccaacc    3720
gggttgaagt agcgcagcag ggcaatgctc cagtccggct gggcttttg cagatcggtg    3780 aggatctgtt ccaccatcag cttgcttttg ccgtaagggc tttgcggtgt gccggtcggg    3840
aagctttcaa cgtatggaat tttgggctga tcgccataaa cggtggcgga ggagctaaaa    3900
ataaagtttt tgacgttagc ggcgcgcatg gcgctaatca ggcgcagagt gccgttgaca    3960
ttgttgtcgt aatattccag cggttttttgt accgattcgc ccacggcttt cagcccggcg    4020
aagtggatca cggtgtcgat agcgtgatcg tgcaggatct cggtcatcaa cgcttcgtta    4080
cgaatatcgc cttcaacaaa cgttggatgt ttgccgccta aacgctcgat aacaggcagt    4140
```

```
acgctgcgct tactgttaca gaggttatca agaatgatga catcatgacc gttttgcagt    4200
aattgcacac aggtatgact ccaatgtaa ccgctaccac cggtaaccag aactctcat     4259

<210> SEQ ID NO 7
<211> LENGTH: 6431
<212> TYPE: DNA
<213> ORGANISM: Artificial Sequence
<220> FEATURE:
<223> OTHER INFORMATION: construct pET-lgtA

<400> SEQUENCE: 7
ggggaattgt gagcggataa caattcccct ctagaaataa ttttgtttaa ctttaagaag      60
gagatatacc atgggcagca gccatcacca tcatcaccac agccaggatc cgaattcgag     120
ctcggcgcgc ctgcaggtcg acaagcttgc ggccgcataa tgcttaagtc gaacagaaag     180
taatcgtatt gtacacggcc gcataatcga aattaatacg actcactata ggggaattgt     240
gagcggataa caattcccca tcttagtata ttagttaagt ataagaagga gatatacata     300
tgccgtccga agcattccgt cgtcaccgtg cttatcgcga aaacaaactg cagccactgg     360
tctctgtcct gatctgcgca tacaacgttg agaaatactt cgcacagtct ctggcagctg     420
tagttaacca gacctggcgt aacctggata tcctgatcgt agatgacggc tctacggatg     480
gtacgctggc gatcgcacag cgtttccagg aacaggacgg tcgtatccgc attctcgctc     540
agccgcgtaa ctctggtctg atcccgtctc tgaacatcgg tctggacgaa ctggccaaat     600
ctggtggtgg tggcgaatac atcgcccgta ctgacgccga cgacattgcg ccccggatt      660 ggatcgaaaa aatcgtaggt gaaatggaga agaccgctc tatcatcgcg atgggtgctt      720
ggctggaagt tctgtccgaa gagaaagacg gtaaccgtct ggcccgtcac catgaacacg     780
gcaaaatctg gaaaaaccg accgtcacg aagatatcgc ggacttcttc ccgttcggta      840
acccgatcca taacaacacc atgatcatgc gtcgtagcgt aatcgacggt ggtctgcgtt     900
acaacaccga acgtgattgg gcagaagact accagttttg gtatgacgtg tctaaactgg     960
gtcgtctggc ttactacccca gaagcgctgg ttaaataccg tctgcacgcc aaccaggtta    1020
gctccaaata ctccatccgt cagcacgaaa tcgcacaggg tatccagaaa acggctcgta    1080
acgacttcct gcagtccatg ggtttcaaaa cccgtttcga ctctctggag taccgtcaga    1140
tcaaagcggt tgcgtatgag ctgctggaga acacctgcc ggaagaggac tttgaacgtg     1200
cgcgtcgttt cctgtaccag tgcttcaaac gtaccgacac tctgccggcg ggtgcatggc    1260
tcgactttgc agcggatggt cgtatgcgtc gtctgttac cctgcgtcag tacttcggta     1320
tcctgcatcg tctcctgaaa accgctaat gagacgtcgg taccctcgag tctggtaaag    1380
aaaccgctgc tgcgaaattt gaacgccagc acatggactc gtctactagc gcagcttaat    1440
taacctaggc tgctgccacc gctgagcaat aactagcata accccttggg gcctctaaac    1500
gggtcttgag gggttttttg ctgaaaggag aactatatc cggattggcg aatgggacgc     1560
gccctgtagc ggcgcattaa gcgcggcggg tgtggtggtt acgcgcagcg tgaccgctac    1620
acttgccagc gccctagcgc ccgctccttt cgctttcttc ccttcctttc tcgccacgtt    1680
cgccggcttt cccctgtcaag ctctaaatcg gggctccct ttagggttcc gatttagtgc    1740
tttacggcac ctcgacccca aaaaacttga ttagggtgat ggttcacgta gtgggccatc    1800
gccctgatag acggtttttc gccctttgac gttggagtcc acgttcttta atagtggact    1860
cttgttccaa actggaacaa cactcaaccc tatctcggtc tattcttttg atttataagg    1920
gattttgccg atttcggcct attggttaaa aaatgagctg atttaacaaa aatttaacgc    1980
```

```
gaattttaac aaaatattaa cgtttacaat ttctggcggc acgatggcat gagattatca  2040
aaaaggatct tcacctagat cctttaaat taaaaatgaa gttttaaatc aatctaaagt   2100
atatatgagt aaacttggtc tgacagttac caatgcttaa tcagtgaggc acctatctca  2160
gcgatctgtc tatttcgttc atccatagtt gcctgactcc ccgtcgtgta gataactacg  2220
atacgggagg gcttaccatc tggccccagt gctgcaatga taccgcgaga cccacgctca  2280
ccggctccag atttatcagc aataaaccag ccagccggaa gggccgagcg cagaagtggt  2340
cctgcaactt tatccgcctc catccagtct attaattgtt gccgggaagc tagagtaagt  2400
agttcgccag ttaatagttt gcgcaacgtt gttgccattg ctacaggcat cgtggtgtca  2460
cgctcgtcgt ttggtatggc ttcattcagc tccggttccc aacgatcaag gcgagttaca  2520
tgatccccca tgttgtgcaa aaaagcggtt agctccttcg gtcctccgat cgttgtcaga  2580
agtaagttgg ccgcagtgtt atcactcatg gttatggcag cactgcataa ttctcttact  2640
gtcatgccat ccgtaagatg cttttctgtg actggtgagt actcaaccaa gtcattctga  2700
gaatagtgta tgcggcgacc gagttgctct tgcccggcgt caatacggga taataccgcg  2760
ccacatagca gaactttaaa agtgctcatc attggaaaac gttcttcggg gcgaaaactc  2820
tcaaggatct taccgctgtt gagatccagt tcgatgtaac ccactcgtgc acccaactga  2880
tcttcagcat cttttacttt caccagcgtt tctgggtgag caaaaacagg aaggcaaaat  2940
gccgcaaaaa agggaataag ggcgacacgg aaatgttgaa tactcatact cttcctttt   3000
caatcatgat tgaagcattt atcagggtta ttgtctcatg agcggataca tatttgaatg  3060
tatttagaaa aataaacaaa taggtcatga ccaaaatccc ttaacgtgag ttttcgttcc  3120
actgagcgtc agaccccgta gaaaagatca aaggatcttc ttgagatcct tttttctgc   3180
gcgtaatctg ctgcttgcaa acaaaaaaac caccgctacc agcggtggtt tgtttgccgg  3240
atcaagagct accaactctt tttccgaagg taactggctt cagcagagcg cagataccaa  3300
atactgtcct tctagtgtag ccgtagttag gccaccactt caagaactct gtagcaccgc  3360
ctacatacct cgctctgcta atcctgttac cagtggctgc tgccagtggc gataagtcgt  3420
gtcttaccgg gttggactca agacgatagt taccggataa ggcgcagcgg tcgggctgaa  3480
cggggggttc gtgcacacag cccagcttgg agcgaacgac ctacaccgaa ctgagatacc  3540
tacagcgtga gctatgagaa agcgccacgc ttcccgaagg gagaaaggcg gacaggtatc  3600
cggtaagcgg cagggtcgga acaggagagc gcacgaggga gcttccaggg ggaaacgcct  3660
ggtatcttta tagtcctgtc gggtttcgcc acctctgact tgagcgtcga ttttgtgat   3720
gctcgtcagg gggcggagc ctatggaaaa acgccagcaa cgcggccttt ttacggttcc   3780
tggccttttg ctggcctttt gctcacatgt tctttcctgc gttatcccct gattctgtgg  3840
ataaccgtat taccgccttt gagtgagctg ataccgctcg ccgcagccga acgaccgagc  3900
gcagcgagtc agtgagcgag gaagcggaag agcgcctgat gcggtatttt ctccttacgc  3960
atctgtgcgg tatttcacac cgcatatatg gtgcactctc agtacaatct gctctgatgc  4020
cgcatagtta agccagtata cactccgcta tcgctacgtg actgggtcat ggctgcgccc  4080
cgacacccgc caacacccgc tgacgcgccc tgacgggctt gtctgctccc ggcatccgct  4140
tacagacaag ctgtgaccgt ctccgggagc tgcatgtgtc agaggttttc accgtcatca  4200
ccgaaacgcg cgaggcagct gcggtaaagc tcatcagcgt ggtcgtgaag cgattcacag  4260
atgtctgcct gttcatccgc gtccagctcg ttgagtttct ccagaagcgt taatgtctgg  4320
```

```
cttctgataa agcgggccat gttaagggcg gttttttcct gtttggtcac tgatgcctcc    4380
gtgtaagggg gatttctgtt catgggggta atgataccga tgaaacgaga gaggatgctc    4440
acgatacggg ttactgatga tgaacatgcc cggttactgg aacgttgtga gggtaaacaa    4500
ctggcggtat ggatgcggcg ggaccagaga aaaatcactc agggtcaatg ccagcgcttc    4560
gttaatacag atgtaggtgt tccacagggt agccagcagc atcctgcgat gcagatccgg    4620
aacataatgg tgcagggcgc tgacttccgc gtttccagac tttacgaaac acggaaaccg    4680
aagaccattc atgttgttgc tcaggtcgca gacgttttgc agcagcagtc gcttcacgtt    4740
cgctcgcgta tcggtgattc attctgctaa ccagtaaggc aaccccgcca gcctagccgg    4800
gtcctcaacg acaggagcac gatcatgcta gtcatgcccc gcgcccaccg aaggagctg    4860 actgggttga aggctctcaa gggcatcggt cgagatcccg gtgcctaatg agtgagctaa    4920
cttacattaa ttgcgttgcg ctcactgccc gctttccagt cgggaaacct gtcgtgccag    4980
ctgcattaat gaatcggcca acgcgcgggg agaggcggtt tgcgtattgg gcgccagggt    5040
ggtttttctt ttcaccagtg agacgggcaa cagctgattg cccttcaccg cctggccctg    5100
agagagttgc agcaagcggt ccacgctggt ttgccccagc aggcgaaaat cctgtttgat    5160
ggtggttaac ggcgggatat aacatgagct gtcttcggta tcgtcgtatc ccactaccga    5220
gatgtccgca ccaacgcgca gcccggactc ggtaatggcg cgcattgcgc ccagcgccat    5280
ctgatcgttg gcaaccagca tcgcagtggg aacgatgccc tcattcagca tttgcatggt    5340
ttgttgaaaa ccggacatgg cactccagtc gccttcccgt tccgctatcg gctgaatttg    5400
attgcgagtg agatatttat gccagccagc cagacgcaga cgcgccgaga cagaacttaa    5460
tgggcccgct aacagcgcga tttgctggtg acccaatgcg accagatgct ccacgcccag    5520
tcgcgtaccg tcttcatggg agaaaataat actgttgatg ggtgtctggt cagagacatc    5580
aagaaataac gccggaacat tagtgcaggc agcttccaca gcaatggcat cctggtcatc    5640
cagcggatag ttaatgatca gcccactgac gcgttgcgcg agaagattgt gcaccgccgc    5700
tttacaggct tcgacgccgc ttcgttctac catcgacacc accacgctgg cacccagttg    5760
atcggcgcga gatttaatcg ccgcgacaat ttgcgacggc gcgtgcaggg ccagactgga    5820
ggtggcaacg ccaatcagca acgactgttt gcccgccagt tgttgtgcca cgcggttggg    5880
aatgtaattc agctccgcca tcgccgcttc cacttttttcc cgcgttttcg cagaaacgtg    5940
gctggcctgg ttcaccacgc gggaaacggt ctgataagag acaccggcat actctgcgac    6000
atcgtataac gttactggtt tcacattcac cacccctgaat tgactctctt ccgggcgcta    6060
tcatgccata ccgcgaaagg ttttgcgcca ttcgatggtg tccgggatct cgacgctctc    6120
ccttatgcga ctcctgcatt aggaagcagc ccagtagtag gttgaggccg ttgagcaccg    6180
ccgccgcaag gaatggtgca tgcaaggaga tggcgcccaa cagtccccg gccacggggc    6240 ctgccaccat acccacgccg aaacaagcgc tcatgagccc gaagtggcga gcccgatctt    6300
ccccatcggt gatgtcggcg atataggcgc cagcaaccgc acctgtggcg ccggtgatgc    6360
cggccacgat gcgtccggcg tagaggatcg agatcgatct cgatcccgcg aaattaatac    6420
gactcactat a                                                          6431
```

<210> SEQ ID NO 8
<211> LENGTH: 5739
<212> TYPE: DNA
<213> ORGANISM: Artificial Sequence
<220> FEATURE:
<223> OTHER INFORMATION: construct pCDF-galT-galE

<400> SEQUENCE: 8

```
ggggaattgt gagcggataa caattcccct gtagaaataa ttttgtttaa ctttaataag    60
gagatatacc atgacgcaat ttaatcccgt tgatcatcca catcgccgct acaacccgct   120
caccgggcaa tggattctgg tttcaccgca ccgcgctaag cgccctggc aggggcgca    180
ggaaacgcca gccaaacagg tgttacctgc gcacgatcca gattgcttcc tctgcgcagg   240
taatgtgcgg gtgacaggcg ataaaaaccc cgattacacc gggacttacg ttttcactaa   300
tgactttgcg gctttgatgt ctgacacgcc agatgcgcca gaaagtcacg atccgctgat   360
gcgttgccag agcgcgcgcg gcaccagccg ggtgatctgc ttttcaccgg atcacagtaa   420
aacgctgcca gagctcagcg ttgcagcatt gacggaaatc gtcaaaacct ggcaggagca   480
aaccgcagaa ctggggaaaa cgtacccatg ggtgcaggtt tttgaaaaca aaggcgcggc   540
gatgggctgc tctaacccgc atccgcacgg tcagatttgg gcaaatagct tcctgcctaa   600
cgaagctgag cgcgaagacc gcctgcaaaa agaatatttt gccgaacaga aatcaccaat   660
gctggtggat tatgttcagc gcgagctggc agacggtagc cgtaccgttg tcgaaaccga   720
acactggtta gccgtcgtgc cttactgggc tgcctggccg ttcgaaacgc tactgctgcc   780
caaagcccac gttttacgga tcaccgattt gaccgacgcc cagcgcagcg atctggcgct   840
ggcgttgaaa aagctgacca gtcgttatga caacctcttc cagtgctcct tccctactc    900
tatgggctgg cacggcgcgc catttaatgg cgaagagaat caacactggc agctgcacgc   960
gcacttttat ccgcctctgc tgcgctccgc caccgtacgt aaatttatgg ttggttatga  1020
aatgctggca gagacccagc gagacctgac cgcagaacag gcagcagagc gtttgcgcgc  1080
agtcagcgat atccattttc gcgaatccgg agtgtaaaag cttgcggccg cataatgctt  1140
aagtcgaaca gaaagtaatc gtattgtaca cggccgcata atcgaaatta atacgactca  1200
ctataggga attgtgagcg gataacaatt cccatctta gtatattagt taagtataag   1260
aaggagatat acagatcaca tatgagagtt ctggttaccg gtggtagcgg ttacattgga  1320
agtcataccct gtgtgcaatt actgcaaaac ggtcatgatg tcatcattct tgataacctc  1380
tgtaacagta agcgcagcgt actgcctgtt atcgagcgtt taggcggcaa acatccaacg  1440
tttgttgaag gcgatattcg taacgaagcg ttgatgaccg agatcctgca cgatcacgct  1500
atcgacaccg tgatccactt cgccgggctg aaagccgtgg cgaatcggt acaaaaaccg   1560
ctggaatatt acgacaacaa tgtcaacggc actctgcgcc tgattagcgc catgcgcgcc  1620
gctaacgtca aaaactttat ttttagctcc tccgccaccg tttatggcga tcagcccaaa  1680
attccatacg ttgaaagctt cccgaccggc acaccgcaaa gcccttacgg caaaagcaag  1740
ctgatggtgg aacagatcct caccgatctg caaaaagccc agccggactg gagcattgcc  1800
ctgctgcgct acttcaaccc ggttggcgcg catccgtcgg gcgatatggg cgaagatccg  1860
caaggcattc cgaataacct gatgccatac atcgcccagg ttgctgtagg ccgtcgcgac  1920
tcgctggcga ttttttggtaa cgattatccg accgaagatg gtactggcgt acgcgattac  1980
atccacgtaa tggatctggc ggacggtcac gtcgtggcga tggaaaaact ggcgaacaag  2040
ccaggcgtac acatctacaa cctcggcgct ggcgtaggca acagcgtgct ggacgtggtt  2100
aatgccttca gcaaagcctg cggcaaaccg gttaattatc attttgcacc gcgtcgcgag  2160
ggcgaccttc cggcctactg gcggacgcc agcaaagccg accgtgaact gaactggcgc  2220
gtaacgcgca cactcgatga aatggcgcag gacacctggc actggcagtc acgccatcca  2280
```

```
cagggatatc cgattaatg actcgagtga tctcgagtct ggtaaagaaa ccgctgctgc    2340
gaaatttgaa cgccagcaca tggactcgtc tactagcgca gcttaattaa cctaggctgc    2400
tgccaccgct gagcaataac tagcataacc ccttggggcc tctaaacggg tcttgagggg    2460
ttttttgctg aaacctcagg catttgagaa gcacacggtc acactgcttc cggtagtcaa    2520
taaaccggta accagcaat agacataagc ggctatttaa cgaccctgcc ctgaaccgac    2580
gaccgggtca tcgtggccgg atcttgcggc ccctcggctt gaacgaattg ttagacatta    2640
tttgccgact accttggtga tctcgccttt cacgtagtgg acaaattctt ccaactgatc    2700
tgcgcgcgag gccaagcgat cttcttcttg tccaagataa gcctgtctag cttcaagtat    2760
gacgggctga tactgggccg gcaggcgctc cattgcccag tcggcagcga catccttcgg    2820
cgcgattttg ccggttactg cgctgtacca aatgcgggac aacgtaagca ctacatttcg    2880
ctcatcgcca gcccagtcgg gcggcgagtt ccatagcgtt aaggtttcat ttagcgcctc    2940
aaatagatcc tgttcaggaa ccggatcaaa gagttcctcc gccgctggac ctaccaaggc    3000
aacgctatgt tctcttgctt ttgtcagcaa gatagccaga tcaatgtcga tcgtggctgg    3060
ctcgaagata cctgcaagaa tgtcattgcg ctgccattct ccaaattgca gttcgcgctt    3120
agctggataa cgccacggaa tgatgtcgtc gtgcacaaca atggtgactt ctacagcgcg    3180
gagaatctcg ctctctccag gggaagccga agtttccaaa aggtcgttga tcaaagctcg    3240
ccgcgttgtt tcatcaagcc ttacggtcac cgtaaccagc aaatcaatat cactgtgtgg    3300
cttcaggccg ccatccactg cggagccgta caaatgtacg ccagcaacg tcggttcgag    3360 atggcgctcg atgacgccaa ctacctctga tagttgagtc gatacttcgg cgatcaccgc    3420
ttccctcata ctcttccttt tcaatatta ttgaagcatt tatcagggtt attgtctcat    3480
gagcggatac atatttgaat gtatttagaa aaataaacaa atagctagct cactcggtcg    3540
ctacgctccg ggcgtgagac tgcggcgggc gctgcggaca catacaaagt tacccacaga    3600
ttccgtggat aagcagggga ctaacatgtg aggcaaaaca gcagggccgc gccggtggcg    3660
tttttccata ggctccgccc tcctgccaga gttcacataa acagacgctt ttccggtgca    3720
tctgtgggag ccgtgaggct caaccatgaa tctgacagta cgggcgaaac ccgacaggac    3780
ttaaagatcc ccaccgtttc cggcgggtcg ctccctcttg cgctctcctg ttccgaccct    3840 gccgttacc ggatacctgt tccgcctttc tcccttacgg gaagtgtggc gctttctcat    3900
agctcacaca ctggtatctc ggctcggtgt aggtcgttcg ctccaagctg gctgtaagc    3960 aagaactccc cgttcagccc gactgctgcg ccttatccgg taactgttca cttgagtcca    4020
acccggaaaa gcacggtaaa acgccactgg cagcagccat ggtaactgg gagttcgcag    4080 aggatttgtt tagctaaaca cgcggttgct cttgaagtgt gcgccaaagt ccggctacac    4140
tggaaggaca gatttggttg ctgtgctctg cgaaagccag ttaccacggt taagcagttc    4200
cccaactgac ttaaccttcg atcaaaccac ctccccaggt ggttttttcg tttacagggc    4260
aaaagattac gcgcagaaaa aaaggatctc aagaagatcc tttgatcttt tctactgaac    4320
cgctctagat ttcagtgcaa tttatctctt caaatgtagc acctgaagtc agccccatac    4380
gatataagtt gtaattctca tgttagtcat gccccgcgcc caccggaagg agctgactgg    4440
gttgaaggct ctcaagggca tcggtcgaga tcccggtgcc taatgagtga gctaacttac    4500
attaattgcg ttgcgctcac tgcccgcttt ccagtcggga aacctgtcgt gccagctgca    4560
ttaatgaatc ggccaacgcg cggggagagg cggtttgcgt attgggcgcc agggtggttt    4620
ttcttttcac cagtgagacg ggcaacagct gattgcccct caccgcctgg ccctgagaga    4680
```

```
gttgcagcaa gcggtccacg ctggtttgcc ccagcaggcg aaaatcctgt tgatggtgg    4740 ttaacggcgg gatataacat gagctgtctt cggtatcgtc gtatcccact accgagatgt    4800
ccgcaccaac gcgcagcccg gactcggtaa tggcgcgcat tgcgcccagc gccatctgat    4860
cgttggcaac cagcatcgca gtgggaacga tgccctcatt cagcatttgc atggtttgtt    4920
gaaaaccgga catggcactc cagtcgcctt cccgttccgc tatcggctga atttgattgc    4980
gagtgagata tttatgccag ccagccagac gcagacgcgc cgagacagaa cttaatgggc    5040
ccgctaacag cgcgatttgc tggtgaccca atgcgaccag atgctccacg cccagtcgcg    5100
taccgtcttc atgggagaaa ataatactgt tgatgggtgt ctggtcagag acatcaagaa    5160
ataacgccgg aacattagtg caggcagctt ccacagcaat ggcatcctgg tcatccagcg    5220
gatagttaat gatcagccca ctgacgcgtt gcgcgagaag attgtgcacc gccgctttac    5280
aggcttcgac gccgcttcgt tctaccatcg acaccaccac gctggcaccc agttgatcgg    5340
cgcgagattt aatcgccgcg acaatttgcg acggcgcgtg cagggccaga ctggaggtgg    5400
caacgccaat cagcaacgac tgtttgcccg ccagttgttg tgccacgcgg ttgggaatgt    5460
aattcagctc cgccatcgcc gcttccactt tttcccgcgt tttcgcagaa acgtggctgg    5520
cctggttcac cacgcgggaa acggtctgat aagagacacc ggcatactct gcgacatcgt    5580
ataacgttac tggtttcaca ttcaccaccc tgaattgact ctcttccggg cgctatcatg    5640
ccataccgcg aaaggttttg cgccattcga tggtgtccgg gatctcgacg ctctccctta    5700
tgcgactcct gcattaggaa attaatacga ctcactata                           5739
```

<210> SEQ ID NO 9
<211> LENGTH: 8232
<212> TYPE: DNA
<213> ORGANISM: Artificial Sequence
<220> FEATURE:
<223> OTHER INFORMATION: construct pCOLA-glmUM-glmS

<400> SEQUENCE: 9

```
cagcccactg acgcgttgcg cgagaagatt gtgcaccgcc gctttacagg cttcgacgcc      60
gcttcgttct accatcgaca ccaccacgct ggcacccagt tgatcggcgc gagatttaat     120
cgccgcgaca atttgcgacg gcgcgtgcag ggccagactg gaggtggcaa cgccaatcag     180
caacgactgt ttgcccgcca gttgttgtgc cacgcgttg ggaatgtaat tcagctccgc     240
catcgccgct ccactttttt cccgcgtttt cgcagaaacg tggctggcct ggttcaccac     300
gcgggaaacg gtctgataag agacaccggc atactctgcg acatcgtata acgttactgg     360
tttcacattc accacctga attgactctc ttccgggcgc tatcatgcca taccgcgaaa     420
ggttttgcgc cattcgatgg tgtccgggat ctcgacgctc tcccttatgc gactcctgca     480
ttaggaaatt aatacgactc actataggg aattgtgagc ggataacaat tcccctgtag     540
aaataatttt gtttaacttt aataaggaga tataccatgc tgaacaacgc gatgtctgtt     600
gttatcctgg cggcgggtaa aggtacccgt atgtactctg acctgccgaa agttctgcac     660
accctggcgg gtaaagcgat ggttcagcac gttatcgacg cggcgaacga actgggtgcg     720
gcgcacgttc acctggttta cggtcacggt ggtgacctgc tgaaacaggc gctgaaagac     780
gacaacctga actgggttct gcaggcggaa cagctgggta ccggtcacgc gatgcagcag     840
gcggcgccgt tcttcgcgga cgacgaagac atcctgatgc tgtacggtga cgttccgctg     900
atctctgttg aaaccctgca gcgtctgcgt gacgcgaaac cgcagggtgg tatcggtctg     960
```

```
ctgaccgtta aactggacga cccgaccggt tacggtcgta tcacccgtga aaacggtaaa    1020
gtaaccggta tcgttgaaca caaagacgcg accgacgaac agcgtcagat ccaggagatc    1080
aacaccggta tcctgatcgc gaacggtgca gacatgaaac gttggctggc gaaactgacc    1140
aacaacaacg cgcagggtga atactacatc accgacatca tcgcgctggc gtaccaggaa    1200
ggtcgtgaaa tcgttgcggt tcacccgcag cgtctgtctg aagttgaagg tgttaacaac    1260
cgtctgcagc tgtctcgtct ggaacgtgtt taccagtctg aacaggcgga aaaactgctg    1320
ctggcgggtg ttatgctgcg tgacccggcg cgtttcgacc tgcgtggtac cctgacccac    1380
ggtcgtgacg ttgaaatcga caccaacgtt atcatcgaag gtaacgttac cctgggtcac    1440
cgtgtaaaaa tcggcaccgg ttgcgttatc aaaaactctg ttatcggtga cgactgcgaa    1500
atctctccgt acaccgttgt tgaagacgcg aacctggcgg cggcgtgcac catcggtccg    1560
ttcgcgcgtc tgcgtccggg tgcggaactg ctggaaggtg cgcacgttgg taacttcgtt    1620
gaaatgaaaa aagcgcgtct gggtaaaggt tctaaagcgg gtcacctgac ctacctgggt    1680
gacgcggaaa tcggtgacaa cgttaacatc ggtgcgggta ccatcacctg caactacgac    1740
ggtgcgaaca aattcaaaac catcatcggt gacgacgttt tcgttggttc tgacacccag    1800
ctggttgcgc cggttaccgt tggtaaaggt gcgaccatcg cggcgggtac caccgttacc    1860
cgtaacgttg gtgaaaacgc gctggcgatc tctcgtgttc cgcagaccca gaaagaaggt    1920
tggcgtcgtc cggttaaaaa aaataacga aggagataga accatgtcca accgtaaata    1980
cttcggtacg gacggtatcc gtggtcgtgt aggtgatgct ccgattacgc cggatttcgt    2040
cctgaaactc ggttgggcag cgggtaaagt tctcgcacgt cacggctctc gtaaaatcat    2100
catcggtaaa gacacccgta tctctggtta catgctcgaa tctgcactgg aagcgggtct    2160
ggctgcagct ggtctgtctg cactgttcac gggtccgatg ccaaccccag ctgtagcgta    2220
cctgactcgc actttccgtg cagaagcagg tatcgtgatc tctgcctctc acaacccgtt    2280
ctacgacaac ggtatcaaat tcttcagcat cgatggtacc aaaactcccag acgcggttga    2340 agaggctatc gaagcggaaa tggagaaaga atctcttgt gtagactctg ccgaactcgg    2400
taaagcgtct cgtatcgttg atgcagcggg tcgttacatc gagttctgca aagccacctt    2460
tccgaacgaa ctgagcctgt ctgagctgaa atcgtcgta gactgtgcca acggtgcgac    2520
ttaccacatt gccccaaacg tactgcgtga gctgggtgct aacgtcatcg cgatcggttg    2580
tgaaccgaac ggtgtcaaca tcaacgcgga agtaggtgcg accgatgttc gtgcactgca    2640
ggctcgtgta ctcgcggaga aagcggatct cggtatcgcc tttgacggtg atggtgaccg    2700
tgttatcatg gttgaccacg aaggtaacaa agtggatggt gaccagatca tgtacatcat    2760
tgcccgtgaa ggtctgcgtc agggtcagct gcgtggtggt gcagtaggta ccctcatgag    2820
caacatgggt ctgaactggg ccctgaaaca gctgggtatc ccattcgctc gtgctaaagt    2880
aggcgaccgt tacgttctgg agaaaatgca ggagaaaggt tggcgtatcg gtgccgaaaa    2940
ctctggtcac gtcatcctgc tggacaaaac cactaccggt gacggtatcg tagcaggtct    3000
gcaggtactc gccgctatgg cccgtaacca catgtccctc catgacctct gctctggtat    3060
gaaaatgttc ccgcagatcc tggttaacgt tcgttacacc gcaggttctg gtgatccgct    3120
ggaacacgag tctgtgaaag ccgttaccgc agaagtggaa gcggccctgg gtaaccgtgg    3180
tcgtgtactg ctgcgtaaat ccggtactga gccactgatc cgtgttatgg ttgagggcga    3240
agatgaagcc caggtcaccg aatttgcgca ccgtattgcc gacgcagtca agcggttta    3300 aatgggcagc agccatcacc atcatcacca cagccaggat ccgaattcga gctcggcgcg    3360
```

```
cctgcaggtc gacaagcttg cggccgcata atgcttaagt cgaacagaaa gtaatcgtat   3420
tgtacacggc cgcataatcg aaattaatac gactcactat aggggaattg tgagcggata   3480
acaattcccc atcttagtat attagttaag tataagaagg agatatacat atgtgcggta   3540
tcgttggtgc tatcgcacag cgtgatgtag cggagatcct cctggaaggt ctgcgtcgtc   3600
tcgaataccg tggttacgac tctgccggtc tggcagtagt ggatgcagaa ggtcacatga   3660
ctcgtctgcg tcgtctgggt aaagtgcaga tgctcgcgca ggcggcgaaa gaacacccac   3720
tccacggtgg tacgggtatc gcacacactc gttgggcaac ccacggtgaa ccgtctgagg   3780
tcaacgcaca cccgcatgtt agcgagcaca tcgtagtcgt tcacaacggt atcatcgaga   3840
accacgaacc actccgtgag gaactcaaag cccgtggtta caccttcgta agcgaaaccg   3900
acacggaagt tatcgcccac ctcgttaact gggaactcaa acagggtggt actctgcgtg   3960
aagcagttct gcgtgccatt ccacagctgc gtggtgcata cggtaccgtg atcatggact   4020
ctcgtcatcc ggatacccctg ctcgccgcac gttctggttc tccactcgtt atcggtctgg   4080
gtatgggtga acttcatc gcctctgatc agctggccct gctcccagtt acccgtcgct   4140
tcatcttcct ggaagagggt gacatcgccg aaatcacccg tcgttccgtt aacatcttcg   4200
acaaaacggg tgcggaagtt aaacgtcagg acatcgagtc taacctgcag tatgacgctg   4260
gtgacaaagg catctaccgt cactacatgc agaaagagat ctacgaacag ccgaacgcga   4320
tcaaaaacac cctgaccggt cgtatctctc acggtcaggt tgacctgtct gagctgggtc   4380
caaacgcgga cgaactcctg tccaaagtcg agcacatcca gatcctggct tgtggtacct   4440
cttacaactc cggtatggtt tctcgttact ggttcgaatc tctggcaggt atcccatgcg   4500
acgttgaaat cgcctccgaa ttccgttatc gtaaatctgc ggtacgtcgt aactccctca   4560
tgatcaccct gtctcagtct ggtgaaaccg ctgatactct ggcaggtctg cgtctcagca   4620
aagaactggg ttacctgggt tctctggcca tctgcaacgt tccggttct agcctggttc   4680 gtgagtctga cctggctctg atgaccaacg cgggtacgga gatcggtgtt gcctctacca   4740
aagcgttcac tacccagctc actgtcctgc tgatgctggt tgccaaactg tctcgtctca   4800
aaggcctcga cgctagcatc gaacacgaca tcgtacacgg tctgcaggcc ctcccatctc   4860
gtatcgagca gatgctgtct caggacaaac gtatcgaagc actggcagaa gacttcagcg   4920
acaaacacca cgcgctgttt ctgggtcgtg gtgaccagta cccaattgcg ctggaaggtg   4980
ccctgaaact gaaagagatc agctacatcc atgcagaggc atacgcagcg ggtgagctga   5040
aacatggtcc actggccctg atcgacgcag atatgccggt tattgtggtt gctccgaaca   5100
acgaactgct ggagaaactg aaatccaaca tcgaggaagt acgtgcgcgt ggtggtcagc   5160
tgtacgtgtt tgctgaccag gacgcgggtt tcgtttccag cgacaacatg cacatcatcg   5220
aaatgccgca tgttgaagag gtaatcgcgc caatcttcta caccgtaccg ctgcagctgc   5280
tggcgtacca tgtagccctg atcaaaggta cggacgttga ccagccgcgt aacctggcga   5340
aatccgtgac cgtggaataa gacgtcggta ccctcgagtc tggtaaagaa accgctgctg   5400
cgaaatttga acgccagcac atggactcgt ctactagcgc agcttaatta acctaggctg   5460
ctgccaccgc tgagcaataa ctagcataac cccttggggc ctctaaacgg tcttgagggg   5520 ttttttgct gaaacctcag gcatttgaga agcacacggt cacactgctt ccggtagtca   5580
ataaaccggt aaaccagcaa tagacataag cggctattta acgaccctgc cctgaaccga   5640
cgacaagctg acgaccgggt ctccgcaagt ggcactttc ggggaaatgt gcgcggaacc   5700
```

```
cctatttgtt tattttttcta aatacattca aatatgtatc cgctcatgaa ttaattctta    5760
gaaaaactca tcgagcatca aatgaaactg caatttattc atatcaggat tatcaatacc    5820 atattttttga aaaagccgtt tctgtaatga aggagaaaac tcaccgaggc agttccatag   5880
gatggcaaga tcctggtatc ggtctgcgat tccgactcgt ccaacatcaa tacaacctat    5940
taatttcccc tcgtcaaaaa taaggttatc aagtgagaaa tcaccatgag tgacgactga    6000
atccggtgag aatggcaaaa gtttatgcat ttctttccag acttgttcaa caggccagcc    6060
attacgctcg tcatcaaaat cactcgcatc aaccaaaccg ttattcattc gtgattgcgc    6120
ctgagcgaga cgaaatacgc ggtcgctgtt aaaaggacaa ttacaaacag gaatcgaatg    6180
caaccggcgc aggaacactg ccagcgcatc aacaatattt tcacctgaat caggatattc    6240
ttctaatacc tggaatgctg ttttcccggg gatcgcagtg gtgagtaacc atgcatcatc    6300
aggagtacgg ataaaatgct tgatggtcgg aagaggcata aattccgtca gccagtttag    6360
tctgaccatc tcatctgtaa catcattggc aacgctacct ttgccatgtt tcagaaacaa    6420
ctctggcgca tcgggcttcc catacaatcg atagattgtc gcacctgatt gcccgacatt    6480
atcgcgagcc catttatacc catataaatc agcatccatg ttggaattta atcgcggcct    6540
agagcaagac gtttcccgtt gaatatggct catactcttc cttttttcaat attattgaag    6600 catttatcag ggttattgtc tcatgagcgg atacatattt gaatgtattt agaaaaataa    6660
acaaataggg atgctagcgc agaaacgtcc tagaagatgc caggaggata cttagcagag    6720
agacaataag gccggagcga agccgttttt ccataggctc cgccccctg acgaacatca     6780 cgaaatctga cgctcaaatc agtggtggcg aaacccgaca ggactataaa gataccaggc    6840
gtttccccct gatggctccc tcttgcgctc tcctgttccc gtcctgcggc gtccgtgttg    6900 tggtggagggc tttacccaaa tcaccacgtc ccgttccgtg tagacagttc gctccaagct    6960
gggctgtgtg caagaaccc ccgttcagcc cgactgctgc gccttatccg gtaactatca     7020
tcttgagtcc aacccggaaa gacacgacaa acgccactg gcagcagcca ttggtaactg     7080
agaattagtg gatttagata tcgagagtct tgaagtggtg gcctaacaga ggctacactg    7140
aaaggacagt atttggtatc tgcgctccac taaagccagt taccaggtta agcagttccc    7200
caactgactt aaccttcgat caaaccgcct ccccaggcgg ttttttcgtt tacagagcag    7260
gagattacga cgatcgtaaa aggatctcaa gaagatcctt tacggattcc cgacaccatc    7320
actctagatt tcagtgcaat ttatctcttc aaatgtagca cctgaagtca gccccatacg    7380
atataagttg taattctcat gttagtcatg ccccgcgccc accggaagga gctgactggg    7440
ttgaaggctc tcaagggcat cggtcgagat cccggtgcct aatgagtgag ctaacttaca    7500
ttaattgcgt tgcgctcact gcccgctttc cagtcgggaa acctgtcgtg ccagctgcat    7560
taatgaatcg gccaacgcgc ggggagaggc ggtttgcgta ttgggcgcca gggtggtttt    7620
tcttttcacc agtgagacgg gcaacagctg attgcccttc accgcctggc cctgagagag    7680
ttgcagcaag cggtccacgc tggtttgccc cagcaggcga aaatcctgtt tgatggtggt    7740
taacggcggg atataacatg agctgtcttc ggtatcgtcg tatcccacta ccgagatgtc    7800
cgcaccaacg cgcagcccgg actcggtaat ggcgcgcatt gcgcccagcg ccatctgatc    7860
gttggcaacc agcatcgcag tgggaacgat gccctcattc agcatttgca tggtttgttg    7920
aaaaccggac atggcactcc agtcgccttc ccgttccgct atcggctgaa tttgattgcg    7980
agtgagatat ttatgccagc cagccagacg cagacgcgcc gagacagaac ttaatgggcc    8040
cgctaacagc gcgatttgct ggtgacccaa tgcgaccaga tgctccacgc ccagtcgcgt    8100
```

```
accgtcttca tgggagaaaa taatactgtt gatgggtgtc tggtcagaga catcaagaaa    8160
taacgccgga acattagtgc aggcagcttc cacagcaatg gcatcctggt catccagcgg    8220
atagttaatg at                                                       8232
```

<210> SEQ ID NO 10
<211> LENGTH: 6792
<212> TYPE: DNA
<213> ORGANISM: Artificial Sequence
<220> FEATURE:
<223> OTHER INFORMATION: construct pINT-malE-PmgalT7

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg  cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct tgatcttttc     420 tacggggtc  tgacgctcag tggaacgaaa actcacgtta agggattttg gtcatgagat     480
tatcaaaaag gatcttcacc tagatccttt taaactagtg aagttaccat cacggaaaaa     540
ggttatgctg cttttaagac ccactttcac atttaagttg ttttttctaat ccgcatatga     600 tcaattcaag gccgaataag aaggctggct ctgcaccttg gtgatcaaat aattcgatag     660
cttgtcgtaa taatggcggc atactatcag tagtaggtgt ttccttttct tctttagcga     720
cttgatgctc ttgatcttcc aatacgcaac ctaaagtaaa atgccccact gcgctgagtg     780
catataatgc attctctagt gaaaaacctt gttggcataa aaaggctaat tgattttcga     840
gagtttcata ctgttttttct gtaggccgtg tacctaaatg tactttttgct ccatcgcgat     900 gacttagtaa agcacatcta aaacttttag cgttattacg taaaaaatct tgccagcttt     960
ccccttctaa agggcaaaag tgagtatggt gcctatctaa catctcaatg gctaaggcgt    1020
cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttcctttttt caatattatt    1200 gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttttg ttgacactct atcattgata gagttatttt accactccct    1380
atcagtgata gagaaaagtg aaatgaatag ttcgacaaaa atctagaaat aattttgttt    1440
aactttaaga aggagatata caaatgaaaa tcgaagaagg taaactggta atctggatta    1500
acggcgataa aggctataac ggtctcgctg aagtcggtaa gaaattcgag aaagataccg    1560
gaattaaagt caccgttgag catccggata aactggaaga gaaattccca caggttgcgg    1620
caactggcga tggccctgac attatcttct gggcacacga ccgctttggt ggctacgctc    1680
aatctggcct gttggctgaa atcaccccgg acaaagcgtt ccaggacaag ctgtatccgt    1740
ttacctggga tgccgtacgt tacaacggca agctgattgc ttacccgatc gctgttgaag    1800
cgttatcgct gatttataac aaagatctgc tgccgaaccc gccaaaaacc tgggaagaga    1860
```

```
tcccggcgct ggataaagaa ctgaaagcga aggtaagag cgcgctgatg ttcaacctgc  1920
aagaaccgta cttcacctgg ccgctgattg ctgctgacgg gggttatgcg ttcaagtatg  1980
aaaacggcaa gtacgacatt aaagacgtgg gcgtggataa cgctggcgcg aaagcgggtc  2040
tgaccttcct ggttgacctg attaaaaaca acacatgaa tgcagacacc gattactcca  2100
tcgcagaagc tgcctttaat aaaggcgaaa cagcgatgac catcaacggc ccgtgggcat  2160
ggtccaacat cgacaccagc aaagtgaatt atggtgtaac ggtactgccg accttcaagg  2220
gtcaaccatc caaaccgttc gttggcgtgc tgagcgcagg tattaacgcc gccagtccga  2280
acaaagagct ggcaaaagag ttcctcgaaa actatctgct gactgatgaa ggtctggaag  2340
cggttaataa agacaaaccg ctgggtgccg tagcgctgaa gtcttacgag aaagagttgg  2400
cgaaagatcc acgtattgcc gccaccatgg aaaacgccca gaaaggtgaa atcatgccga  2460
acatcccgca gatgtccgct ttctggtatg ccgtgcgtac tgcggtgatc aacgccgcca  2520
gcggtcgtca gactgtcgat gaagccctga agacgcgca gactatgagc ggtgaacact  2580
atgtcattag cctgtcgtcg gcagttgaac gtcgccagca cattcgtaac cagttttcgc  2640
agaagaacat cccgtttcag ttttttcgatg caatttcacc gtcgccgctg ctggaccagc  2700
tggtgctgca atttttcccg cgtctggcgg atagctctct gaccggcggt gaaaaagcct  2760
gctttatgag ccatctgtct ctgtggcaca aatgtgtgga agaaaacctg ccgtatattg  2820
tggttttga agatgacatc gttctgggca agatgcgca caagttcctg attggtgatg  2880
aatggctgtt ttctcgtttc gacccggaag aaatctttat tatccgcctg gaaaccttcc  2940
tgcagaaagt cgtgtgcgaa agcacccata ttgccccgta tacgcaccgc gattttctga  3000
gtctgaaatc cgcacatttc ggcacggctg gttacgtcat cagtcagggc gcggccaaat  3060
ttctgctgga tattttcaag aacatctcca atgaacacat tgcgccgatc gacgaactga  3120
tttttaacca gttcctggtt aagaactcat tcaacgtcta ccaactgtcg ccggcaatct  3180
gtgttcagga actgcaactg aacaatgaaa gttccgctct gcagagccaa ctggaactgg  3240
aacgtaacaa attccgcaat aaaaagtctg aagaactgaa gcgtaaccgc aagaacttca  3300
tcgaaaagtt catctacatc ctgaaaaagc cgaagcgtat gctggataac aataagcgta  3360
agcgcgaaga gagtaagatc gaaaacgaca agatgatcat cgaatttaaa tgagcggccg  3420
cgtcgacacg caaaaaggcc atccgtcagg atggccttct gcttaattat ctagatgcct  3480
ggcagtttat ggcgggcgtc ctgcccgcca ccctccgggc cgttgcttcg caacgttcaa  3540
atccgctccc ggcggatttg tcctactcag gagagcgttc accgacaaac aacagataaa  3600
acgaaaggcc cagtctttcg actgagcctt tcgttttatt tgatgcctgg cagttcccta  3660
ctctcgcatg gggagacccc acactaccat catgtatgaa tatcctcctt agttcctatt  3720
ccgaagggta atggcatcag ggaatggcga acgcgctccc cacactacca tcatgtatga  3780
atatcctcct tagttcctat tccgaagttc ctattctcta gaaagtatag gaacttcggt  3840
ggaacgacgc gtaactcacg ttaagggatt ttggtcatga tcagcacgtg ttgacaatta  3900
atcatcggca tagtatatcg gcatagtata atacgacaag gtgaggaact aaaccatggc  3960
caagttgacc agtgccgttc cggtgctcac cgcgcgcgac gtcgccggag cggtcgagtt  4020
ctggaccgac cggctcgggt tctcccggga cttcgtggag gacgacttcg ccggtgtggt  4080
ccgggacgac gtgaccctgt tcatcagcgc ggtccaggac caggtggtgc ggacaacac  4140
cctggcctgg gtgtgggtgc gcggcctgga cgagctgtac gccgagtggt cggaggtcgt  4200
gtccacgaac ttccgggacg cctccgggcc ggccatgacc gagatcggcg agcagccgtg  4260
```

```
ggggcgggag ttcgccctgc gcgacccggc cggcaactgc gtgcacttcg tggccgagga      4320
gcaggactga gtggcagggc ggggcgtaag gcgcgccatt taaatgaagt tcctattccg      4380
aagttcctat tctctagaaa gtataggaac ttcgaagcag ctccagccta cacaatcgct      4440
caagacggaa cccgcgcttg gcaggaaagt aataggata gcagctccag cctacacaat       4500
cgctcaagac gtgtaatgct gcacaataac cctgctgcag aggcctgcat gcaagcttgg      4560
cgtaatcatg gtcatagctg tttcctgtgt gaaattgtta ccgctcaca attccacaca      4620 acatacgagc cggaagcata aagtgtaaag cctggggtgc ctaatgagtg agctaactca     4680
cattaattgc gttgcgctca ctgcccgctt tccagtcggg aaacctgtcg tgccagctgc      4740
attaatgaat cggccaacgc gcggggagag gcggtttgcg tattgggcgc tcttccgctt      4800
cctcgctcac tgactcgctg cgctcggtcg ttcggctgcg gcgagcggta tcagctcact     4860
caaaggcggt aatacggtta tccacagaat caggggataa cgcaggaaag aacatgtgag     4920
caaaaggcca gcaaaaggcc aggaaccgta aaaaggccgc gttgctggcg tttttccata     4980
ggctccgccc ccctgacgag catcacaaaa atcgacgctc aagtcagagg tggcgaaacc     5040
cgacaggact ataaagatac caggcgtttc ccctggaag ctcccctgtg cgctctcctg      5100
ttccgaccct gccgcttacc ggatacctgt ccgcctttct cccttcggga agcgtggcgc     5160
tttctcatag ctcacgctgt aggtatctca gttcggtgta ggtcgttcgc tccaagctgg     5220
gctgtgtgca cgaaccccc gttcagcccg accgctgcgc cttatccggt aactatcgtc      5280
ttgagtccaa cccggtaaga cacgacttat cgccactggc agcagccact ggtaacagga     5340
ttagcagagc gaggtatgta ggcggtgcta cagagttctt gaagtggtgg cctaactacg     5400
gctacactag aagaacagta tttggtatct gcgctctgct gaagccagtt accttcggaa     5460
aaagagttgg tagctcttga tccggcaaac aaaccaccgc tggtagcggt ggtttttttg     5520
tttgcaagca gcagattacg cgcagaaaaa aaggatctca agaagatcct ttgatctttt     5580
ctacggggtc tgacgctcag tggaacgaaa actcacgtta agggattttg gtcatgagat     5640
tatcaaaaag gatcttcacc tagatccttt taaattaaaa atgaagtttt aaatcaatct     5700
aaagtatata tgagtaaact tggtctgaca gttaccaatg cttaatcagt gaggcaccta     5760
tctcagcgat ctgtctattt cgttcatcca tagttgcctg actccccgtc gtgtagataa     5820
ctacgatacg ggagggctta ccatctggcc ccagtgctgc aatgataccg cgagacccac     5880
gctcaccggc tccagattta tcagcaataa accagccagc cggaagggcc gagcgcagaa     5940
gtggtcctgc aactttatcc gcctccatcc agtctattaa ttgttgccgg gaagctagag     6000
taagtagttc gccagttaat agtttgcgca acgttgttgc cattgctaca ggcatcgtgg     6060
tgtcacgctc gtcgtttggt atggcttcat tcagctccgg ttcccaacga tcaaggcgag     6120
ttacatgatc ccccatgttg tgcaaaaaag cggttagctc cttcggtcct ccgatcgttg     6180
tcagaagtaa gttggccgca gtgttatcac tcatggttat ggcagcactg cataattctc     6240
ttactgtcat gccatccgta agatgctttt ctgtgactgg tgagtactca accaagtcat     6300
tctgagaata gtgtatgcgg cgaccgagtt gctcttgccc ggcgtcaata cgggataata     6360
ccgcgccaca tagcagaact ttaaaagtgc tcatcattgg aaaacgttct cggggcgaa      6420 aactctcaag gatcttaccg ctgttgagat ccagttcgat gtaacccact cgtgcaccca     6480
actgatcttc agcatctttt actttcacca gcgtttctgg gtgagcaaaa acaggaaggc     6540
aaaatgccgc aaaaaaggga ataagggcga cacggaaatg ttgaatactc atactcttcc     6600
```

-continued

```
tttttcaata ttattgaagc atttatcagg gttattgtct catgagcgga tacatatttg    6660
aatgtattta gaaaaataaa caaatagggg ttccgcgcac atttccccga aaagtgccac    6720
ctgacgtcta agaaaccatt attatcatga cattaaccta taaaaatagg cgtatcacga    6780
ggccctttcg tc                                                        6792

<210> SEQ ID NO 11
<211> LENGTH: 6702
<212> TYPE: DNA
<213> ORGANISM: Artificial Sequence
<220> FEATURE:
<223> OTHER INFORMATION: construct pINT-malE-MsgalT8

<400> SEQUENCE: 11
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct ttgatctttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg cttttaagac ccactttcac atttaagttg ttttctaat ccgcatatga      600 tcaattcaag gccgaataag aaggctggct ctgcaccttg gtgatcaaat aattcgatag     660
cttgtcgtaa taatggcggc atactatcag tagtaggtgt ttccctttct tctttagcga     720
cttgatgctc ttgatcttcc aatacgcaac ctaaagtaaa atgccccact gcgctgagtg     780
catataatgc attctctagt gaaaaacctt gttggcataa aaaggctaat tgattttcga     840
gagtttcata ctgttttttct gtaggccgtg tacctaaatg tactttgct ccatcgcgat     900 gacttagtaa agcacatcta aaacttttag cgttattacg taaaaaatct tgccagcttt     960 cccccttctaa agggcaaaag tgagtatggt gcctatctaa catctcaatg gctaaggcgt    1020
cgagcaaagc ccgcttattt tttacatgcc aatacaatgt aggctgctct acacctagct    1080
tctgggcgag tttacggggt gttaaacctt cgattccgac ctcattaagc agctctaatg    1140
cgctgttaat cacttacttt ttatctaaac gagacatact cttcctttt caatattatt     1200 gaagcatta tcagggttat tgtctcatga gcggatacat atttgaatgt atttagaaaa    1260
ataaacaaat aggggttccg cgcacatttc ccgaaaagt gccacctgaa attggcaga     1320 tgattaattc ctaattttg ttgacactct atcattgata gagttatttt accactccct     1380
atcagtgata gagaaaagtg aaatgaatag ttcgacaaaa atctagaaat aattttgttt    1440
aactttaaga aggagatata caaatgaaaa tcgaagaagg taaactggta atctggatta    1500
acggcgataa aggctataac ggtctcgctg aagtcggtaa gaaattcgag aaagataccg    1560
gaattaaagt caccgttgag catccggata aactggaaga gaaattccca caggttgcgg    1620
caactggcga tggccctgac attatcttct gggcacacga ccgctttggt ggctacgctc    1680
aatctggcct gttggctgaa atcaccccgg acaaagcgtt ccaggacaag ctgtatccgt    1740
taccctggga tgccgtacgt tacaacggca agctgattgc ttacccgatc gctgttgaag    1800
cgttatcgct gatttataac aaagatctgc tgccgaaccc gccaaaaacc tgggaagaga    1860
```

```
tcccggcgct ggataaagaa ctgaaagcga aaggtaagag cgcgctgatg ttcaacctgc   1920
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca aacacatgaa tgcagacacc gattactcca   2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag aagagttgg   2400 cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga agacgcgca gactatggat gaaatcaaac   2580
tgtcggtggt tatgccgtat tacaaacgtc tgcgtgaatt tatgcgtgtc ctgccgctga   2640
atgcccgctt ctttagccgt catgaatatg aagtggttct gagtcggac gaaccgtccg   2700 aagaagccga tctgctgcgt gtcctgcgcg acttcccgtc tattcgttgg cgcgttctgg   2760
tcaatgacct ggatcacccg tggcgtccgc cgtgccgtgc actgaacgtt ggcatccgta   2820
atgctctggg tgaaaacgtc ctggtcgtga gcccggaatc tgcgtttgtg accgatgttc   2880
cggcacgcgc tctggatcat attgcagcaa acccgggtac cgcagctctg ggtcacgttt   2940
gttttgcaac gttcgatgcg ctggaagccc gtcagggcag cctggaaaaa acgtgcgctc   3000
cgccgtggaa tctgtatggt tctatctgtg tcccgcgtga acgtctggca cgtgtgcatg   3060
gctacgacga aagcttcgat cgctggggcg gtgatgacga taacctgcgt attcgcctga   3120
tgcagaccga aacgtatctg catccgctgg acgatatgcg catcctgcac ctgagttttg   3180
aagcccgtaa agtgcgtcaa gcagcagaac cgccgtcccc ggaatacgca gaacgtattt   3240
tccagccggt gtcaccgcaa gcaaatccgg gcggttgggg tgaatcgttt cagcgcgttg   3300
cgttcgattg gcgtcgccaa tgagcggccg cgtcgacacg caaaaaggcc atccgtcagg   3360
atggccttct gcttaattat ctagatgcct ggcagtttat ggcgggcgtc ctgcccgcca   3420
ccctccgggc cgttgcttcg caacgttcaa atccgctccc ggcggatttg tcctactcag   3480
gagagcgttc accgacaaac aacagataaa acgaaaggcc cagtctttcg actgagcctt   3540
tcgttttatt tgatgcctgg cagttcccta ctctcgcatg gggagacccc acactaccat   3600
catgtatgaa tatcctcctt agttcctatt ccgaagggta atggcatcag ggaatggcga   3660
acgcgctccc cacactacca tcatgtatga atatcctcct tagttcctat tccgaagttc   3720
ctattctcta gaaagtatag gaacttcggt ggaacgacgc gtaactcacg ttaagggatt   3780
ttggtcatga tcagcacgtg ttgacaatta atcatcggca tagtatatcg gcatagtata   3840
atacgacaag gtgaggaact aaaccatggc caagttgacc agtgccgttc cggtgctcac   3900
cgcgcgcgac gtcgccggag cggtcgagtt ctggaccgac cggctcgggt ctcccgggga   3960
cttcgtggag gacgacttcg ccggtgtggt ccggacgacg gtgaccctgt tcatcagcgc   4020
ggtccaggac caggtggtgc cggacaacac cctggcctgg gtgtgggtgc gcggcctgga   4080
cgagctgtac gccgagtggt cggaggtcgt gtccacgaac ttccgggacg cctccggcc   4140 ggccatgacc gagatcggcg agcagccgtg ggggcgggag ttcgccctgc gcgacccggc   4200
```

-continued

```
cggcaactgc gtgcacttcg tggccgagga gcaggactga gtggcagggc ggggcgtaag    4260
gcgcgccatt taaatgaagt tcctattccg aagttcctat tctctagaaa gtataggaac    4320
ttcgaagcag ctccagccta cacaatcgct caagacggaa cccgcgcttg gcaggaaagt    4380
aatagggata gcagctccag cctacacaat cgctcaagac gtgtaatgct gcacaataac    4440
cctgctgcag aggcctgcat gcaagcttgg cgtaatcatg gtcatagctg tttcctgtgt    4500
gaaattgtta tccgctcaca attccacaca catacgagcc ggaagcata aagtgtaaag     4560
cctggggtgc ctaatgagtg agctaactca cattaattgc gttgcgctca ctgcccgctt    4620
tccagtcggg aaacctgtcg tgccagctgc attaatgaat cggccaacgc gcggggagag    4680
gcggtttgcg tattgggcgc tcttccgctt cctcgctcac tgactcgctg cgctcggtcg    4740
ttcggctgcg gcgagcggta tcagctcact caaaggcggt aatacggtta tccacagaat    4800
caggggataa cgcaggaaag aacatgtgag caaaaggcca gcaaaaggcc aggaaccgta    4860
aaaaggccgc gttgctggcg tttttccata ggctccgccc ccctgacgag catcacaaaa    4920
atcgacgctc aagtcagagg tggcgaaacc cgacaggact ataaagatac caggcgtttc    4980
ccctggaag ctccctcgtg cgctctcctg ttccgaccct gccgcttacc ggatacctgt      5040
ccgcctttct cccttcggga agcgtggcgc tttctcatag ctcacgctgt aggtatctca    5100
gttcggtgta ggtcgttcgc tccaagctgg gctgtgtgca cgaaccccc gttcagcccg     5160
accgctgcgc cttatccggt aactatcgtc ttgagtccaa cccggtaaga cacgacttat    5220
cgccactggc agcagccact ggtaacagga ttagcagagc gaggtatgta ggcggtgcta    5280
cagagttctt gaagtggtgg cctaactacg gctacactag aagaacagta tttggtatct    5340
gcgctctgct gaagccagtt accttcggaa aaagagttgg tagctcttga tccggcaaac    5400
aaaccaccgc tggtagcggt ggtttttttg tttgcaagca gcagattacg cgcagaaaaa    5460
aaggatctca agaagatcct ttgatctttt ctacgggtc tgacgctcag tggaacgaaa     5520
actcacgtta agggattttg gtcatgagat tatcaaaaag gatcttcacc tagatccttt    5580
taaattaaaa atgaagtttt aaatcaatct aaagtatata tgagtaaact tggtctgaca    5640
gttaccaatg cttaatcagt gaggcaccta tctcagcgat ctgtctattt cgttcatcca    5700
tagttgcctg actccccgtc gtgtagataa ctacgatacg ggagggctta ccatctggcc    5760
ccagtgctgc aatgataccg cgagacccac gctcaccggc tccagattta tcagcaataa    5820
accagccagc cggaagggcc gagcgcagaa gtggtcctgc aactttatcc gcctccatcc    5880
agtctattaa ttgttgccgg gaagctagag taagtagttc gccagttaat agtttgcgca    5940
acgttgttgc cattgctaca ggcatcgtgg tgtcacgctc gtcgtttggt atggcttcat    6000
tcagctccgg ttcccaacga tcaaggcgag ttacatgatc ccccatgttg tgcaaaaaag    6060
cggttagctc cttcggtcct ccgatcgttg tcagaagtaa gttggccgca gtgttatcac    6120
tcatggttat ggcagcactg cataattctc ttactgtcat gccatccgta agatgctttt    6180
ctgtgactgg tgagtactca accaagtcat tctgagaata gtgtatgcgg cgaccgagtt    6240
gctcttgccc ggcgtcaata cgggataata ccgcgccaca tagcagaact ttaaaagtgc    6300
tcatcattgg aaaacgttct tcggggcgaa aactctcaag gatcttaccg ctgttgagat    6360
ccagttcgat gtaaccact cgtgcaccca actgatcttc agcatctttt actttcacca     6420
gcgtttctgg gtgagcaaaa acaggaaggc aaaatgccgc aaaaaaggga ataagggcga    6480
cacgaaaatg ttgaatactc atactcttcc ttttcaata ttattgaagc atttatcagg     6540
gttattgtct catgagcgga tacatatttg aatgtattta gaaaaataaa caaatagggg    6600
```

```
ttccgcgcac atttccccga aaagtgccac ctgacgtcta agaaaccatt attatcatga   6660
cattaaccta taaaaatagg cgtatcacga ggccctttcg tc                     6702
```

<210> SEQ ID NO 12
<211> LENGTH: 6777
<212> TYPE: DNA
<213> ORGANISM: Artificial Sequence
<220> FEATURE:
<223> OTHER INFORMATION: construct pINT-malE-KdgalT10

<400> SEQUENCE: 12

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt taaactagtg aagttaccat cacgaaaaa    540 ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgttttct gtaggccgtg tacctaaatg tacttttgct ccatcgcgat    900
gacttagtaa agcacatcta aactttttag cgttattacg taaaaaatct gccagctttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaaacctt cgattccgac ctcattaagc agctctaatg   1140
cgctgttaat cactttactt ttatctaaac gagacatact cttcctttt caatattatt    1200 gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactccct    1380
atcagtgata gagaaaagtg aaatgaatag ttcgacaaaa atctagaaat aattttgttt   1440
aactttaaga aggagatata caaatgaaaa tcgaagaagg taaactggta atctggatta   1500
acggcgataa aggctataac ggtctcgctg aagtcggtaa gaaattcgag aaagataccg   1560
gaattaaagt caccgttgag catccggata aactggaaga gaaattccca caggttgcgg   1620
caactggcga tgggcctgac attatcttct gggcacacga ccgctttggt ggctacgctc   1680
aatctggcct gttggctgaa atcaccccgg acaaagcgtt ccaggacaag ctgtatccgt   1740
ttacctggga tgccgtacgt tacaacggca agctgattgc ttaccccgatc gctgttgaag   1800 cgttatcgct gatttataac aaagatctgc tgccgaaccc gccaaaaacc tgggaagaga   1860
tcccggcgct ggataaagaa ctgaaagcga aaggtaagag cgcgctgatg ttcaacctgc   1920
```

```
aagaaccgta cttcacctgg ccgctgattg ctgctgacgg gggttatgcg ttcaagtatg   1980
aaaacggcaa gtacgacatt aaagacgtgg gcgtggataa cgctggcgcg aaagcgggtc   2040
tgaccttcct ggttgacctg attaaaaaca acacatgaa tgcagacacc gattactcca    2100
tcgcagaagc tgcctttaat aaaggcgaaa cagcgatgac catcaacggc ccgtgggcat   2160
ggtccaacat cgacaccagc aaagtgaatt atggtgtaac ggtactgccg accttcaagg   2220
gtcaaccatc caaaccgttc gttggcgtgc tgagcgcagg tattaacgcc gccagtccga   2280
acaaagagct ggcaaaagag ttcctcgaaa actatctgct gactgatgaa ggtctggaag   2340
cggttaataa agacaaaccg ctgggtgccg tagcgctgaa gtcttacgag aagagttgg    2400 cgaaagatcc acgtattgcc gccaccatgg aaaacgccca gaaaggtgaa atcatgccga   2460
acatcccgca gatgtccgct ttctggtatg ccgtgcgtac tgcggtgatc aacgccgcca   2520
gcggtcgtca gactgtcgat gaagccctga agacgcgca gactatggaa aactatgtcg    2580
tctctatccg caccgcagcc caacgccgcc agcatgtcgc cgccgaattc aataagcacc   2640
aaatcgcctt tcatttcttt gatgcggtga ccccggaaac gctggcggaa agcatcgcag   2700
aacactgccc gaacctggca gacgcctttc tgaccggcgg tgaaaagggc tgtttcatgt   2760
ctcatgtctg cctgtgggca aatgtgtgg ctgatgacct gccgtatatt ggcatctttg    2820
aagatgacgt tattttcggt cagaacagct ctcgttttct gaatgatacc aaatggctgg   2880
acgaacgttt tcagaaccaa tcattcatta tccgcatgga aacgtttctg aaggcgaacc   2940
cggttgccct gagcaaatct ggcgtccgtc cgttcaatgg tcgtaagatc ctgcgcctgc   3000
agagttttgg cttcggtacc gcggcctatc tgatttccca gcaaaccgca atcacgctgc   3060
tgaattggat tcgcgaagtc gctccggaaa aactggaacc gattgataac atgctgttta   3120
atgcagcttc agaaattccg gaaatccaga tgtaccaaat ctcgccggcc ctgtgcattc   3180
aggaactgca actgaaccgc gcagatagtt ccctgtcatc gaccctggaa gacggtcgtc   3240
tggcacgtca ccagcaactg gatggcggta aacccagcc ggaacagacg caagaaaacc    3300
gtaacatctt cgcatgggct aagaacaaga tcgtgaagga atacaagcgc gttaaacgtc   3360
gctggacgga tgacaaaaag attgttccgt tcaaatgagc ggccgcgtcg acacgcaaaa   3420
aggccatccg tcaggatggc cttctgctta attatctaga tgcctggcag tttatggcgg   3480
gcgtcctgcc cgccaccctc cgggccgttg cttcgcaacg ttcaaatccg ctcccggcgg   3540
atttgtccta ctcaggagag cgttcaccga caaacaacag ataaaacgaa aggcccagtc   3600
tttcgactga gcctttcgtt ttatttgatg cctggcagtt ccctactctc gcatggggag   3660
accccacact accatcatgt atgaatatcc tccttagttc ctattccgaa gggtaatggc   3720
atcagggaat ggcgaacgcg ctccccacac taccatcatg tatgaatatc ctccttagtt   3780
cctattccga agttcctatt ctctagaaag tataggaact tcggtggaac gacgcgtaac   3840
tcacgttaag ggattttggt catgatcagc acgtgttgac aattaatcat cggcatagta   3900
tatcggcata gtataatacg acaaggtgag gaactaaacc atggccaagt tgaccagtgc   3960
cgttccggtg ctcaccgcgc gcgacgtcgc cggagcggtc gagttctgga ccgaccggct   4020
cgggttctcc cggacttcg tggaggacga cttcgccggt gtggtccggg acgacgtgac    4080
cctgttcatc agcgcggtcc aggaccaggt ggtgccggac aacaccctgg cctgggtgtg   4140
ggtgcgcggc ctggacgagc tgtacgccga gtggtcggag gtcgtgtcca cgaacttccg   4200
ggacgcctcc gggccggcca tgaccgagat cggcgagcag ccgtggggc gggagttcgc    4260 cctgcgcgac ccggccggca actgcgtgca cttcgtggcc gaggagcagg actgagtggc   4320
```

-continued

```
agggcggggc gtaaggcgcg ccatttaaat gaagttccta ttccgaagtt cctattctct    4380
agaaagtata ggaacttcga agcagctcca gcctacacaa tcgctcaaga cggaacccgc    4440
gcttggcagg aaagtaatag ggatagcagc tccagcctac acaatcgctc aagacgtgta    4500
atgctgcaca ataaccctgc tgcagaggcc tgcatgcaag cttggcgtaa tcatggtcat    4560
agctgtttcc tgtgtgaaat tgttatccgc tcacaattcc acacaacata cgagccggaa    4620
gcataaagtg taaagcctgg ggtgcctaat gagtgagcta actcacatta attgcgttgc    4680
gctcactgcc cgctttccag tcgggaaacc tgtcgtgcca gctgcattaa tgaatcggcc    4740
aacgcgcggg gagaggcggt ttgcgtattg ggcgctcttc cgcttcctcg ctcactgact    4800
cgctgcgctc ggtcgttcgg ctgcggcgag cggtatcagc tcactcaaag gcggtaatac    4860
ggttatccac agaatcaggg gataacgcag gaaagaacat gtgagcaaaa ggccagcaaa    4920
aggccaggaa ccgtaaaaag gccgcgttgc tggcgttttt ccataggctc cgcccccctg    4980
acgagcatca caaaaatcga cgctcaagtc agaggtggcg aaacccgaca ggactataaa    5040
gataccaggc gtttccccct ggaagctccc tcgtgcgctc tcctgttccg accctgccgc    5100
ttaccggata cctgtccgcc tttctccctt cgggaagcgt ggcgctttct catagctcac    5160
gctgtaggta tctcagttcg gtgtaggtcg ttcgctccaa gctgggctgt gtgcacgaac    5220
cccccgttca gcccgaccgc tgcgccttat ccggtaacta tcgtcttgag tccaacccgg    5280
taagacacga cttatcgcca ctggcagcag ccactggtaa caggattagc agagcgaggt    5340
atgtaggcgg tgctacagag ttcttgaagt ggtggcctaa ctacggctac actagaagaa    5400
cagtatttgg tatctgcgct ctgctgaagc cagttacctt cggaaaaaga gttggtagct    5460
cttgatccgg caaacaaacc accgctggta gcggtggttt ttttgtttgc aagcagcaga    5520
ttacgcgcag aaaaaaagga tctcaagaag atcctttgat cttttctacg gggtctgacg    5580
ctcagtggaa cgaaaactca cgttaaggga ttttggtcat gagattatca aaaaggatct    5640
tcacctagat ccttttaaat taaaaatgaa gttttaaatc aatctaaagt atatatgagt    5700
aaacttggtc tgacagttac caatgcttaa tcagtgaggc acctatctca gcgatctgtc    5760
tatttcgttc atccatagtt gcctgactcc ccgtcgtgta gataactacg atacgggagg    5820
gcttaccatc tggccccagt gctgcaatga taccgcgaga cccacgctca ccggctccag    5880
atttatcagc aataaaccag ccagccggaa gggccgagcg cagaagtggt cctgcaactt    5940
tatccgcctc catccagtct attaattgtt gccgggaagc tagagtaagt agttcgccag    6000
ttaatagttt cgcaacgtt gttgccattg ctacaggcat cgtggtgtca cgctcgtcgt    6060
ttggtatggc ttcattcagc tccggttccc aacgatcaag gcgagttaca tgatccccca    6120
tgttgtgcaa aaaagcggtt agctccttcg gtcctccgat cgttgtcaga gtaagttgg    6180 ccgcagtgtt atcactcatg gttatggcag cactgcataa ttctcttact gtcatgccat    6240
ccgtaagatg cttttctgtg actggtgagt actcaaccaa gtcattctga aatagtgta    6300 tgcggcgacc gagttgctct tgcccggcgt caatacggga taataccgcg ccacatagca    6360
gaactttaaa agtgctcatc attggaaaac gttcttcggg gcgaaaactc tcaaggatct    6420
taccgctgtt gagatccagt tcgatgtaac ccactcgtgc acccaactga tcttcagcat    6480
cttttacttt caccagcgtt tctgggtgag caaaaacagg aaggcaaaat gccgcaaaaa    6540
agggaataag ggcgacacgg aaatgttgaa tactcatact cttcctttt caatattatt    6600 gaagcattta tcagggttat tgtctcatga gcggatacat atttgaatgt atttagaaaa    6660
```

| | | | | |
|---|---|---|---|---|
| ataaacaaat | agggggttccg | cgcacatttc | cccgaaaagt | gccacctgac gtctaagaaa | 6720 |
| ccattattat | catgacatta | acctataaaa | ataggcgtat | cacgaggccc tttcgtc | 6777 |

<210> SEQ ID NO 13
<211> LENGTH: 6786
<212> TYPE: DNA
<213> ORGANISM: Artificial Sequence
<220> FEATURE:
<223> OTHER INFORMATION: construct pINT-malE-gatD

<400> SEQUENCE: 13

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcagggcgcg tcagcgggtg | 120 |
| ttggcgggtg | tcggggctgg | cttaactatg | cggcatcaga | gcagattgta ctgagagtgc | 180 |
| accatatgcg | gtgtgaaata | ccgcacagat | gcgtaaggag | aaaataccgc atcaggcgcc | 240 |
| attcgccatt | caggctgcgc | aactgttggg | aagggcgatc | ggtgcgggcc tcttcgctat | 300 |
| tacgccagct | ggcgaaaggg | ggatgtgctg | caaggcgatt | aagttgggta acgccagggt | 360 |
| tttcccagtc | acgacgttgt | aaaacgacgg | ccagtgaatt | cgaagatcct ttgatctttt | 420 |
| ctacgggtc | tgacgctcag | tggaacgaaa | actcacgtta | agggattttg gtcatgagat | 480 |
| tatcaaaaag | gatcttcacc | tagatccttt | taaactagtg | aagttaccat cacggaaaaa | 540 |
| ggttatgctg | cttttaagac | ccactttcac | atttaagttg | ttttctaat ccgcatga | 600 |
| tcaattcaag | gccgaataag | aaggctggct | ctgcaccttg | gtgatcaaat aattcgatag | 660 |
| cttgtcgtaa | taatggcggc | atactatcag | tagtaggtgt | ttccctttct tctttagcga | 720 |
| cttgatgctc | ttgatcttcc | aatacgcaac | ctaaagtaaa | atgccccact gcgctgagtg | 780 |
| catataatgc | attctctagt | gaaaaacctt | gttggcataa | aaaggctaat tgattttcga | 840 |
| gagtttcata | ctgtttttct | gtaggccgtg | tacctaaatg | tactttgct ccatcgcgat | 900 |
| gacttagtaa | agcacatcta | aaactttag | cgttattacg | taaaaaatct tgccagcttt | 960 |
| ccccttctaa | agggcaaaag | tgagtatggt | gcctatctaa | catctcaatg gctaaggcgt | 1020 |
| cgagcaaagc | ccgcttattt | tttacatgcc | aatacaatgt | aggctgctct acacctagct | 1080 |
| tctgggcgag | tttacgggtt | gttaaacctt | cgattccgac | ctcattaagc agctctaatg | 1140 |
| cgctgttaat | cactttactt | ttatctaaac | gagacatact | cttcctttt caatattatt | 1200 |
| gaagcattta | tcagggttat | tgtctcatga | gcggatacat | atttgaatgt atttagaaaa | 1260 |
| ataaacaaat | aggggttccg | cgcacatttc | cccgaaaagt | gccacctgaa attggccaga | 1320 |
| tgattaattc | ctaatttttg | ttgacactct | atcattgata | gagttatttt accactccct | 1380 |
| atcagtgata | gagaaaagtg | aaatgaatag | ttcgacaaaa | atctagaaat aattttgttt | 1440 |
| aactttaaga | aggagatata | caaatgaaaa | tcgaagaagg | taaactggta atctggatta | 1500 |
| acggcgataa | aggctataac | ggtctcgctg | aagtcggtaa | gaaattcgag aaagataccg | 1560 |
| gaattaaagt | caccgttgag | catccggata | aactggaaga | gaaattccca caggttgcgg | 1620 |
| caactggcga | tggccctgac | attatcttct | gggcacacga | ccgctttggt ggctacgctc | 1680 |
| aatctggcct | gttggctgaa | atcaccccgg | acaaagcgtt | ccaggacaag ctgtatccgt | 1740 |
| ttacctggga | tgccgtacgt | tacaacggca | agctgattgc | ttacccgatc gctgttgaag | 1800 |
| cgttatcgct | gatttataac | aaagatctgc | tgccgaaccc | gccaaaaacc tgggaagaga | 1860 |
| tcccggcgct | ggataaagaa | ctgaaagcga | aaggtaagag | cgcgctgatg ttcaacctgc | 1920 |
| aagaaccgta | cttcacctgg | ccgctgattg | ctgctgacgg | gggttatgcg ttcaagtatg | 1980 |

```
aaaacggcaa gtacgacatt aaagacgtgg gcgtggataa cgctggcgcg aaagcgggtc    2040
tgaccttcct ggttgacctg attaaaaaca aacacatgaa tgcagacacc gattactcca    2100
tcgcagaagc tgcctttaat aaaggcgaaa cagcgatgac catcaacggc ccgtgggcat    2160
ggtccaacat cgacaccagc aaagtgaatt atggtgtaac ggtactgccg accttcaagg    2220
gtcaaccatc caaaccgttc gttggcgtgc tgagcgcagg tattaacgcc gccagtccga    2280
acaaagagct ggcaaaagag ttcctcgaaa actatctgct gactgatgaa ggtctggaag    2340
cggttaataa agacaaaccg ctgggtgccg tagcgctgaa gtcttacgag gaagagttgg    2400
cgaaagatcc acgtattgcc gccaccatgg aaaacgccca gaaaggtgaa atcatgccga    2460
acatcccgca gatgtccgct ttctggtatg ccgtgcgtac tgcggtgatc aacgccgcca    2520
gcggtcgtca gactgtcgat gaagcccctga aagacgcgca gactatgtcc tcagcttttcc   2580 attacgtcat tagcctggca tcggcagttg aacgccgtca gcacattagc gaacagttt    2640 cccaatacga cattccgttt cagttttcg atgcgatcag tccgtccccg ctgctgaacc    2700
agctggtgtc tcaatttttc ccgtccctgg ccgatagctc tctgaccgac ggcgaaaaag    2760
gttgctttat ttcacatctg tcgctgtggc acaagtgtgt tgaaaagaac ctgccgtata    2820
ttgtggtttt tgaagatgac atcctgctgg gcaagaatgc agataaattc ctgattgaag    2880
acgaatggtt tttctctcgt tttaacacga atgatgtctt catcgtgcgc ctggaaacct    2940
ttctgcagaa agtgtattgc caaccgagct acatcaagtc ttactacaac cgtgaactgc    3000
tgaccctgaa aagcacgcat ttcggcaccg caggttatat tatcagtctg ggtgcggcca    3060
agtttctgct gtccctgttc aacaaaatgc acattgaaga agttgctccg atcgatgaac    3120
tgctgtttaa taagttcctg gaacgcaaag actttacggt ctaccagttc agtccggcac    3180
tgtgcattca ggaactgcaa ctgaacaaat cagatgctgt cctgctgtcg caactggaac    3240
tggaacgtag caaatgtcgc attatgaccg aatctcgtat cggccgcgaa aagaaaaaac    3300
tgaaggataa gatcatccat gttctgacga agccgaaacg tatgctggaa aagaaacgtc    3360
agcgcaatga agacaagaaa atcaccatga ttatcgaatt tgaatgagcg gccgcgtcga    3420
cacgcaaaaa ggccatccgt caggatggcc ttctgcttaa ttatctagat gcctggcagt    3480
ttatggcggg cgtcctgccc gccaccctcc gggccgttgc ttcgcaacgt tcaaatccgc    3540
tcccggcgga tttgtcctac tcaggagagc gttcaccgac aaacaacaga taaaacgaaa    3600
ggcccagtct ttcgactgag cctttcgttt tatttgatgc ctggcagttc cctactctcg    3660 catgggggaga ccccacacta ccatcatgta tgaatatcct ccttagttcc tattccgaag   3720
ggtaatggca tcagggaatg gcgaacgcgc tccccacact accatcatgt atgaatatcc    3780
tccttagttc ctattccgaa gttcctattc tctagaaagt ataggaactt cggtggaacg    3840
acgcgtaact cacgttaagg gattttggtc atgatcagca cgtgttgaca attaatcatc    3900
ggcatagtat atcggcatag tataatacga caaggtgagg aactaaacca tggccaagtt    3960
gaccagtgcc gttccggtgc tcaccgcgcg cgacgtcgcc ggagcggtcg agttctggac    4020
cgaccggctc gggttctccc gggacttcgt ggaggacgac ttcgccggtg tggtccggga    4080
cgacgtgacc ctgttcatca gcgcggtcca ggaccaggtg gtgccggaca acaccctggc    4140
ctgggtgtgg gtgcgcggcc tggacgagct gtacgccgag tggtcggagg tcgtgtccac    4200
gaacttccgg gacgcctccg gccggccat gaccgagatc ggcgagcagc gtgggggcg    4260 ggagttcgcc ctgcgcgacc cggccggcaa ctgcgtgcac ttcgtggccg aggagcagga    4320
```

```
ctgagtggca gggcggggcg taaggcgcgc catttaaatg aagttcctat tccgaagttc   4380
ctattctcta gaaagtatag gaacttcgaa gcagctccag cctacacaat cgctcaagac   4440
ggaacccgcg cttggcagga agtaataggg atagcagct ccagcctaca caatcgctca   4500
agacgtgtaa tgctgcacaa taaccctgct gcagaggcct gcatgcaagc ttggcgtaat   4560
catggtcata gctgtttcct gtgtgaaatt gttatccgct cacaattcca cacaacatac   4620
gagccggaag cataaagtgt aaagcctggg gtgcctaatg agtgagctaa ctcacattaa   4680
ttgcgttgcg ctcactgccc gctttccagt cgggaaacct gtcgtgccag ctgcattaat   4740
gaatcggcca acgcgcgggg agaggcggtt tgcgtattgg gcgctcttcc gcttcctcgc   4800
tcactgactc gctgcgctcg tcgttcggc tgcggcgagc ggtatcagct cactcaaagg   4860
cggtaatacg gttatccaca gaatcagggg ataacgcagg aaagaacatg tgagcaaaag   4920
gccagcaaaa ggccaggaac cgtaaaaagg ccgcgttgct ggcgtttttc cataggctcc   4980
gcccccctga cgagcatcac aaaaatcgac gctcaagtca gaggtggcga acccgacag   5040 gactataaag ataccaggcg tttcccctg gaagctccct cgtgcgctct cctgttccga   5100
ccctgccgct taccggatac ctgtccgcct ttctcccttc gggaagcgtg gcgctttctc   5160
atagctcacg ctgtaggtat ctcagttcgg tgtaggtcgt tcgctccaag ctgggctgtg   5220
tgcacgaacc ccccgttcag cccgaccgct gcgccttatc cggtaactat cgtcttgagt   5280
ccaacccggt aagacacgac ttatcgccac tggcagcagc cactggtaac aggattagca   5340
gagcgaggta tgtaggcggt gctacagagt tcttgaagtg gtggcctaac tacggctaca   5400
ctagaagaac agtatttggt atctgcgctc tgctgaagcc agttaccttc ggaaaaagag   5460
ttggtagctc ttgatccggc aaacaaacca ccgctggtag cggtggtttt tttgtttgca   5520
agcagcagat tacgcgcaga aaaaaggat ctcaagaaga tcctttgatc ttttctacgg   5580
ggtctgacgc tcagtggaac gaaaactcac gttaagggat tttggtcatg agattatcaa   5640
aaaggatctt cacctagatc cttttaaatt aaaaatgaag ttttaaatca atctaaagta   5700
tatatgagta aacttggtct gacagttacc aatgcttaat cagtgaggca cctatctcag   5760
cgatctgtct atttcgttca tccatagttg cctgactccc cgtcgtgtag ataactacga   5820
tacgggaggg cttaccatct ggccccagtg ctgcaatgat accgcgagac ccacgctcac   5880
cggctccaga tttatcagca ataaaccagc cagccggaag ggccgagcgc agaagtggtc   5940
ctgcaacttt atccgcctcc atccagtcta ttaattgttg ccgggaagct agagtaagta   6000
gttcgccagt taatagtttg cgcaacgttg ttgccattgc tacaggcatc gtggtgtcac   6060
gctcgtcgtt tggtatggct tcattcagct ccggttccca acgatcaagg cgagttacat   6120 gatccccat gttgtgcaaa aaagcggtta gctccttcgg tcctccgatc gttgtcagaa   6180
gtaagttggc cgcagtgtta tcactcatgg ttatggcagc actgcataat tctcttactg   6240
tcatgccatc cgtaagatgc ttttctgtga ctggtgagta ctcaaccaag tcattctgag   6300
aatagtgtat gcggcgaccg agttgctctt gcccggcgtc aatacgggat aataccgcgc   6360
cacatagcag aactttaaaa gtgctcatca ttggaaaacg ttcttcgggg cgaaaactct   6420
caaggatctt accgctgttg agatccagtt cgatgtaacc cactcgtgca cccaactgat   6480
cttcagcatc ttttactttc accagcgttt ctgggtgagc aaaaacagga aggcaaaatg   6540
ccgcaaaaaa gggaataagg gcgacacgga aatgttgaat actcatactc ttcctttttc   6600
aatattattg aagcatttat cagggttatt gtctcatgag cggatacata tttgaatgta   6660
tttagaaaaa taaacaaata ggggttccgc gcacatttcc ccgaaaagtg ccacctgacg   6720
```
tctaagaaac cattattatc atgacattaa cctataaaaa taggcgtatc acgaggccct  6780
ttcgtc                                                              6786

<210> SEQ ID NO 14
<211> LENGTH: 7506
<212> TYPE: DNA
<213> ORGANISM: Artificial Sequence
<220> FEATURE:
<223> OTHER INFORMATION: construct pINT-malE-BFgalT2

<400> SEQUENCE: 14
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgaagatcct ttgatctttt   420
ctacggggtc tgacgctcag tggaacgaaa actcacgtta agggattttg gtcatgagat   480
tatcaaaaag gatcttcacc tagatccttt taaactagtg aagttaccat cacgaaaaaa   540
ggttatgctg cttttaagac ccactttcac atttaagttg ttttttctaat ccgcatatga   600 tcaattcaag gccgaataag aaggctggct ctgcaccttg gtgatcaaat aattcgatag   660
cttgtcgtaa taatggcggc atactatcag tagtaggtgt ttccctttct tctttagcga   720
cttgatgctc ttgatcttcc aatacgcaac ctaaagtaaa atgccccact gcgctgagtg   780
catataatgc attctctagt gaaaaacctt gttggcataa aaaggctaat tgattttcga   840
gagtttcata ctgttttttct gtaggccgtg tacctaaatg tacttttgct ccatcgcgat   900
gacttagtaa agcacatcta aaactttag cgttattacg taaaaaatct tgccagcttt   960
ccccttctaa agggcaaaag tgagtatggt gcctatctaa catctcaatg gctaaggcgt  1020
cgagcaaagc ccgcttattt tttacatgcc aatacaatgt aggctgctct acacctagct  1080
tctgggcgag tttacgggtt gttaaacctt cgattccgac ctcattaagc agctctaatg  1140
cgctgttaat cactttactt ttatctaaac gagacatact cttcctttt caatattatt  1200 gaagcattta tcagggttat tgtctcatga gcggatacat atttgaatgt atttagaaaa  1260
ataaacaaat aggggttccg cgcacatttc cccgaaaagt gccacctgaa attggccaga  1320
tgattaattc ctaattttg ttgacactct atcattgata gagttatttt accactccct  1380
atcagtgata gagaaaagtg aaatgaatag ttcgacaaaa atctagaaat aattttgttt  1440
aactttaaga aggagatata caaatgaaaa tcgaagaagg taaactggta atctggatta  1500
acggcgataa aggctataac ggtctcgctg aagtcggtaa gaaattcgag aaagataccg  1560
gaattaaagt caccgttgag catccggata aactggaaga gaaattccca caggttgcgg  1620
caactggcga tggccctgac attatcttct gggcacacga ccgctttggt ggctacgctc  1680
aatctggcct gttggctgaa atcaccccgg acaaagcgtt ccaggacaag ctgtatccgt  1740
ttacctggga tgccgtacgt tacaacggca agctgattgc ttacccgatc gctgttgaag  1800
cgttatcgct gatttataac aaagatctgc tgccgaaccc gccaaaaacc tgggaagaga  1860
tcccggcgct ggataaagaa ctgaaagcga aaggtaagag cgcgctgatg ttcaacctgc  1920

```
aagaaccgta cttcacctgg ccgctgattg ctgctgacgg gggttatgcg ttcaagtatg    1980
aaaacggcaa gtacgacatt aaagacgtgg gcgtggataa cgctggcgcg aaagcgggtc    2040
tgaccttcct ggttgacctg attaaaaaca acacatgaa tgcagacacc gattactcca     2100
tcgcagaagc tgcctttaat aaaggcgaaa cagcgatgac catcaacggc ccgtgggcat    2160
ggtccaacat cgacaccagc aaagtgaatt atggtgtaac ggtactgccg accttcaagg    2220
gtcaaccatc caaaccgttc gttggcgtgc tgagcgcagg tattaacgcc gccagtccga    2280
acaaagagct ggcaaaagag ttcctcgaaa actatctgct gactgatgaa ggtctggaag    2340
cggttaataa agacaaaccg ctgggtgccg tagcgctgaa gtcttacgag aagagttgg     2400 cgaaagatcc acgtattgcc gccaccatgg aaaacgccca gaaggtgaa atcatgccga     2460 acatcccgca gatgtccgct ttctggtatg ccgtgcgtac tgcggtgatc aacgccgcca    2520
gcggtcgtca gactgtcgat gaagcccga aagacgcgca gactatgaac gtgaataagc     2580
cgaccaccga aaagaaactg attgacctga caacgacat tatccataac tttgatgtga     2640
gcattgtgat gagcttctat aagcgttaca ccgaatttcg caaagtgctg ccgcataacg    2700
cgccgtatct gcagcgtaat ggcattgaag tcattatcgt gctggatgac ccggatgaaa    2760
aaagcgaact gctgatgctg ctgcaaaact atccgttcat caattggaag ctgattatca    2820
acgaacgtaa acatgcaccg cgcaaccacg cttctgttct gaatgtcggt ctgaaacatg    2880
cgaccaaaaa gtatattctg cagatcgatc cggaagttga atttctgacg gatattatct    2940
ggcaaatgcg tgacgccatt gaaaaatatc cgatgcacta catcctggcg atgatggcct    3000
atgtcccgta cgaacaggaa ctgaccgaaa acaacatcaa ggaactggat ttcatcccgt    3060
ggggcaacct gatggtggaa cgcaatcatc tgtataaact gcacggttac gatgaaacct    3120
tcattacgtg gggcggtgaa gataacaata tgcgtgcgcg cctggacatg tcaggcatta    3180
aaaagtttat cctgccggaa gccaagacca tccatcgtga aaagaactat gatccgaatg    3240
aacgttcgaa gcgcattaat aaacacagta tctccgactg gcgcaaaatg aactacccgt    3300
cagaagcaat tgctaataag gatatctggg gctcggaatt caacaaagtt atttatgatt    3360
ggcaggacaa tcaatacgcc aaagatctgt gctataccta cctgcagcaa tttattggtt    3420
tcgaaatccg tcatccggcg gcctttcgta acgccacaa aaagattgtc ctgtgtcagg    3480
catataacga agaaaaactg atcgaaggct tcctgacgaa catggctaat tactttgatg    3540
gtattatcct gctggatgac gaaagtaccg atcgcacgtg ggacctggca atccatgata    3600
agatcatcct gaaggtgaaa aagaaacgtt ccggttttaa tgatctggaa accgcaata     3660 ttctgctgga cctgtcagcg ttttccagt cggaatggtt ttgcttcatg gatatcgacg     3720
aacgtttcga tgaacgcttt accaacttca gcgaattcga aaacaacaag gaaatccacg    3780
tggtttcttt tcgtggcgtg tatctgtgga atgatgaaca gagctacaag ggcgacattc    3840
cgaactctaa taaaggtatc ctgaccgttt atcgtatgtt ccgcccgatt ggtcataccc    3900
acatcaacac gcataagaaa ctgcacttca ttgcgacgcc gtattttacc aacacgtggc    3960
agagtaatat cctgtttaag gattacggct ccatgaaaga aaatgaccgt attcgcaagt    4020
atgaacgcta catccaggaa gatcagcaaa agacatgag ctctggttat gattacctgc     4080
tgaacagcga aaatctgtat caactggaca aaattgaaga atactgagcg gccgcgtcga    4140
cacgcaaaaa ggccatccgt caggatggcc ttctgcttaa ttatctagat gcctggcagt    4200
ttatggcggg cgtcctgccc gccacccctcc gggccgttgc ttcgcaacgt tcaaatccgc    4260
tcccggcgga tttgtcctac tcaggagagc gttcaccgac aaacaacaga taaaacgaaa    4320
```

```
ggcccagtct ttcgactgag cctttcgttt tatttgatgc ctggcagttc cctactctcg   4380
catgggagac cccacactac catcatgtat gaatatcct ccttagttcc tattccgaag    4440
ggtaatggca tcagggaatg gcgaacgcgc tccccacact accatcatgt atgaatatcc   4500
tccttagttc ctattccgaa gttcctattc tctagaaagt ataggaactt cggtggaacg   4560
acgcgtaact cacgttaagg gattttggtc atgatcagca cgtgttgaca attaatcatc   4620
ggcatagtat atcggcatag tataatacga caaggtgagg aactaaacca tggccaagtt   4680
gaccagtgcc gttccggtgc tcaccgcgcg cgacgtcgcc ggagcggtcg agttctggac   4740
cgaccggctc gggttctccc gggacttcgt ggaggacgac ttcgccggtg tggtccggga   4800
cgacgtgacc ctgttcatca gcgcggtcca ggaccaggtg gtgccggaca cacccctggc   4860
ctgggtgtgg gtgcgcggcc tggacgagct gtacgccgag tggtcggagg tcgtgtccac   4920
gaacttccgg gacgcctccg ggccggccat gaccgagatc ggcgagcagc cgtggggcg    4980 ggagttcgcc ctgcgcgacc cggccggcaa ctgcgtgcac ttcgtggccg aggagcagga   5040
ctgagtggca gggcggggcg taaggcgcgc catttaaatg aagttcctat tccgaagttc   5100
ctattctcta gaaagtatag gaacttcgaa gcagctccag cctacacaat cgctcaagac   5160
ggaacccgcg cttggcagga aagtaatagg gatagcagct ccagcctaca caatcgctca   5220
agacgtgtaa tgctgcacaa taaccctgct gcagaggcct gcatgcaagc ttggcgtaat   5280
catggtcata gctgtttcct gtgtgaaatt gttatccgct cacaattcca cacaacatac   5340
gagccggaag cataaagtgt aaagcctggg gtgcctaatg agtgagctaa ctcacattaa   5400
ttgcgttgcg ctcactgccc gctttccagt cgggaaacct gtcgtgccag ctgcattaat   5460
gaatcggcca acgcgcgggg agaggcggtt tgcgtattgg gcgctcttcc gcttcctcgc   5520
tcactgactc gctgcgctcg gtcgttcggc tgcggcgagc ggtatcagct cactcaaagg   5580
cggtaatacg gttatccaca gaatcagggg ataacgcagg aaagaacatg tgagcaaaag   5640
gccagcaaaa ggccaggaac cgtaaaaagg ccgcgttgct ggcgtttttc cataggctcc   5700
gcccccctga cgagcatcac aaaaatcgac gctcaagtca gaggtggcga aacccgacag   5760
gactataaag ataccaggcg tttccccctg gaagctccct cgtgcgctct cctgttccga   5820
ccctgccgct taccggatac ctgtccgcct ttctcccttc gggaagcgtg gcgctttctc   5880
atagctcacg ctgtaggtat ctcagttcgg tgtaggtcgt tcgctccaag ctgggctgtg   5940
tgcacgaacc ccccgttcag cccgaccgct gcgccttatc cggtaactat cgtcttgagt   6000
ccaacccggt aagacacgac ttatcgccac tggcagcagc cactggtaac aggattagca   6060
gagcgaggta tgtaggcggt gctacagagt tcttgaagtg gtggcctaac tacggctaca   6120
ctagaagaac agtatttggt atctgcgctc tgctgaagcc agttaccttc ggaaaaagag   6180
ttggtagctc ttgatccggc aaacaaacca ccgctggtag cggtggtttt tttgtttgca   6240
agcagcagat tacgcgcaga aaaaaaggat ctcaagaaga tcctttgatc ttttctacgg   6300
ggtctgacgc tcagtggaac gaaaactcac gttaagggat tttggtcatg agattatcaa   6360
aaaggatctt cacctagatc cttttaaatt aaaaatgaag ttttaaatca atctaaagta   6420
tatatgagta aacttggtct gacagttacc aatgcttaat cagtgaggca cctatctcag   6480
cgatctgtct atttcgttca tccatagttg cctgactccc cgtcgtgtag ataactacga   6540
tacgggaggg cttaccatct ggccccagtg ctgcaatgat accgcgagac ccacgctcac   6600
cggctccaga tttatcagca ataaaccagc cagccggaag ggccgagcgc agaagtggtc   6660
```

```
ctgcaacttt atccgcctcc atccagtcta ttaattgttg ccgggaagct agagtaagta    6720
gttcgccagt taatagtttg cgcaacgttg ttgccattgc tacaggcatc gtggtgtcac    6780
gctcgtcgtt tggtatggct tcattcagct ccggttccca acgatcaagg cgagttacat    6840
gatccccat gttgtgcaaa aaagcggtta gctccttcgg tcctccgatc gttgtcagaa     6900
gtaagttggc cgcagtgtta tcactcatgg ttatggcagc actgcataat tctcttactg    6960
tcatgccatc cgtaagatgc ttttctgtga ctggtgagta ctcaaccaag tcattctgag    7020
aatagtgtat gcggcgaccg agttgctctt gcccggcgtc aatacgggat aataccgcgc    7080
cacatagcag aactttaaaa gtgctcatca ttggaaaacg ttcttcgggg cgaaaactct    7140
caaggatctt accgctgttg agatccagtt cgatgtaacc cactcgtgca cccaactgat    7200
cttcagcatc ttttactttc accagcgttt ctgggtgagc aaaaacagga aggcaaaatg    7260
ccgcaaaaaa gggaataagg gcgacacgga aatgttgaat actcatactc ttcctttttc    7320
aatattattg aagcatttat cagggttatt gtctcatgag cggatacata tttgaatgta    7380
tttagaaaaa taaacaaata ggggttccgc gcacatttcc ccgaaaagtg ccacctgacg    7440
tctaagaaac cattattatc atgacattaa cctataaaaa taggcgtatc acgaggccct    7500
ttcgtc                                                               7506

<210> SEQ ID NO 15
<211> LENGTH: 6717
<212> TYPE: DNA
<213> ORGANISM: Artificial Sequence
<220> FEATURE:
<223> OTHER INFORMATION: construct pINT-malE-lsgD

<400> SEQUENCE: 15
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct ttgatctttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg cttttaagac ccactttcac atttaagttg ttttttctaat ccgcatatga    600
tcaattcaag gccgaataag aaggctggct ctgcaccttg gtgatcaaat aattcgatag     660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgttttttct gtaggccgtg tacctaaatg tacttttgct ccatcgcgat    900
gacttagtaa agcacatcta aaactttag cgttattacg taaaaaatct tgccagcttt     960
cccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttttt caatattatt   1200
```

```
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg ttgacactct atcattgata gagttatttt accactccct    1380
atcagtgata gagaaaagtg aaatgaatag ttcgacaaaa atctagaaat aattttgttt    1440
aactttaaga aggagatata caaatgaaaa tcgaagaagg taaactggta atctggatta    1500
acggcgataa aggctataac ggtctcgctg aagtcggtaa gaaattcgag aaagataccg    1560
gaattaaagt caccgttgag catccggata aactggaaga gaaattccca caggttgcgg    1620
caactggcga tggccctgac attatcttct gggcacacga ccgctttggt ggctacgctc    1680
aatctggcct gttggctgaa atcaccccgg acaaagcgtt ccaggacaag ctgtatccgt    1740
ttacctggga tgccgtacgt tacaacggca agctgattgc ttacccgatc gctgttgaag    1800
cgttatcgct gatttataac aaagatctgc tgccgaaccc gccaaaaacc tgggaagaga    1860
tcccggcgct ggataaagaa ctgaaagcga aggtaagag cgcgctgatg ttcaacctgc    1920
aagaaccgta cttcacctgg ccgctgattg ctgctgacgg gggttatgcg ttcaagtatg    1980
aaaacggcaa gtacgacatt aaagacgtgg gcgtggataa cgctggcgcg aaagcgggtc    2040
tgaccttcct ggttgacctg attaaaaaca acacatgaa tgcagacacc gattactcca    2100
tcgcagaagc tgcctttaat aaaggcgaaa cagcgatgac catcaacggc ccgtgggcat    2160
ggtccaacat cgacaccagc aaagtgaatt atggtgtaac ggtactgccg accttcaagg    2220
gtcaaccatc caaaccgttc gttggcgtgc tgagcgcagg tattaacgcc gccagtccga    2280
acaaagagct ggcaaaagag ttcctcgaaa actatctgct gactgatgaa ggtctggaag    2340
cggttaataa agacaaaccg ctgggtgccg tagcgctgaa gtcttacgag gaagagttgg    2400
cgaaagatcc acgtattgcc gccaccatgg aaaacgccca gaaggtgaa atcatgccga    2460 acatcccgca gatgtccgct ttctggtatg ccgtgcgtac tgcggtgatc aacgccgcca    2520
gcggtcgtca gactgtcgat gaagcccga agacgcgca gactatgctg aagaagtacc    2580
tgattagcct ggataaggac attcaacgcc gcaagctgtt tttctcgcag aagaacacgg    2640
aagattttca aattttctca gcgatcaaca ccatgcagaa agattgggac gaactggcat    2700
cgatcttcaa catcgaacaa ttcaaggctc attacttccg taacgtcacc aagggcgaaa    2760
ttggttgcac gctgagtcac ctgtccgtct atcagaaaat tgtggaagat aacgacatcg    2820
cagaagattc atacgctctg gtttgtgaag atgacgccct gtttcatctg gatttccagc    2880
aaaatctgac cgcactgctg agtgaaaaac tggaagctga aattatcctg ctgggccagt    2940
ccaacattaa caatttttaat gatacggacc tggaaatcaa ttacccgacc acgtttagct    3000
tcctgtgcaa aaagaccggt aacgtgaatt atgcgttccc gtataaatct tactttgccg    3060
gcacggttgg ttacctgatt aaaagagcg cggcccgtcg cttcattcag caaatctctc    3120
agaacaaacc gttttggctg gcggatgact ttctgctgtt cgaacaaaac ttcaatatcc    3180
gtaataaggt ggttcgcccg ctgatggtta ttgaaaaccc ggtcctgatc tcaaatctgg    3240
aatcggtgcg cggcagcctg tctaacaatc tgctgaaaaa gctgatgaaa tatccgctga    3300
aaagattttt tgcgatcaaa aagaacctgg ccaattaagc ggccgcgtcg acacgcaaaa    3360
aggccatccg tcaggatggc cttctgctta attatctaga tgcctggcag tttatggcgg    3420
gcgtcctgcc cgccacccte cgggccgttg cttcgcaacg ttcaaatccg ctcccggcgg    3480
atttgtccta ctcaggagag cgttcaccga caaacaacag ataaaacgaa aggcccagtc    3540
```

```
tttcgactga gcctttcgtt ttatttgatg cctggcagtt ccctactctc gcatggggag    3600
accccacact accatcatgt atgaatatcc tccttagttc ctattccgaa gggtaatggc    3660
atcagggaat ggcgaacgcg ctccccacac taccatcatg tatgaatatc ctccttagtt    3720
cctattccga agttcctatt ctctagaaag tataggaact tcggtggaac gacgcgtaac    3780
tcacgttaag ggattttggt catgatcagc acgtgttgac aattaatcat cggcatagta    3840
tatcggcata gtataatacg acaaggtgag gaactaaacc atggccaagt tgaccagtgc    3900
cgttccggtg ctcaccgcgc gcgacgtcgc cggagcggtc gagttctgga ccgaccggct    3960
cgggttctcc cgggacttcg tggaggacga cttcgccggt gtggtccggg acgacgtgac    4020
cctgttcatc agcgcggtcc aggaccaggt ggtgccggac aacaccctgg cctgggtgtg    4080
ggtgcgcggc ctggacgagc tgtacgccga gtggtcggag gtcgtgtcca cgaacttccg    4140
ggacgcctcc gggccggcca tgaccgagat cggcgagcag ccgtgggggc gggagttcgc    4200
cctgcgcgac ccggccggca actgcgtgca cttcgtggcc gaggagcagg actgagtggc    4260
agggcggggc gtaaggcgcg ccatttaaat gaagttccta ttccgaagtt cctattctct    4320
agaaagtata ggaacttcga agcagctcca gcctacacaa tcgctcaaga cggaacccgc    4380
gcttggcagg aaagtaatag ggatagcagc tccagcctac acaatcgctc aagacgtgta    4440
atgctgcaca taaccctgc tgcagaggcc tgcatgcaag cttggcgtaa tcatggtcat    4500
agctgtttcc tgtgtgaaat tgttatccgc tcacaattcc acacaacata cgagccggaa    4560
gcataaagtg taaagcctgg ggtgcctaat gagtgagcta actcacatta attgcgttgc    4620
gctcactgcc cgctttccag tcgggaaacc tgtcgtgcca gctgcattaa tgaatcggcc    4680
aacgcgcggg gagaggcggt ttgcgtattg ggcgctcttc cgcttcctcg ctcactgact    4740
cgctgcgctc ggtcgttcgg ctgcggcgag cggtatcagc tcactcaaag gcggtaatac    4800
ggttatccac agaatcaggg gataacgcag gaaagaacat gtgagcaaaa ggccagcaaa    4860
aggccaggaa ccgtaaaaag gccgcgttgc tggcgttttt ccataggctc cgcccccctg    4920
acgagcatca caaaaatcga cgctcaagtc agaggtggcg aaacccgaca ggactataaa    4980
gataccaggc gtttccccct ggaagctccc tcgtgcgctc tcctgttccg accctgccgc    5040
ttaccggata cctgtccgcc tttctccctt cgggaagcgt ggcgctttct catagctcac    5100
gctgtaggta tctcagttcg gtgtaggtcg ttcgctccaa gctgggctgt gtgcacgaac    5160
cccccgttca gcccgaccgc tgcgccttat ccggtaacta tcgtcttgag tccaacccgg    5220
taagacacga cttatcgcca ctggcagcag ccactggtaa caggattagc agagcgaggt    5280
atgtaggcgg tgctacagag ttcttgaagt ggtggcctaa ctacggctac actagaagaa    5340
cagtatttgg tatctgcgct ctgctgaagc cagttacctt cggaaaaaga gttggtagct    5400
cttgatccgg caaacaaacc accgctggta gcggtggttt ttttgtttgc aagcagcaga    5460
ttacgcgcag aaaaaaagga tctcaagaag atcctttgat cttttctacg ggtctgacg    5520 ctcagtggaa cgaaaactca cgttaaggga ttttggtcat gagattatca aaaaggatct    5580
tcacctagat cctttttaaat taaaaatgaa gttttaaatc aatctaaagt atatatgagt    5640
aaacttggtc tgacagttac caatgcttaa tcagtgaggc acctatctca gcgatctgtc    5700
tatttcgttc atccatagtt gcctgactcc ccgtcgtgta gataactacg atacgggagg    5760
gcttaccatc tggccccagt gctgcaatga taccgcgaga cccacgctca ccggctccag    5820
atttatcagc aataaaccag ccagccggaa gggccgagcg cagaagtggt cctgcaactt    5880
tatccgcctc catccagtct attaattgtt gccgggaagc tagagtaagt agttcgccag    5940
```

```
ttaatagttt gcgcaacgtt gttgccattg ctacaggcat cgtggtgtca cgctcgtcgt    6000
ttggtatggc ttcattcagc tccggttccc aacgatcaag gcgagttaca tgatccccca    6060
tgttgtgcaa aaaagcggtt agctccttcg gtcctccgat cgttgtcaga agtaagttgg    6120
ccgcagtgtt atcactcatg gttatggcag cactgcataa ttctcttact gtcatgccat    6180
ccgtaagatg cttttctgtg actggtgagt actcaaccaa gtcattctga gaatagtgta    6240
tgcggcgacc gagttgctct tgcccggcgt caatacggga taataccgcg ccacatagca    6300
gaactttaaa agtgctcatc attggaaaac gttcttcggg gcgaaaactc tcaaggatct    6360
taccgctgtt gagatccagt tcgatgtaac ccactcgtgc acccaactga tcttcagcat    6420
cttttacttt caccagcgtt tctgggtgag caaaaacagg aaggcaaaat gccgcaaaaa    6480
agggaataag ggcgacacgg aaatgttgaa tactcatact cttcctttt caatattatt    6540 gaagcattta tcagggttat tgtctcatga gcggatacat atttgaatgt atttagaaaa    6600
ataaacaaat aggggttccg cgcacatttc cccgaaaagt gccacctgac gtctaagaaa    6660
ccattattat catgacatta acctataaaa ataggcgtat cacgaggccc tttcgtc      6717

<210> SEQ ID NO 16
<211> LENGTH: 6769
<212> TYPE: DNA
<213> ORGANISM: Artificial Sequence
<220> FEATURE:
<223> OTHER INFORMATION: construct pINT-malE-HPgalT

<400> SEQUENCE: 16
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct ttgatctttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg cttttaagac ccactttcac atttaagttg ttttctaat ccgcatatga    600 tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgttttct gtaggccgtg tacctaaatg tacttttgct ccatcgcgat    900
gacttagtaa agcacatcta aaactttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatg aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
```

```
ataaacaaat agggggttccg cgcacatttc cccgaaaagt gccacctgaa attggccaga    1320
tgattaattc ctaattttg ttgacactct atcattgata gagttatttt accactccct    1380
atcagtgata gagaaaagtg aaatgaatag ttcgacaaaa atctagaaat aattttgttt    1440
aactttaaga aggagatata caaatgaaaa tcgaagaagg taaactggta atctggatta    1500
acggcgataa aggctataac ggtctcgctg aagtcggtaa gaaattcgag aaagataccg    1560
gaattaaagt caccgttgag catccggata aactggaaga gaaattccca caggttgcgg    1620
caactggcga tggccctgac attatcttct gggcacacga ccgctttggt ggctacgctc    1680
aatctggcct gttggctgaa atcaccccgg acaaagcgtt ccaggacaag ctgtatccgt    1740
ttacctggga tgccgtacgt tacaacggca agctgattgc ttacccgatc gctgttgaag    1800
cgttatcgct gatttataac aaagatctgc tgccgaaccc gccaaaaacc tgggaagaga    1860
tcccggcgct ggataaagaa ctgaaagcga aggtaagag cgcgctgatg ttcaacctgc    1920
aagaaccgta cttcacctgg ccgctgattg ctgctgacgg gggttatgcg ttcaagtatg    1980
aaaacggcaa gtacgacatt aaagacgtgg gcgtggataa cgctggcgcg aaagcgggtc    2040
tgaccttcct ggttgacctg attaaaaaca aacacatgaa tgcagacacc gattactcca    2100
tcgcagaagc tgcctttaat aaaggcgaaa cagcgatgac catcaacggc ccgtgggcat    2160
ggtccaacat cgacaccagc aaagtgaatt atggtgtaac ggtactgccg accttcaagg    2220
gtcaaccatc caaaccgttc gttggcgtgc tgagcgcagg tattaacgcc gccagtccga    2280
acaaagagct ggcaaaagag ttcctcgaaa actatctgct gactgatgaa ggtctggaag    2340
cggttaataa agacaaaccg ctgggtgccg tagcgctgaa gtcttacgag gaagagttgg    2400
cgaaagatcc acgtattgcc gccaccatgg aaaacgccca gaaggtgaa atcatgccga    2460 acatcccgca gatgtccgct ttctggtatg ccgtgcgtac tgcggtgatc aacgccgcca    2520
gcggtcgtca gactgtcgat gaagccctga agacgcgca gactatgcgt gtgtttatta    2580
tttccctgaa tcaaaaagtg tgtgatacct tcggtctggt gttccgtgat acgacgaccc    2640
tgctgaacaa cattaacgcg acccatcacc aggcccaaat ttttgatgca atctactcca    2700
aaacgttcga aggcggtctg catccgctgg ttaaaaaaca tctgcacccg tactttatta    2760
cccagaacat caaagacatg ggcattacca cgaatctgat cagcgaagtc tctaaattct    2820
actacgctct gaaataccat gcgaaattca tgagcctggg cgaactgggt tgctatgcta    2880
gtcactactc cctgtgggaa aaatgcattg aactgaacga agcgatttgt atcctggaag    2940
atgacatcac gctgaaagaa gattttaaag aaggcctgga cttcctggaa aaacatattc    3000
aggaactggg ttatgtgcgt ctgatgcacc tgctgtacga tccgaatgtt aaaagcgaac    3060
cgctgaacca taaaaatcac gaaatccagg aacgcgtggg cattatcaaa gcctattctc    3120
atggcgttgg cacccaaggt tacgtcatta cgccgaaaat cgcaaaagtc ttcaaaaaac    3180
atagtcgtaa atgggtggtt ccggtggata ccattatgga cgcgacgttt atccacggtg    3240
tcaaaaatct ggtgctgcaa ccgttcgtta ttgccgatga cgaacaaatt tcaaccatcg    3300
cacgcaaaga agaaccgtat tcgccgaaaa tcgccctgat gcgtgaactg cacttcaaat    3360
acctgaaata ctggcaattc gtctaagcgg ccgcgtcgac acgcaaaaag gccatccatc    3420
cgtcaggatg gccttctgct taattatcta gatgcctggc agtttatggc gggcgtcctg    3480
cccgccaccc tccgggccgt tgcttcgcaa cgttcaaatc cgctcccggc ggatttgtcc    3540
tactcaggag agcgttcacc gacaaacaac agataaaacg aaaggcccag tctttcgact    3600
gagcctttcg ttttatttga tgcctggcag ttccctactc tcgcatgggg agaccccaca    3660
```

-continued

```
ctaccatcat gtatgaatat cctccttagt tcctattccg aagggtaatg gcatcaggga    3720
atggcgaacg cgctccccac actaccatca tgtatgaata tcctccttag ttcctattcc    3780
gaagttccta ttctctagaa agtataggaa cttcggtgga acgacgcgta actcacgtta    3840
agggattttg gtcatgatca gcacgtgttg acaattaatc atcggcatag tatatcggca    3900
tagtataata cgacaaggtg aggaactaaa ccatggccaa gttgaccagt gccgttccgg    3960
tgctcaccgc gcgcgacgtc gccggagcgg tcgagttctg gaccgaccgg ctcgggttct    4020
cccgggactt cgtggaggac gacttcgccg gtgtggtccg ggacgacgtg accctgttca    4080
tcagcgcggt ccaggaccag gtggtgccgg acaacaccct ggcctgggtg tgggtgcgcg    4140
gcctggacga gctgtacgcc gagtggtcgg aggtcgtgtc cacgaacttc cgggacgcct    4200
ccgggccggc catgaccgag atcggcgagc agccgtgggg cgggagttc gccctgcgcg    4260 acccggccgg caactgcgtg cacttcgtgg ccgaggagca ggactgagtg gcagggcggg    4320
gcgtaaggcg cgccatttaa atgaagttcc tattccgaag ttcctattct ctagaaagta    4380
taggaacttc gaagcagctc cagcctacac aatcgctcaa gacggaaccc gcgcttggca    4440
ggaaagtaat agggatagca gctccagcct acacaatcgc tcaagacgtg taatgctgca    4500
caataaccct gctgcagagg cctgcatgca agcttggcgt aatcatggtc atagctgttt    4560
cctgtgtgaa attgttatcc gctcacaatt ccacacaaca tacgagccgg aagcataaag    4620
tgtaaagcct ggggtgccta atgagtgagc taactcacat taattgcgtt gcgctcactg    4680
cccgctttcc agtcgggaaa cctgtcgtgc cagctgcatt aatgaatcgg ccaacgcgcg    4740
gggagaggcg gtttgcgtat tgggcgctct tccgcttcct cgctcactga ctcgctgcgc    4800
tcggtcgttc ggctgcggcg agcggtatca gctcactcaa aggcggtaat acggttatcc    4860
acagaatcag gggataacgc aggaaagaac atgtgagcaa aaggccagca aaaggccagg    4920
aaccgtaaaa aggccgcgtt gctggcgttt ttccataggc tccgcccccc tgacgagcat    4980
cacaaaaatc gacgctcaag tcagaggtgg cgaaacccga caggactata aagataccag    5040
gcgtttcccc ctggaagctc cctcgtgcgc tctcctgttc cgaccctgcc gcttaccgga    5100
tacctgtccg cctttctccc ttcgggaagc gtggcgcttt ctcatagctc acgctgtagg    5160
tatctcagtt cggtgtaggt cgttcgctcc aagctgggct gtgtgcacga accccccgtt    5220
cagcccgacc gctgcgcctt atccggtaac tatcgtcttg agtccaaccc ggtaagacac    5280
gacttatcgc cactggcagc agccactggt aacaggatta gcagagcgag gtatgtaggc    5340
ggtgctacag agttcttgaa gtggtggcct aactacggct acactagaag aacagtattt    5400
ggtatctgcg ctctgctgaa gccagttacc ttcggaaaaa gagttggtag ctcttgatcc    5460
ggcaaacaaa ccaccgctgg tagcggtggt ttttttgttt gcaagcagca gattacgcgc    5520
agaaaaaaag gatctcaaga agatcctttg atcttttcta cggggtctga cgctcagtgg    5580
aacgaaaact cacgttaagg gattttggtc atgagattat caaaaaggat cttcacctag    5640
atccttttaa attaaaaatg aagttttaaa tcaatctaaa gtatatatga gtaaacttgg    5700
tctgacagtt accaatgctt aatcagtgag gcacctatct cagcgatctg tctatttcgt    5760
tcatccatag ttgcctgact ccccgtcgtg tagataacta cgatacggga gggcttacca    5820
tctggcccca gtgctgcaat gataccgcga gacccacgct caccggctcc agatttatca    5880
gcaataaacc agccagccgg aagggccgag cgcagaagtg gtcctgcaac tttatccgcc    5940
tccatccagt ctattaattg ttgccgggaa gctagagtaa gtagttcgcc agttaatagt    6000
```

| | |
|---|---:|
| ttgcgcaacg ttgttgccat tgctacaggc atcgtggtgt cacgctcgtc gtttggtatg | 6060 |
| gcttcattca gctccggttc ccaacgatca aggcgagtta catgatcccc catgttgtgc | 6120 |
| aaaaaagcgg ttagctcctt cggtcctccg atcgttgtca gaagtaagtt ggccgcagtg | 6180 |
| ttatcactca tggttatggc agcactgcat aattctctta ctgtcatgcc atccgtaaga | 6240 |
| tgcttttctg tgactggtga gtactcaacc aagtcattct gagaatagtg tatgcggcga | 6300 |
| ccgagttgct cttgcccggc gtcaatacgg gataataccg cgccacatag cagaacttta | 6360 |
| aaagtgctca tcattggaaa acgttcttcg gggcgaaaac tctcaaggat cttaccgctg | 6420 |
| ttgagatcca gttcgatgta acccactcgt gcacccaact gatcttcagc atcttttact | 6480 |
| ttcaccagcg tttctgggtg agcaaaaaca ggaaggcaaa atgccgcaaa aaagggaata | 6540 |
| agggcgacac ggaaatgttg aatactcata ctcttccttt ttcaatatta ttgaagcatt | 6600 |
| tatcagggtt attgtctcat gagcggatac atatttgaat gtatttagaa aaataaacaa | 6660 |
| ataggggttc cgcgcacatt tccccgaaaa gtgccacctg acgtctaaga aaccattatt | 6720 |
| atcatgacat taacctataa aaataggcgt atcacgaggc cctttcgtc | 6769 |

<210> SEQ ID NO 17
<211> LENGTH: 4714
<212> TYPE: DNA
<213> ORGANISM: Artificial Sequence
<220> FEATURE:
<223> OTHER INFORMATION: construct pACYC-waaX

<400> SEQUENCE: 17

| | |
|---|---:|
| ggggaattgt gagcggataa caattcccct gtagaaataa ttttgtttaa ctttaataag | 60 |
| gagatatacc atgaaagtgt tgtggtcaa cctggataag gataaggata aaaaagaaaa | 120 |
| aatcaagaat gaatgccgca acgcagaact ggactatgaa attatctcag cagttgatgg | 180 |
| ccgtgaactg agctacaacg aactgaaatc taaggtccat ccggtgtcac tgaattatct | 240 |
| gtcgaaaggc gaaattggtt gcgtcctgtc ccaccagcgt atttacaaac gcatcctgga | 300 |
| tgacgatatt gactatgctc tgatcctgga agacgatgtg gaactgagtc aagatatcaa | 360 |
| ggttttcctg aaggaattcc tgtccgtcaa agacaagaac aaaggcgatg tgtttctgct | 420 |
| gtacccgtca ggtctgcgtt tcctgaaccg tcgcatcaac gtgtcgcatg attatttctt | 480 |
| ttatgaagcg tacaacagct cttgtgccca cggttatatt atcagcaaca aagcggccaa | 540 |
| aaagctgatt cgcatcaata ccccgattat cctggttgca gatgcttggc tgtggtttta | 600 |
| ccagatttct ctgctgaaag tgtatgttct gaacaaagaa ctggttcgtg catatgacgt | 660 |
| cgataaaagt ctgtccacca tcgaaacgga acgcagcctg ctgctggacg aaaaggaaaa | 720 |
| gcatcagatg caaatcatca aaagcaacc gctgtactac ctgatcaagt actaccacaa | 780 |
| gtacatccgt cgcctgttca tcaataagga taaataagaa ttcgagctcg gcgcgcctgc | 840 |
| aggtcgacaa gcttgcggcc gcataatgct taagtcgaac agaaagtaat cgtattgtac | 900 |
| acggccgcat aatcgaaatt aatacgactc actataggg aattgtgagc ggataacaat | 960 |
| tccccatctt agtatattag ttaagtataa gaaggagata tacatatggc agatctcaat | 1020 |
| tggatatcgg ccggccacgc gatcgctgac gtcggtaccc tcgagtctgg taaagaaacc | 1080 |
| gctgctgcga atttgaacg ccagcacatg gactcgtcta ctagcgcagc ttaattaacc | 1140 |
| taggctgctg ccaccgctga gcaataacta gcataacccc ttggggcctc taaacgggtc | 1200 |
| ttgaggggtt ttttgctgaa acctcaggca tttgagaagc acacggtcac actgcttccg | 1260 |
| gtagtcaata aaccggtaaa ccagcaatag acataagcgg ctatttaacg accctgccct | 1320 |

| | |
|---|---|
| gaaccgacga ccgggtcgaa tttgctttcg aatttctgcc attcatccgc ttattatcac | 1380 |
| ttattcaggc gtagcaccag gcgtttaagg caccaataa ctgccttaaa aaaattacgc | 1440 |
| cccgccctgc cactcatcgc agtactgttg taattcatta agcattctgc cgacatggaa | 1500 |
| gccatcacag acggcatgat gaacctgaat cgccagcggc atcagcacct tgtcgccttg | 1560 |
| cgtataatat ttgcccatag tgaaaacggg ggcgaagaag ttgtccatat tggccacgtt | 1620 |
| taaatcaaaa ctggtgaaac tcacccaggg attggctgag acgaaaaaca tattctcaat | 1680 |
| aaacccttta gggaaatagg ccaggttttc accgtaacac gccacatctt gcgaatatat | 1740 |
| gtgtagaaac tgccggaaat cgtcgtggta ttcactccag agcgatgaaa acgtttcagt | 1800 |
| ttgctcatgg aaaacggtgt aacaagggtg aacactatcc catatcacca gctcaccgtc | 1860 |
| tttcattgcc atacgaact ccggatgagc attcatcagg cgggcaagaa tgtgaataaa | 1920 |
| ggccggataa aacttgtgct tattttcctt tacggtcttt aaaaaggccg taatatccag | 1980 |
| ctgaacggtc tggttatagg tacattgagc aactgactga aatgcctcaa aatgttcttt | 2040 |
| acgatgccat tgggatatat caacggtggt atatccagtg attttttct ccatttagc | 2100 |
| ttccttagct cctgaaaatc tcgataactc aaaaaatacg cccggtagtg atcttatttc | 2160 |
| attatggtga aagttggaac ctcttacgtg ccgatcaacg tctcatttc gccaaaagtt | 2220 |
| ggcccagggc ttcccggtat caacagggac caggattt atttattctg cgaagtgatc | 2280 |
| ttccgtcaca ggtatttatt cggcgcaaag tgcgtcgggt gatgctgcca acttactgat | 2340 |
| ttagtgtatg atggtgtttt tgaggtgctc cagtggcttc tgtttctatc agctgtccct | 2400 |
| cctgttcagc tactgacggg gtggtgcgta acggcaaaag caccgccgga catcagcgct | 2460 |
| agcggagtgt atactggctt actatgttgg cactgatgag ggtgtcagtg aagtgcttca | 2520 |
| tgtggcagga gaaaaaggc tgcaccggtg cgtcagcaga atatgtgata caggatatat | 2580 |
| tccgcttcct cgctcactga ctcgctacgc tcggtcgttc gactgcggcg agcggaaatg | 2640 |
| gcttacgaac ggggcggaga tttcctggaa gatgccagga agatacttaa cagggaagtg | 2700 |
| agagggccgc ggcaaagccg ttttccata ggctccgccc ccctgacaag catcacgaaa | 2760 |
| tctgacgctc aaatcagtgg tggcgaaacc cgacaggact ataaagatac caggcgtttc | 2820 |
| ccctggcggc tccctcgtgc gctctcctgt tcctgccttt cggtttaccg gtgtcattcc | 2880 |
| gctgttatgg ccgcgtttgt ctcattccac gcctgacact cagttccggg taggcagttc | 2940 |
| gctccaagct ggactgtatg cacgaacccc ccgttcagtc cgaccgctgc gccttatccg | 3000 |
| gtaactatcg tcttgagtcc aacccggaaa gacatgcaaa agcaccactg gcagcagcca | 3060 |
| ctggtaattg atttagagga gttagtcttg aagtcatgcg ccggttaagg ctaaactgaa | 3120 |
| aggacaagtt tggtgactg cgctcctcca agccagttac ctcggttcaa agagttggta | 3180 |
| gctcagagaa ccttcgaaaa accgccctgc aaggcggttt tttcgttttc agagcaagag | 3240 |
| attacgcgca gaccaaaacg atctcaagaa gatcatctta ttaatcagat aaaatatttc | 3300 |
| tagatttcag tgcaatttat ctcttcaaat gtagcacctg aagtcagccc catacgatat | 3360 |
| aagttgtaat tctcatgtta gtcatgcccc gcgcccaccg gaaggagctg actgggttga | 3420 |
| aggctctcaa gggcatcggt cgagatcccg gtgcctaatg agtgagctaa cttacattaa | 3480 |
| ttgcgttgcg ctcactgccc gctttccagt cgggaaacct gtcgtgccag ctgcattaat | 3540 |
| gaatcggcca acgcgcgggg agaggcggtt tgcgtattgg gcgccagggt ggttttctt | 3600 |
| ttcaccagtg agacgggcaa cagctgattg cccttcaccg cctggccctg agagagttgc | 3660 |

-continued

| | |
|---|---|
| agcaagcggt ccacgctggt tgccccagc aggcgaaaat cctgtttgat ggtggttaac | 3720 |
| ggcgggatat aacatgagct gtcttcggta tcgtcgtatc ccactaccga gatgtccgca | 3780 |
| ccaacgcgca gcccggactc ggtaatggcg cgcattgcgc ccagcgccat ctgatcgttg | 3840 |
| gcaaccagca tcgcagtggg aacgatgccc tcattcagca tttgcatggt ttgttgaaaa | 3900 |
| ccggacatgg cactccagtc gccttcccgt tccgctatcg gctgaatttg attgcgagtg | 3960 |
| agatatttat gccagccagc cagacgcaga gcgcgccgaga cagaacttaa tgggcccgct | 4020 |
| aacagcgcga tttgctggtg acccaatgcg accagatgct ccacgcccag tcgcgtaccg | 4080 |
| tcttcatggg agaaaataat actgttgatg ggtgtctggt cagagacatc aagaaataac | 4140 |
| gccggaacat tagtgcaggc agcttccaca gcaatggcat cctggtcatc cagcggatag | 4200 |
| ttaatgatca gcccactgac gcgttgcgcg agaagattgt gcaccgccgc tttacaggct | 4260 |
| tcgacgccgc ttcgttctac catcgacacc accacgctgg cacccagttg atcggcgcga | 4320 |
| gatttaatcg ccgcgacaat ttgcgacggc gcgtgcaggg ccagactgga ggtggcaacg | 4380 |
| ccaatcagca acgactgttt gcccgccagt tgttgtgcca cgcggttggg aatgtaattc | 4440 |
| agctccgcca tcgccgcttc cacttttttcc cgcgttttcg cagaaacgtg gctggcctgg | 4500 |
| ttcaccacgc gggaaacggt ctgataagag acaccggcat actctgcgac atcgtataac | 4560 |
| gttactggtt tcacattcac caccctgaat tgactctctt ccgggcgcta tcatgccata | 4620 |
| ccgcgaaagg ttttgcgcca ttcgatggtg tccgggatct cgacgctctc ccttatgcga | 4680 |
| ctcctgcatt aggaaattaa tacgactcac tata | 4714 |

<210> SEQ ID NO 18
<211> LENGTH: 4760
<212> TYPE: DNA
<213> ORGANISM: Artificial Sequence
<220> FEATURE:
<223> OTHER INFORMATION: construct pACYC-wbdO

<400> SEQUENCE: 18

| | |
|---|---|
| ggggaattgt gagcggataa caattcccct gtagaaataa ttttgtttaa ctttaataag | 60 |
| gagatatacc atgctgacgg aagtgcgccc ggtctctacg acgaaaccgc tggtgtctgt | 120 |
| gattctgccg gtgaacaaat tcaacccgta tctggatcgt gcaattcatt caatcctgag | 180 |
| tcagtcctat ccgtcgattg aactgattat cattgcaaac aattgcacca atgactttt | 240 |
| cgatgctctg aaaaaacgtg aatgtgaaac cattaaagtg ctgcgcacga acatcgcgta | 300 |
| tctgccgtac tgcctgaata aaggcctgga tctgtgtaac ggtgactttg ttgcccgcat | 360 |
| ggattcagat gacatttcgc acccggaacg tatcgatcgc caggtcgact tcctgattaa | 420 |
| caatccggac atcgatgtgg ttggcaccaa tgcagtctat attgatgaag atgacatcga | 480 |
| actggaaaaa agcaacctgc cggtgaacaa taacgctatt cgtaaaatgc tgccgtataa | 540 |
| atgctgtctg gtgcatccgt ctgttatgtt tcgcaaaaat gtcgtgatca ccagcggcgg | 600 |
| ttacatgttc gcgaattatt ctgaagatta cgaactgtgg aaccgtctgg ccgttgaagg | 660 |
| ccgcaatttt tataacctga gcgaatacct gctgtattac cgtctgcaca ataaccaatc | 720 |
| aacgtcgaaa ataacctgt ttatggtgat ggcgaacgat gtcgccatta agtgaaata | 780 |
| tttcctgctg accaagaaaa ttagctacct gctgggtatc attcgcacgg tcttttctgt | 840 |
| gttctattgc aaatacatca atgaattcg agctcggcgc gcctgcaggt cgacaagctt | 900 |
| gcggccgcat aatgcttaag tcgaacagaa agtaatcgta ttgtacacgg ccgcataatc | 960 |
| gaaattaata cgactcacta tagggggaatt gtgagcggat aacaattccc catcttagta | 1020 |

```
tattagttaa gtataagaag gagatataca tatggcagat ctcaattgga tatcggccgg   1080
ccacgcgatc gctgacgtcg gtaccctcga gtctggtaaa gaaaccgctg ctgcgaaatt   1140
tgaacgccag cacatggact cgtctactag cgcagcttaa ttaacctagg ctgctgccac   1200
cgctgagcaa taactagcat aacccottgg ggcctctaaa cgggtcttga ggggtttttt   1260
gctgaaacct caggcatttg agaagcacac ggtcacactg cttccggtag tcaataaacc   1320
ggtaaaccag caatagacat aagcggctat ttaacgaccc tgccctgaac cgacgaccgg   1380
gtcgaatttg ctttcgaatt tctgccattc atccgcttat tatcacttat tcaggcgtag   1440
caccaggcgt ttaagggcac caataactgc cttaaaaaaa ttacgccccg ccctgccact   1500
catcgcagta ctgttgtaat tcattaagca ttctgccgac atggaagcca tcacagacgg   1560
catgatgaac ctgaatcgcc agcggcatca gcaccttgtc gccttgcgta taatatttgc   1620
ccatagtgaa aacggggggcg aagaagttgt ccatattggc cacgtttaaa tcaaaactgg   1680
tgaaactcac ccagggattg gctgagacga aaaacatatt ctcaataaac cctttaggga   1740
aataggccag gttttcaccg taacacgcca catcttgcga atatatgtgt agaaactgcc   1800
ggaaatcgtc gtggtattca ctccagagcg atgaaaacgt ttcagtttgc tcatggaaaa   1860
cggtgtaaca agggtgaaca ctatcccata tcaccagctc accgtctttc attgccatac   1920
ggaactccgg atgagcattc atcaggcggg caagaatgtg aataaaggcc ggataaaact   1980
tgtgcttatt tttctttacg gtctttaaaa aggccgtaat atccagctga acggtctggt   2040
tataggtaca ttgagcaact gactgaaatg cctcaaaatg ttctttacga tgccattggg   2100
atatatcaac ggtggtatat ccagtgattt ttttctccat tttagcttcc ttagctcctg   2160
aaaatctcga taactcaaaa aatacgcccg gtagtgatct tatttcatta tggtgaaagt   2220
tggaacctct tacgtgccga tcaacgtctc attttcgcca aaagttggcc cagggcttcc   2280
cggtatcaac agggacacca ggatttattt attctgcgaa gtgatcttcc gtcacaggta   2340
tttattcggc gcaaagtgcg tcgggtgatg ctgccaactt actgatttag tgtatgatgg   2400 tgttttgag gtgctccagt ggcttctgtt tctatcagct gtccctcctg ttcagctact   2460
gacggggtgg tgcgtaacgg caaaagcacc gccggacatc agcgctagcg gagtgtatac   2520
tggcttacta tgttggcact gatgagggtg tcagtgaagt gcttcatgtg gcaggagaaa   2580
aaaggctgca ccggtgcgtc agcagaatat gtgatacagg atatattccg cttcctcgct   2640
cactgactcg ctacgctcgg tcgttcgact gcggcgagcg gaaatggctt acgaacgggg   2700
cggagatttc ctggaagatg ccaggaagat acttaacagg gaagtgagag ggccgcggca   2760
aagccgtttt tccataggct ccgcccccct gacaagcatc acgaaatctg acgctcaaat   2820
cagtggtggc gaaacccgac aggactataa agataccagg cgtttcccct ggcggctccc   2880
tcgtgcgctc tcctgttcct gcctttcggt ttaccggtgt cattccgctg ttatggccgc   2940
gtttgtctca ttccacgcct gacactcagt tccgggtagg cagttcgctc caagctggac   3000
tgtatgcacg aaccccccgt tcagtccgac cgctgcgcct tatccggtaa ctatcgtctt   3060
gagtccaacc cggaaagaca tgcaaaagca ccactggcag cagccactgg taattgattt   3120
agaggagtta gtcttgaagt catgcgccgg ttaaggctaa actgaaagga caagttttgg   3180
tgactgcgct cctccaagcc agttacctcg gttcaaagag ttggtagctc agagaacctt   3240
cgaaaaaccg ccctgcaagg cggttttttc gttttcagag caagagatta cgcgcagacc   3300
aaaacgatct caagaagatc atcttattaa tcagataaaa tatttctaga tttcagtgca   3360
```

```
atttatctct tcaaatgtag cacctgaagt cagccccata cgatataagt tgtaattctc    3420
atgttagtca tgccccgcgc ccaccggaag gagctgactg ggttgaaggc tctcaagggc    3480
atcggtcgag atcccggtgc ctaatgagtg agctaactta cattaattgc gttgcgctca    3540
ctgcccgctt tccagtcggg aaacctgtcg tgccagctgc attaatgaat cggccaacgc    3600
gcggggagag gcggtttgcg tattgggcgc cagggtggtt tttcttttca ccagtgagac    3660
gggcaacagc tgattgccct tcaccgcctg gccctgagag agttgcagca agcggtccac    3720
gctggtttgc cccagcaggc gaaaatcctg tttgatggtg gttaacggcg ggatataaca    3780
tgagctgtct tcggtatcgt cgtatcccac taccgagatg tccgcaccaa cgcgcagccc    3840
ggactcggta atggcgcgca ttgcgcccag cgccatctga tcgttggcaa ccagcatcgc    3900
agtgggaacg atgccctcat tcagcatttg catggtttgt tgaaaaccgg acatggcact    3960
ccagtcgcct tcccgttccg ctatcggctg aatttgattg cgagtgagat atttatgcca    4020
gccagccaga cgcagacgcg ccgagacaga acttaatggg cccgctaaca gcgcgatttg    4080
ctggtgaccc aatgcgacca gatgctccac gcccagtcgc gtaccgtctt catgggagaa    4140
aataatactg ttgatgggtg tctggtcaga gacatcaaga aataacgccg gaacattagt    4200
gcaggcagct tccacagcaa tggcatcctg gtcatccagc ggatagttaa tgatcagccc    4260
actgacgcgt tgcgcgagaa gattgtgcac cgccgcttta caggcttcga cgccgcttcg    4320
ttctaccatc gacaccacca cgctggcacc cagttgatcg gcgcgagatt taatcgccgc    4380
gacaatttgc gacggcgcgt gcagggccag actggaggtg gcaacgccaa tcagcaacga    4440
ctgtttgccc gccagttgtt gtgccacgcg gttgggaatg taattcagct ccgccatcgc    4500
cgcttccact ttttcccgcg ttttcgcaga acgtggctg gcctggttca ccacgcggga    4560
aacggtctga taagagacac cggcatactc tgcgacatcg tataacgtta ctggtttcac    4620
attcaccacc ctgaattgac tctcttccgg gcgctatcat gccataccgc gaaaggtttt    4680
gcgccattcg atggtgtccg ggatctcgac gctctcccctt atgcgactcc tgcattagga    4740
aattaatacg actcactata                                                4760
```

<210> SEQ ID NO 19
<211> LENGTH: 4795
<212> TYPE: DNA
<213> ORGANISM: Artificial Sequence
<220> FEATURE:
<223> OTHER INFORMATION: construct pACYC-furA

<400> SEQUENCE: 19

```
ggggaattgt gagcggataa caattcccct gtagaaataa ttttgtttaa ctttaataag      60
gagatatacc atggataaaa tcaaacaggg cagcgcctct ctggttgtcg gtgaccagca     120
agaaaaacat ccggtggttt cagtgctgct gccggttaat cgtgtcgatc gcttttttcat    180
tccggcagtt gaatcgatcc tgacccaaac gctgcaggat tttgaactga tcattatcgc    240
taatggctgt agcaccgaac atctgaacaa aattcgtctg acgtatggtg atcacaatcg    300
tgttcgcatt ctgaacaccg aaatcaaagg cctgccgttt gcgctgaatc tgggcgtgca    360
caacgcccgt ggtctgtata ttgcacgcat ggatgctgat gacatttcta tcccggaacg    420
cctggaaaaa caactgaata cgctggaaca gaacaagaaa attggcgtcg tgagctctgg    480
tgtggacttt attgatgaaa atgaccaggc gatccgtgag ggtaaattcc cggaactgac    540
cgacaaagat catcgtcgcc tgctgccgct gatttgctgt atcgcccacc cgacggttat    600
ggtccgcaaa gaaattatca acaaactggg cggttatagt tttggtagtt ctccgaaga     660
```

```
ctacgatctg tggctgcgta ttatgcgcga actgccggaa gttgaatttt atcgtatccc    720
ggaatccctg ctgaaatacc gtcgccatgg caatcaggcc accagttcca aaacattaa    780 gaaaattcgc gcgtacaact cagccctgaa aattcgtgaa ctgtttctgt cgcgcaaact    840
gaaattcatt atcggtatta tcctgccggc acgtatggtg accctgtggc gcaaatgaga    900
attcgagctc ggcgcgcctg caggtcgaca agcttgcggc cgcataatgc ttaagtcgaa    960
cagaaagtaa tcgtattgta cacggccgca taatcgaaat taatacgact cactataggg   1020
gaattgtgag cggataacaa ttccccatct tagtatatta gttaagtata agaaggagat   1080
atacatatgg cagatctcaa ttggatatcg gccggccacg cgatcgctga cgtcggtacc   1140
ctcgagtctg gtaaagaaac cgctgctgcg aaatttgaac gccagcacat ggactcgtct   1200
actagcgcag cttaattaac ctaggctgct gccaccgctg agcaataact agcataaccc   1260
cttggggcct ctaaacgggt cttgaggggt tttttgctga aacctcaggc atttgagaag   1320
cacacggtca cactgcttcc ggtagtcaat aaaccggtaa accagcaata gacataagcg   1380
gctatttaac gaccctgccc tgaaccgacg accgggtcga atttgctttc gaatttctgc   1440
cattcatccg cttattatca cttattcagg cgtagcacca ggcgtttaag ggcaccaata   1500
actgccttaa aaaaattacg ccccgccctg ccactcatcg cagtactgtt gtaattcatt   1560
aagcattctg ccgacatgga agccatcaca gacggcatga tgaacctgaa tcgccagcgg   1620
catcagcacc ttgtcgcctt gcgtataata tttgcccata gtgaaaacgg ggcgaagaa   1680 gttgtccata ttggccacgt ttaaatcaaa actggtgaaa ctcacccagg gattggctga   1740
gacgaaaaac atattctcaa taaacccttt agggaaatag gccaggtttt caccgtaaca   1800
cgccacatct tgcgaatata tgtgtagaaa ctgccggaaa tcgtcgtggt attcactcca   1860
gagcgatgaa aacgtttcag tttgctcatg gaaaacggtg taacaagggt gaacactatc   1920
ccatatcacc agctcaccgt ctttcattgc catacggaac tccggatgag cattcatcag   1980
gcgggcaaga atgtgaataa aggccggata aaacttgtgc ttattttttct ttacggtctt   2040 taaaaaggcc gtaatatcca gctgaacggt ctggttatag gtacattgag caactgactg   2100
aaatgcctca aaatgttctt tacgatgcca ttgggatata tcaacggtgg tatatccagt   2160
gatttttttc tccattttag cttccttagc tcctgaaaat ctcgataact caaaaaatac   2220
gcccggtagt gatcttattt cattatggtg aaagttggaa cctcttacgt gccgatcaac   2280
gtctcatttt cgccaaaagt tggcccaggg cttcccggta tcaacaggga caccaggatt   2340
tatttattct gcgaagtgat cttccgtcac aggtatttat tcggcgcaaa gtgcgtcggg   2400
tgatgctgcc aacttactga tttagtgtat gatggtgttt ttgaggtgct ccagtggctt   2460
ctgtttctat cagctgtccc tcctgttcag ctactgacgg ggtggtgcgt aacggcaaaa   2520
gcaccgccgg acatcagcgc tagcggagtg tatactggct tactatgttg gcactgatga   2580
gggtgtcagt gaagtgcttc atgtggcagg agaaaaaagg ctgcaccggt gcgtcagcag   2640
aatatgtgat acaggatata ttccgcttcc tcgctcactg actcgctacg ctcggtcgtt   2700
cgactgcggc gagcggaaat ggcttacgaa cggggcggag atttcctgga agatgccagg   2760
aagatactta acagggaagt gagagggccg cggcaaagcc gttttttccat aggctccgcc   2820 cccctgacaa gcatcacgaa atctgacgct caaatcagtg gtggcgaaac ccgacaggac   2880
tataaagata ccaggcgttt cccctggcgg ctccctcgtg cgctctcctg ttcctgcctt   2940
tcggtttacc ggtgtcattc cgctgttatg gccgcgtttg tctcattcca cgcctgacac   3000
```

```
tcagttccgg gtaggcagtt cgctccaagc tggactgtat gcacgaaccc cccgttcagt      3060
ccgaccgctg cgccttatcc ggtaactatc gtcttgagtc aacccggaa agacatgcaa       3120 aagcaccact ggcagcagcc actggtaatt gatttagagg agttagtctt gaagtcatgc     3180
gccggttaag gctaaactga aaggacaagt tttggtgact gcgctcctcc aagccagtta      3240
cctcggttca aagagttggt agctcagaga accttcgaaa aaccgccctg caaggcggtt     3300
ttttcgtttt cagagcaaga gattacgcgc agaccaaaac gatctcaaga agatcatctt      3360
attaatcaga taaatatttt ctagatttca gtgcaattta tctcttcaaa tgtagcacct     3420
gaagtcagcc ccatacgata taagttgtaa ttctcatgtt agtcatgccc cgcgcccacc     3480
ggaaggagct gactgggttg aaggctctca agggcatcgg tcgagatccc ggtgcctaat    3540
gagtgagcta acttacatta attgcgttgc gctcactgcc cgctttccag tcggaaaacc    3600
tgtcgtgcca gctgcattaa tgaatcggcc aacgcgcggg gagaggcggt ttgcgtattg    3660
ggcgccaggg tggtttttct tttcaccagt gagacgggca acagctgatt gcccttcacc    3720
gcctggccct gagagagttg cagcaagcgg tccacgctgg tttgccccag caggcgaaaa   3780
tcctgtttga tggtggttaa cggcgggata taacatgagc tgtcttcggt atcgtcgtat    3840
cccactaccg agatgtccgc accaacgcgc agcccggact cggtaatggc gcgcattgcg    3900
cccagcgcca tctgatcgtt ggcaaccagc atcgcagtgg gaacgatgcc ctcattcagc    3960
atttgcatgg tttgttgaaa accggacatg gcactccagt cgccttcccg ttccgctatc    4020
ggctgaattt gattgcgagt gagatattta tgccagccag ccagacgcag acgcgccgag    4080
acagaactta atgggcccgc taacagcgcg atttgctggt gacccaatgc gaccagatgc   4140
tccacgccca gtcgcgtacc gtcttcatgg gagaaaataa tactgttgat gggtgtctgg   4200
tcagagacat caagaaataa cgccggaaca ttagtgcagg cagcttccac agcaatggca    4260
tcctggtcat ccagcggata gttaatgatc agcccactga cgcgttgcgc gagaagattg    4320
tgcaccgccg ctttacaggc ttcgacgccg cttcgttcta ccatcgacac caccacgctg   4380
gcacccagtt gatcggcgcg agatttaatc gccgcgacaa tttgcgacgg cgcgtgcagg    4440
gccagactgg aggtggcaac gccaatcagc aacgactgtt tgcccgccag ttgttgtgcc   4500
acgcggttgg gaatgtaatt cagctccgcc atcgccgctt ccacttttc ccgcgttttc    4560 gcagaaacgt ggctggcctg gttcaccacg cgggaaacgg tctgataaga gacaccggca  4620
tactctgcga catcgtataa cgttactggt ttcacattca ccaccctgaa ttgactctct    4680
tccgggcgct atcatgccat accgcgaaag ttttgcgcc attcgatggt gtccgggatc   4740
tcgacgctct cccttatgcg actcctgcat taggaaatta atacgactca ctata       4795
```

<210> SEQ ID NO 20
<211> LENGTH: 6383
<212> TYPE: DNA
<213> ORGANISM: Artificial Sequence
<220> FEATURE:
<223> OTHER INFORMATION: construct pET-PmnagT

<400> SEQUENCE: 20

```
ggggaattgt gagcggataa caattcccct ctagaaataa ttttgtttaa ctttaagaag       60
gagatatacc atgggcagca gccatcacca tcatcaccac agccaggatc cgaattcgag      120
ctcggcgcgc ctgcaggtcg acaagcttgc ggccgcataa tgcttaagtc gaacagaaag    180
taatcgtatt gtacacggcc gcataatcga aattaatacg actcactata ggggaattgt    240
gagcggataa caattcccca tcttagtata ttagttaagt ataagaagga gatatacata    300
```

```
tggaaaataa acctttagtt tcagttttga tttgtgctta taatgtcgag aaatatattg      360
aagaatgtat taatgcagtg attaatcaga catataagaa cttagaaatt attattgtga      420
atgatggttc ttctgataat acttattttc ttttaaaaaa gttagctgaa aaagataatc      480
gtataaaaat attaaatttc aataatcata ttggaataat ttctgcttta aatgaaggtt      540
taaaagagat agctggagaa tatattgctc gaacagattc tgatgatata actaagccag      600
attggattga gaaatattta acttgtatgc aaaatgatcc taaaatcatc gctatgggat      660
cttatcttac tgtcttgtca gaagaaaata atggtagtgt gcttgctaat catcataaaa      720
ataaagttga atggaaaaat ccattagagc acaaagatat tgttgagaaa atgttatttg      780
gtaatcctat tcataataat tcaatggtta tgagaagtga gatatataca aagtatcact      840
taatttatga tccagattat cattatgctg aagattataa attttggctg gaagttagtc      900
gaattgggaa attagcaaat tatcctgagt cactcgtata ttatagactt caccgaaatc      960
aaacatcttc tattcataat agccaacaag aaataaatgg taaaaaatta cgtttacaag     1020
ctcttaatta ttatttaaaa gatcttggta ttgattatca gttacctgaa aaatttttat     1080
tcaaagatat agcgttattg caagaaatat tttatgaacg aggtatgttt agagaaaata     1140
taataaggcg tatcatctac gaatgttatc tttccttggg agagtataat tataaagata     1200
tttattattt tttaataaat aaaaataact ttctttctat aaaagacaaa tttaaaataa     1260
taaaaaaata tcttcgtcct gataaatatt catctactta ttaggacgtc ggtaccctcg     1320
agtctggtaa agaaaccgct gctgcgaaat ttgaacgcca gcacatggac tcgtctacta     1380
gcgcagctta attaacctag gctgctgcca ccgctgagca ataactagca taaccccttg     1440
gggcctctaa acgggtcttg agggttttt tgctgaaagg aggaactata tccggattgg      1500
cgaatgggac gcgccctgta gcggcgcatt aagcgcggcg ggtgtggtgg ttacgcgcag     1560
cgtgaccgct acacttgcca gcgccctagc gcccgctcct ttcgctttct tcccttcctt     1620
tctcgccacg ttcgccggct ttccccgtca gctctaaat cggggctcc ctttagggtt      1680 ccgatttagt gctttacggc acctcgaccc caaaaaactt gattagggtg atggttcacg     1740
tagtgggcca tcgccctgat agacggtttt tcgccctttg acgttggagt ccacgttctt     1800
taatagtgga ctcttgttcc aaactggaac aacactcaac cctatctcgg tctattcttt     1860
tgatttataa gggattttgc cgatttcggc ctattggtta aaaaatgagc tgatttaaca     1920
aaaatttaac gcgaatttta acaaaatatt aacgtttaca atttctggcg gcacgatggc     1980
atgagattat caaaaaggat cttcacctag atccttttaa attaaaaatg aagttttaaa     2040
tcaatctaaa gtatatatga gtaaacttgg tctgacagtt accaatgctt aatcagtgag     2100
gcacctatct cagcgatctg tctatttcgt tcatccatag ttgcctgact ccccgtcgtg     2160
tagataacta cgatacggga gggcttacca tctggcccca gtgctgcaat gataccgcga     2220
gacccacgct caccggctcc agatttatca gcaataaacc agccagccgg aagggccgag     2280
cgcagaagtg gtcctgcaac tttatccgcc tccatccagt ctattaattg ttgccgggaa     2340
gctagagtaa gtagttcgcc agttaatagt ttgcgcaacg ttgttgccat tgctacaggc     2400
atcgtggtgt cacgctcgtc gtttggtatg gcttcattca gctccggttc caacgatca      2460 aggcgagtta catgatcccc catgttgtgc aaaaaagcgg ttagctcctt cggtcctccg     2520
atcgttgtca gaagtaagtt ggccgcagtg ttatcactca tggttatggc agcactgcat     2580
aattctctta ctgtcatgcc atccgtaaga tgcttttctg tgactggtga gtactcaacc     2640
```

```
aagtcattct gagaatagtg tatgcggcga ccgagttgct cttgcccggc gtcaatacgg    2700
gataataccg cgccacatag cagaacttta aaagtgctca tcattggaaa acgttcttcg    2760
gggcgaaaac tctcaaggat cttaccgctg ttgagatcca gttcgatgta acccactcgt    2820
gcacccaact gatcttcagc atcttttact ttcaccagcg tttctgggtg agcaaaaaca    2880
ggaaggcaaa atgccgcaaa aaagggaata agggcgacac ggaaatgttg aatactcata    2940
ctcttccttt ttcaatcatg attgaagcat ttatcagggt tattgtctca tgagcggata    3000
catatttgaa tgtatttaga aaataaaca aataggtcat gaccaaaatc ccttaacgtg     3060
agttttcgtt ccactgagcg tcagaccccg tagaaaagat caaggatctc tcttgagatc    3120
ctttttttct gcgcgtaatc tgctgcttgc aaacaaaaaa accaccgcta ccagcggtgg    3180
tttgtttgcc ggatcaagag ctaccaactc tttttccgaa ggtaactggc ttcagcagag    3240
cgcagatacc aaatactgtc cttctagtgt agccgtagtt aggccaccac ttcaagaact    3300
ctgtagcacc gcctacatac ctcgctctgc taatcctgtt accagtggct gctgccagtg    3360
gcgataagtc gtgtcttacc gggttggact caagacgata gttaccggat aaggcgcagc    3420
ggtcgggctg aacggggggt tcgtgcacac agcccagctt ggagcgaacg acctacaccg    3480
aactgagata cctacagcgt gagctatgag aaagcgccac gcttcccgaa gggagaaagg    3540
cggacaggta tccggtaagc ggcagggtcg gaacaggaga gcgcacgagg gagcttccag    3600
ggggaaacgc ctggtatctt tatagtcctg tcgggtttcg ccacctctga cttgagcgtc    3660
gatttttgtg atgctcgtca gggggggcgga gcctatggaa aaacgccagc aacgcggcct    3720
ttttacggtt cctggccttt tgctggcctt ttgctcacat gttctttcct gcgttatccc    3780
ctgattctgt ggataaccgt attaccgcct ttgagtgagc tgataccgct cgccgcagcc    3840
gaacgaccga gcgcagcgag tcagtgagcg aggaagcgga agagcgcctg atgcggtatt    3900
ttctccttac gcatctgtgc ggtatttcac accgcatata tggtgcactc tcagtacaat    3960
ctgctctgat gccgcatagt taagccagta tacactccgc tatcgctacg tgactgggtc    4020
atggctgcgc cccgacaccc gccaacaccc gctgacgcgc cctgacgggc ttgtctgctc    4080
ccggcatccg cttacagaca agctgtgacc gtctccggga gctgcatgtg tcagaggttt    4140
tcaccgtcat caccgaaacg cgcgaggcag ctgcggtaaa gctcatcagc gtggtcgtga    4200
agcgattcac agatgtctgc ctgttcatcc gcgtccagct cgttgagttt ctccagaagc    4260
gttaatgtct ggcttctgat aaagcgggcc atgttaaggg cggttttttc ctgtttggtc    4320
actgatgcct ccgtgtaagg gggatttctg ttcatggggg taatgatacc gatgaaacga    4380
gagaggatgc tcacgatacg ggttactgat gatgaacatg cccggttact ggaacgttgt    4440
gagggtaaac aactggcggt atggatgcgg cgggaccaga gaaaaatcac tcagggtcaa    4500
tgccagcgct tcgttaatac agatgtaggt gttccacagg gtagccagca gcatcctgcg    4560
atgcagatcc ggaacataat ggtgcagggc gctgacttcc gcgtttccag actttacgaa    4620
acacggaaac cgaagaccat tcatgttgtt gctcaggtcg cagacgtttt gcagcagcag    4680
tcgcttcacg ttcgctcgcg tatcggtgat tcattctgct aaccagtaag caaccccgc     4740 cagcctagcc gggtcctcaa cgacaggagc acgatcatgc tagtcatgcc ccgcgcccac    4800
cggaaggagc tgactgggtt gaaggctctc aagggcatcg gtcgagatcc cggtgcctaa    4860
tgagtgagct aacttacatt aattgcgttg cgctcactgc ccgctttcca gtcgggaaac    4920
ctgtcgtgcc agctgcatta atgaatcggc caacgcgcgg ggagaggcgg tttgcgtatt    4980
gggcgccagg gtggtttttc ttttcaccag tgagacgggc aacagctgat tgcccttcac    5040
```

-continued

```
cgcctggccc tgagagagtt gcagcaagcg gtccacgctg gtttgcccca gcaggcgaaa    5100
atcctgtttg atggtggtta acggcgggat ataacatgag ctgtcttcgg tatcgtcgta    5160
tcccactacc gagatgtccg caccaacgcg cagcccggac tcggtaatgg cgcgcattgc    5220
gcccagcgcc atctgatcgt tggcaaccag catcgcagtg ggaacgatgc cctcattcag    5280
catttgcatg gtttgttgaa aaccggacat ggcactccag tcgccttccc gttccgctat    5340
cggctgaatt tgattgcgag tgagatattt atgccagcca gcagacgca gacgcgccga     5400 gacagaactt aatgggcccg ctaacagcgc gatttgctgg tgacccaatg cgaccagatg    5460
ctccacgccc agtcgcgtac cgtcttcatg ggagaaaata atactgttga tgggtgtctg    5520
gtcagagaca tcaagaaata acgccggaac attagtgcag gcagcttcca cagcaatggc    5580
atcctggtca tccagcggat agttaatgat cagcccactg acgcgttgcg cgagaagatt    5640
gtgcaccgcc gctttacagg cttcgacgcc gcttcgttct accatcgaca ccaccacgct    5700
ggcacccagt tgatcggcgc gagatttaat cgccgcgaca atttgcgacg cgcgcgtgcag   5760 ggccagactg gaggtggcaa cgccaatcag caacgactgt ttgcccgcca gttgttgtgc    5820
cacgcggttg ggaatgtaat tcagctccgc catcgccgct tccactttttt cccgcgtttt   5880 cgcagaaacg tggctggcct ggttcaccac gcgggaaacg gtctgataag agacaccggc    5940
atactctgcg acatcgtata acgttactgg tttcacattc accaccctga attgactctc    6000
ttccgggcgc tatcatgcca taccgcgaaa ggttttgcgc cattcgatgg tgtccgggat    6060
ctcgacgctc tcccttatgc gactcctgca ttaggaagca gcccagtagt aggttgaggc    6120
cgttgagcac cgccgccgca aggaatggtg catgcaagga gatggcgccc aacagtcccc    6180
cggccacggg gcctgccacc atacccacgc cgaaacaagc gctcatgagc cgaagtggc    6240 gagcccgatc ttccccatcg gtgatgtcgg cgatataggc gccagcaacc gcacctgtgg    6300
cgccggtgat gccggccacg atgcgtccgg cgtagaggat cgagatcgat ctcgatcccg    6360
cgaaattaat acgactcact ata                                           6383
```

<210> SEQ ID NO 21
<211> LENGTH: 6711
<212> TYPE: DNA
<213> ORGANISM: Artificial Sequence
<220> FEATURE:
<223> OTHER INFORMATION: construct pINT-yjhB

<400> SEQUENCE: 21

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420 ctacgggtc tgacgctcag tggaacgaaa actcacgtta agggattttg gtcatgagat     480
tatcaaaaag gatcttcacc tagatccttt taaactagtg aagttaccat cacggaaaaa    540
ggttatgctg cttttaagac ccactttcac atttaagttg ttttttctaat ccgcatatga   600 tcaattcaag gccgaataag aaggctggct ctgcaccttg gtgatcaaat aattcgatag    660
```

```
cttgtcgtaa taatggcggc atactatcag tagtaggtgt ttcccttttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaactttag cgttattacg taaaaaatct tgccagcttt    960
cccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacggggtt gttaaacctt cgattccgac ctcattaagc agctctaatg   1140
cgctgttaat cactttactt ttatctaaac gagacatact cttcctttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tggcaacagc   1500
atggtataaa caagttaatc caccacaacg gaaagctctt ttttccgcat ggcttggata   1560
tgtatttgat ggctttgatt ttatgatgat attttacatt cttcatatta taaaagcaga   1620
tcttggcatt acggatattc aggctacttt aataggagca gtggccttca tagccagacc   1680
tattggaggt ggttttttg gtgccatggc tgataaatat ggtcgtaagc caatgatgat   1740
gtgggcaatt ttcatttact cagtcggaac aggccttagc ggtattgcta caaacttata   1800
tatgctcgca gtttgccgtt ttattgttgg cttaggatg tctggtgaat atgcatgtgc   1860
ttcaacttat gcggtagaaa gttggcctaa aaatcttcaa tctaaagcta gtgctttttt   1920
ggtaagtggt ttttctgttg gaaatattat tgcggcacaa ataatccctc agtttgctga   1980
agtatatgga tggagaaact cttttttttat aggcctgtta ccagttttac tagttctttg   2040
gatcagaaaa agtgctccag aaagtcagga gtggattgaa gataaatata aggataaatc   2100
aacatttttg tctgtcttca gaaaaccaca tctttcaatc tctatgatcg tttttcctcgt   2160
ctgtttttgt ctatttggtg caaactggcc gataaacgga ctacttcctt cctacctggc   2220
agataatgga gttaatacag tggtcatttc aactctgatg acaatagcag gtttaggaac   2280
actgacaggt acaatatttt ttggttttgt tggtgataag attggtgtaa aaaaagcctt   2340
tgtagtcggt ctaataactt catttatttt cctttgtcct ctttttttta tttctgtgaa   2400
aaactcttct cttataggat tatgtctctt tggattaatg tttacaaatt taggtattgc   2460
agggttggtt ccaaaattta tatatgatta ctttccaaca aaattaagag gattagggac   2520
cggtcttatt tataacttag gggcaactgg aggaatggcc gcacctgtat tagctacata   2580
catttcagga tattatggct taggtgtttc attattcatt gttacggttg cattctctgc   2640
cttattaatt ttgttagttg gttttgatat tccaggtaaa atttataaac tatccgtggc   2700
taaatgataa atcgatacta gcataacccc ttggggcctc taaacgcgtc gacacgcaaa   2760
aaggccatcc gtcaggatgg ccttctgctt aatttgatgc ctggcagttt atggcgggcg   2820
tcctgcccgc caccctccgg gccgttgctt cgcaacgttc aaatccgctc ccggcggatt   2880
tgtcctactc aggagagcgt tcaccgacaa caacagata aaacgaaagg cccagtcttt   2940
cgactgagcc tttcgtttta tttgatgcct ggcagttccc tactctcgca tggggagacc   3000
ccacactacc atcatgtatg aatatcctcc ttagttccta ttccgaagtt cctattctct   3060
```

```
agaaagtata ggaacttcgg cgcgtcctac ctgtgacgga agatcacttc gcagaataaa    3120
taaatcctgg tgtccctgtt gataccggga agccctgggc caacttttgg cgaaaatgag    3180
acgttgatcg gcacgtaaga ggttccaact ttcaccataa tgaaataaga tcactaccgg    3240
gcgtattttt tgagttgtcg agattttcag gagctaagga agctaaaatg gagaaaaaaa    3300
tcactggata taccaccgtt gatatatccc aatggcatcg taaagaacat tttgaggcat    3360
ttcagtcagt tgctcaatgt acctataacc agaccgttca gctggatatt acggcctttt    3420
taaagaccgt aaagaaaaat aagcacaagt tttatccggc ctttattcac attcttgccc    3480
gcctgatgaa tgctcatccg gaattacgta tggcaatgaa agacggtgag ctggtgatat    3540
gggatagtgt tcacccttgt tacaccgttt tccatgagca aactgaaacg ttttcatcgc    3600
tctggagtga ataccacgac gatttccggc agtttctaca catatattcg caagatgtgg    3660
cgtgttacgg tgaaaacctg gcctatttcc ctaaagggtt tattgagaat atgttttttcg    3720 tctcagccaa tccctgggtg agtttcacca gttttgattt aaacgtggcc aatatggaca    3780
acttcttcgc ccccgttttc accatgggca atattatac gcaaggcgac aaggtgctga    3840
tgccgctggc gattcaggtt catcatgccg tttgtgatgg cttccatgtc ggcagatgct    3900
taatgaatac aacagtactg cgatgagtgg cagggcgggg cgtaaggcgc gccatttaaa    3960
tgaagttcct attccgaagt tcctattctc tagaaagtat aggaacttcg aagcagctcc    4020
agcctacaca atcgctcaag acgtgtaatg ctgcaatctg catgcaagct tggcactggc    4080
cacgcaaaaa ggccatccgt caggatggcc ttctgcttaa tttgatgcct ggcagtttat    4140
ggcgggcgtc ctgcccgcca ccctccgggc cgttgcttcg caacgttcaa atccgctccc    4200
ggcggatttg tcctactcag gagagcgttc accgacaaac aacagataaa acgaaaggcc    4260
cagtctttcg actgagcctt tcgttttatt tgatgcctgg cagttcccta ctctcgcatg    4320
gggagacccc acactaccat cgggggggcca tcgatgcagg tggcactttt cggggaaatg    4380
tgcgcggaac ccctatttgt ttatttttct aaatacattc aaatatgtat ccgctcatga    4440
gacaataacc ctgctgcaga ggcctgcatg caagcttggc gtaatcatgg tcatagctgt    4500
ttcctgtgtg aaattgttat ccgctcacaa ttccacacaa catacgagcc ggaagcataa    4560
agtgtaaagc ctggggtgcc taatgagtga gctaactcac attaattgcg ttgcgctcac    4620
tgcccgcttt ccagtcggga aacctgtcgt gccagctgca ttaatgaatc ggccaacgcg    4680
cggggagagg cggtttgcgt attgggcgct cttccgcttc ctcgctcact gactcgctgc    4740
gctcggtcgt tcggctgcgg cgagcggtat cagctcactc aaaggcggta atacggttat    4800
ccacagaatc aggggataac gcaggaaaga acatgtgagc aaaaggccag caaaaggcca    4860
ggaaccgtaa aaaggccgcg ttgctggcgt ttttccatag gctccgcccc cctgacgagc    4920
atcacaaaaa tcgacgctca agtcagaggt ggcgaaaccc gacaggacta taaagatacc    4980
aggcgtttcc ccctggaagc tccctcgtgc gctctcctgt tccgaccctg ccgcttaccg    5040
gatacctgtc cgcctttctc ccttcgggaa gcgtggcgct ttctcatagc tcacgctgta    5100
ggtatctcag ttcggtgtag gtcgttcgct ccaagctggg ctgtgtgcac gaaccccccg    5160
ttcagcccga ccgctgcgcc ttatccggta actatcgtct tgagtccaac ccggtaagac    5220
acgacttatc gccactggca gcagccactg gtaacaggat tagcagagcg aggtatgtag    5280
gcggtgctac agagttcttg aagtggtggc ctaactacgg ctacactaga agaacagtat    5340
ttggtatctg cgctctgctg aagccagtta ccttcggaaa aagagttggt agctcttgat    5400
```

| | |
|---|---|
| ccggcaaaca aaccaccgct ggtagcggtg gttttttgt ttgcaagcag cagattacgc | 5460 |
| gcagaaaaaa aggatctcaa gaagatcctt tgatcttttc tacggggtct gacgctcagt | 5520 |
| ggaacgaaaa ctcacgttaa gggattttgg tcatgagatt atcaaaaagg atcttcacct | 5580 |
| agatccttt aaattaaaaa tgaagtttta aatcaatcta agtatatat gagtaaactt | 5640 |
| ggtctgacag ttaccaatgc ttaatcagtg aggcacctat ctcagcgatc tgtctatttc | 5700 |
| gttcatccat agttgcctga ctccccgtcg tgtagataac tacgatacgg gagggcttac | 5760 |
| catctggccc cagtgctgca atgataccgc gagacccacg ctcaccggct ccagatttat | 5820 |
| cagcaataaa ccagccagcc ggaagggccg agcgcagaag tggtcctgca actttatccg | 5880 |
| cctccatcca gtctattaat tgttgccggg aagctagagt aagtagttcg ccagttaata | 5940 |
| gtttgcgcaa cgttgttgcc attgctacag gcatcgtggt gtcacgctcg tcgtttggta | 6000 |
| tggcttcatt cagctccggt tcccaacgat caaggcgagt tacatgatcc cccatgttgt | 6060 |
| gcaaaaaagc ggttagctcc ttcggtcctc cgatcgttgt cagaagtaag ttggccgcag | 6120 |
| tgttatcact catggttatg gcagcactgc ataattctct tactgtcatg ccatccgtaa | 6180 |
| gatgcttttc tgtgactggt gagtactcaa ccaagtcatt ctgagaatag tgtatgcggc | 6240 |
| gaccgagttg ctcttgcccg gcgtcaatac gggataatac cgcgccacat agcagaactt | 6300 |
| taaaagtgct catcattgga aaacgttctt cggggcgaaa actctcaagg atcttaccgc | 6360 |
| tgttgagatc cagttcgatg taacccactc gtgcacccaa ctgatcttca gcatctttta | 6420 |
| ctttcaccag cgtttctggg tgagcaaaaa caggaaggca aaatgccgca aaaagggaa | 6480 |
| taagggcgac acgaaaatgt tgaatactca tactcttcct ttttcaatat tattgaagca | 6540 |
| tttatcaggg ttattgtctc atgagcggat acatatttga atgtatttag aaaaataaac | 6600 |
| aaatagggg tccgcgcaca tttccccgaa aagtgccacc tgacgtctaa gaaaccatta | 6660 |
| ttatcatgac attaacctat aaaaataggc gtatcacgag gcccttcgt c | 6711 |

<210> SEQ ID NO 22
<211> LENGTH: 6867
<212> TYPE: DNA
<213> ORGANISM: Artificial Sequence
<220> FEATURE:
<223> OTHER INFORMATION: construct pINT-yebQ

<400> SEQUENCE: 22

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgaagatcct tgatcttttt | 420 |
| ctacggggtc tgacgctcag tggaacgaaa actcacgtta agggattttg tcatgagat | 480 |
| tatcaaaaag gatcttcacc tagatccttt taaactagtg aagttaccat cacgaaaaa | 540 |
| ggttatgctg cttttaagac ccactttcac atttaagttg ttttttctaat ccgcatatga | 600 |
| tcaattcaag gccgaataag aaggctggct ctgcaccttg gtgatcaaat aattcgatag | 660 |
| cttgtcgtaa taatggcggc atactatcag tagtaggtgt ttccctttct tctttagcga | 720 |
| cttgatgctc ttgatcttcc aatacgcaac ctaaagtaaa atgccccact gcgctgagtg | 780 |

| | |
|---|---|
| catataatgc attctctagt gaaaaacctt gttggcataa aaaggctaat tgattttcga | 840 |
| gagtttcata ctgtttttct gtaggccgtg tacctaaatg tacttttgct ccatcgcgat | 900 |
| gacttagtaa agcacatcta aaacttttag cgttattacg taaaaaatct tgccagcttt | 960 |
| cccttctaa agggcaaaag tgagtatggt gcctatctaa catctcaatg gctaaggcgt | 1020 |
| cgagcaaagc ccgcttattt tttacatgcc aatacaatgt aggctgctct acacctagct | 1080 |
| tctgggcgag tttacgggtt gttaaacctt cgattccgac ctcattaagc agctctaatg | 1140 |
| cgctgttaat cactttactt ttatctaaac gagacatact cttccttttt caatattatt | 1200 |
| gaagcattta tcagggttat tgtctcatga gcggatacat atttgaatgt atttagaaaa | 1260 |
| ataaacaaat aggggttccg cgcacatttc cccgaaaagt gccacctgaa attggccaga | 1320 |
| tgattaattc ctaattttg ttgacactct atcattgata gagttatttt accactccct | 1380 |
| atcagtgata gagaaaagtg aaatgaatag ttcgacaaaa atctagaaat aattttgttt | 1440 |
| aactttaaga aggagatata caagagctcg agtcgaagga gatagaacca tgccaaaagt | 1500 |
| tcaggccgac ggcctgccat tgccccagcg atacggtgcg atattaacca ttgtgattgg | 1560 |
| tatttcgatg gccgtccttg acggcgcaat cgccaacgtc gccctgccaa caatcgccac | 1620 |
| ggaccttcat gccacgccag ccagttccat ctgggtagtg aacgcctatc aaatcgccat | 1680 |
| tgtcatctcc ctgctctcgt tttcgtttct gggcgatatg tttggctatc gacgtattta | 1740 |
| taaatgcggt ctggtcgttt ttctgttgtc ttcactgttc tgcgcccttt ctgattcgct | 1800 |
| gcaaatgctc acccttgcgc gtgtcataca aggtttcggc ggtgcagcgt tgatgagcgt | 1860 |
| taataccgca cttatccgcc tgatctatcc acaacgtttt ctgggtagag ggatgggcat | 1920 |
| aaactcgttt attgttgccg tctcttctgc tgccgggccg acaattgctg cagcaatcct | 1980 |
| ctccatcgca tcctggaaat ggttatttt aatcaacgta ccgttaggta ttatcgccct | 2040 |
| gcttctggcg atgcgttttc tgccacccaa tggttctcgc gccagtaaac ccgtttcga | 2100 |
| cctgcccagc gccgtgatga acgcgttaac cttcggcctg cttatcactg cgttgagtgg | 2160 |
| tttcgctcag gggcaatcgc tgacgttaat tgctgcggaa ctggtggtaa tggttgttgt | 2220 |
| tggtattttc tttattcgcc gccagctttc tcttcccgta ccgctgctac cggtggattt | 2280 |
| actgcgtatc ccgctgtttt cacttttctat ttgcacatct gtttgctctt tctgcgcaca | 2340 |
| aatgctggca atggtttccc tgcccttta cctgcaaacc gtgctcgggc gtagtgaagt | 2400 |
| cgaaacaggt ttacttctga caccgtggcc gttagcaacg atggtgatgg ctccgctggc | 2460 |
| aggctatttg attgaacgcg tacatgcagg attgctgggg ctttagggt tgttcatcat | 2520 |
| ggctgcgggg ctttttccc tggttctgct gcccgcgtca cctgcggata tcaatattat | 2580 |
| ctggccgatg atcttatgtg gtgctggatt tggcttattc cagtcaccca ataaccacac | 2640 |
| cattattacc tccgcgcctc gcgaacgtag cggtggagcc agtggcatgt taggaacggc | 2700 |
| tcgtctactg ggtcagagta gcggcgcggc gctggtggcg ctgatgctaa atcagtttgg | 2760 |
| agataatggt acacacgtct cgctgatggc tgcggctatt ctggcagtga ttgctgcctg | 2820 |
| tgtcagtggt ttacgtatca ctcagccacg atccagggca taataaatcg atactagcat | 2880 |
| aacccttgg ggcctctaaa cgcgtcgaca cgcaaaaagg ccatccgtca ggatggcctt | 2940 |
| ctgcttaatt tgatgcctgg cagtttatgg cgggcgtcct gcccgccacc ctccgggccg | 3000 |
| ttgcttcgca acgttcaaat ccgctcccgg cggatttgtc ctactcagga gagcgttcac | 3060 |
| cgacaaacaa cagataaaac gaaaggccca gtctttcgac tgagcctttc gttttatttg | 3120 |

```
atgcctggca gttccctact ctcgcatggg gagaccccac actaccatca tgtatgaata   3180
tcctccttag ttcctattcc gaagttccta ttctctagaa agtataggaa cttcggcgcg   3240
tcctacctgt gacggaagat cacttcgcag aataaataaa tcctggtgtc cctgttgata   3300
ccgggaagcc ctgggccaac ttttggcgaa aatgagacgt tgatcggcac gtaagaggtt   3360
ccaactttca ccataatgaa ataagatcac taccggcgt atttttttgag ttgtcgagat   3420
tttcaggagc taaggaagct aaaatggaga aaaaaatcac tggatatacc accgttgata   3480
tatcccaatg gcatcgtaaa gaacattttg aggcatttca gtcagttgct caatgtacct   3540
ataaccagac cgttcagctg gatattacgg ccttttttaaa gaccgtaaag aaaaataagc   3600
acaagtttta tccggccttt attcacattc ttgcccgcct gatgaatgct catccggaat   3660
tacgtatggc aatgaaagac ggtgagctgg tgatatggga tagtgttcac ccttgttaca   3720
ccgtttttcca tgagcaaact gaaacgtttt catcgctctg gagtgaatac cacgacgatt   3780
tccggcagtt tctacacata tattcgcaag atgtggcgtg ttacggtgaa aacctggcct   3840
atttccctaa agggtttatt gagaatatgt ttttcgtctc agccaatccc tgggtgagtt   3900
tcaccagttt tgatttaaac gtggccaata tggacaactt cttcgccccc gttttcacca   3960
tgggcaaata ttatacgcaa ggcgacaagg tgctgatgcc gctggcgatt caggttcatc   4020
atgccgtttg tgatggcttc catgtcggca gatgcttaat gaatacaaca gtactgcgat   4080
gagtggcagg gcgggggcgta aggcgcgcca tttaaatgaa gttcctattc cgaagttcct   4140
attctctaga aagtatagga acttcgaagc agctccagcc tacacaatcg ctcaagacgt   4200
gtaatgctgc aatctgcatg caagcttggc actggccacg caaaaaggcc atccgtcagg   4260
atggccttct gcttaatttg atgcctggca gtttatggcg ggcgtcctgc ccgccaccct   4320
ccgggccgtt gcttcgcaac gttcaaatcc gctcccggcg gatttgtcct actcaggaga   4380
gcgttcaccg acaaacaaca gataaaacga aaggcccagt ctttcgactg agcctttcgt   4440
tttatttgat gcctggcagt tccctactct cgcatgggga gaccccacac taccatcggg   4500
gggccatcga tgcaggtggc acttttcggg gaaatgtgcg cggaacccct atttgtttat   4560
ttttctaaat acattcaaat atgtatccgc tcatgagaca ataaccctgc tgcagaggcc   4620
tgcatgcaag cttggcgtaa tcatggtcat agctgtttcc tgtgtgaaat tgttatccgc   4680
tcacaattcc acacaacata cgagccggaa gcataaagtg taaagcctgg ggtgcctaat   4740
gagtgagcta actcacatta attgcgttgc gctcactgcc cgctttccag tcgggaaacc   4800
tgtcgtgcca gctgcattaa tgaatcggcc aacgcgcggg gagaggcggt ttgcgtattg   4860
ggcgctcttc cgcttcctcg ctcactgact cgctgcgctc ggtcgttcgg ctgcggcgag   4920
cggtatcagc tcactcaaag gcggtaatac ggttatccac agaatcaggg gataacgcag   4980
gaaagaacat gtgagcaaaa ggccagcaaa aggccaggaa ccgtaaaaag gccgcgttgc   5040
tggcgttttt ccataggctc cgcccccctg acgagcatca caaaaatcga cgctcaagtc   5100
agaggtggcg aaacccgaca ggactataaa gataccaggc gtttccccct ggaagctccc   5160
tcgtgcgctc tcctgttccg accctgccgc ttaccggata cctgtccgcc tttctccctt   5220
cgggaagcgt ggcgctttct catagctcac gctgtaggta tctcagttcg gtgtaggtcg   5280
ttcgctccaa gctgggctgt gtgcacgaac cccccgttca gcccgaccgc tgcgccttat   5340
ccggtaacta tcgtcttgag tccaacccgg taagacacga cttatcgcca ctggcagcag   5400
ccactggtaa caggattagc agagcgaggt atgtaggcgg tgctacagag ttcttgaagt   5460
ggtggcctaa ctacggctac actagaagaa cagtatttgg tatctgcgct ctgctgaagc   5520
```

```
cagttacctt cggaaaaaga gttggtagct cttgatccgg caaacaaacc accgctggta    5580
gcggtggttt ttttgtttgc aagcagcaga ttacgcgcag aaaaaaagga tctcaagaag    5640
atcctttgat cttttctacg gggtctgacg ctcagtggaa cgaaaactca cgttaaggga    5700
ttttggtcat gagattatca aaaggatct tcacctagat cctttaaat taaaaatgaa     5760 gttttaaatc aatctaaagt atatatgagt aaacttggtc tgacagttac caatgcttaa    5820
tcagtgaggc acctatctca gcgatctgtc tatttcgttc atccatagtt gcctgactcc    5880
ccgtcgtgta gataactacg atacgggagg gcttaccatc tggccccagt gctgcaatga    5940
taccgcgaga cccacgctca ccggctccag atttatcagc aataaaccag ccagccggaa    6000
gggccgagcg cagaagtggt cctgcaactt tatccgcctc catccagtct attaattgtt    6060
gccgggaagc tagagtaagt agttcgccag ttaatagttt gcgcaacgtt gttgccattg    6120
ctacaggcat cgtggtgtca cgctcgtcgt ttggtatggc ttcattcagc tccggttccc    6180
aacgatcaag gcgagttaca tgatccccca tgttgtgcaa aaaagcggtt agctccttcg    6240
gtcctccgat cgttgtcaga agtaagttgg ccgcagtgtt atcactcatg gttatggcag    6300
cactgcataa ttctcttact gtcatgccat ccgtaagatg cttttctgtg actggtgagt    6360
actcaaccaa gtcattctga aatagtgta tgcggcgacc gagttgctct tgcccggcgt    6420
caatacggga taataccgcg ccacatagca gaactttaaa agtgctcatc attggaaaac    6480
gttcttcggg gcgaaaactc tcaaggatct taccgctgtt gagatccagt tcgatgtaac    6540
ccactcgtgc acccaactga tcttcagcat cttttacttt caccagcgtt tctgggtgag    6600
caaaaacagg aaggcaaaat gccgcaaaaa agggaataag ggcgacacgg aaatgttgaa    6660
tactcatact cttccttttt caatattatt gaagcattta tcagggttat tgtctcatga    6720
gcggatacat atttgaatgt atttagaaaa ataaacaaat aggggttccg cgcacatttc    6780
cccgaaaagt gccacctgac gtctaagaaa ccattattat catgacatta acctataaaa    6840
ataggcgtat cacgaggccc tttcgtc                                        6867
```

<210> SEQ ID NO 23
<211> LENGTH: 6768
<212> TYPE: DNA
<213> ORGANISM: Artificial Sequence
<220> FEATURE:
<223> OTHER INFORMATION: construct pINT-proP

<400> SEQUENCE: 23

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct ttgatctttt    420
ctacggggtc tgacgctcag tggaacgaaa actcacgtta agggattttg gtcatgagat    480
tatcaaaaag gatcttcacc tagatccttt aaactagtg aagttaccat cacggaaaaa    540
ggttatgctg cttttaagac ccactttcac atttaagttg ttttttctaat ccgcatatga    600 tcaattcaag gccgaataag aaggctggct ctgcaccttg gtgatcaaat aattcgatag    660
```

```
cttgtcgtaa taatggcggc atactatcag tagtaggtgt ttcccttttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgttttttct gtaggccgtg tacctaaatg tactttttgct ccatcgcgat    900
gacttagtaa agcacatcta aaacttttag cgttattacg taaaaaatct tgccagcttt    960
cccctttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacggggtt gttaaacctt cgattccgac ctcattaagc agctctaatg   1140
cgctgttaat cactttactt ttatctaaac gagacatact cttcctttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgccgaacaa   1500
agctgaaacc tccccggcga aactgcgtct gaaagccttc ctgaaacgta tcaagattat   1560
gaacaccacc gaaaacagca aacagaagcc ggttaacgtg gttgcatttg ctttcctgct   1620
gaccgcgttt ctgacgggta tcgccagctc tttccaaacc ccgacgctga gcctgtttct   1680
ggcgcaggaa attcaagtct ctccgtttat ggtgggcatg ttctatacct caaatgcagt   1740
gctgggcatc gttctgtcgc agattctggc taaatacagt gattcccaag atgaccgtcg   1800
caagattatc attttctgca gtctgctggc gatcggcggt tgtatcaccct tcgcctacaa   1860
ccgtaactac tacgtgctga tgttttttcgc gacgttcctg ctgtccctgg gtagttccgc   1920
aaacccgcag gcatttgcac tggcacgtga atatgcagac tacaccaaac gcgaagctat   1980
catgttacc acgattatgc gcacgcagat cagcctggca tggattgttg gcccgccgct   2040
gtcattctcg attgcgctgg gctggggttt tgaatatatg tacatggtcg cggcctcagc   2100
atttctgctg tgcgctatca ttgctaaagc gctgctgccg tatgtgccgc gtaaagccgt   2160
cgtgccgctg accaagccgg atgaagttgc gggtctgccg gccaaaaata aaaagcagag   2220
tgacaagcaa tccatccgcc tgctgtttat tacgtgcttc ctgatgtgga gttgtaacgg   2280
catgtatctg atctccatgc cgctgcatgt tattaatgaa ctgcacctga gtgaacgtct   2340
ggcgggcatt ctgatgggta ccgcagctgg cctggaaatc ccggtgatgc tgattgccgg   2400
ctatctgacc aaatacctga cgaaaaagtc tctgatcctg accgccctgt tcatgggtct   2460
gttttttctat attggcatgc tgtttgcaga acagacgtgg caactggtcg ccctgcaggc   2520
atttaacgct atcttcattg gtatcattgc gaccctgggc atggtgtact ttcaagatct   2580
gatgccgggc aaaatggggtt cagccaccac gctgttctcg aacgcggcca aatcatcgtg   2640
gatcgttgca ggtccgtttg tcggcatcat tgctcagatt tggaattata gctctgtgtt   2700
ctacatcagc attgttctgg tcgcggtgtc tctgtttagc atgtctaaag ttaagagcgt   2760
ctaataaatc gatactagca taccccttg gggcctctaa acgcgtcgac acgcaaaaag   2820
gccatccgtc aggatggcct tctgcttaat ttgatgcctg gcagtttatg gcgggcgtcc   2880
tgcccgccac cctccgggcc gttgcttcgc aacgttcaaa tccgctcccg gcggatttgt   2940
cctactcagg agagcgttca ccgacaaaca acagataaaa cgaaaggccc agtctttcga   3000
ctgagccttt cgttttattt gatgcctggc agttccctac tctcgcatgg ggagaccca    3060
```

```
cactaccatc atgtatgaat atcctcctta gttcctattc cgaagttcct attctctaga    3120
aagtatagga acttcggcgc gtcctacctg tgacggaaga tcacttcgca gaataaataa    3180
atcctggtgt ccctgttgat accgggaagc cctgggccaa cttttggcga aaatgagacg    3240
ttgatcggca cgtaagaggt tccaactttc accataatga aataagatca ctaccgggcg    3300
tattttttga gttgtcgaga ttttcaggag ctaaggaagc taaaatggag aaaaaaatca    3360
ctggatatac caccgttgat atatcccaat ggcatcgtaa agaacatttt gaggcatttc    3420
agtcagttgc tcaatgtacc tataaccaga ccgttcagct ggatattacg gcctttttaa    3480
agaccgtaaa gaaaaataag cacaagtttt atccggcctt tattcacatt cttgcccgcc    3540
tgatgaatgc tcatccggaa ttacgtatgg caatgaaaga cggtgagctg gtgatatggg    3600
atagtgttca cccttgttac accgttttcc atgagcaaac tgaaacgttt tcatcgctct    3660
ggagtgaata ccacgacgat ttccggcagt ttctacacat atattcgcaa gatgtggcgt    3720
gttacggtga aaacctggcc tatttcccta aagggtttat tgagaatatg tttttcgtct    3780
cagccaatcc ctgggtgagt ttcaccagtt ttgatttaaa cgtggccaat atggacaact    3840
tcttcgcccc cgttttcacc atgggcaaat attatacgca aggcgacaag gtgctgatgc    3900
cgctggcgat tcaggttcat catgccgttt gtgatggctt ccatgtcggc agatgcttaa    3960
tgaatacaac agtactgcga tgagtggcag ggcggggcgt aaggcgcgcc atttaaatga    4020
agttcctatt ccgaagttcc tattctctag aaagtatagg aacttcgaag cagctccagc    4080
ctacacaatc gctcaagacg tgtaatgctg caatctgcat gcaagcttgg cactggccac    4140
gcaaaaaggc catccgtcag gatggccttc tgcttaattt gatgcctggc agtttatggc    4200
gggcgtcctg cccgccaccc tccgggccgt tgcttcgcaa cgttcaaatc cgctcccggc    4260
ggatttgtcc tactcaggag agcgttcacc gacaaacaac agataaaacg aaaggcccag    4320
tctttcgact gagcctttcg ttttatttga tgcctggcag ttccctactc tcgcatgggg    4380
agaccccaca ctaccatcgg ggggccatcg atgcaggtgg cacttttcgg ggaaatgtgc    4440
gcggaacccc tatttgttta ttttttctaaa tacattcaaa tatgtatccg ctcatgagac    4500
aataaccctg ctgcagaggc ctgcatgcaa gcttggcgta atcatggtca tagctgtttc    4560
ctgtgtgaaa ttgttatccg ctcacaattc cacacaacat acgagccgga agcataaagt    4620
gtaaagcctg gggtgcctaa tgagtgagct aactcacatt aattgcgttg cgctcactgc    4680
ccgctttcca gtcgggaaac ctgtcgtgcc agctgcatta atgaatcggc caacgcgcgg    4740
ggagaggcgg tttgcgtatt gggcgctctt ccgcttcctc gctcactgac tcgctgcgct    4800
cggtcgttcg gctgcggcga gcggtatcag ctcactcaaa ggcggtaata cggttatcca    4860
cagaatcagg ggataacgca ggaaagaaca tgtgagcaaa aggccagcaa aaggccagga    4920
accgtaaaaa ggccgcgttg ctggcgtttt tccataggct ccgcccccct gacgagcatc    4980
acaaaaatcg acgctcaagt cagaggtggc gaaacccgac aggactataa agataccagg    5040
cgtttccccc tggaagctcc ctcgtgcgct ctcctgttcc gaccctgccg cttaccggat    5100
acctgtccgc ctttctccct tcgggaagcg tggcgctttc tcatagctca cgctgtaggt    5160
atctcagttc ggtgtaggtc gttcgctcca agctgggctg tgtgcacgaa ccccccgttc    5220
agcccgaccg ctgcgcctta tccggtaact atcgtcttga gtccaacccg gtaagacacg    5280
acttatcgcc actggcagca gccactggta acaggattag cagagcgagg tatgtaggcg    5340
gtgctacaga gttcttgaag tggtggccta actacggcta cactagaaga acagtatttg    5400
```

```
gtatctgcgc tctgctgaag ccagttacct tcggaaaaag agttggtagc tcttgatccg    5460
gcaaacaaac caccgctggt agcggtggtt tttttgtttg caagcagcag attacgcgca    5520 gaaaaaagg atctcaagaa gatcctttga tcttttctac ggggtctgac gctcagtgga     5580
acgaaaactc acgttaaggg attttggtca tgagattatc aaaaaggatc ttcacctaga    5640
tccttttaaa ttaaaaatga gttttaaat caatctaaag tatatatgag taaacttggt     5700
ctgacagtta ccaatgctta atcagtgagg cacctatctc agcgatctgt ctatttcgtt    5760
catccatagt tgcctgactc cccgtcgtgt agataactac gatacgggag ggcttaccat    5820
ctggccccag tgctgcaatg ataccgcgag acccacgctc accggctcca gatttatcag    5880
caataaacca gccagccgga agggccgagc gcagaagtgg tcctgcaact ttatccgcct    5940
ccatccagtc tattaattgt tgccgggaag ctagagtaag tagttcgcca gttaatagtt    6000
tgcgcaacgt tgttgccatt gctacaggca tcgtggtgtc acgctcgtcg tttggtatgg    6060
cttcattcag ctccggttcc caacgatcaa ggcgagttac atgatccccc atgttgtgca    6120
aaaaagcggt tagctccttc ggtcctccga tcgttgtcag aagtaagttg gccgcagtgt    6180
tatcactcat ggttatggca gcactgcata attctcttac tgtcatgcca tccgtaagat    6240
gcttttctgt gactggtgag tactcaacca agtcattctg agaatagtgt atgcggcgac    6300
cgagttgctc ttgcccggcg tcaatacggg ataataccgc gccacatagc agaactttaa    6360
aagtgctcat cattggaaaa cgttcttcgg ggcgaaaact ctcaaggatc ttaccgctgt    6420
tgagatccag ttcgatgtaa cccactcgtg cacccaactg atcttcagca tcttttactt    6480
tcaccagcgt ttctgggtga gcaaaaacag gaaggcaaaa tgccgcaaaa aagggaataa    6540
gggcgacacg gaaatgttga atactcatac tcttcctttt tcaatattat tgaagcattt    6600
atcagggtta ttgtctcatg agcggataca tatttgaatg tatttagaaa aataaacaaa    6660
taggggttcc gcgcacattt ccccgaaaag tgccacctga cgtctaagaa accattatta    6720
tcatgacatt aacctataaa aataggcgta tcacgaggcc ctttcgtc                 6768

<210> SEQ ID NO 24
<211> LENGTH: 6672
<212> TYPE: DNA
<213> ORGANISM: Artificial Sequence
<220> FEATURE:
<223> OTHER INFORMATION: construct pINT-Cn-setA

<400> SEQUENCE: 24
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct tgatcttttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctg cttttaagac ccactttcac atttaagttg ttttttctaat ccgcatatga     600 tcaattcaag gccgaataag aaggctggct ctgcaccttg gtgatcaaat aattcgatag     660
cttgtcgtaa taatggcggc atactatcag tagtaggtgt ttccctttct tctttagcga     720
```

-continued

```
cttgatgctc ttgatcttcc aatacgcaac ctaaagtaaa atgccccact gcgctgagtg      780
catataatgc attctctagt gaaaaacctt gttggcataa aaaggctaat tgattttcga      840
gagtttcata ctgttttcct gtaggccgtg tacctaaatg tacttttgct ccatcgcgat      900 gactagtaa agcacatcta aaacttttag cgttattacg taaaaaatct tgccagcttt      960
ccccttctaa agggcaaaag tgagtatggt gcctatctaa catctcaatg gctaaggcgt     1020
cgagcaaagc ccgcttattt tttacatgcc aatacaatgt aggctgctct acacctagct     1080
tctgggcgag tttacgggtt gttaaacctt cgattccgac ctcattaagc agctctaatg     1140
cgctgttaat cactttactt ttatctaaac gagacatact cttccttttt caatattatt     1200
gaagcattta tcagggttat tgtctcatga gcggatacat atttgaatgt atttagaaaa     1260
ataaacaaat aggggttccg cgcacatttc cccgaaaagt gccacctgaa attggcagaa    1320
tgattaattc ctaattttg ttgacactct atcattgata gagttatttt accactccct      1380
atcagtgata gagaaaagtg aaatgaatag ttcgacaaaa atctagaaat aattttgttt     1440
aactttaaga aggagatata caagagctcg agtcgaagga gatagaacca tgctgtggtt    1500
tctgacccgt gctcgtcgct tcaatccggt ttatgcggcc tttatggccg tcagcttcat    1560
gattggtgtg gccggtgcac tgcaggcacc gaccctgtct ctgtttctga cgcgtgaagt    1620
tgaagtccgc ccgttttggg ttggtctgtt ctacacggtc aacgcaattg ctggcatcgg    1680
tgtgagtctg ctgctggcca aacgtagtga ttcccaaggc gaccgtcgca aactgattat    1740
ggtgtgctgt gttatggcgg tcgccaactg cgtcctgttt gcattcaatc gccattatct    1800
gaccctgatc acgctgggtg tgatgtttgc aagcattgct aataccgcga tgccgcagat    1860
cttcgcactg gctcgtgaat acgccgatcg ttctgcacgc gaagtggtta tgtttagctc    1920
tattatgcgc gcccaactga gtctggcatg ggttattggc ccgccgctgt ccttcatgct    1980
ggccctgaaa tatggttta ccacgatgtt cctgattgca gctggcattt ttgtgatctc     2040
actggctctg attatcttcg cgctgccgtc ggtgccgcgt gttgaacagc cggccgaagt    2100
ggcaattacc caagttagcg gttggaaaga ttctaacgtt cgcatgctgt ttatcgcctc    2160
aatgctgatg tggacctgta atacgatgta tattatcgac atgccgctgt ggatttcgca    2220
ggatctgggt ctgccggatg aactggccgg tctgctgatg ggtaccgccg caggcattga    2280
aatcccggct atgatcctgg cgggttatta cgtgaaacgt tttggcaaac gcaacatgat    2340
ggtcgcagct gtggcggccg gtattctgtt ttacgttggc ctgatcctgt tccatagcaa    2400
aacggcgctg gtcgtgctgc agctgtttaa tgccgtcttc attggtatta tgcaggcat     2460 cggtatgctg tggtttcaag atctgatgcc gggtcgtccg ggtagcgcaa ccaccctgtt    2520
caccaactca atttcgacgg gcgtgattct ggccggtatt ctgcagggtg ccctggcaga    2580
aggttttggt cactatagtg tgtactggct gatggcagct ctggctgtta tcgcgctgtt    2640
cctgaccagc cgcgttaaaa acgtctaata aatcgatact agcataaccc cttgggcct    2700 ctaaacgcgt cgacacgcaa aaaggccatc cgtcaggatg gccttctgct taatttgatg    2760
cctggcagtt tatggcgggc gtcctgcccg ccaccctccg ggccgttgct tcgcaacgtt    2820
caaatccgct cccggcggat ttgtcctact caggagagcg ttcaccgaca acaacagat     2880 aaaacgaaag gcccagtctt tcgactgagc ctttcgtttt atttgatgcc tggcagttcc    2940
ctactctcgc atggggagac cccacactac catcatgtat gaatatcctc cttagttcct    3000
attccgaagt tcctattctc tagaaagtat aggaacttcg gcgcgtccta cctgtgacgg    3060
```

```
aagatcactt cgcagaataa ataaatcctg gtgtccctgt tgataccggg aagccctggg   3120 ccaactttg gcgaaaatga gacgttgatc ggcacgtaag aggttccaac tttcaccata    3180
atgaaataag atcactaccg ggcgtatttt ttgagttgtc gagattttca ggagctaagg   3240
aagctaaaat ggagaaaaaa atcactggat ataccaccgt tgatatatcc caatggcatc   3300
gtaaagaaca ttttgaggca tttcagtcag ttgctcaatg tacctataac cagaccgttc   3360
agctggatat tacggccttt ttaaagaccg taaagaaaaa taagcacaag ttttatccgg   3420
cctttattca cattcttgcc cgcctgatga atgctcatcc ggaattacgt atggcaatga   3480
aagacggtga gctggtgata tgggatagtg ttcacccttg ttacaccgtt ttccatgagc   3540
aaactgaaac gttttcatcg ctctggagtg aataccacga cgatttccgg cagtttctac   3600
acatatattc gcaagatgtg gcgtgttacg gtgaaaacct ggcctatttc cctaaagggt   3660
ttattgagaa tatgtttttc gtctcagcca atccctgggt gagtttcacc agttttgatt   3720
taaacgtggc caatatggac aacttcttcg cccccgtttt caccatgggc aaatattata   3780
cgcaaggcga caaggtgctg atgccgctgg cgattcaggt tcatcatgcc gtttgtgatg   3840
gcttccatgt cggcagatgc ttaatgaata caacagtact gcgatgagtg gcagggcggg   3900
gcgtaaggcg cgccatttaa atgaagttcc tattccgaag ttcctattct ctagaaagta   3960
taggaacttc gaagcagctc cagcctacac aatcgctcaa gacgtgtaat gctgcaatct   4020
gcatgcaagc ttggcactgg ccacgcaaaa aggccatccg tcaggatggc cttctgctta   4080
atttgatgcc tggcagttta tggcgggcgt cctgcccgcc accctccggg ccgttgcttc   4140
gcaacgttca aatccgctcc cggcggattt gtcctactca ggagagcgtt caccgacaaa   4200
caacagataa aacgaaaggc ccagtctttc gactgagcct ttcgttttat ttgatgcctg   4260
gcagttccct actctcgcat ggggagaccc cacactacca tcgggggggcc atcgatgcag   4320 gtggcacttt tcggggaaat gtgcgcggaa cccctatttg tttatttttc taaatacatt   4380
caaatatgta tccgctcatg agacaataac cctgctgcag aggcctgcat gcaagcttgg   4440
cgtaatcatg gtcatagctg tttcctgtgt gaaattgtta tccgctcaca attccacaca   4500
acatacgagc cggaagcata aagtgtaaag cctggggtgc ctaatgagtg agctaactca   4560
cattaattgc gttgcgctca ctgcccgctt tccagtcggg aaacctgtcg tgccagctgc   4620
attaatgaat cggccaacgc gcggggagag gcggtttgcg tattgggcgc tcttccgctt   4680
cctcgctcac tgactcgctg cgctcggtcg ttcggctgcg gcgagcggta tcagctcact   4740
caaaggcggt aatacggtta tccacagaat caggggataa cgcaggaaag aacatgtgag   4800
caaaaggcca gcaaaaggcc aggaaccgta aaaaggccgc gttgctggcg ttttttccata   4860 ggctccgccc ccctgacgag catcacaaaa atcgacgctc aagtcagagg tggcgaaacc   4920
cgacaggact ataaagatac caggcgtttc ccctggaag ctccctcgtg cgctctcctg   4980
ttccgaccct gccgcttacc ggatacctgt ccgcctttct cccttcggga agcgtggcgc   5040
tttctcatag ctcacgctgt aggtatctca gttcggtgta ggtcgttcgc tccaagctgg   5100
gctgtgtgca cgaaccccc gttcagcccg accgctgcgc cttatccggt aactatcgtc   5160
ttgagtccaa cccggtaaga cacgacttat cgccactggc agcagccact ggtaacagga   5220
ttagcagagc gaggtatgta ggcggtgcta cagagttctt gaagtggtgg cctaactacg   5280
gctacactag aagaacagta tttggtatct gcgctctgct gaagccagtt accttcggaa   5340
aaagagttgg tagctcttga tccggcaaac aaaccaccgc tggtagcggt ggttttttg    5400 tttgcaagca gcagattacg cgcagaaaaa aaggatctca agaagatcct ttgatctttt    5460
```

```
ctacggggtc tgacgctcag tggaacgaaa actcacgtta agggattttg gtcatgagat    5520
tatcaaaaag gatcttcacc tagatccttt taaattaaaa atgaagtttt aaatcaatct    5580
aaagtatata tgagtaaact tggtctgaca gttaccaatg cttaatcagt gaggcaccta    5640
tctcagcgat ctgtctattt cgttcatcca tagttgcctg actcccgtc gtgtagataa     5700 ctacgatacg ggagggctta ccatctggcc ccagtgctgc aatgataccg cgagacccac    5760
gctcaccggc tccagattta tcagcaataa accagccagc cggaagggcc gagcgcagaa    5820
gtggtcctgc aactttatcc gcctccatcc agtctattaa ttgttgccgg gaagctagag    5880
taagtagttc gccagttaat agtttgcgca acgttgttgc cattgctaca ggcatcgtgg    5940
tgtcacgctc gtcgtttggt atggcttcat tcagctccgg ttcccaacga tcaaggcgag    6000
ttacatgatc ccccatgttg tgcaaaaaag cggttagctc cttcggtcct ccgatcgttg    6060
tcagaagtaa gttggccgca gtgttatcac tcatggttat ggcagcactg cataattctc    6120
ttactgtcat gccatccgta agatgctttt ctgtgactgg tgagtactca accaagtcat    6180
tctgagaata gtgtatgcgg cgaccgagtt gctcttgccc ggcgtcaata cgggataata    6240
ccgcgccaca tagcagaact ttaaaagtgc tcatcattgg aaaacgttct cggggcgaa     6300 aactctcaag gatcttaccg ctgttgagat ccagttcgat gtaacccact cgtgcaccca    6360
actgatcttc agcatctttt actttcacca gcgtttctgg gtgagcaaaa acaggaaggc    6420
aaaatgccgc aaaaaaggga ataagggcga cacggaaatg ttgaatactc atactcttcc    6480
tttttcaata ttattgaagc atttatcagg gttattgtct catgagcgga tacatatttg    6540
aatgtattta gaaaaataaa caaatagggg ttccgcgcac atttccccga aaagtgccac    6600
ctgacgtcta agaaaccatt attatcatga cattaaccta taaaaatagg cgtatcacga    6660 ggcccttcg tc                                                         6672
```

<210> SEQ ID NO 25
<211> LENGTH: 7074
<212> TYPE: DNA
<213> ORGANISM: Artificial Sequence
<220> FEATURE:
<223> OTHER INFORMATION: construct pINT-spoVB

<400> SEQUENCE: 25

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct tgatctttt    420 ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg ctttttaagac ccactttcac atttaagttg ttttttctaat ccgcatatga    600 tcaattcaag gccgaataag aaggctggct ctgcaccttg gtgatcaaat aattcgatag    660
cttgtcgtaa taatgcggc atactatcag tagtaggtgt ttcccttct tctttagcga    720 cttgatgctc ttgatcttcc aatacgcaac ctaaagtaaa atgccccact gcgctgagtg    780
```

| | |
|---|---|
| catataatgc attctctagt gaaaaacctt gttggcataa aaaggctaat tgattttcga | 840 |
| gagtttcata ctgtttttct gtaggccgtg tacctaaatg tacttttgct ccatcgcgat | 900 |
| gacttagtaa agcacatcta aaacttttag cgttattacg taaaaaatct tgccagcttt | 960 |
| cccttctaa agggcaaaag tgagtatggt gcctatctaa catctcaatg gctaaggcgt | 1020 |
| cgagcaaagc ccgcttattt tttacatgcc aatacaatgt aggctgctct acacctagct | 1080 |
| tctgggcgag tttacgggtt gttaaacctt cgattccgac ctcattaagc agctctaatg | 1140 |
| cgctgttaat cactttactt ttatctaaac gagacatact cttccttttt caatattatt | 1200 |
| gaagcattta tcagggttat tgtctcatga gcggatacat atttgaatgt atttagaaaa | 1260 |
| ataaacaaat aggggttccg cgcacatttc cccgaaaagt gccacctgaa attggccaga | 1320 |
| tgattaattc ctaattttg ttgacactct atcattgata gagttatttt accactccct | 1380 |
| atcagtgata gagaaaagtg aaatgaatag ttcgacaaaa atctagaaat aattttgttt | 1440 |
| aactttaaga aggagatata caagagctcg agtcgaagga gatagaacca tgaatgactc | 1500 |
| ggtcggtgct aagcgtcaaa gtgcgtggaa gggtgcgttc gtcctggtcg ttgcgggcat | 1560 |
| cgttaccaag atcctgtctg ccgtgtatcg tgttccgttt cagaacattg tcggcgatgt | 1620 |
| gggtttctat atctaccagc aagtttaccc gtttctgggc attgcggtca tgctgagtac | 1680 |
| ctccggtttt ccggtgatca tctcgaagct gatgaacgat tacagcgacc ataaacagaa | 1740 |
| gattatgaag atcagtgcac tgtatgtgac ggcagcaggt ctggttctgt ttgccctgat | 1800 |
| gtacgcaggt gcagctccgc tggcgggctt catgggtgat gaccgtctgg tcatgctgat | 1860 |
| tcgcgtggcg gcctttgctt tcatcctgtt tccgttcacc gcggttttc gcggctattt | 1920 |
| ccagggtgtg cacgacatga tgccgtctgc tctgagtcag attacggaac aactgctgcg | 1980 |
| tgtggcagtt ctgctgggcc tgtcttttg gctgctgaaa tccggtcgtt cactgtacgc | 2040 |
| agctggtgca ggtgcagcat caggttcgat tgcaggtagt ctggcagctc tgtgcgttct | 2100 |
| ggcagtcttc tggtataaac gtgaagaaac caaaaaggat ggcggtcata tcgaaacggc | 2160 |
| ggttattatc aaaaagctgc tgctgtactc cgtgaccatt tgtatcagct ctgttctgat | 2220 |
| gctgctgctg cagctggttg atgcgctgaa cctgtattcg ctgctgagcg acggcaccga | 2280 |
| atcacatgcg gccaaacaac tgaagggcat ttacgaccgt ggtcagccgc tgctgcaact | 2340 |
| gggtacggtg tttgcggttt ccattgcagc ttcactggtc ccgagcatct ctaaagccgt | 2400 |
| gcacgaaaat aagccgttca ttatcaaaga aaaggctacc tctgcggtca aactgtgcct | 2460 |
| ggcggtgggc attggtgcta gtgcgggcct gttttgtatt ctggaaccgg ttaacatcat | 2520 |
| gctgttccag aattccgaag gtacccagac gctgcaaatc tttagtctgt ccattttctt | 2580 |
| tgcctcaatc gcactgaccg cagcagcaat cctgcaaggt gcaggtcata cggtgttccc | 2640 |
| ggcagtcagc gtgctggctg gcggtgcgct gaaatgggtc ctgaacgtgt ggctggttcc | 2700 |
| gggtggggt attaccggtg ctgcactggc tacggttctg gcatttgcag cagtcgcatg | 2760 |
| cctgaacctg cgtcgcatct ggtcgaaagg ttggctgacc aatattggcg gtgtgatcgc | 2820 |
| acgtctgtgc tggtgtagcc tgctgatggt gttttcctg ctggtctata tgaaactgtg | 2880 |
| gcagctgttt gttccggtca gccgtgccgg cgcagtttgc gaatcactgt cggccagcgt | 2940 |
| gattggcggt ctgctgttca tctactgtat gatccgcatg aagatcttca ccgatgaaga | 3000 |
| actgagcggc ctgccgttcg gttctgcgct gagtaaactg aaaaagcgtc gcgaaaagca | 3060 |
| cggtcgctaa taaatcgata ctagcataac cccttgggc ctctaaacgc gtcgacacgc | 3120 |
| aaaaaggcca tccgtcagga tggccttctg cttaatttga tgcctggcag tttatggcgg | 3180 |

```
gcgtcctgcc cgccaccctc cgggccgttg cttcgcaacg ttcaaatccg ctcccggcgg    3240
atttgtccta ctcaggagag cgttcaccga caaacaacag ataaaacgaa aggcccagtc    3300
tttcgactga gcctttcgtt ttatttgatg cctggcagtt ccctactctc gcatggggag    3360
accccacact accatcatgt atgaatatcc tccttagttc ctattccgaa gttcctattc    3420
tctagaaagt ataggaactt cggcgcgtcc tacctgtgac ggaagatcac ttcgcagaat    3480
aaataaatcc tggtgtccct gttgataccg ggaagccctg gccaactttt ggcgaaaat    3540 gagacgttga tcggcacgta agaggttcca actttcacca taatgaaata agatcactac    3600
cgggcgtatt ttttgagttg tcgagatttt caggagctaa ggaagctaaa atggagaaaa    3660
aaatcactgg ataccaccg gttgatatat cccaatggca tcgtaaagaa cattttgagg    3720
catttcagtc agttgctcaa tgtacctata accagaccgt tcagctggat attacggcct    3780
ttttaaagac cgtaaagaaa aataagcaca agttttatcc ggcctttatt cacattcttg    3840
cccgcctgat gaatgctcat ccggaattac gtatggcaat gaaagacggt gagctggtga    3900
tatgggatag tgttcacccct tgttacaccg ttttccatga gcaaactgaa acgttttcat    3960
cgctctggag tgaataccac gacgatttcc ggcagtttct acacatatat tcgcaagatg    4020
tggcgtgtta cggtgaaaac ctggcctatt ccctaaagg gtttattgag aatatgtttt    4080
tcgtctcagc caatccctgg gtgagtttca ccagttttga tttaaacgtg gccaatatgg    4140
acaacttctt cgcccccgtt ttcaccatgg gcaaatatta tacgcaaggc gacaaggtgc    4200
tgatgccgct ggcgattcag gttcatcatg ccgtttgtga tggcttccat gtcggcagat    4260
gcttaatgaa tacaacagta ctgcgatgag tggcagggcg gggcgtaagg cgcgccattt    4320
aaatgaagtt cctattccga agttcctatt ctctagaaag tataggaact tcgaagcagc    4380
tccagcctac acaatcgctc aagacgtgta atgctgcaat ctgcatgcaa gcttggcact    4440
ggccacgcaa aaaggccatc cgtcaggatg gccttctgct taatttgatg cctggcagtt    4500
tatgcggggc gtcctgcccg ccaccctccg ggccgttgct tcgcaacgtt caaatccgct    4560
cccggcggat ttgtcctact caggagagcg ttcaccgaca acaacagat aaaacgaaag    4620 gcccagtctt tcgactgagc ctttcgtttt atttgatgcc tggcagttcc ctactctcgc    4680
atggggagac cccacactac catcgggggg ccatcgatgc aggtggcact tttcggggaa    4740
atgtgcgcgg aacccctatt tgtttatttt tctaaataca ttcaaatatg tatccgctca    4800
tgagacaata accctgctgc agaggcctgc atgcaagctt ggcgtaatca tggtcatagc    4860
tgtttcctgt gtgaaattgt tatccgctca caattccaca caacatacga ccggaagca    4920 taaagtgtaa agcctggggt gcctaatgag tgagctaact cacattaatt gcgttgcgct    4980
cactgcccgc tttccagtcg ggaaacctgt cgtgccagct gcattaatga atcggccaac    5040
gcgcggggag aggcggtttg cgtattgggc gctcttccgc ttcctcgctc actgactcgc    5100
tgcgctcggt cgttcggctg cggcgagcgg tatcagctca ctcaaaggcg gtaatacggt    5160
tatccacaga atcagggat aacgcaggaa agaacatgtg agcaaaaggc cagcaaaagg    5220
ccaggaaccg taaaaaggcc gcgttgctgg cgttttttcca taggctccgc ccccctgacg    5280
agcatcacaa aaatcgacgc tcaagtcaga ggtggcgaaa cccgacagga ctataaagat    5340
accaggcgtt tcccctgga agctccctcg tgcgctctcc tgttccgacc ctgccgctta    5400
ccggatacct gtccgccttt ctcccttcgg gaagcgtggc gctttctcat agctcacgct    5460
gtaggtatct cagttcggtg taggtcgttc gctccaagct gggctgtgtg cacgaacccc    5520
```

```
ccgttcagcc cgaccgctgc gccttatccg gtaactatcg tcttgagtcc aacccggtaa    5580
gacacgactt atcgccactg gcagcagcca ctggtaacag gattagcaga gcgaggtatg    5640
taggcggtgc tacagagttc ttgaagtggt ggcctaacta cggctacact agaagaacag    5700
tatttggtat ctgcgctctg ctgaagccag ttaccttcgg aaaaagagtt ggtagctctt    5760
gatccggcaa acaaaccacc gctggtagcg gtggtttttt tgtttgcaag cagcagatta    5820
cgcgcagaaa aaaaggatct caagaagatc ctttgatctt ttctacgggg tctgacgctc    5880
agtggaacga aaactcacgt taagggattt tggtcatgag attatcaaaa aggatcttca    5940
cctagatcct tttaaattaa aaatgaagtt ttaaatcaat ctaaagtata tatgagtaaa    6000
cttggtctga cagttaccaa tgcttaatca gtgaggcacc tatctcagcg atctgtctat    6060
ttcgttcatc catagttgcc tgactccccg tcgtgtagat aactacgata cgggagggct    6120
taccatctgg ccccagtgct gcaatgatac cgcgagaccc acgctcaccg gctccagatt    6180
tatcagcaat aaaccagcca gccggaaggg ccgagcgcag aagtggtcct gcaactttat    6240
ccgcctccat ccagtctatt aattgttgcc gggaagctag agtaagtagt tcgccagtta    6300
atagtttgcg caacgttgtt gccattgcta caggcatcgt ggtgtcacgc tcgtcgtttg    6360
gtatggcttc attcagctcc ggttcccaac gatcaaggcg agttacatga tcccccatgt    6420
tgtgcaaaaa agcggttagc tccttcggtc ctccgatcgt tgtcagaagt aagttggccg    6480
cagtgttatc actcatggtt atggcagcac tgcataattc tcttactgtc atgccatccg    6540
taagatgctt ttctgtgact ggtgagtact caaccaagtc attctgagaa tagtgtatgc    6600
ggcgaccgag ttgctcttgc ccggcgtcaa tacgggataa taccgcgcca catagcagaa    6660
ctttaaaagt gctcatcatt ggaaaacgtt cttcggggcg aaaactctca aggatcttac    6720
cgctgttgag atccagttcg atgtaaccca ctcgtgcacc caactgatct tcagcatctt    6780
ttactttcac cagcgtttct gggtgagcaa aaacaggaag gcaaaatgcc gcaaaaaagg    6840
gaataagggc gacacggaaa tgttaatac tcatactctt ccttttcaa tattattgaa    6900
gcatttatca gggttattgt ctcatgagcg gatacatatt tgaatgtatt tagaaaaata    6960
aacaaatagg ggttccgcgc acatttcccc gaaaagtgcc acctgacgtc taagaaacca    7020
ttattatcat gacattaacc tataaaaata ggcgtatcac gaggccctt cgtc           7074
```

<210> SEQ ID NO 26
<211> LENGTH: 6699
<212> TYPE: DNA
<213> ORGANISM: Artificial Sequence
<220> FEATURE:
<223> OTHER INFORMATION: construct pINT-yabM

<400> SEQUENCE: 26

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct tgatctttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
```

-continued

```
ggttatgctg cttttaagac ccactttcac atttaagttg tttttctaat ccgcatatga    600
tcaattcaag gccgaataag aaggctggct ctgcaccttg gtgatcaaat aattcgatag    660
cttgtcgtaa taatggcggc atactatcag tagtaggtgt ttcccttcct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960 cccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttcctttt caatattatt    1200 gaagcattta tcaggggttat tgtctcatga gcggatacat atttgaatgt atttagaaaa   1260
ataaacaaat aggggttccg cgcacatttc cccgaaaagt gccacctgaa attggccaga   1320
tgattaattc ctaatttttg ttgacactct atcattgata gagttatttt accactccct   1380
atcagtgata gagaaaagtg aaatgaatag ttcgacaaaa atctagaaat aatttttgttt  1440 aactttaaga aggagatata caagagctcg agtcgaagga gatagaacca tgaaggctct   1500
gtggtcgcgt cgccgtcgta tccacccggt ctatctggct tttatggcag tttcgtttat   1560
ggttggcatc gcaggtgcgc tgcagtcacc gaccctgtcg ctgtttctga gccgtgaagt   1620
gggtgttcgc ccgttttggg tgggcctgtt ctatacggtt aacgcagtcg ctggtattat   1680
cgtttccctg ctgctggcca aacgttcaga taatcagggc gaccgtcgca tgctgattct   1740
gttctgctgt gttatggcga tcgccaacgc agtcctgttt gccttcaatc gccattatct   1800
gaccctggtc attgcaggtg tgctgctgag ctctatcgct agcgtggcga tgccgcagat   1860
ttttgctctg gcgcgtgaat acgcagatag ttccgcccgc gaagcagtca tgttctcatc   1920
ggtgatgcgt gcccaactgt cgctggcatg ggttatcggt ccgccgctga gctttgccat   1980
tgcactgaac tacggcttta ccgcgatgtt cctggtggcg gccctgctgt ttttcgtctg   2040
cgtggctctg atttggttca ccctgccgag cgttccgcgt gcagaaaaca cggcagctga   2100
accgctgagt gatatctccg gttggaaaca ccgtgacgtg cgcatgctgt ttattgcctc   2160
tgttttcatg tggacctgta atacgatgta tgttatcgat atgccgctgt acattagtat   2220
cgtcctgggt ctgccggaca agctggcagg tctgctgatg ggtaccgcag caggcctgga   2280
aattccggtc atgctgctgg ctggtcatta tgtgaaacgt tttggcaagc gcccgatgat   2340
gctgctggcg gttggctgcg gtgtcctgtt ttacctgggt ctggtgctgt tccacggccg   2400
tacggaactg atgctgctgc agctgctgaa cgctctgttt atcggcatta tcgcgggcat   2460
tggtatgatc tggttccaag atctgatgcc gggtcgtccg ggttctgcaa ccacgctgtt   2520
taccaatagc atttctacgg gtgtgatcct ggcaggtgtg ctgcagggcg ttatggccga   2580
aacctttggc catcacgcag tctattggct ggcttccctg ctggcgctga tttctttcgc   2640
tctgagttgg caagttcgtg aagcgcgcac ggtgaagagt gttccgctgg cctaataaat   2700
cgatactagc ataaccccct ggggcctcta aacgcgtcga cacgcaaaaa ggccatccgt   2760
caggatggcc ttctgcttaa tttgatgcct ggcagtttat ggcgggcgtc ctgcccgcca   2820
ccctccgggc cgttgcttcg caacgttcaa atccgctccc ggcggatttg tcctactcag   2880
```

```
gagagcgttc accgacaaac aacagataaa acgaaaggcc cagtctttcg actgagcctt    2940
tcgttttatt tgatgcctgg cagttcccta ctctcgcatg gggagacccc acactaccat    3000
catgtatgaa tatcctcctt agttcctatt ccgaagttcc tattctctag aaagtatagg    3060
aacttcggcg cgtcctacct gtgacggaag atcacttcgc agaataaata aatcctggtg    3120
tccctgttga taccgggaag ccctgggcca acttttggcg aaaatgagac gttgatcggc    3180
acgtaagagg ttccaacttt caccataatg aaataagatc actaccgggc gtattttttg    3240
agttgtcgag attttcagga gctaaggaag ctaaaatgga gaaaaaatc actggatata    3300 ccaccgttga tatatcccaa tggcatcgta aagaacattt tgaggcattt cagtcagttg    3360
ctcaatgtac ctataaccag accgttcagc tggatattac ggcctttttta aagaccgtaa    3420 agaaaaataa gcacaagttt tatccggcct ttattcacat tcttgcccgc ctgatgaatg    3480
ctcatccgga attacgtatg gcaatgaaag acggtgagct ggtgatatgg atagtgttc    3540 acccttgtta caccgttttc catgagcaaa ctgaaacgtt ttcatcgctc tggagtgaat    3600
accacgacga tttccggcag tttctacaca tatattcgca agatgtggcg tgttacggtg    3660
aaaacctggc ctatttccct aaagggttta ttgagaatat gttttttcgtc tcagccaatc    3720 cctgggtgag tttcaccagt tttgatttaa acgtggccaa tatggacaac ttcttcgccc    3780
ccgttttcac catgggcaaa tattatacgc aaggcgacaa ggtgctgatg ccgctggcga    3840
ttcaggttca tcatgccgtt tgtgatggct tccatgtcgg cagatgctta atgaatacaa    3900
cagtactgcg atgagtggca gggcggggcg taaggcgcgc catttaaatg aagttcctat    3960
tccgaagttc ctattctcta gaaagtatag gaacttcgaa gcagtccag cctacacaat    4020 cgctcaagac gtgtaatgct gcaatctgca tgcaagcttg gcactggcca cgcaaaaagg    4080
ccatccgtca ggatggcctt ctgcttaatt tgatgcctgg cagtttatgg cgggcgtcct    4140
gcccgccacc ctccgggccg ttgcttcgca acgttcaaat ccgctcccgg cggatttgtc    4200
ctactcagga gagcgttcac cgacaaacaa cagataaaac gaaaggccca gtctttcgac    4260
tgagcctttc gttttatttg atgcctggca gttccctact ctcgcatggg gagaccccac    4320
actaccatcg ggggccatc gatgcaggtg gcacttttcg gggaaatgtg cgcggaaccc    4380
ctatttgttt attttttctaa atacattcaa atatgtatcc gctcatgaga caataaccct    4440
gctgcagagg cctgcatgca agcttggcgt aatcatggtc atagctgttt cctgtgtgaa    4500
attgttatcc gctcacaatt ccacacaaca tacgagccgg aagcataaag tgtaaagcct    4560
ggggtgccta atgagtgagc taactcacat taattgcgtt gcgctcactg cccgctttcc    4620
agtcgggaaa cctgtcgtgc cagctgcatt aatgaatcgg ccaacgcgcg gggagaggcg    4680
gtttgcgtat tgggcgctct tccgcttcct cgctcactga ctcgctgcgc tcggtcgttc    4740
ggctgcggcg agcggtatca gctcactcaa aggcggtaat acggttatcc acagaatcag    4800
gggataacgc aggaaagaac atgtgagcaa aaggccagca aaaggccagg aaccgtaaaa    4860
aggccgcgtt gctggcgttt ttccataggc tccgcccccc tgacgagcat cacaaaaatc    4920
gacgctcaag tcagaggtgg cgaaacccga caggactata aagataccag gcgtttcccc    4980
ctggaagctc cctcgtgcgc tctcctgttc cgaccctgcc gcttaccgga tacctgtccg    5040
cctttctccc ttcgggaagc gtggcgcttt ctcatagctc acgctgtagg tatctcagtt    5100
cggtgtaggt cgttcgctcc aagctgggct gtgtgcacga accccccgtt cagcccgacc    5160
gctgcgcctt atccggtaac tatcgtcttg agtccaaccc ggtaagacac gacttatcgc    5220
cactggcagc agccactggt aacaggatta gcagagcgag gtatgtaggc ggtgctacag    5280
```

```
agttcttgaa gtggtggcct aactacggct acactagaag aacagtattt ggtatctgcg      5340
ctctgctgaa gccagttacc ttcggaaaaa gagttggtag ctcttgatcc ggcaaacaaa      5400
ccaccgctgg tagcggtggt tttttgttt gcaagcagca gattacgcgc agaaaaaaag      5460
gatctcaaga agatcctttg atctttcta cggggtctga cgctcagtgg aacgaaaact      5520
cacgttaagg gattttggtc atgagattat caaaaaggat cttcacctag atccttttaa      5580
attaaaaatg aagttttaaa tcaatctaaa gtatatatga gtaaacttgg tctgacagtt      5640
accaatgctt aatcagtgag gcacctatct cagcgatctg tctatttcgt tcatccatag      5700
ttgcctgact ccccgtcgtg tagataacta cgatacggga gggcttacca tctggcccca      5760
gtgctgcaat gataccgcga gacccacgct caccggctcc agatttatca gcaataaacc      5820
agccagccgg aagggccgag cgcagaagtg gtcctgcaac tttatccgcc tccatccagt      5880
ctattaattg ttgccgggaa gctagagtaa gtagttcgcc agttaatagt ttgcgcaacg      5940
ttgttgccat tgctacaggc atcgtggtgt cacgctcgtc gtttggtatg gcttcattca      6000
gctccggttc ccaacgatca aggcgagtta catgatcccc catgttgtgc aaaaaagcgg      6060
ttagctcctt cggtcctccg atcgttgtca gaagtaagtt ggccgcagtg ttatcactca      6120
tggttatggc agcactgcat aattctctta ctgtcatgcc atccgtaaga tgcttttctg      6180
tgactggtga gtactcaacc aagtcattct gagaatagtg tatgcggcga ccgagttgct      6240
cttgcccggc gtcaatacgg gataataccg cgccacatag cagaacttta aaagtgctca      6300
tcattggaaa acgttcttcg gggcgaaaac tctcaaggat cttaccgctg ttgagatcca      6360
gttcgatgta acccactcgt gcacccaact gatcttcagc atcttttact ttcaccagcg      6420
tttctgggtg agcaaaaaca ggaaggcaaa atgccgcaaa aaagggaata agggcgacac      6480
ggaaatgttg aatactcata ctcttccttt ttcaatatta ttgaagcatt tatcagggtt      6540
attgtctcat gagcggatac atatttgaat gtatttagaa aaataaacaa ataggggttc      6600
cgcgcacatt tccccgaaaa gtgccacctg acgtctaaga aaccattatt atcatgacat      6660
taacctataa aaataggcgt atcacgaggc cctttcgtc                             6699
```

<210> SEQ ID NO 27
<211> LENGTH: 6684
<212> TYPE: DNA
<213> ORGANISM: Artificial Sequence
<220> FEATURE:
<223> OTHER INFORMATION: construct pINT-ydeA

<400> SEQUENCE: 27

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgccagct ggcgaaaggg ggatgtgctg caaggcgatt aagttgggta acgccagggt       360
tttcccagtc acgacgttgt aaaacgacgg ccagtgaatt cgaagatcct tgatcttttt      420
ctacggggtc tgacgctcag tggaacgaaa actcacgtta agggattttg gtcatgagat       480
tatcaaaaag gatcttcacc tagatccttt taaactagtg aagttaccat cacggaaaaa       540
ggttatgctg cttttaagac ccactttcac atttaagttg ttttttctaat ccgcatatga      600
```

```
tcaattcaag gccgaataag aaggctggct ctgcaccttg gtgatcaaat aattcgatag    660
cttgtcgtaa taatggcggc atactatcag tagtaggtgt ttcccttct tctttagcga     720 cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgttttct gtaggccgtg tacctaaatg tacttttgct ccatcgcgat     900
gacttagtaa agcacatcta aaacttttag cgttattacg taaaaaatct tgccagcttt    960
ccccttctaa agggcaaaag tgagtatggt gcctatctaa catctcaatg gctaaggcgt    1020
cgagcaaagc ccgcttattt tttacatgcc aatacaatgt aggctgctct acacctagct    1080
tctgggcgag tttacgggtt gttaaaccct cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg ttgacactct atcattgata gagttatttt accactcct      1380 atcagtgata gagaaaagtg aaatgaatag ttcgacaaaa atctagaaat aattttgttt    1440
aactttaaga aggagatata caagagctcg agtcgaagga gatagaacca tgacaacaaa    1500
cactgtttcc cgcaaagtgg cgtggctacg ggtcgttacg ctggcagtcg ccgccttcat    1560
cttcaacacc accgaatttg tccctgttgg cctgctctct gacattgcgc aaagttttca    1620
catgcaaacc gctcaggtcg gcatcatgtt gaccatttac gcatgggtag tagcgctaat    1680
gtcattgcct tttatgttaa tgaccagtca ggttgaacgg cgcaaattac tgatctgcct    1740
gtttgtggtg tttattgcca gccacgtact gtcgttttg tcgtggagct ttaccgttct     1800
ggtgatcagt cgcattggtg tggcttttgc acatgcgatt ttctggtcga ttacggcgtc    1860
tctggcgatc cgtatggctc cggccgggaa gcgagcacag gcattgagtt taattgccac    1920
cggtacagca ctggcgatgg tcttaggtttt acctctcggg cgcattgtgg gccagtattt   1980
cggttggcga atgaccttct tcgcgattgg tattgggggcg cttatcaccc tttttgtgcct  2040 gattaagtta cttcccttac tgcccagtga gcattccggt tcactgaaaa gcctcccgct    2100
attgttccgc cgcccggcat tgatgagcat ttatttgtta actgtggtgg ttgtcaccgc    2160 ccattcacg gcatacagct atatcgagcc ttttgtacaa acattgcgg gattcagcgc      2220 caactttgcc acggcattac tgttattact cggtggtgcg ggcattattg gcagcgtgat    2280
tttcggtaaa ctgggtaatc agtatgcgtc tgcgttggtg agtacggcga ttgcgctgtt    2340
gctggtgtgc ctggcattgc tgttacctgc ggcgaacagt gaaatacacc tcggggtgct    2400
gagtattttc tggggggatcg cgatgatgat catcggcctt ggtatgcagg ttaaagtgct    2460
ggcgctggca ccagatgcta ccgacgtcgc gatggcgcta ttctccggca tatttaatat    2520
tggaatcggg gcgggtgcgt tggtaggtaa tcaggtgagt ttgcactggt caatgtcgat    2580
gattggttat gtgggcgcgg tgcctgcttt tgccgcgtta atttggtcaa tcattatatt    2640
tcgccgctgg ccagtgacac tcgaagaaca gacgcaatag taaatcgata ctagcataac    2700 cccttgggc ctctaaacgc gtcgacacgc aaaaaggcca tccgtcagga tggccttctg     2760
cttaatttga tgcctggcag tttatggcgg gcgtcctgcc cgccaccctc cgggccgttg    2820
cttcgcaacg ttcaaatccg ctcccggcgg atttgtccta ctcaggagag cgttcaccga    2880
caaacaacag ataaaacgaa aggcccagtc tttcgactga gcctttcgtt ttatttgatg    2940
cctggcagtt ccctactctc gcatggggag accccacact accatcatgt atgaatatcc    3000
```

```
tccttagttc ctattccgaa gttcctattc tctagaaagt ataggaactt cggcgcgtcc   3060
tacctgtgac ggaagatcac ttcgcagaat aaataaatcc tggtgtccct gttgataccg   3120
ggaagccctg ggccaacttt tggcgaaaat gagacgttga tcggcacgta agaggttcca   3180
actttcacca taatgaaata agatcactac cgggcgtatt ttttgagttg tcgagatttt   3240
caggagctaa ggaagctaaa atggagaaaa aaatcactgg atataccacc gttgatatat   3300
cccaatggca tcgtaaagaa cattttgagg catttcagtc agttgctcaa tgtacctata   3360
accagaccgt tcagctggat attacggcct ttttaaagac cgtaaagaaa aataagcaca   3420
agttttatcc ggcctttatt cacattcttg cccgcctgat gaatgctcat ccggaattac   3480
gtatggcaat gaaagacggt gagctggtga tatgggatag tgttcaccct tgttacaccg   3540
ttttccatga gcaaactgaa acgttttcat cgctctggag tgaataccac gacgatttcc   3600
ggcagtttct acacatatat tcgcaagatg tggcgtgtta cggtgaaaac ctggcctatt   3660
tccctaaagg gtttattgag aatatgtttt tcgtctcagc caatccctgg gtgagtttca   3720
ccagttttga tttaaacgtg gccaatatgg acaacttctt cgcccccgtt ttcaccatgg   3780
gcaaatatta tacgcaaggc gacaaggtgc tgatgccgct ggcgattcag gttcatcatg   3840
ccgtttgtga tggcttccat gtcggcagat gcttaatgaa tacaacagta ctgcgatgag   3900
tggcagggcg gggcgtaagg cgcgccattt aaatgaagtt cctattccga agttcctatt   3960
ctctagaaag tataggaact tcgaagcagc tccagcctac acaatcgctc aagacgtgta   4020
atgctgcaat ctgcatgcaa gcttggcact ggccacgcaa aaaggccatc cgtcaggatg   4080
gccttctgct taatttgatg cctggcagtt tatggcgggc gtcctgcccg ccaccctccg   4140
ggccgttgct tcgcaacgtt caaatccgct cccggcggat ttgtcctact caggagagcg   4200
ttcaccgaca acaacagat aaaacgaaag gcccagtctt tcgactgagc ctttcgtttt   4260
atttgatgcc tggcagttcc ctactctcgc atggggagac cccacactac catcgggggg   4320
ccatcgatgc aggtggcact tttcggggaa atgtgcgcgg aacccctatt tgtttatttt   4380
tctaaataca ttcaaatatg tatccgctca tgagacaata accctgctgc agaggcctgc   4440
atgcaagctt ggcgtaatca tggtcatagc tgtttcctgt gtgaaattgt tatccgctca   4500
caattccaca acatacga gccggaagca taaagtgtaa agcctggggt gcctaatgag   4560
tgagctaact cacattaatt gcgttgcgct cactgcccgc tttccagtcg ggaaacctgt   4620
cgtgccagct gcattaatga atcggccaac gcgcggggag aggcggtttg cgtattgggc   4680
gctcttccgc ttcctcgctc actgactcgc tgcgctcggt cgttcggctg cggcgagcgg   4740
tatcagctca ctcaaaggcg gtaatacggt tatccacaga atcagggat aacgcaggaa   4800 agaacatgtg agcaaaaggc cagcaaaagg ccaggaaccg taaaaaggcc gcgttgctgg   4860
cgttttccca taggctccgc cccctgacg agcatcacaa aatcgacg tcaagtcaga   4920 ggtggcgaaa cccgacagga ctataaagat accaggcgtt tccccctgga agctccctcg   4980
tgcgctctcc tgttccgacc ctgccgctta ccggatacct gtccgccttt ctcccttcgg   5040
gaagcgtggc gctttctcat agctcacgct gtaggtatct cagttcggtg taggtcgttc   5100
gctccaagct gggctgtgtg cacgaacccc cgttcagcc cgaccgctgc gccttatccg   5160
gtaactatcg tcttgagtcc aacccggtaa gacacgactt atcgccactg gcagcagcca   5220
ctggtaacag gattagcaga gcgaggtatg taggcggtgc tacagagttc ttgaagtggt   5280
ggcctaacta cggctacact agaagaacag tatttggtat ctgcgctctg ctgaagccag   5340
```

```
ttaccttcgg aaaaagagtt ggtagctctt gatccggcaa acaaaccacc gctggtagcg      5400
gtggttttt tgtttgcaag cagcagatta cgcgcagaaa aaaaggatct caagaagatc       5460
ctttgatctt ttctacgggg tctgacgctc agtggaacga aaactcacgt taagggattt     5520
tggtcatgag attatcaaaa aggatcttca cctagatcct tttaaattaa aaatgaagtt     5580
ttaaatcaat ctaaagtata tatgagtaaa cttggtctga cagttaccaa tgcttaatca     5640
gtgaggcacc tatctcagcg atctgtctat ttcgttcatc catagttgcc tgactccccg     5700
tcgtgtagat aactacgata cgggagggct taccatctgg ccccagtgct gcaatgatac     5760
cgcgagaccc acgctcaccg gctccagatt tatcagcaat aaaccagcca gccgaaggg      5820
ccgagcgcag aagtggtcct gcaactttat ccgcctccat ccagtctatt aattgttgcc     5880
gggaagctag agtaagtagt tcgccagtta atagtttgcg caacgttgtt gccattgcta     5940
caggcatcgt ggtgtcacgc tcgtcgtttg gtatggcttc attcagctcc ggttcccaac     6000
gatcaaggcg agttacatga tcccccatgt tgtgcaaaaa agcggttagc tccttcggtc     6060
ctccgatcgt tgtcagaagt aagttggccg cagtgttatc actcatggtt atggcagcac     6120
tgcataattc tcttactgtc atgccatccg taagatgctt ttctgtgact ggtgagtact     6180
caaccaagtc attctgagaa tagtgtatgc ggcgaccgag ttgctcttgc ccggcgtcaa     6240
tacgggataa taccgcgcca catagcagaa ctttaaaagt gctcatcatt ggaaaacgtt     6300
cttcggggcg aaaactctca aggatcttac cgctgttgag atccagttcg atgtaaccca     6360
ctcgtgcacc caactgatct tcagcatctt ttactttcac cagcgtttct gggtgagcaa     6420
aaacaggaag gcaaaatgcc gcaaaaaagg gaataagggc gacacggaaa tgttgaatac     6480
tcatactctt cctttttcaa tattattgaa gcatttatca gggttattgt ctcatgagcg     6540
gatacatatt tgaatgtatt tagaaaaata aacaataggg gttccgcgc acatttcccc      6600
gaaaagtgcc acctgacgtc taagaaacca ttattatcat gacattaacc tataaaaata     6660
ggcgtatcac gaggcccttt cgtc                                            6684
```

<210> SEQ ID NO 28
<211> LENGTH: 6738
<212> TYPE: DNA
<213> ORGANISM: Artificial Sequence
<220> FEATURE:
<223> OTHER INFORMATION: construct pINT-propP2

<400> SEQUENCE: 28

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgagatcct ttgatctttt       420
ctacggggtc tgacgctcag tggaacgaaa actcacgtta agggattttg gtcatgagat     480
tatcaaaaag gatcttcacc tagatccttt aaactagtg aagttaccat cacggaaaaa      540
ggttatgctg cttttaagac ccactttcac atttaagttg ttttttctaat ccgcatatga    600
tcaattcaag gccgaataag aaggctggct ctgcaccttg gtgatcaaat aattcgatag     660
cttgtcgtaa taatggcggc atactatcag tagtaggtgt ttccctttct tctttagcga    720
```

```
cttgatgctc ttgatcttcc aatacgcaac ctaaagtaaa atgccccact gcgctgagtg      780
catataatgc attctctagt gaaaaacctt gttggcataa aaaggctaat tgattttcga      840
gagtttcata ctgttttcct gtaggccgtg tacctaaatg tacttttgct ccatcgcgat      900
gacttagtaa agcacatcta aaactttag cgttattacg taaaaaatct tgccagcttt      960 cccttctaa agggcaaaag tgagtatggt gcctatctaa catctcaatg ctaaggcgt      1020 cgagcaaagc ccgcttattt tttacatgcc aatacaatgt aggctgctct acacctagct     1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggcaga     1320 tgattaattc ctaatttttg ttgacactct atcattgata gagttatttt accactccct   1380
atcagtgata gagaaaagtg aaatgaatag ttcgacaaaa atctagaaat aatttgtt    1440 aactttaaga aggagatata caagagctcg agtcgaagga gatagaacca tgaatgaatc    1500
cgccgtgaaa atcaaccgca cctttatctc ccactatgct ctgctgctga aactgatgac    1560
catgttcgtc caacaacaga acagtacccc gtccaatatt gtggcgttta acttcctgct    1620
gatcgccttt ctgacgggta ttgcgagcgc cttccagacc ccgacgctgt cactgtatct    1680
gtcgcaagaa atcaatgtta gtccgttttt cgttggtctg ttttactccg ttaacgcgat    1740
tatcggcatt atcctgagcc agattctggc caaatattct gataagcaag atgaccgtcg    1800
caaagtcatg attgtgtgct gtctgatcgc agtgctgggt tgcctgatct ttgcttacag   1860
ccgtaattat tacgttctga ttatcattgg caccacgctg ctgggcctgg gtagctctgc   1920
aaacccgcag tcatttgcac tggctcgtga atatgcagaa agttcccatc gcgaagctgt   1980
tatgttcacc acgattatgc gcacccagat cagtctggca tggattgtcg gtccgccgct   2040 gtccttttc attgctctga attggggctt tgattatatg tacctggtcg caggttcagc   2100
tttcctgctg tgcgccggcg tgtcgaaact gctgccgaag atcccgcgtc agtctgcagt   2160
caaaaatcaa gaaattctgg acaacacccc gccgcgtcgc agtgtgattt acctgtttat   2220
cgccaatctg ctgctgtgga cgtgtaattc catgtacctg atcaacatgc cgctgttcgt   2280
gattaacgaa ctgcacctgg gtaaagaact ggcaggtacc ctgatgggta cggcagcagg   2340
cctggaaatt ccggtgatga tctttgccgg ctatctgacc aaatacttct caaaaaagcg   2400
cctgatgatg attgcactgg tttcgggtct ggcttttat tcatcgctgc tgttcagcga    2460
tcagacctgg caactgatcg gcctgcagat gctgaacgcg atctttattg gtatcaccgc   2520
cacgattggc atggtttat tccaagacct gatgccgacc aaaatgggta cggcgaccac    2580
gctgtttagt aatgcagcta agagctcttg gatcattggc ggtccgatcg cgggcatcat    2640
tgccgaaatc tggcattaca actctgtgtt ttatgtggcg gttgccctga ttttcatcag   2700
cgtcggctgt atgtggaagg ttaagtctgt ctaataaatc gatactagca taacccttg    2760 gggcctctaa acgcgtcgac acgcaaaaag gccatccgtc aggatggcct tctgcttaat    2820
ttgatgcctg gcagtttatg gcgggcgtcc tgcccgccac cctccgggcc gttgcttcgc    2880
aacgttcaaa tccgctcccg gcggatttgt cctactcagg agagcgttca ccgacaaaca    2940
acagataaaa cgaaaggccc agtctttcga ctgagccttt cgttttattt gatgcctggc    3000
agttccctac tctcgcatgg ggagacccca cactaccatc atgtatgaat atcctcctta    3060
```

```
gttcctattc cgaagttcct attctctaga aagtatagga acttcggcgc gtcctacctg      3120
tgacggaaga tcacttcgca gaataaataa atcctggtgt ccctgttgat accgggaagc      3180
cctgggccaa cttttggcga aaatgagacg ttgatcggca cgtaagaggt tccaactttc      3240
accataatga aataagatca ctaccgggcg tattttttga gttgtcgaga ttttcaggag      3300
ctaaggaagc taaatggag aaaaaaatca ctggatatac caccgttgat atatcccaat      3360
ggcatcgtaa agaacatttt gaggcatttc agtcagttgc tcaatgtacc tataaccaga      3420
ccgttcagct ggatattacg gcctttttaa agaccgtaaa gaaaaataag cacaagtttt      3480
atccggcctt tattcacatt cttgcccgcc tgatgaatgc tcatccggaa ttacgtatgg      3540
caatgaaaga cggtgagctg gtgatatggg atagtgttca cccttgttac accgttttcc      3600
atgagcaaac tgaaacgttt tcatcgctct ggagtgaata ccacgacgat ttccggcagt      3660
ttctacacat atattcgcaa gatgtggcgt gttacggtga aaacctggcc tatttcccta      3720
aagggtttat tgagaatatg ttttcgtct cagccaatcc ctgggtgagt ttcaccagtt      3780
ttgatttaaa cgtggccaat atggacaact tcttcgcccc cgttttcacc atgggcaaat      3840
attatacgca aggcgacaag gtgctgatgc cgctggcgat tcaggttcat catgccgttt      3900
gtgatggctt ccatgtcggc agatgcttaa tgaatacaac agtactgcga tgagtggcag      3960
ggcggggcgt aaggcgcgcc atttaaatga agttcctatt ccgaagttcc tattctctag      4020
aaagtatagg aacttcgaag cagctccagc ctacacaatc gctcaagacg tgtaatgctg      4080
caatctgcat gcaagcttgg cactggccac gcaaaaaggc catccgtcag gatggccttc      4140
tgcttaattt gatgcctggc agtttatggc gggcgtcctg cccgccaccc tccgggccgt      4200
tgcttcgcaa cgttcaaatc cgctcccggc ggatttgtcc tactcaggag agcgttcacc      4260
gacaaacaac agataaaacg aaaggcccag tctttcgact gagcctttcg ttttatttga      4320
tgcctggcag ttccctactc tcgcatgggg agaccccaca ctaccatcgg ggggccatcg      4380
atgcaggtgg cacttttcgg ggaaatgtgc gcggaacccc tatttgttta ttttctaaa      4440 tacattcaaa tatgtatccg ctcatgagac aataaccctg ctgcagaggc ctgcatgcaa      4500
gcttggcgta atcatggtca tagctgtttc ctgtgtgaaa ttgttatccg ctcacaattc      4560
cacacaacat acgagccgga agcataaagt gtaaagcctg gggtgcctaa tgagtgagct      4620
aactcacatt aattgcgttg cgctcactgc ccgctttcca gtcgggaaac ctgtcgtgcc      4680
agctgcatta atgaatcggc caacgcgcgg ggagaggcgg tttgcgtatt gggcgctctt      4740
ccgcttcctc gctcactgac tcgctgcgct cggtcgttcg gctgcggcga gcggtatcag      4800
ctcactcaaa ggcggtaata cggttatcca cagaatcagg ggataacgca ggaaagaaca      4860
tgtgagcaaa aggccagcaa aaggccagga accgtaaaaa ggccgcgttg ctggcgtttt      4920
tccataggct ccgcccccct gacgagcatc acaaaaatcg acgctcaagt cagaggtggc      4980
gaaacccgac aggactataa agataccagg cgtttccccc tggaagctcc ctcgtgcgct      5040
ctcctgttcc gaccctgccg cttaccggat acctgtccgc ctttctccct tcgggaagcg      5100
tggcgctttc tcatagctca cgctgtaggt atctcagttc ggtgtaggtc gttcgctcca      5160
agctgggctg tgtgcacgaa ccccccgttc agcccgaccg ctgcgcctta tccggtaact      5220
atcgtcttga gtccaacccg gtaagacacg acttatcgcc actggcagca gccactggta      5280
acaggattag cagagcgagg tatgtaggcg gtgctacaga gttcttgaag tggtggccta      5340
actacggcta cactagaaga acagtatttg gtatctgcgc tctgctgaag ccagttacct      5400
tcggaaaaag agttggtagc tcttgatccg gcaaacaaac caccgctggt agcggtggtt      5460
```

```
tttttgtttg caagcagcag attacgcgca gaaaaaaagg atctcaagaa gatcctttga   5520
tcttttctac ggggtctgac gctcagtgga acgaaaactc acgttaaggg attttggtca   5580
tgagattatc aaaaaggatc ttcacctaga tccttttaaa ttaaaaatga agttttaaat   5640
caatctaaag tatatatgag taaacttggt ctgacagtta ccaatgctta atcagtgagg   5700
cacctatctc agcgatctgt ctatttcgtt catccatagt tgcctgactc cccgtcgtgt   5760
agataactac gatacgggag ggcttaccat ctggccccag tgctgcaatg ataccgcgag   5820
acccacgctc accggctcca gatttatcag caataaacca gccagccgga agggccgagc   5880
gcagaagtgg tcctgcaact ttatccgcct ccatccagtc tattaattgt tgccgggaag   5940
ctagagtaag tagttcgcca gttaatagtt tgcgcaacgt tgttgccatt gctacaggca   6000
tcgtggtgtc acgctcgtcg tttggtatgg cttcattcag ctccggttcc caacgatcaa   6060
ggcgagttac atgatccccc atgttgtgca aaaaagcggt tagctccttc ggtcctccga   6120
tcgttgtcag aagtaagttg gccgcagtgt tatcactcat ggttatggca gcactgcata   6180
attctcttac tgtcatgcca tccgtaagat gcttttctgt gactggtgag tactcaacca   6240
agtcattctg agaatagtgt atgcggcgac cgagttgctc ttgcccggcg tcaatacggg   6300
ataataccgc gccacatagc agaactttaa aagtgctcat cattggaaaa cgttcttcgg   6360
ggcgaaaact ctcaaggatc ttaccgctgt tgagatccag ttcgatgtaa cccactcgtg   6420
cacccaactg atcttcagca tcttttactt tcaccagcgt ttctgggtga gcaaaaacag   6480
gaaggcaaaa tgccgcaaaa aagggaataa gggcgacacg gaaatgttga atactcatac   6540
tcttcctttt tcaatattat tgaagcattt atcagggtta ttgtctcatg agcggataca   6600
tatttgaatg tatttagaaa aataaacaaa taggggttcc gcgcacattt ccccgaaaag   6660
tgccacctga cgtctaagaa accattatta tcatgacatt aacctataaa aataggcgta   6720
tcacgaggcc ctttcgtc                                                6738
```

<210> SEQ ID NO 29
<211> LENGTH: 6513
<212> TYPE: DNA
<213> ORGANISM: Artificial Sequence
<220> FEATURE:
<223> OTHER INFORMATION: construct pINT-Pc-setA

<400> SEQUENCE: 29

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct tgatcttttt    420
ctacggggtc tgacgctcag tggaacgaaa actcacgtta agggattttg gtcatgagat    480
tatcaaaaag gatcttcacc tagatccttt taaactagta agttaccat cacgaaaaaa    540
ggttatgctg cttttaagac ccactttcac atttaagttg ttttttctaat ccgcatatga    600
tcaattcaag gccgaataag aaggctggct ctgcaccttg gtgatcaaat aattcgatag    660
cttgtcgtaa taatggcggc atactatcag tagtaggtgt ttcccttttct tctttagcga    720
```

```
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
ccccttctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc cccgaaaagt gccacctgaa attggccaga   1320
tgattaattc ctaattttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgttctacac   1500
gggctcggca gttattggta tcgtcgtctc gcagatgctg gctacgcgct cggatcgtca   1560
gggtgaccgc aagtcgctga tcttcgtttg ctgtctgctg ggtgcgctgg cctgcatgct   1620
gtttgcgtgg aaccgcaatt atttcatcct gctgtttatt ggtgtgctgc tgagctcttt   1680
cggcagtacc gccaacccgc agctgtttgc actggctcgc gaacatgcag ataaaacggg   1740
tcgtgaagcg gccatgttca gttccatcct gcgtgcccaa atttccctgg catgggtggt   1800
tggtccgccg attgcgtttg ccctggcact gggcttcggt tttaccacga tgtacctgac   1860
cgcagctgtc gtgttcatcc tgtgtggtat tctggtgaag ctgtttctgc cgagcatgcc   1920
gaaagccgtt gaaaagacca cgagcaccct ggaatctccg cgtcgcaatc gtcgcgacac   1980
gctgctgctg tttgttgcgt gcaccctgat gtggacgtgt aacggcatct atctgattaa   2040
tatgccgctg tacctggttc atgaactgca cctgccggaa aaactggcag gtatcatgat   2100
gggtgtcgca gcaggtctgg aaatcccggt tatgctgatt gccggttatg tcgcaaaacg   2160
tttcggcaag cgcttttctga tgcgtctggc tgtcgcgagc ggtctgctgt ttttcggcgg   2220
tctgctggtg ctggatggcg aaatcgccct gctggcactg caggctctga acgcgatttt   2280
catcggcatt ctggctggca ttggtatgct gtactttcag gacctgatgc cgggccaagc   2340
aggtgcagct accacgctgt ttaccaacac cacgcgcgtg ggttggatta tctcaggttc   2400
gctggctggc atcgtggcgg aaatttggaa ttatcacgct gtgttttcct ttgcgctgct   2460
gatgatcgtc ggctctattt actgcatgtg gcgtattaaa gatgcgtaat aaatcgatac   2520
tagcataacc ccttggggcc tctaaacgcg tcgacacgca aaaaggccat ccgtcaggat   2580
ggccttctgc ttaatttgat gcctggcagt ttatggcggg cgtcctgccc gccaccctcc   2640
gggccgttgc ttcgcaacgt tcaaatccgc tcccggcgga tttgtcctac tcaggagagc   2700
gttcaccgac aaacaacaga taaaacgaaa ggcccagtct ttcgactgag cctttcgttt   2760
tatttgatgc ctggcagttc cctactctcg catggggaga ccccacacta ccatcatgta   2820
tgaatatcct ccttagttcc tattccgaag ttcctattct ctagaaagta taggaacttc   2880
ggcgcgtcct acctgtgacg gaagatcact tcgcagaata aataaatcct ggtgtccctg   2940
ttgataccgg gaagccctgg gccaacttttt ggcgaaaatg agacgttgat cggcacgtaa   3000
gaggttccaa ctttcaccat aatgaaataa gatcactacc gggcgtattt tttgagttgt   3060
cgagattttc aggagctaag gaagctaaaa tggagaaaaa aatcactgga tataccaccg   3120
```

```
ttgatatatc ccaatggcat cgtaaagaac attttgaggc atttcagtca gttgctcaat    3180
gtacctataa ccagaccgtt cagctggata ttacggcctt tttaaagacc gtaaagaaaa    3240
ataagcacaa gttttatccg gcctttattc acattcttgc ccgcctgatg aatgctcatc    3300
cggaattacg tatggcaatg aaagacggtg agctggtgat atgggatagt gttcacccctt   3360 gttacaccgt tttccatgag caaactgaaa cgttttcatc gctctggagt gaataccacg    3420
acgatttccg gcagtttcta cacatatatt cgcaagatgt ggcgtgttac ggtgaaaacc    3480
tggcctattt ccctaaaggg tttattgaga atatgttttt cgtctcagcc aatccctggg    3540
tgagtttcac cagttttgat ttaaacgtgg ccaatatgga caacttcttc gccccccgttt  3600 tcaccatggg caaatattat acgcaaggcg acaaggtgct gatgccgctg gcgattcagg    3660
ttcatcatgc cgtttgtgat ggcttccatg tcggcagatg cttaatgaat acaacagtac    3720
tgcgatgagt ggcagggcgg ggcgtaaggc gcgccattta aatgaagttc ctattccgaa    3780
gttcctattc tctagaaagt ataggaactt cgaagcagct ccagcctaca caatcgctca    3840
agacgtgtaa tgctgcaatc tgcatgcaag cttggcactg ccacgcaaa aaggccatcc     3900 gtcaggatgg ccttctgctt aatttgatgc ctggcagttt atggcgggcg tcctgcccgc    3960
caccctccgg gccgttgctt cgcaacgttc aaatccgctc ccggcggatt tgtcctactc    4020
aggagagcgt tcaccgacaa acaacagata aaacgaaagg cccagtcttt cgactgagcc    4080
tttcgtttta tttgatgcct ggcagttccc tactctcgca tggggagacc ccacactacc    4140 atcgggggc catcgatgca ggtggcactt tcggggaaa tgtgcgcgga accctatt      4200 gtttatttt ctaaatacat tcaaatatgt atccgctcat gagacaataa ccctgctgca    4260
gaggcctgca tgcaagcttg gcgtaatcat ggtcatagct gtttcctgtg tgaaattgtt    4320
atccgctcac aattccacac aacatacgag ccggaagcat aaagtgtaaa gcctggggtg    4380
cctaatgagt gagctaactc acattaattg cgttgcgctc actgcccgct ttccagtcgg    4440
gaaacctgtc gtgccagctg cattaatgaa tcggccaacg cgcggggaga ggcggtttgc    4500
gtattgggcg ctcttccgct tcctcgctca ctgactcgct gcgctcggtc gttcggctgc    4560
ggcgagcggt atcagctcac tcaaaggcgg taatacggtt atccacagaa tcaggggata    4620
acgcaggaaa gaacatgtga gcaaaaggcc agcaaaaggc caggaaccgt aaaaaggccg    4680
cgttgctggc gtttttccat aggctccgcc cccctgacga gcatcacaaa aatcgacgct    4740
caagtcagag gtggcgaaac ccgacaggac tataaagata ccaggcgttt ccccctggaa    4800
gctccctcgt gcgctctcct gttccgaccc tgccgcttac cggatacctg tccgcctttc    4860
tcccttcggg aagcgtggcg ctttctcata gctcacgctg taggtatctc agttcggtgt    4920
aggtcgttcg ctccaagctg ggctgtgtgc acgaaccccc cgttcagccc gaccgctgcg    4980
ccttatccgg taactatcgt cttgagtcca acccggtaag acacgactta tcgccactgg    5040
cagcagccac tggtaacagg attagcagag cgaggtatgt aggcggtgct acagagttct    5100
tgaagtggtg gcctaactac ggctacacta agaacagt atttggtatc tgcgctctgc      5160
tgaagccagt taccttcgga aaagagttg gtagctcttg atccggcaaa caaaccaccg    5220
ctggtagcgg tggttttttt gtttgcaagc agcagattac gcgcagaaaa aaggatctc     5280 aagaagatcc tttgatcttt tctacgggt ctgacgctca gtggaacgaa aactcacgtt     5340
aagggatttt ggtcatgaga ttatcaaaaa ggatcttcac ctagatcctt ttaaattaaa    5400
aatgaagttt taaatcaatc taaagtatat atgagtaaac ttggtctgac agttaccaat    5460
```

```
gcttaatcag tgaggcacct atctcagcga tctgtctatt tcgttcatcc atagttgcct    5520
gactccccgt cgtgtagata actacgatac gggagggctt accatctggc cccagtgctg    5580
caatgatacc gcgagaccca cgctcaccgg ctccagattt atcagcaata aaccagccag    5640
ccggaagggc cgagcgcaga agtggtcctg caactttatc cgcctccatc cagtctatta    5700
attgttgccg ggaagctaga gtaagtagtt cgccagttaa tagtttgcgc aacgttgttg    5760
ccattgctac aggcatcgtg gtgtcacgct cgtcgtttgg tatggcttca ttcagctccg    5820
gttcccaacg atcaaggcga gttacatgat cccccatgtt gtgcaaaaaa gcggttagct    5880
ccttcggtcc tccgatcgtt gtcagaagta agttggccgc agtgttatca ctcatggtta    5940
tggcagcact gcataattct cttactgtca tgccatccgt aagatgcttt tctgtgactg    6000
gtgagtactc aaccaagtca ttctgagaat agtgtatgcg gcgaccgagt tgctcttgcc    6060
cggcgtcaat acgggataat accgcgccac atagcagaac tttaaaagtg ctcatcattg    6120
gaaaacgttc ttcggggcga aaactctcaa ggatcttacc gctgttgaga tccagttcga    6180
tgtaacccac tcgtgcaccc aactgatctt cagcatcttt tactttcacc agcgtttctg    6240
ggtgagcaaa aacaggaagg caaaatgccg caaaaaaggg aataagggcg acacggaaat    6300
gttgaatact catactcttc cttttccaat attattgaag catttatcag ggttattgtc    6360
tcatgagcgg atacatattt gaatgtattt agaaaaataa acaaataggg gttccgcgca    6420
catttccccg aaaagtgcca cctgacgtct aagaaaccat tattatcatg acattaacct    6480
ataaaaatag gcgtatcacg aggcccttc gtc    6513
```

<210> SEQ ID NO 30
<211> LENGTH: 6810
<212> TYPE: DNA
<213> ORGANISM: Artificial Sequence
<220> FEATURE:
<223> OTHER INFORMATION: construct pINT-fucP

<400> SEQUENCE: 30

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct tgatcttttt    420
ctacggggtc tgacgctcag tggaacgaaa actcacgtta agggattttg gtcatgagat    480
tatcaaaaag gatcttcacc tagatccttt taaactagtg aagttaccat cacggaaaaa    540
ggttatgctg cttttaagac ccactttcac atttaagttg ttttctaat ccgcatatga    600 tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact cgctgagtg    780 catataatgc attctctagt gaaaaacctt gttggcataa aaaggctaat tgattttcga    840
gagtttcata ctgttttttct gtaggccgtg tacctaaatg tacttttgct ccatcgcgat    900
gacttagtaa agcacatcta aaactttag cgttattacg taaaaaatct tgccagcttt    960
ccccttctaa agggcaaaag tgagtatggt gcctatctaa catctcaatg gctaaggcgt   1020
```

```
cgagcaaagc cgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg ttgacactct atcattgata gagttatttt accactccct    1380
atcagtgata gagaaaagtg aaatgaatag ttcgacaaaa atctagaaat aattttgttt    1440
aactttaaga aggagatata caagagctcg agtcgaagga gatagaacca tgggaaacac    1500
atcaatacaa acgcagagtt accgtgcggt agataaagat gcagggcaaa gcagaagtta    1560
cattattcca ttcgcgctgc tgtgctcact gttttttctt tgggcggtag ccaataacct    1620
taacgacatt ttattacctc aattccagca ggcttttacg ctgacaaatt ccaggctgg    1680 cctgatccaa tcggccttt actttggtta tttcattatc ccaatccctg ctgggatatt    1740 gatgaaaaa ctcagttata aagcagggat tattaccggg ttatttttat atgccttggg    1800
tgctgcatta ttctggcccg ccgcagaaat aatgaactac accttgtttt tagttggcct    1860 attattatt gcagccggat taggttgtct ggaaactgcc gcaaaccctt ttgttacggt    1920
attagggccg gaaagtagtg gtcacttccg cttaaatctt gcgcaaacat ttaactcgtt    1980
tggcgcaatt atcgcggttg tctttgggca aagtcttatt ttgtctaacg tgccacatca    2040
atcgcaagac gttctcgata aaatgtctcc agagcaattg agtgcgtata aacacagcct    2100
ggtattatcg gtacagacac cttatatgat catcgtggct atcgtgttac tggtcgccct    2160
gctgatcatg ctgacgaaat tcccggcatt gcagagtgat aatcacagtg acgccaaaca    2220
aggatcgttc tccgcatcgc tttctcgcct ggcgcgtatt cgccactggc gctgggcggt    2280
attagcgcaa ttctgctatg tcggcgcaca aacggcctgc tggagctatt tgattcgcta    2340
cgctgtagaa gaaattccag gtatgactgc aggctttgcc gctaactatt taaccggaac    2400
catggtgtgc ttctttattg gtcgtttcac cggtacctgg ctcatcagtc gcttcgcacc    2460
acacaaagtc ctggccgcct acgcattaat cgctatggca ctgtgcctga tctcagcctt    2520
cgctggcggt catgtgggct aatagcccct gactttatgc agcgccttta tgtcgattca    2580
gtacccaaca atcttctcgc tgggcattaa gaatctcggc caggacacca atatggttc    2640 gtccttcatc gttatgacca ttattggcgg cggtattgtc actccggtca tgggttttgt    2700
cagtgacgcg gcgggcaaca tccccactgc tgaactgatc cccgcactct gcttcgcggt    2760
catctttatc tttgcccgtt tccgttctca aacggcaact aactgataaa tcgatactag    2820
cataacccct tggggcctct aaacgcgtcg acacgcaaaa aggccatccg tcaggatggc    2880
cttctgctta atttgatgcc tggcagttta tggcgggcgt cctgcccgcc accctccggg    2940
ccgttgcttc gcaacgttca aatcgctcc cggcggattt gtcctactca ggagagcgtt    3000
caccgacaaa caacagataa aacgaaaggc ccagtctttc gactgagcct ttcgttttat    3060
ttgatgcctg gcagttccct actctcgcat ggggagaccc cacactacca tcatgtatga    3120
atatcctcct tagttcctat tccgaagttc ctattctcta gaaagtatag gaacttcggc    3180
gcgtcctacc tgtgacggaa gatcacttcg cagaataaat aaatcctggt gtccctgttg    3240
ataccgggaa gccctgggcc aacttttggc gaaaatgaga cgttgatcgg cacgtaagag    3300
gttccaactt tcaccataat gaaataagat cactaccggg cgtattttt gagttgtcga    3360
```

| | |
|---|---|
| gattttcagg agctaaggaa gctaaaatgg agaaaaaaat cactggatat accaccgttg | 3420 |
| atatatccca atggcatcgt aaagaacatt ttgaggcatt tcagtcagtt gctcaatgta | 3480 |
| cctataacca gaccgttcag ctggatatta cggcctttt aaagaccgta agaaaaata | 3540 |
| agcacaagtt ttatccggcc tttattcaca ttcttgcccg cctgatgaat gctcatccgg | 3600 |
| aattacgtat ggcaatgaaa gacggtgagc tggtgatatg ggatagtgtt cacccttgtt | 3660 |
| acaccgtttt ccatgagcaa actgaaacgt tttcatcgct ctggagtgaa taccacgacg | 3720 |
| atttccggca gtttctacac atatattcgc aagatgtggc gtgttacggt gaaaacctgg | 3780 |
| cctatttccc taaagggttt attgagaata tgttttcgt ctcagccaat ccctgggtga | 3840 |
| gtttcaccag ttttgattta acgtggcca atatggacaa cttcttcgcc cccgttttca | 3900 |
| ccatgggcaa atattatacg caaggcgaca aggtgctgat gccgctggcg attcaggttc | 3960 |
| atcatgccgt ttgtgatggc ttccatgtcg gcagatgctt aatgaataca acagtactgc | 4020 |
| gatgagtggc agggcgggc gtaaggcgcg ccatttaaat gaagttccta ttccgaagtt | 4080 |
| cctattctct agaaagtata ggaacttcga agcagctcca gcctacacaa tcgctcaaga | 4140 |
| cgtgtaatgc tgcaatctgc atgcaagctt ggcactggcc acgcaaaaag gccatccgtc | 4200 |
| aggatggcct tctgcttaat tgatgcctg gcagtttatg gcgggcgtcc tgcccgccac | 4260 |
| cctccgggcc gttgcttcgc aacgttcaaa tccgctcccg gcggatttgt cctactcagg | 4320 |
| agagcgttca ccgacaaaca acagataaaa cgaaaggccc agtctttcga ctgagccttt | 4380 |
| cgttttattt gatgcctggc agttccctac tctcgcatgg ggagaccca cactaccatc | 4440 |
| gggggggccat cgatgcaggt ggcacttttc ggggaaatgt gcgcggaacc ctatttgtt | 4500 |
| tatttttcta aatacattca aatatgtatc cgctcatgag acaataaccc tgctgcagag | 4560 |
| gcctgcatgc aagcttggcg taatcatggt catagctgtt tcctgtgtga aattgttatc | 4620 |
| cgctcacaat tccacacaac atacgagccg gaagcataaa gtgtaaagcc tggggtgcct | 4680 |
| aatgagtgag ctaactcaca ttaattgcgt tgcgctcact gcccgctttc cagtcgggaa | 4740 |
| acctgtcgtg ccagctgcat taatgaatcg gccaacgcgc ggggagaggc ggtttgcgta | 4800 |
| ttgggcgctc ttccgcttcc tcgctcactg actcgctgcg ctcggtcgtt cggctgcggc | 4860 |
| gagcggtatc agctcactca aaggcggtaa tacggttatc cacagaatca ggggataacg | 4920 |
| caggaaagaa catgtgagca aaaggccagc aaaaggccag gaaccgtaaa aaggccgcgt | 4980 |
| tgctggcgtt tttccatagg ctccgccccc ctgacgagca tcacaaaaat cgacgctcaa | 5040 |
| gtcagaggtg gcgaaacccg acaggactat aaagatacca ggcgtttccc cctggaagct | 5100 |
| ccctcgtgcg ctctcctgtt ccgaccctgc cgcttaccgg atacctgtcc gcctttctcc | 5160 |
| cttcgggaag cgtggcgctt tctcatagct cacgctgtag gtatctcagt tcggtgtagg | 5220 |
| tcgttcgctc caagctgggc tgtgtgcacg aaccccccgt tcagcccgac cgctgcgcct | 5280 |
| tatccggtaa ctatcgtctt gagtccaacc cggtaagaca cgacttatcg ccactggcag | 5340 |
| cagccactgg taacaggatt agcagagcga ggtatgtagg cggtgctaca gagttcttga | 5400 |
| agtggtggcc taactacggc tacactagaa gaacagtatt tggtatctgc gctctgctga | 5460 |
| agccagttac cttcggaaaa agagttggta gctcttgatc cggcaaacaa accaccgctg | 5520 |
| gtagcggtgg tttttttgtt tgcaagcagc agattacgcg cagaaaaaaa ggatctcaag | 5580 |
| aagatccttt gatcttttct acggggtctg acgctcagtg gaacgaaaac tcacgttaag | 5640 |
| ggattttggt catgagatta tcaaaaagga tcttcaccta gatccttta aattaaaaat | 5700 |
| gaagttttaa atcaatctaa agtatatatg agtaaacttg gtctgacagt taccaatgct | 5760 |

```
taatcagtga ggcacctatc tcagcgatct gtctatttcg ttcatccata gttgcctgac    5820
tccccgtcgt gtagataact acgatacggg agggcttacc atctggcccc agtgctgcaa    5880
tgataccgcg agacccacgc tcaccggctc cagatttatc agcaataaac cagccagccg    5940
gaagggccga gcgcagaagt ggtcctgcaa ctttatccgc ctccatccag tctattaatt    6000
gttgccggga agctagagta agtagttcgc cagttaatag tttgcgcaac gttgttgcca    6060
ttgctacagg catcgtggtg tcacgctcgt cgtttggtat ggcttcattc agctccggtt    6120
cccaacgatc aaggcgagtt acatgatccc ccatgttgtg caaaaaagcg gttagctcct    6180
tcggtcctcc gatcgttgtc agaagtaagt tggccgcagt gttatcactc atggttatgg    6240
cagcactgca taattctctt actgtcatgc catccgtaag atgcttttct gtgactggtg    6300
agtactcaac caagtcattc tgagaatagt gtatgcggcg accgagttgc tcttgcccgg    6360
cgtcaatacg ggataatacc gcgccacata gcagaacttt aaaagtgctc atcattggaa    6420
aacgttcttc ggggcgaaaa ctctcaagga tcttaccgct gttgagatcc agttcgatgt    6480
aacccactcg tgcacccaac tgatcttcag catcttttac tttcaccagc gtttctgggt    6540
gagcaaaaac aggaaggcaa aatgccgcaa aaagggaat aagggcgaca cggaaatgtt    6600
gaatactcat actcttcctt tttcaatatt attgaagcat ttatcagggt tattgtctca    6660
tgagcggata catatttgaa tgtatttaga aaaataaaca ataggggtt ccgcgcacat    6720 ttccccgaaa agtgccacct gacgtctaag aaaccattat tatcatgaca ttaacctata    6780
aaaataggcg tatcacgagg ccctttcgtc                                    6810

<210> SEQ ID NO 31
<211> LENGTH: 6933
<212> TYPE: DNA
<213> ORGANISM: Artificial Sequence
<220> FEATURE:
<223> OTHER INFORMATION: construct pINT-mdeA

<400> SEQUENCE: 31
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgaagatcct tgatcttttt     420
ctacggggtc tgacgctcag tggaacgaaa actcacgtta agggattttg gtcatgagat     480
tatcaaaaag gatcttcacc tagatccttt taaactagtg aagttaccat cacggaaaaa     540
ggttatgctc ttttaagacc cactttcac atttaagttg ttttttctaat ccgcatatga     600 tcaattcaag gccgaataag aaggctggct ctgcaccttg gtgatcaaat aattcgatag     660
cttgtcgtaa taatggcggc atactatcag tagtaggtgt ttcccttttct tctttagcga     720 cttgatgctc ttgatcttcc aatacgcaac ctaaagtaaa atgccccact gcgctgagtg     780
catataatgc attctctagt gaaaaacctt gttggcataa aaaggctaat tgattttcga     840
gagtttcata ctgttttttct gtaggccgtg tacctaaatg tacttttgct ccatcgcgat     900
gacttagtaa agcacatcta aactttttag cgttattacg taaaaaatct tgccagcttt     960
```

-continued

```
cccccttctaa agggcaaaag tgagtatggt gcctatctaa catctcaatg gctaaggcgt    1020
cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttg ttgacactct atcattgata gagttatttt accactccct    1380
atcagtgata gagaaaagtg aaatgaatag ttcgacaaaa atctagaaat aattttgttt    1440
aactttaaga aggagatata caagagctcg agtcgaagga gatagaacca tgtccaaaaa    1500
acaaaaactg acgatgatta ttacgatgct gatgggtggc ttcttcggtc tgctgaatga    1560
aacgctgctg gtgacggcac tgccgagcat catgaaagac ttcgaaattt cttatacgca    1620
ggttcaatgg ctgaccacgg catttctgct gaccaacggc atcgttattc cgctgtcagc    1680
tctggtcatt cagcgttaca ccacgcgcca agttttcctg gtcggtatct ctattttctt    1740
tctgggcacg ctgctgtcag gtctgtcgcc gcattttgcg accctgctgg ttgcgcgtat    1800
tatccaggca ctgggcgctg gtatcatgat gccgctgatg atgaccacga ttctggatgt    1860
cttccaaccg cacgaacgcg gcaaatatat gggcattttt ggtctggtga tcggtctggc    1920
accggcaatc ggtccgaccc tgagtggtta tctggttgaa tacttcaact ggcgttccct    1980
gtttcatgtg gttgcgccga tcgcggccgt tacctttctg attggcttca aaacgatcaa    2040
aaatgtgggt accacgatta agttccgat cgactttatt tcagtcatct ctcggtgct    2100 gggctttggc ggtctgctgt atggtaccag ctctatttca gaaaaaggct cgataatcc    2160 gatcgtcctg gtgtcgatga ttggcggtgt cgtgctggtt gcactgtttg tcctgcgtca    2220
gtaccgcctg agcaccccgc tgctgaactt cgctgtgttc aaaaacaaac aattcaccgt    2280
tggcattatc attatgggtg tgacgatggt tagcatgatc ggctctgaaa ccattctgcc    2340
gatctttgtt cagaacctgc tgcatcgtag tgcactggac tccggtctga cgctgctgcc    2400
gggtgcaatt gtgatggcct tcatgagcat gacctctggc gccctgtatg aaaaatttgg    2460
tccgcgcaat ctggcactgg tgggtatggc tattgttgtc atcaccacgg catattttgt    2520
ggttatggat gaacagacca gtacgattat gctggcaacc gtctacgcta ttcgcatggt    2580
gggcatcgcg ctgggtctga ttccggttat gacccatacg atgaaccagc tgaaaccgga    2640
aatgaatgcg cacggcagtt ccatgaccaa cacggtgcag caaattgccg gcagcatcgg    2700
taccgcagct ctgatcacga ttctgagtca cgcctccaaa aacttttcac cgaccatgtc    2760
ggattacaac ggtatgaaca aaatcgacat gatgaaccag atcaaagtcg ataccatgct    2820
gcatggctac cacgcgggtt ttctgttcgc cctgctgatt accgtggtgt cgttcttctg    2880
ttcatttatg ctgcaaggca aaagaaaga agtggattcc cgccagtaat aaatcgatac    2940
tagcataacc ccttggggcc tctaaacgcg tcgacacgca aaaaggccat ccgtcaggat    3000
ggccttctgc ttaatttgat gcctggcagt ttatggcggg cgtcctgccc gccaccctcc    3060
gggccgttgc ttcgcaacgt tcaaatccgc tcccggcgga tttgtcctac tcaggagagc    3120
gttcaccgac aaacaacaga taaaacgaaa ggcccagtct ttcgactgag cctttcgttt    3180
tatttgatgc ctggcagttc cctactctcg catggggaga ccccacacta ccatcatgta    3240
tgaatatcct ccttagttcc tattccgaag ttcctattct ctagaaagta taggaacttc    3300
ggcgcgtcct acctgtgacg gaagatcact tcgcagaata aataaatcct ggtgtccctg    3360
```

| | |
|---|---|
| ttgataccgg gaagccctgg gccaactttt ggcgaaaatg agacgttgat cggcacgtaa | 3420 |
| gaggttccaa ctttcaccat aatgaaataa gatcactacc gggcgtattt tttgagttgt | 3480 |
| cgagattttc aggagctaag gaagctaaaa tggagaaaaa aatcactgga tataccaccg | 3540 |
| ttgatatatc ccaatggcat cgtaaagaac attttgaggc atttcagtca gttgctcaat | 3600 |
| gtacctataa ccagaccgtt cagctggata ttacggcctt tttaaagacc gtaaagaaaa | 3660 |
| ataagcacaa gttttatccg gcctttattc acattcttgc ccgcctgatg aatgctcatc | 3720 |
| cggaattacg tatggcaatg aaagacggtg agctggtgat atgggatagt gttcacccct | 3780 |
| gttacaccgt tttccatgag caaactgaaa cgttttcatc gctctggagt gaataccacg | 3840 |
| acgatttccg gcagtttcta cacatatatt cgcaagatgt ggcgtgttac ggtgaaaacc | 3900 |
| tggcctattt ccctaaaggg tttattgaga atatgttttt cgtctcagcc aatccctggg | 3960 |
| tgagtttcac cagttttgat ttaaacgtgg ccaatatgga caacttcttc gcccccgttt | 4020 |
| tcaccatggg caaatattat acgcaaggcg acaaggtgct gatgccgctg gcgattcagg | 4080 |
| ttcatcatgc cgtttgtgat ggcttccatg tcggcagatg cttaatgaat acaacagtac | 4140 |
| tgcgatgagt ggcagggcgg ggcgtaaggc gcgccattta aatgaagttc ctattccgaa | 4200 |
| gttcctattc tctagaaagt ataggaactt cgaagcagct ccagcctaca caatcgctca | 4260 |
| agacgtgtaa tgctgcaatc tgcatgcaag cttggcactg gccacgcaaa aaggccatcc | 4320 |
| gtcaggatgg ccttctgctt aatttgatgc ctggcagttt atggcgggcg tcctgcccgc | 4380 |
| caccctccgg gccgttgctt cgcaacgttc aaatccgctc ccggcggatt tgtcctactc | 4440 |
| aggagagcgt tcaccgacaa acaacagata aaacgaaagg cccagtcttt cgactgagcc | 4500 |
| tttcgtttta tttgatgcct ggcagttccc tactctcgca tggggagacc ccacactacc | 4560 |
| atcgggggc catcgatgca ggtggcactt ttcggggaaa tgtgcgcgga acccctattt | 4620 |
| gtttatttt ctaaatacat tcaaatatgt atccgctcat gagacaataa ccctgctgca | 4680 |
| gaggcctgca tgcaagcttg gcgtaatcat ggtcatagct gtttcctgtg tgaaattgtt | 4740 |
| atccgctcac aattccacac aacatacgag ccggaagcat aaagtgtaaa gcctggggtg | 4800 |
| cctaatgagt gagctaactc acattaattg cgttgcgctc actgcccgct ttccagtcgg | 4860 |
| gaaacctgtc gtgccagctg cattaatgaa tcggccaacg cgcgggaga ggcggtttgc | 4920 |
| gtattgggcg ctcttccgct tcctcgctca ctgactcgct gcgctcggtc gttcggctgc | 4980 |
| ggcgagcggt atcagctcac tcaaaggcgg taatacggtt atccacagaa tcaggggata | 5040 |
| acgcaggaaa gaacatgtga gcaaaaggcc agcaaaaggc caggaaccgt aaaaaggccg | 5100 |
| cgttgctggc gttttccat aggctccgcc cccctgacga gcatcacaaa aatcgacgct | 5160 |
| caagtcagag gtggcgaaac ccgacaggac tataaagata ccaggcgttt ccccctggaa | 5220 |
| gctccctcgt gcgctctcct gttccgaccc tgccgcttac cggatacctg tccgcctttc | 5280 |
| tcccttcggg aagcgtggcg ctttctcata gctcacgctg taggtatctc agttcggtgt | 5340 |
| aggtcgttcg ctccaagctg ggctgtgtgc acgaaccccc cgttcagccc gaccgctgcg | 5400 |
| ccttatccgg taactatcgt cttgagtcca acccggtaag acacgactta tcgccactgg | 5460 |
| cagcagccac tggtaacagg attagcagag cgaggtatgt aggcggtgct acagagttct | 5520 |
| tgaagtggtg gcctaactac ggctacacta agaacagt atttggtatc tgcgctctgc | 5580 |
| tgaagccagt taccttcgga aaagagttg gtagctcttg atccggcaaa caaaccaccg | 5640 |
| ctggtagcgg tggttttttt gtttgcaagc agcagattac gcgcagaaaa aaaggatctc | 5700 |

```
aagaagatcc tttgatcttt tctacggggt ctgacgctca gtggaacgaa aactcacgtt     5760
aagggatttt ggtcatgaga ttatcaaaaa ggatcttcac ctagatcctt ttaaattaaa     5820
aatgaagttt taaatcaatc taaagtatat atgagtaaac ttggtctgac agttaccaat     5880
gcttaatcag tgaggcacct atctcagcga tctgtctatt tcgttcatcc atagttgcct     5940
gactccccgt cgtgtagata actacgatac gggagggctt accatctggc cccagtgctg     6000
caatgatacc gcgagaccca cgctcaccgg ctccagattt atcagcaata aaccagccag     6060
ccggaagggc cgagcgcaga agtggtcctg caactttatc cgcctccatc cagtctatta     6120
attgttgccg ggaagctaga gtaagtagtt cgccagttaa tagtttgcgc aacgttgttg     6180
ccattgctac aggcatcgtg gtgtcacgct cgtcgtttgg tatggcttca ttcagctccg     6240
gttcccaacg atcaaggcga gttacatgat cccccatgtt gtgcaaaaaa gcggttagct     6300
ccttcggtcc tccgatcgtt gtcagaagta agttggccgc agtgttatca ctcatggtta     6360
tggcagcact gcataattct cttactgtca tgccatccgt aagatgcttt tctgtgactg     6420
gtgagtactc aaccaagtca ttctgagaat agtgtatgcg gcgaccgagt tgctcttgcc     6480
cggcgtcaat acgggataat accgcgccac atagcagaac tttaaaagtg ctcatcattg     6540
gaaaacgttc ttcggggcga aaactctcaa ggatcttacc gctgttgaga tccagttcga     6600
tgtaacccac tcgtgcaccc aactgatctt cagcatcttt tactttcacc agcgtttctg     6660
ggtgagcaaa aacaggaagg caaaatgccg caaaaaaggg aataagggcg acacggaaat     6720
gttgaatact catactcttc ctttttcaat attattgaag catttatcag ggttattgtc     6780
tcatgagcgg atacatattt gaatgtattt agaaaaataa acaaataggg gttccgcgca     6840
catttccccg aaaagtgcca cctgacgtct aagaaaccat tattatcatg acattaacct     6900
ataaaaatag gcgtatcacg aggccctttc gtc                                 6933
```

<210> SEQ ID NO 32
<211> LENGTH: 7248
<212> TYPE: DNA
<213> ORGANISM: Artificial Sequence
<220> FEATURE:
<223> OTHER INFORMATION: construct pINT-lmrA

<400> SEQUENCE: 32

```
tcgcgcgttt cggtgatgac ggtgaaaacc tctgacacat gcagctcccg gagacggtca       60
cagcttgtct gtaagcggat gccggagcag acaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt cgaagatcct ttgatctttt      420
ctacggggtc tgacgctcag tggaacgaaa actcacgtta agggattttg gtcatgagat      480
tatcaaaaag gatcttcacc tagatccttt aaactagtg aagttaccat cacggaaaaa      540
ggttatgctg cttttaagac ccactttcac atttaagttg ttttttctaat ccgcatatga      600 tcaattcaag gccgaataag aaggctggct ctgcaccttg gtgatcaaat aattcgatag      660
cttgtcgtaa taatggcggc atactatcag tagtaggtgt ttcccttttct tctttagcga      720 cttgatgctc ttgatcttcc aatacgcaac ctaaagtaaa atgccccact gcgctgagtg      780
catataatgc attctctagt gaaaaacctt gttggcataa aaaggctaat tgattttcga      840
```

-continued

```
gagtttcata ctgtttttct gtaggccgtg tacctaaatg tacttttgct ccatcgcgat     900
gacttagtaa agcacatcta aaacttttag cgttattacg taaaaaatct tgccagcttt     960
ccccttctaa agggcaaaag tgagtatggt gcctatctaa catctcaatg gctaaggcgt    1020
cgagcaaagc ccgcttattt tttacatgcc aatacaatgt aggctgctct acacctagct    1080
tctgggcgag tttacgggtt gttaaacctt cgattccgac ctcattaagc agctctaatg    1140
cgctgttaat cactttactt ttatctaaac gagacatact cttccttttt caatattatt    1200
gaagcattta tcagggttat tgtctcatga gcggatacat atttgaatgt atttagaaaa    1260
ataaacaaat aggggttccg cgcacatttc cccgaaaagt gccacctgaa attggccaga    1320
tgattaattc ctaattttgt tgacactct atcattgata gagttatttt accactccct     1380
atcagtgata gagaaaagtg aaatgaatag ttcgacaaaa atctagaaat aattttgttt    1440
aactttaaga aggagatata caagagctcg agtcgaagga gatagaacca tggcgaaccg    1500
tatcgaaggc aaagctgtgg acaaaacctc aatcaaacat tcattaaaac tgatccgtgc    1560
cgcaaaaccg cgttacctgt ttttcattat cggtattctg gcgggtatcg tgggcaccct    1620
gattcagctg caagtcccga aaatggtgca gccgctggtt aactcttttg gtcatggcgt    1680
taatggcggt aaagttgccc tggtcattgc actgtatatc ggtagtgcag cagtctccgc    1740
aattgcagct atcgtgctgg gtatctttgg cgaaagcgtg gttaaaaacc tgcgtacgcg    1800
cgtttgggat aaaatgattc acctgccggt gaaatacttc gacgaagtta aaaccggtga    1860
aatgagctct cgtctggcga atgataccac gcaagtgaaa aacctgattg caaatagcat    1920
cccgcaggct tttacgtcta ttctgctgct ggtcggcagt atcgtgttca tgctgcagat    1980
gcaatgcgcc ctgacccctgg ctatgattat cgcggttccg gtcgtgatgc tgattatgtt    2040
tccgatcatg acgttcggtc agaaaattgg ccgtacccgc caagatagcc tggcgaactt    2100
tcagggtatt gcctcagaat cgctgagcga aatccgtctg gtgaaaagtt ccaatgccga    2160
aaaacaggca tccaaaaaag ctgaaaacga cgttaatgca ctgtataaaa ttggtgtcaa    2220
agaagcgatc tttgatggcc tgatgagtcc ggtcatgatg ctgtccatga tgctgatgat    2280
cttcggtctg ctggcctatg gcatttacct gatcagcacg ggtgtgatgt ctctgggtac    2340
cctgctgggc atgatgatgt acctgatgaa cctgattggc gcggtgccga ccgttgccac    2400 gttttttcacc gaactggcga aagcctctgg tagtacgggc cgtctgaccg aactgctgga    2460
tgaagaacag gaagttctgc atcagggtga atcgctggat ctggaaggca aaaccctgag    2520
cgcacgtcac gtcgactttg cttatgatga ctctgaacaa attctgcgcg atatctcctt    2580
tgaagcgcag ccgaattcaa ttatcgcatt cgctggcccg agtggcggtg gcaaatcaac    2640 catctttttcg ctgctggaac gcttctacca accgacggcc ggtgaaatta ccatcgatgg    2700
ccagccgatt gacaacatct cactggaaaa ttggcgttcg cagattggtt tcgttagcca    2760
agactctgct attatggcgg gcacgatccg cgaaaacctg acctatggtc tggaaggcga    2820
ttacacggat gaagacctgt ggcaggtcct ggacctggcg tttgcccgtt cattcgtgga    2880
aaacatgccg gatcagctga ataccgaagt tggtgaacgc ggcgtcaaaa tttcgggtgg    2940
ccagcgtcaa cgcctggcaa tcgctcgtgc gtttctgcgc aatccgaaaa ttctgatgct    3000
ggatgaagcc accgcatctc tggactccga atcagaatcg atggtgcaga agcgctggaa    3060
tagtctgatg aaaggtcgta ccacgctggt gattgcccat cgcctgtcca cgatcgttga    3120
tgcagacaaa atctacttca tcgaaaaagg ccagatcacc ggtagcggca aacacaacga    3180
```

-continued

```
actggtcgca acccacccgc tgtacgcaaa atatgtctcg gaacaactga cggtcggcca    3240
ataataaatc gatactagca taacccctttg gggcctctaa acgcgtcgac acgcaaaaag   3300
gccatccgtc aggatggcct tctgcttaat ttgatgcctg gcagtttatg gcgggcgtcc   3360
tgcccgccac cctccgggcc gttgcttcgc aacgttcaaa tccgctcccg gcggatttgt   3420
cctactcagg agagcgttca ccgacaaaca acagataaaa cgaaaggccc agtctttcga   3480
ctgagccttt cgttttattt gatgcctggc agttccctac tctcgcatgg ggagacccca   3540
cactaccatc atgtatgaat atcctcctta gttcctattc cgaagttcct attctctaga   3600
aagtatagga acttcggcgc gtcctacctg tgacggaaga tcacttcgca gaataaataa   3660
atcctggtgt ccctgttgat accgggaagc cctgggccaa cttttggcga aaatgagacg   3720
ttgatcggca cgtaagaggt tccaactttc accataatga aataagatca ctaccgggcg   3780
tatttttga gttgtcgaga ttttcaggag ctaaggaagc taaaatggag aaaaaaatca   3840
ctggatatac caccgttgat atatcccaat ggcatcgtaa agaacatttt gaggcatttc   3900
agtcagttgc tcaatgtacc tataaccaga ccgttcagct ggatattacg gcctttttaa   3960
agaccgtaaa gaaaaataag cacaagtttt atccggcctt tattcacatt cttgcccgcc   4020
tgatgaatgc tcatccggaa ttacgtatgg caatgaaaga cggtgagctg gtgatatggg   4080
atagtgttca cccttgttac accgttttcc atgagcaaac tgaaacgttt tcatcgctct   4140
ggagtgaata ccacgacgat ttccggcagt ttctacacat atattcgcaa gatgtggcgt   4200
gttacggtga aaacctggcc tatttcccta aagggtttat tgagaatatg ttttcgtct   4260
cagccaatcc ctgggtgagt ttcaccagtt ttgatttaaa cgtggccaat atggacaact   4320
tcttcgcccc cgtttttcacc atgggcaaat attatacgca aggcgacaag gtgctgatgc   4380
cgctggcgat tcaggttcat catgccgttt gtgatggctt ccatgtcggc agatgcttaa   4440
tgaatacaac agtactgcga tgagtggcag ggcggggcgt aaggcgcgcc atttaaatga   4500
agttcctatt ccgaagttcc tattctctag aaagtatagg aacttcgaag cagctccagc   4560
ctacacaatc gctcaagacg tgtaatgctg caatctgcat gcaagcttgg cactggccac   4620
gcaaaaggc catccgtcag gatggccttc tgcttaattt gatgcctggc agtttatggc   4680
gggcgtcctg cccgccaccc tccgggccgt tgcttcgcaa cgttcaaatc cgctcccggc   4740
ggatttgtcc tactcaggag agcgttcacc gacaaacaac agataaaacg aaaggcccag   4800
tctttcgact gagcctttcg ttttatttga tgcctggcag ttccctactc tcgcatgggg   4860
agacccaca ctaccatcgg ggggccatcg atgcaggtgg cacttttcgg ggaaatgtgc   4920
gcggaacccc tatttgttta ttttttctaaa tacattcaaa tatgtatccg ctcatgagac   4980
aataaccctg ctgcagaggc ctgcatgcaa gcttggcgta atcatggtca tagctgtttc   5040
ctgtgtgaaa ttgttatccg ctcacaattc cacacaacat acgagccgga agcataaagt   5100
gtaaagcctg gggtgcctaa tgagtgagct aactcacatt aattgcgttg cgctcactgc   5160
ccgctttcca gtcgggaaac ctgtcgtgcc agctgcatta atgaatcggc caacgcgcgg   5220
ggagaggcgg tttgcgtatt gggcgctctt ccgcttcctc gctcactgac tcgctgcgct   5280
cggtcgttcg gctgcggcga gcggtatcag ctcactcaaa ggcggtaata cggttatcca   5340
cagaatcagg ggataacgca ggaaagaaca tgtgagcaaa aggccagcaa aaggccagga   5400
accgtaaaaa ggccgcgttg ctggcgtttt tccataggct ccgcccccct gacgagcatc   5460
acaaaaatcg acgctcaagt cagaggtggc gaaacccgac aggactataa agataccagg   5520
cgtttccccc tggaagctcc ctcgtgcgct ctcctgttcc gaccctgccg cttaccggat   5580
```

```
acctgtccgc ctttctccct tcgggaagcg tggcgctttc tcatagctca cgctgtaggt    5640
atctcagttc ggtgtaggtc gttcgctcca agctgggctg tgtgcacgaa ccccccgttc    5700
agcccgaccg ctgcgcctta tccggtaact atcgtcttga gtccaacccg gtaagacacg    5760
acttatcgcc actggcagca gccactggta acaggattag cagagcgagg tatgtaggcg    5820
gtgctacaga gttcttgaag tggtggccta actacggcta cactagaaga acagtatttg    5880
gtatctgcgc tctgctgaag ccagttacct tcggaaaaag agttggtagc tcttgatccg    5940
gcaaacaaac caccgctggt agcggtggtt ttttgtttg caagcagcag attacgcgca    6000
gaaaaaaagg atctcaagaa gatcctttga tcttttctac ggggtctgac gctcagtgga    6060
acgaaaactc acgttaaggg attttggtca tgagattatc aaaaaggatc ttcacctaga    6120
tccttttaaa ttaaaatga agttttaaat caatctaaag tatatatgag taaacttggt    6180
ctgacagtta ccaatgctta atcagtgagg cacctatctc agcgatctgt ctatttcgtt    6240
catccatagt tgcctgactc cccgtcgtgt agataactac gatacgggag ggcttaccat    6300
ctggccccag tgctgcaatg ataccgcgag acccacgctc accggctcca gatttatcag    6360
caataaacca gccagccgga agggccgagc gcagaagtgg tcctgcaact ttatccgcct    6420
ccatccagtc tattaattgt tgccgggaag ctagagtaag tagttcgcca gttaatagtt    6480
tgcgcaacgt tgttgccatt gctacaggca tcgtggtgtc acgctcgtcg tttggtatgg    6540
cttcattcag ctccggttcc caacgatcaa ggcgagttac atgatccccc atgttgtgca    6600
aaaaagcggt tagctccttc ggtcctccga tcgttgtcag aagtaagttg gccgcagtgt    6660
tatcactcat ggttatggca gcactgcata attctcttac tgtcatgcca tccgtaagat    6720
gcttttctgt gactggtgag tactcaacca agtcattctg agaatagtgt atgcggcgac    6780
cgagttgctc ttgcccggcg tcaatacggg ataataccgc gccacatagc agaactttaa    6840
aagtgctcat cattggaaaa cgttcttcgg ggcgaaaact ctcaaggatc ttaccgctgt    6900
tgagatccag ttcgatgtaa cccactcgtg cacccaactg atcttcagca tcttttactt    6960
tcaccagcgt ttctgggtga gcaaaaacag gaaggcaaaa tgccgcaaaa aagggaataa    7020
gggcgacacg gaaatgttga atactcatac tcttcctttt tcaatattat tgaagcattt    7080
atcagggtta ttgtctcatg agcggataca tatttgaatg tatttagaaa aataaacaaa    7140
taggggttcc gcgcacattt ccccgaaaag tgccacctga cgtctaagaa accattatta    7200
tcatgacatt aacctataaa aataggcgta tcacgaggcc ctttcgtc                 7248

<210> SEQ ID NO 33
<211> LENGTH: 6684
<212> TYPE: DNA
<213> ORGANISM: Artificial Sequence
<220> FEATURE:
<223> OTHER INFORMATION: construct pINT-Ps-setA

<400> SEQUENCE: 33
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aaggggcgatc ggtgcgggcc tcttcgctat     300
tacgccagct ggcgaaaggg ggatgtgctg caaggcgatt aagttgggta acgccagggt     360
```

```
tttcccagtc acgacgttgt aaaacgacgg ccagtgaatt cgaagatcct tgatctttt    420
ctacggggtc tgacgctcag tggaacgaaa actcacgtta agggattttg gtcatgagat    480
tatcaaaaag gatcttcacc tagatccttt aaactagtg aagttaccat cacggaaaaa    540
ggttatgctg cttttaagac ccactttcac atttaagttg ttttctaat ccgcatatga    600
tcaattcaag gccgaataag aaggctggct ctgcaccttg gtgatcaaat aattcgatag    660
cttgtcgtaa taatggcggc atactatcag tagtaggtgt ttccctttct tctttagcga    720
cttgatgctc ttgatcttcc aatacgcaac ctaaagtaaa atgccccact gcgctgagtg    780
catataatgc attctctagt gaaaaacctt gttggcataa aaaggctaat tgattttcga    840
gagtttcata ctgtttttct gtaggccgtg tacctaaatg tacttttgct ccatcgcgat    900
gacttagtaa agcacatcta aaacttttag cgttattacg taaaaaatct tgccagcttt    960
cccctctaa agggcaaaag tgagtatggt gcctatctaa catctcaatg gctaaggcgt   1020
cgagcaaagc ccgcttattt tttacatgcc aatacaatgt aggctgctct acacctagct   1080
tctgggcgag tttacgggtt gttaaacctt cgattccgac ctcattaagc agctctaatg   1140
cgctgttaat cactttactt ttatctaaac gagacatact cttccttttt caatattatt   1200
gaagcattta tcagggttat tgtctcatga gcggatacat atttgaatgt atttagaaaa   1260
ataaacaaat aggggttccg cgcacatttc ccgaaaagt gccacctgaa attggccaga   1320
tgattaattc ctaattttg ttgacactct atcattgata gagttatttt accactccct   1380
atcagtgata gagaaaagtg aaatgaatag ttcgacaaaa atctagaaat aattttgttt   1440
aactttaaga aggagatata caagagctcg agtcgaagga gatagaacca tgaacgaaag   1500
ccagagctct catggcggtt catggctgtc ggttattgcg ctggccctgg cggcctttat   1560
cttcaatacc acggaattcg ttccggtcgc gctgctgtca gatattggcc gttcgtttga   1620
catgccgcca tcacaagtgg gtctgatgct gaccatctat gcgtgggtgg ttgccctgat   1680
gtcgctgccg atgatgctgc tgacccgcaa cgtcgaacgt cgcacgctgc tgattttgt   1740
gttcgtcgtg ttcatcggca gtcatctggt gagttccgtg gcgtcatcgt ttagcatgct   1800
gatgatttct cgtattggta tcgcactgtc ccacgctgtg ttttggagta tcaccgcatc   1860
cctggctgtg cgtgttgcac cggctggtaa acaggcccag gcactgggtc tgctggcaac   1920
cggttcagca ctggctatgg tcctgggtat tccgctgggc cgtgttgtcg gtgaactgct   1980
ggattggcgc accacgttcc tgagcattgc catcgtggca gctctggtgg ttctgtgtct   2040
ggcacgtacc ctgccgctgc tgccgagtca gaatagtggt tccctgcgtt ccctgccgat   2100
gctgtttaaa cgtccggcgc tggttgcggc atatgttctg accgccctgg ttattacggc   2160
gcagtttacc gcctatacgt acattgaacc gttcgcacaa accatcgctc atctgtctgg   2220
caacatgacc acggcactgc tgctgctgtt tggcggtgct ggtattctgg gcacggtgct   2280
gttcagccgt tattctaatc gctacccgaa aggttttctg atcgcagcta ttagtatcat   2340
ggcaatgtgt ctgctgctgc tgctgccggc ctcccgcgat agctctctgc tggccgccct   2400
ggtcgtggtt tgggggtattg cgggcatgtg tttcggcctg gcgctgcagg ccaaagttct   2460
gaacctggca agcgatgcta ccgacgtcgc gatggccctg tttctggca tttataatgt   2520
tggtatcggc ggtggcgccc tgctgggttc actggttacg gcacacctgg gcctgtcgga   2580
cgttggtatt gtcggtggcc tgctggccct gagcggcgtc gtgctgtgct gttttgccac   2640
ctatcgcttt gcacgtccgg tgggttctgc agctctgtaa taaatcgata ctagcataac   2700
cccttggggc ctctaaacgc gtcgacacgc aaaaaggcca tccgtcagga tggccttctg   2760
```

-continued

```
cttaatttga tgcctggcag tttatggcgg gcgtcctgcc cgccaccctc cgggccgttg    2820
cttcgcaacg ttcaaatccg ctcccggcgg atttgtccta ctcaggagag cgttcaccga    2880
caaacaacag ataaaacgaa aggcccagtc tttcgactga gcctttcgtt ttatttgatg    2940
cctggcagtt ccctactctc gcatggggag accccacact accatcatgt atgaatatcc    3000
tccttagttc ctattccgaa gttcctattc tctagaaagt ataggaactt cggcgcgtcc    3060
tacctgtgac ggaagatcac ttcgcagaat aaataaatcc tggtgtccct gttgataccg    3120
ggaagccctg ggccaacttt tggcgaaaat gagacgttga tcggcacgta agaggttcca    3180
actttcacca taatgaaata agatcactac cgggcgtatt ttttgagttg tcgagatttt    3240
caggagctaa ggaagctaaa atggagaaaa aaatcactgg atataccacc gttgatatat    3300
cccaatggca tcgtaaagaa cattttgagg catttcagtc agttgctcaa tgtacctata    3360
accagaccgt tcagctggat attacggcct ttttaaagac cgtaaagaaa aataagcaca    3420
agttttatcc ggcctttatt cacattcttg cccgcctgat gaatgctcat ccggaattac    3480
gtatggcaat gaaagacggt gagctggtga tatgggatag tgttcaccct tgttacaccg    3540
ttttccatga gcaaactgaa acgttttcat cgctctggag tgaataccac gacgatttcc    3600
ggcagtttct acacatatat tcgcaagatg tggcgtgtta cggtgaaaac ctggcctatt    3660
tccctaaagg gtttattgag aatatgtttt tcgtctcagc caatccctgg gtgagtttca    3720
ccagttttga tttaaacgtg gccaatatgg acaacttctt cgcccccgtt ttcaccatgg    3780
gcaaatatta tacgcaaggc gacaaggtgc tgatgccgct ggcgattcag gttcatcatg    3840
ccgtttgtga tggcttccat gtcggcagat gcttaatgaa tacaacagta ctgcgatgag    3900
tggcagggcg gggcgtaagg cgcgccattt aaatgaagtt cctattccga agttcctatt    3960
ctctagaaag tataggaact tcgaagcagc tccagcctac acaatcgctc aagacgtgta    4020
atgctgcaat ctgcatgcaa gcttggcact ggccacgcaa aaaggccatc cgtcaggatg    4080
gccttctgct taatttgatg cctggcagtt tatggcgggc gtcctgcccg ccaccctccg    4140
ggccgttgct tcgcaacgtt caaatccgct cccggcggat ttgtcctact caggagagcg    4200
ttcaccgaca aacaacagat aaaacgaaag gcccagtctt tcgactgagc ctttcgtttt    4260
atttgatgcc tggcagttcc ctactctcgc atggggagac cccacactac catcgggggg    4320
ccatcgatgc aggtggcact tttcggggaa atgtgcgcgg aacccctatt tgtttatttt    4380
tctaaataca ttcaaatatg tatccgctca tgagacaata accctgctgc agaggcctgc    4440
atgcaagctt ggcgtaatca tggtcatagc tgtttcctgt gtgaaattgt tatccgctca    4500
caattccaca acatacgagc cggaagcata aagtgtaaa gcctggggt gcctaatgag    4560 tgagctaact cacattaatt gcgttgcgct cactgcccgc tttccagtcg ggaaacctgt    4620
cgtgccagct gcattaatga atcggccaac gcgcggggag aggcggtttg cgtattgggc    4680
gctcttccgc ttcctcgctc actgactcgc tgcgctcggt cgttcggctg cggcgagcgg    4740
tatcagctca ctcaaaggcg gtaatacggt tatccacaga atcaggggat aacgcaggaa    4800
agaacatgtg agcaaaaggc cagcaaaagg ccaggaaccg taaaaaggcc gcgttgctgg    4860
cgttttccca taggctccgc cccctgacg agcatcacaa aaatcgacgc tcaagtcaga    4920
ggtggcgaaa cccgacagga ctataaagat accaggcgtt tcccctggaa gctccctcg    4980 tgcgctctcc tgttccgacc ctgccgctta ccggatacct gtccgccttt ctcccttcgg    5040
gaagcgtggc gctttctcat agctcacgct gtaggtatct cagttcggtg taggtcgttc    5100
```

```
gctccaagct gggctgtgtg cacgaaccce cegttcagee egacegetge gccttatccg    5160
gtaactateg tcttgagtcc aacccggtaa gacacgactt atcgccactg gcagcagcca    5220
ctggtaacag gattagcaga gcgaggtatg taggcggtgc tacagagttc ttgaagtggt    5280
ggcctaacta cggctacact agaagaacag tatttggtat ctgcgctctg ctgaagccag    5340
ttaccttcgg aaaagagtt ggtagctctt gatccggcaa acaaaccacc gctggtagcg    5400
gtggtttttt tgtttgcaag cagcagatta cgcgcagaaa aaaggatct caagaagatc    5460
ctttgatctt ttctacgggg tctgacgctc agtggaacga aaactcacgt taagggattt    5520
tggtcatgag attatcaaaa aggatcttca cctagatcct tttaaattaa aaatgaagtt    5580
ttaaatcaat ctaaagtata tatgagtaaa cttggtctga cagttaccaa tgcttaatca    5640
gtgaggcacc tatctcagcg atctgtctat ttcgttcatc catagttgcc tgactccccg    5700
tcgtgtagat aactacgata cgggagggct taccatctgg ccccagtgct gcaatgatac    5760
cgcgagaccc acgctcaccg gctccagatt tatcagcaat aaaccagcca gccgaaggg    5820
ccgagcgcag aagtggtcct gcaactttat ccgcctccat ccagtctatt aattgttgcc    5880
gggaagctag agtaagtagt tcgccagtta atagtttgcg caacgttgtt gccattgcta    5940
caggcatcgt ggtgtcacgc tcgtcgtttg gtatggcttc attcagctcc ggttcccaac    6000
gatcaaggcg agttacatga tcccccatgt tgtgcaaaaa agcggttagc tccttcggtc    6060
ctccgatcgt tgtcagaagt aagttggccg cagtgttatc actcatggtt atggcagcac    6120
tgcataattc tcttactgtc atgccatccg taagatgctt ttctgtgact ggtgagtact    6180
caaccaagtc attctgagaa tagtgtatgc ggcgaccgag ttgctcttgc ccggcgtcaa    6240
tacgggataa taccgcgcca catagcagaa ctttaaaagt gctcatcatt ggaaaacgtt    6300
cttcggggcg aaaactctca aggatcttac cgctgttgag atccagttcg atgtaaccca    6360
ctcgtgcacc caactgatct tcagcatctt ttactttcac cagcgtttct gggtgagcaa    6420
aaacaggaag gcaaaatgcc gcaaaaaagg aataagggc gacacggaaa tgttgaatac    6480
tcatactctt cctttttcaa tattattgaa gcatttatca gggttattgt ctcatgagcg    6540
gatacatatt tgaatgtatt tagaaaaata aacaataggg gttccgcgc acatttcccc    6600
gaaaagtgcc acctgacgtc taagaaacca ttattatcat gacattaacc tataaaaata    6660
ggcgtatcac gaggcccttt cgtc                                           6684

<210> SEQ ID NO 34
<211> LENGTH: 6692
<212> TYPE: DNA
<213> ORGANISM: Artificial Sequence
<220> FEATURE:
<223> OTHER INFORMATION: construct pINT-Bb-setA

<400> SEQUENCE: 34
tcgcgcgttt cggtgatgac ggtgaaaacc tctgacacat gcagctcccg gagacggtca     60
cagcttgtct gtaagcggat gccggagcag acaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgaagatcct tgatctttt    420
ctacggggtc tgacgctcag tggaacgaaa actcacgtta agggattttg gtcatgagat    480
```

| | |
|---|---|
| tatcaaaaag gatcttcacc tagatccttt taaactagtg aagttaccat cacggaaaaa | 540 |
| ggttatgctg cttttaagac ccactttcac atttaagttg tttttctaat ccgcatatga | 600 |
| tcaattcaag gccgaataag aaggctggct ctgcaccttg gtgatcaaat aattcgatag | 660 |
| cttgtcgtaa taatggcggc atactatcag tagtaggtgt ttccctttct tctttagcga | 720 |
| cttgatgctc ttgatcttcc aatacgcaac ctaaagtaaa atgccccact gcgctgagtg | 780 |
| catataatgc attctctagt gaaaaacctt gttggcataa aaaggctaat tgattttcga | 840 |
| gagtttcata ctgttttcct gtaggccgtg tacctaaatg tacttttgct ccatcgcgat | 900 |
| gacttagtaa agcacatcta aaacttttag cgttattacg taaaaaatct tgccagcttt | 960 |
| ccccttctaa agggcaaaag tgagtatggt gcctatctaa catctcaatg gctaaggcgt | 1020 |
| cgagcaaagc ccgcttattt tttacatgcc aatacaatgt aggctgctct acacctagct | 1080 |
| tctgggcgag tttacgggtt gttaaacctt cgattccgac ctcattaagc agctctaatg | 1140 |
| cgctgttaat cactttactt ttatctaaac gagacatact cttcctttt caatattatt | 1200 |
| gaagcattta tcagggttat tgtctcatga gcggatacat atttgaatgt atttagaaaa | 1260 |
| ataaacaaat aggggttccg cgcacatttc cccgaaaagt gccacctgaa attggccaga | 1320 |
| tgattaattc ctaattttg ttgacactct atcattgata gagttatttt accactccct | 1380 |
| atcagtgata gagaaaagtg aaatgaatag ttcgacaaaa atctagaaat aattttgttt | 1440 |
| aactttaaga aggagatata caagagctcg agtcgaagga gatagaacca tgaccattgc | 1500 |
| aacggtttcc cgcaaaaccg cttggctgcg tgtggttacc ctggccgttg ccgcctttat | 1560 |
| cttcaacacc acgaatttg tcccggtggg cctgctgagt gatattgcgc agtccttcgg | 1620 |
| catgaaaacc gcccaagtgg gtattatgct gacgatctat gcctggggttg tggcactgat | 1680 |
| gagcctgccg tttatgctga tgacctctca ggtggaacgt cgccgtctgc tgattagcat | 1740 |
| cttttctgctg ttcatcgcaa gtcatgttct gtcctttctg gcgtggaatt tcaccgttct | 1800 |
| ggtcatttct cgcattggta tcgcgtttgc ccacgcaatt ttctggtcaa tcacggcttc | 1860 |
| gctggcgatt cgtatggctc cggcgggcaa gaaagcgcag gcactgagtc tgctggcgac | 1920 |
| cggtacggct ctggcgatgg ttctgggtct gccgatcggc cgcattgtcg gtcaatactt | 1980 |
| tggctggcgt accacgtttt tcgtgattgg cgttgtcgca gctatcaccc tgttctgcct | 2040 |
| gattaaactg ctgccgaaac tgccgagcga acatagtggt tccctgagct ctgtgccgaa | 2100 |
| actgtttcgc cgtccggcgc tggttaacat ctatgccctg attgcaatcg tggttaccgc | 2160 |
| acactacacg gcttatagtt acatcgaacc gttcgtgcag caaattgccg gcctgtccgc | 2220 |
| taactttgcg accctgctgc tgctgctgtt tggcggtgcg ggtattatcg gctctgttct | 2280 |
| gtttggtaaa tggggcaata acatgccag cggtctggtc tctggcgcca ttgcactgat | 2340 |
| ggccgcatgt ctggtgctgc tgctgccggc agctcagggt gaactgaccc tggccggcct | 2400 |
| gtcactgttt tggggtattt cgatcatgat tgtcgcactg gtatgcaag tgaaagttct | 2460 |
| ggctctggcc ccggatgcca ccgatgttgc catgagcctg ttttctggca tcttcaacat | 2520 |
| cggcattggt gccggcgcac tgctgggtaa tcaggtgtca ctgcacattt caatgtcgga | 2580 |
| catcggtttt attggcgcca tcccggcaat tatcgctctg gtctggtcga ttctggtgtc | 2640 |
| cgccgttggc cggttgccct ggaagaacat ccgcaggcaa cccactaata aatcgatact | 2700 |
| agcataaccc cttggggcct ctaaacgcgt cgacacgcaa aaaggccatc cgtcaggatg | 2760 |
| gccttctgct taatttgatg cctggcagtt tatggcgggc gtcctgcccg ccaccctccg | 2820 |

-continued

```
ggccgttgct tcgcaacgtt caaatccgct cccggcggat ttgtcctact caggagagcg   2880
ttcaccgaca acaacagat aaaacgaaag gcccagtctt tcgactgagc ctttcgtttt    2940
atttgatgcc tggcagttcc ctactctcgc atggggagac cccacactac catcatgtat   3000
gaatatcctc cttagttcct attccgaagt tcctattctc tagaaagtat aggaacttcg   3060
gcgcgtccta cctgtgacgg aagatcactt cgcagaataa ataaatcctg gtgtccctgt   3120
tgataccggg aagccctggg ccaacttttg gcgaaaatga dacgttgatc ggcacgtaag   3180
aggttccaac tttcaccata atgaaataag atcactaccg ggcgtatttt ttgagttgtc   3240
gagattttca ggagctaagg aagctaaaat ggagaaaaaa atcactggat ataccaccgt   3300
tgatatatcc caatggcatc gtaaagaaca ttttgaggca tttcagtcag ttgctcaatg   3360
tacctataac cagaccgttc agctggatat tacggccttt ttaaagaccg taagaaaaa    3420 taagcacaag ttttatccgg cctttattca cattcttgcc cgcctgatga atgctcatcc   3480
ggaattacgt atggcaatga agacggtga gctggtgata tgggatagtg ttcacccttg    3540
ttacaccgtt ttccatgagc aaactgaaac gttttcatcg ctctggagtg aataccacga   3600
cgatttccgg cagtttctac acatatattc gcaagatgtg gcgtgttacg gtgaaaacct   3660
ggcctatttc cctaaagggt ttattgagaa tatgtttttc gtctcagcca tccctgggt    3720 gagtttcacc agttttgatt taaacgtggc caatatggac aacttcttcg cccccgtttt   3780
caccatgggc aaatattata cgcaaggcga caaggtgctg atgccgctgg cgattcaggt   3840
tcatcatgcc gtttgtgatg gcttccatgt cggcagatgc ttaatgaata caacagtact   3900
gcgatgagtg gcagggcggg gcgtaaggcg cgccatttaa atgaagttcc tattccgaag   3960
ttcctattct ctagaaagta taggaacttc gaagcagctc cagcctacac aatcgctcaa   4020
gacgtgtaat gctgcaatct gcatgcaagc ttggcactgg ccacgcaaaa aggccatccg   4080
tcaggatggc cttctgctta atttgatgcc tggcagttta tggcgggcgt cctgcccgcc   4140
accctccggg ccgttgcttc gcaacgttca aatccgctcc cggcggattt gtcctactca   4200
ggagagcgtt caccgacaaa caacagataa acgaaaggc ccagtctttc gactgagcct    4260
ttcgttttat ttgatgcctg gcagttccct actctcgcat ggggagaccc cacactacca   4320
tcggggggcc atcgatgcag gtggcacttt tcggggaaat gtgcgcggaa cccctatttg   4380
tttatttttc taaatacatt caaatatgta tccgctcatg agacaataac cctgctgcag   4440
aggcctgcat gcaagcttgg cgtaatcatg gtcatagctg tttcctgtgt gaaattgtta   4500
tccgctcaca attccacaca acatacgagc cggaagcata aagtgtaaag cctggggtgc   4560
ctaatgagtg agctaactca cattaattgc gttgcgctca ctgcccgctt tccagtcggg   4620
aaacctgtcg tgccagctgc attaatgaat cggccaacgc gcgggagag gcggtttgcg    4680 tattgggcgc tcttccgctt cctcgctcac tgactcgctg cgctcggtcg ttcggctgcg   4740
gcgagcggta tcagctcact caaaggcggt aatacggtta ccacagaat cagggataa     4800 cgcaggaaag aacatgtgag caaaaggcca gcaaaaggcc aggaaccgta aaaaggccgc    4860
gttgctggcg ttttccata ggctccgccc ccctgacgag catcacaaaa atcgacgctc     4920
aagtcagagg tggcgaaacc cgacaggact ataaagatac caggcgtttc ccctggaag    4980 ctccctcgtg cgctctcctg ttccgaccct gccgcttacc ggatacctgt ccgcctttct   5040
cccttcggga agcgtggcgc tttctcatag ctcacgctgt aggtatctca gttcggtgta   5100
ggtcgttcgc tccaagctgg gctgtgtgca cgaacccccc gttcagcccg accgctgcgc   5160
cttatccggt aactatcgtc ttgagtccaa cccggtaaga cacgacttat cgccactggc   5220
```

```
agcagccact ggtaacagga ttagcagagc gaggtatgta ggcggtgcta cagagttctt    5280
gaagtggtgg cctaactacg gctacactag aagaacagta tttggtatct gcgctctgct    5340
gaagccagtt accttcggaa aaagagttgg tagctcttga tccggcaaac aaaccaccgc    5400
tggtagcggt ggttttttg tttgcaagca gcagattacg cgcagaaaaa aaggatctca    5460
agaagatcct ttgatctttt ctacggggtc tgacgctcag tggaacgaaa actcacgtta    5520
agggattttg gtcatgagat tatcaaaaag gatcttcacc tagatccttt taaattaaaa    5580
atgaagtttt aaatcaatct aaagtatata tgagtaaact tggtctgaca gttaccaatg    5640
cttaatcagt gaggcaccta tctcagcgat ctgtctattt cgttcatcca tagttgcctg    5700
actccccgtc gtgtagataa ctacgatacg ggagggctta ccatctggcc ccagtgctgc    5760
aatgataccg cgagacccac gctcaccggc tccagattta tcagcaataa accagccagc    5820
cggaagggcc gagcgcagaa gtggtcctgc aactttatcc gcctccatcc agtctattaa    5880
ttgttgccgg gaagctagag taagtagttc gccagttaat agtttgcgca acgttgttgc    5940
cattgctaca ggcatcgtgg tgtcacgctc gtcgtttggt atggcttcat tcagctccgg    6000
ttcccaacga tcaaggcgag ttacatgatc ccccatgttg tgcaaaaaag cggttagctc    6060
cttcggtcct ccgatcgttg tcagaagtaa gttggccgca gtgttatcac tcatggttat    6120
ggcagcactg cataattctc ttactgtcat gccatccgta agatgctttt ctgtgactgg    6180
tgagtactca accaagtcat tctgagaata gtgtatgcgg cgaccgagtt gctcttgccc    6240
ggcgtcaata cgggataata ccgcgccaca tagcagaact ttaaaagtgc tcatcattgg    6300
aaaacgttct cggggcgaaa actctcaag gatcttaccg ctgttgagat ccagttcgat    6360
gtaacccact cgtgcaccca actgatcttc agcatctttt actttcacca gcgtttctgg    6420
gtgagcaaaa acaggaaggc aaaatgccgc aaaaaaggga ataagggcga cacggaaatg    6480
ttgaatactc atactcttcc tttttcaata ttattgaagc atttatcagg gttattgtct    6540
catgagcgga tacatatttg aatgtattta gaaaaataaa caaatagggg ttccgcgcac    6600
atttccccga aaagtgccac ctgacgtcta agaaaccatt attatcatga cattaaccta    6660
taaaaatagg cgtatcacga ggccctttcg tc                                    6692
```

<210> SEQ ID NO 35
<211> LENGTH: 35
<212> TYPE: DNA
<213> ORGANISM: Artificial Sequence
<220> FEATURE:
<223> OTHER INFORMATION: Primer

<400> SEQUENCE: 35
ttactcagca ataaactgat attccgtcag gctgg                                 35

<210> SEQ ID NO 36
<211> LENGTH: 83
<212> TYPE: DNA
<213> ORGANISM: Artificial Sequence
<220> FEATURE:
<223> OTHER INFORMATION: Primer

<400> SEQUENCE: 36
ttgtaatctc gcgctcttca catcagactt tccatataga gcgtaatttc cgttaacgtc     60
ggtagtgctg accttgccgg agg                                              83

<210> SEQ ID NO 37

```
<211> LENGTH: 53
<212> TYPE: DNA
<213> ORGANISM: Artificial Squence
<220> FEATURE:
<223> OTHER INFORMATION: Primer

<400> SEQUENCE: 37
ctgtctctta tcacatctcc tgaaatggcc agatgtaatt cctaattttt gtt          53

<210> SEQ ID NO 38
<211> LENGTH: 44
<212> TYPE: DNA
<213> ORGANISM: Artificial Sequence
<220> FEATURE:
<223> OTHER INFORMATION: Primer

<400> SEQUENCE: 38
ctgtctctta tcacatctca cattacatct gagcgattgt tagg                   44

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
gatcacatat gagagttctg gttaccggtg                                   30

<210> SEQ ID NO 40
<211> LENGTH: 40
<212> TYPE: DNA
<213> ORGANISM: Artificial Sequence
<220> FEATURE:
<223> OTHER INFORMATION: Primer

<400> SEQUENCE: 40
gatcactcga gtcattaatc gggatatccc tgtggatggc                        40

<210> SEQ ID NO 41
<211> LENGTH: 60
<212> TYPE: DNA
<213> ORGANISM: Artificial Sequence
<220> FEATURE:
<223> OTHER INFORMATION: Primer

<400> SEQUENCE: 41
gtcgatgaag ccctgaaaga cgcgcagact atgcacttca ttgaaaacaa aaacttcgtc   60

<210> SEQ ID NO 42
<211> LENGTH: 60
<212> TYPE: DNA
<213> ORGANISM: Artificial Sequence
<220> FEATURE:
<223> OTHER INFORMATION: Primer

<400> SEQUENCE: 42
gatggccttt ttgcgtgtcg acgcggccgc ctagataaac aggatgatat ttttgccttg   60

<210> SEQ ID NO 43
<211> LENGTH: 60
<212> TYPE: DNA
<213> ORGANISM: Artificial Sequence
<220> FEATURE:
<223> OTHER INFORMATION: Primer

<400> SEQUENCE: 43
```

```
caaggcaaaa atatcatcct gtttatctag gcggccgcgt cgacacgcaa aaaggccatc    60
```

<210> SEQ ID NO 44
<211> LENGTH: 60
<212> TYPE: DNA
<213> ORGANISM: Artificial Sequence
<220> FEATURE:
<223> OTHER INFORMATION: Primer

<400> SEQUENCE: 44

```
gacgaagttt ttgttttcaa tgaagtgcat agtctgcgcg tctttcaggg cttcatcgac    60
```

<210> SEQ ID NO 45
<211> LENGTH: 60
<212> TYPE: DNA
<213> ORGANISM: Artificial Sequence
<220> FEATURE:
<223> OTHER INFORMATION: Primer

<400> SEQUENCE: 45

```
atggcctttt tgcgtgtcga cgcggccgct taattcgagc gggtaaagat cttcatcagg    60
```

<210> SEQ ID NO 46
<211> LENGTH: 60
<212> TYPE: DNA
<213> ORGANISM: Artificial Sequence
<220> FEATURE:
<223> OTHER INFORMATION: Primer

<400> SEQUENCE: 46

```
atggcctttt tgcgtgtcga cgcggccgct taattcgagc gggtaaagat cttcatcagg    60
```

<210> SEQ ID NO 47
<211> LENGTH: 60
<212> TYPE: DNA
<213> ORGANISM: Artificial Sequence
<220> FEATURE:
<223> OTHER INFORMATION: Primer

<400> SEQUENCE: 47

```
ctgatgaaga tctttacccg ctcgaattaa gcggccgcgt cgacacgcaa aaaggccatc    60
```

<210> SEQ ID NO 48
<211> LENGTH: 60
<212> TYPE: DNA
<213> ORGANISM: Artificial Sequence
<220> FEATURE:
<223> OTHER INFORMATION: Primer

<400> SEQUENCE: 48

```
cggggtacgc ttaatcaggt tatcaatcat agtctgcgcg tctttcaggg cttcatcgac    60
```

<210> SEQ ID NO 49
<211> LENGTH: 60
<212> TYPE: DNA
<213> ORGANISM: Artificial Sequence
<220> FEATURE:
<223> OTHER INFORMATION: Primer

<400> SEQUENCE: 49

```
gtcgatgaag ccctgaaaga cgcgcagact atgagcggtg aacactatgt cattagcctg    60
```

<210> SEQ ID NO 50
<211> LENGTH: 60
<212> TYPE: DNA

```
<213> ORGANISM: Artificial Sequence
<220> FEATURE:
<223> OTHER INFORMATION: Primer

<400> SEQUENCE: 50
gatggccttt ttgcgtgtcg acgcggccgc tcatttaaat tcgatgatca tcttgtcgtt      60

<210> SEQ ID NO 51
<211> LENGTH: 60
<212> TYPE: DNA
<213> ORGANISM: Artificial Sequence
<220> FEATURE:
<223> OTHER INFORMATION: Primer

<400> SEQUENCE: 51
aacgacaaga tgatcatcga atttaaatga gcggccgcgt cgacacgcaa aaaggccatc      60

<210> SEQ ID NO 52
<211> LENGTH: 60
<212> TYPE: DNA
<213> ORGANISM: Artificial Sequence
<220> FEATURE:
<223> OTHER INFORMATION: Primer

<400> SEQUENCE: 52
caggctaatg acatagtgtt caccgctcat agtctgcgcg tctttcaggg cttcatcgac      60

<210> SEQ ID NO 53
<211> LENGTH: 60
<212> TYPE: DNA
<213> ORGANISM: Artificial Sequence
<220> FEATURE:
<223> OTHER INFORMATION: Primer

<400> SEQUENCE: 53
gtcgatgaag ccctgaaaga cgcgcagact atggatgaaa tcaaactgtc ggtggttatg      60

<210> SEQ ID NO 54
<211> LENGTH: 60
<212> TYPE: DNA
<213> ORGANISM: Artificial Sequence
<220> FEATURE:
<223> OTHER INFORMATION: Primer

<400> SEQUENCE: 54
gatggccttt ttgcgtgtcg acgcggccgc tcattggcga cgccaatcga acgcaacgcg      60

<210> SEQ ID NO 55
<211> LENGTH: 60
<212> TYPE: DNA
<213> ORGANISM: Artificial Sequence
<220> FEATURE:
<223> OTHER INFORMATION: Primer

<400> SEQUENCE: 55
cgcgttgcgt tcgattggcg tcgccaatga gcggccgcgt cgacacgcaa aaaggccatc      60

<210> SEQ ID NO 56
<211> LENGTH: 60
<212> TYPE: DNA
<213> ORGANISM: Artificial Sequence
<220> FEATURE:
<223> OTHER INFORMATION: Primer

<400> SEQUENCE: 56
cataaccacc gacagtttga tttcatccat agtctgcgcg tctttcaggg cttcatcgac      60
```

<210> SEQ ID NO 57
<211> LENGTH: 60
<212> TYPE: DNA
<213> ORGANISM: Artificial Sequence
<220> FEATURE:
<223> OTHER INFORMATION: Primer

<400> SEQUENCE: 57
gtcgatgaag ccctgaaaga cgcgcagact atggaaaact atgtcgtctc tatccgcacc    60

<210> SEQ ID NO 58
<211> LENGTH: 60
<212> TYPE: DNA
<213> ORGANISM: Artificial Sequence
<220> FEATURE:
<223> OTHER INFORMATION: Primer

<400> SEQUENCE: 58
gatggccttt ttgcgtgtcg acgcggccgc tcatttgaac ggaacaatct ttttgtcatc    60

<210> SEQ ID NO 59
<211> LENGTH: 60
<212> TYPE: DNA
<213> ORGANISM: Artificial Sequence
<220> FEATURE:
<223> OTHER INFORMATION: Primer

<400> SEQUENCE: 59
gatgacaaaa agattgttcc gttcaaatga gcggccgcgt cgacacgcaa aaaggccatc    60

<210> SEQ ID NO 60
<211> LENGTH: 60
<212> TYPE: DNA
<213> ORGANISM: Artificial Sequence
<220> FEATURE:
<223> OTHER INFORMATION: Primer

<400> SEQUENCE: 60
ggtgcggata gagacgacat agttttccat agtctgcgcg tctttcaggg cttcatcgac    60

<210> SEQ ID NO 61
<211> LENGTH: 60
<212> TYPE: DNA
<213> ORGANISM: Artificial Sequence
<220> FEATURE:
<223> OTHER INFORMATION: Primer

<400> SEQUENCE: 61
gtcgatgaag ccctgaaaga cgcgcagact atgtcctcag ctttccatta cgtcattagc    60

<210> SEQ ID NO 62
<211> LENGTH: 60
<212> TYPE: DNA
<213> ORGANISM: Artificial Sequence
<220> FEATURE:
<223> OTHER INFORMATION: Primer

<400> SEQUENCE: 62
gatggccttt ttgcgtgtcg acgcggccgc tcattcaaat tcgataatca tggtgatttt    60

<210> SEQ ID NO 63
<211> LENGTH: 60
<212> TYPE: DNA
<213> ORGANISM: Artificial Sequence
<220> FEATURE:

<223> OTHER INFORMATION: Primer

<400> SEQUENCE: 63
aaaatcacca tgattatcga atttgaatga gcggccgcgt cgacacgcaa aaaggccatc    60

<210> SEQ ID NO 64
<211> LENGTH: 60
<212> TYPE: DNA
<213> ORGANISM: Artificial Sequence
<220> FEATURE:
<223> OTHER INFORMATION: Primer

<400> SEQUENCE: 64
gctaatgacg taatggaaag ctgaggacat agtctgcgcg tctttcaggg cttcatcgac    60

<210> SEQ ID NO 65
<211> LENGTH: 60
<212> TYPE: DNA
<213> ORGANISM: Artificial Sequence
<220> FEATURE:
<223> OTHER INFORMATION: Primer

<400> SEQUENCE: 65
gtcgatgaag ccctgaaaga cgcgcagact atgaacgtga ataagccgac caccgaaaag    60

<210> SEQ ID NO 66
<211> LENGTH: 60
<212> TYPE: DNA
<213> ORGANISM: Artificial Sequence
<220> FEATURE:
<223> OTHER INFORMATION: Primer

<400> SEQUENCE: 66
gatggccttt ttgcgtgtcg acgcggccgc tcagtattct tcaattttgt ccagttgata    60

<210> SEQ ID NO 67
<211> LENGTH: 60
<212> TYPE: DNA
<213> ORGANISM: Artificial Sequence
<220> FEATURE:
<223> OTHER INFORMATION: Primer

<400> SEQUENCE: 67
tatcaactgg acaaaattga agaatactga gcggccgcgt cgacacgcaa aaaggccatc    60

<210> SEQ ID NO 68
<211> LENGTH: 60
<212> TYPE: DNA
<213> ORGANISM: Artificial Sequence
<220> FEATURE:
<223> OTHER INFORMATION: Primer

<400> SEQUENCE: 68
cttttcggtg gtcggcttat tcacgttcat agtctgcgcg tctttcaggg cttcatcgac    60

<210> SEQ ID NO 69
<211> LENGTH: 60
<212> TYPE: DNA
<213> ORGANISM: Artificial Sequence
<220> FEATURE:
<223> OTHER INFORMATION: Primer

<400> SEQUENCE: 69
gtgatcaacg ccgccagcgg tcgtcagact gtcgatgaag ccctgaaaga cgcgcagact    60

```
<210> SEQ ID NO 70
<211> LENGTH: 60
<212> TYPE: DNA
<213> ORGANISM: Artificial Sequence
<220> FEATURE:
<223> OTHER INFORMATION: Primer

<400> SEQUENCE: 70
gcggccgcgt cgacacgcaa aaaggccatc catccgtcag gatggccttc tgcttaattt    60

<210> SEQ ID NO 71
<211> LENGTH: 60
<212> TYPE: DNA
<213> ORGANISM: Artificial Sequence
<220> FEATURE:
<223> OTHER INFORMATION: Primer

<400> SEQUENCE: 71
aaattaagca gaaggccatc ctgacggatg gatggccttt ttgcgtgtcg acgcggccgc    60

<210> SEQ ID NO 72
<211> LENGTH: 60
<212> TYPE: DNA
<213> ORGANISM: Artificial Sequence
<220> FEATURE:
<223> OTHER INFORMATION: Primer

<400> SEQUENCE: 72
agtctgcgcg tctttcaggg cttcatcgac agtctgacga ccgctggcgg cgttgatcac    60

<210> SEQ ID NO 73
<211> LENGTH: 66
<212> TYPE: DNA
<213> ORGANISM: Artificial Sequence
<220> FEATURE:
<223> OTHER INFORMATION: Primer

<400> SEQUENCE: 73
gtttaacttt aataaggaga tataccatgc tgacggaagt gcgcccggtc tctacgacga    60
aaccgc                                                              66

<210> SEQ ID NO 74
<211> LENGTH: 66
<212> TYPE: DNA
<213> ORGANISM: Artificial Sequence
<220> FEATURE:
<223> OTHER INFORMATION: Primer

<400> SEQUENCE: 74
cgacctgcag gcgcgccgag ctcgaattca tttgatgtat ttgcaataga acacagaaaa    60
gaccgt                                                              66

<210> SEQ ID NO 75
<211> LENGTH: 66
<212> TYPE: DNA
<213> ORGANISM: Artificial Sequence
<220> FEATURE:
<223> OTHER INFORMATION: Primer

<400> SEQUENCE: 75
gtgttctatt gcaaatacat caaatgaatt cgagctcggc gcgcctgcag gtcgacaagc    60
ttgcgg                                                              66

<210> SEQ ID NO 76
```

<211> LENGTH: 69
<212> TYPE: DNA
<213> ORGANISM: Artificial Sequence
<220> FEATURE:
<223> OTHER INFORMATION: Primer

<400> SEQUENCE: 76
gagaccgggc gcacttccgt cagcatggta tatctcctta ttaaagttaa acaaaattat    60
ttctacagg                                                             69

<210> SEQ ID NO 77
<211> LENGTH: 62
<212> TYPE: DNA
<213> ORGANISM: Artificial Sequence
<220> FEATURE:
<223> OTHER INFORMATION: Primer

<400> SEQUENCE: 77
gtatggtgac cctgtggcgc aaatgagaat tcgagctcgg cgcgcctgca ggtcgacaag    60
ct                                                                    62

<210> SEQ ID NO 78
<211> LENGTH: 64
<212> TYPE: DNA
<213> ORGANISM: Artificial Sequence
<220> FEATURE:
<223> OTHER INFORMATION: Primer

<400> SEQUENCE: 78
gcgctgccct gtttgatttt atccatggta tatctcctta ttaaagttaa acaaaattat    60
ttct                                                                  64

<210> SEQ ID NO 79
<211> LENGTH: 63
<212> TYPE: DNA
<213> ORGANISM: Artificial Sequence
<220> FEATURE:
<223> OTHER INFORMATION: Primer

<400> SEQUENCE: 79
cctgcaggcg cgccgagctc gaattctcat ttgcgccaca gggtcaccat acgtgccggc    60
agg                                                                   63

<210> SEQ ID NO 80
<211> LENGTH: 66
<212> TYPE: DNA
<213> ORGANISM: Artificial Sequence
<220> FEATURE:
<223> OTHER INFORMATION: Primer

<400> SEQUENCE: 80
gtttaacttt aataaggaga tataccatgg ataaaatcaa acagggcagc gcctctctgg    60
ttgtcg                                                                66

<210> SEQ ID NO 81
<211> LENGTH: 57
<212> TYPE: DNA
<213> ORGANISM: Artificial Sequence
<220> FEATURE:
<223> OTHER INFORMATION: Primer

<400> SEQUENCE: 81
cagactcgag ggtaccgacg tcctaataag tagatgaata tttatcagga cgaagat       57

<210> SEQ ID NO 82
<211> LENGTH: 55
<212> TYPE: DNA
<213> ORGANISM: Artificial Sequence
<220> FEATURE:
<223> OTHER INFORMATION: Primer

<400> SEQUENCE: 82
aactaaaggt ttattttcca tatgtatatc tccttcttat acttaactaa tatac        55

<210> SEQ ID NO 83
<211> LENGTH: 64
<212> TYPE: DNA
<213> ORGANISM: Artificial Sequence
<220> FEATURE:
<223> OTHER INFORMATION: Primer

<400> SEQUENCE: 83
taaatattca tctacttatt aggacgtcgg taccctcgag tctggtaaag aaaccgctgc    60
tgcg                                                                64

<210> SEQ ID NO 84
<211> LENGTH: 59
<212> TYPE: DNA
<213> ORGANISM: Artificial Sequence
<220> FEATURE:
<223> OTHER INFORMATION: Primer

<400> SEQUENCE: 84
gtataagaag gagatataca tatggaaaat aaaccttag tttcagtttt gatttgtgc     59

<210> SEQ ID NO 85
<211> LENGTH: 75
<212> TYPE: DNA
<213> ORGANISM: Artificial Sequence
<220> FEATURE:
<223> OTHER INFORMATION: Primer

<400> SEQUENCE: 85
taactttaag aaggagatat acaagagctc gagtcgaagg agatagaacc atggcaacag    60
catggtataa acaag                                                    75

<210> SEQ ID NO 86
<211> LENGTH: 82
<212> TYPE: DNA
<213> ORGANISM: Artificial Sequence
<220> FEATURE:
<223> OTHER INFORMATION: Primer

<400> SEQUENCE: 86
gcgtgtcgac gcgtttagag gccccaaggg gttatgctag tatcgattta tcatttagcc    60
acggatagtt tataaatttt ac                                            82

<210> SEQ ID NO 87
<211> LENGTH: 80
<212> TYPE: DNA
<213> ORGANISM: Artificial Sequence
<220> FEATURE:
<223> OTHER INFORMATION: Primer

<400> SEQUENCE: 87
ggttctatct ccttcgactc gagctcttgt atatctcctt cttaaagtta aacaaaatta    60

```
tttctagatt tttgtcgaac                                              80

<210> SEQ ID NO 88
<211> LENGTH: 63
<212> TYPE: DNA
<213> ORGANISM: Artificial Sequence
<220> FEATURE:
<223> OTHER INFORMATION: Primer

<400> SEQUENCE: 88
taaatcgata ctagcataac cccttggggc tctaaacgc gtcgacacgc aaaaaggcca    60
tcc                                                                63

<210> SEQ ID NO 89
<211> LENGTH: 80
<212> TYPE: DNA
<213> ORGANISM: Artificial Sequence
<220> FEATURE:
<223> OTHER INFORMATION: Primer

<400> SEQUENCE: 89
gttcgacaaa aatctagaaa taattttgtt taactttaag aaggagatat acaagagctc   60
gagtcgaagg agatagaacc                                              80

<210> SEQ ID NO 90
<211> LENGTH: 63
<212> TYPE: DNA
<213> ORGANISM: Artificial Sequence
<220> FEATURE:
<223> OTHER INFORMATION: Primer

<400> SEQUENCE: 90
ggatggcctt tttgcgtgtc gacgcgttta gaggccccaa ggggttatgc tagtatcgat   60
tta                                                                63

<210> SEQ ID NO 91
<211> LENGTH: 34
<212> TYPE: DNA
<213> ORGANISM: Artificial Sequence
<220> FEATURE:
<223> OTHER INFORMATION: Primer

<400> SEQUENCE: 91
atatgacgtc tcattagcgg tttttcagga gacg                              34

<210> SEQ ID NO 92
<211> LENGTH: 35
<212> TYPE: DNA
<213> ORGANISM: Artificial Sequence
<220> FEATURE:
<223> OTHER INFORMATION: Primer

<400> SEQUENCE: 92
atatcatatg ccgtccgaag cattccgtcg tcacc                             35

<210> SEQ ID NO 93
<211> LENGTH: 62
<212> TYPE: DNA
<213> ORGANISM: Artificial Sequence
<220> FEATURE:
<223> OTHER INFORMATION: Primer

<400> SEQUENCE: 93
taactttaat aaggagatat accatgacgc aatttaatcc cgttgatcat ccacatcgcc   60
```

```
gc                                                              62

<210> SEQ ID NO 94
<211> LENGTH: 67
<212> TYPE: DNA
<213> ORGANISM: Artificial Sequence
<220> FEATURE:
<223> OTHER INFORMATION: Primer

<400> SEQUENCE: 94
attttcgcga atccggagtg taaaagcttg cggccgcata atgcttaagt cgaacagaaa    60
gtaatcg                                                              67

<210> SEQ ID NO 95
<211> LENGTH: 72
<212> TYPE: DNA
<213> ORGANISM: Artificial Sequence
<220> FEATURE:
<223> OTHER INFORMATION: Primer

<400> SEQUENCE: 95
aagcattatg cggccgcaag cttttacact ccggattcgc gaaaatggat atcgctgact    60
gcgcgcaaac gc                                                        72

<210> SEQ ID NO 96
<211> LENGTH: 68
<212> TYPE: DNA
<213> ORGANISM: Artificial Sequence
<220> FEATURE:
<223> OTHER INFORMATION: Primer

<400> SEQUENCE: 96
tcaacgggat taaattgcgt catggtatat ctccttatta agttaaaca aaattatttc     60 tacagggg                                                             68

<210> SEQ ID NO 97
<211> LENGTH: 57
<212> TYPE: DNA
<213> ORGANISM: Artificial Sequence
<220> FEATURE:
<223> OTHER INFORMATION: Primer

<400> SEQUENCE: 97
atggtgatgg ctgctgccca tttaaaccgc tttgactgcg tcggcaatac ggtgcgc       57

<210> SEQ ID NO 98
<211> LENGTH: 60
<212> TYPE: DNA
<213> ORGANISM: Artificial Sequence
<220> FEATURE:
<223> OTHER INFORMATION: Primer

<400> SEQUENCE: 98
gtttaacttt aataaggaga tataccatgc tgaacaacgc gatgtctgtt gttatcctgg    60

<210> SEQ ID NO 99
<211> LENGTH: 53
<212> TYPE: DNA
<213> ORGANISM: Artificial Sequence
<220> FEATURE:
<223> OTHER INFORMATION: Primer

<400> SEQUENCE: 99
```

```
cgcagtcaaa gcggtttaaa tgggcagcag ccatcaccat catcaccaca gcc          53

<210> SEQ ID NO 100
<211> LENGTH: 59
<212> TYPE: DNA
<213> ORGANISM: Artificial Sequence
<220> FEATURE:
<223> OTHER INFORMATION: Primer

<400> SEQUENCE: 100
tcgcgttgtt cagcatggta tatctcctta ttaaagttaa acaaaattat ttctacagg    59

<210> SEQ ID NO 101
<211> LENGTH: 35
<212> TYPE: DNA
<213> ORGANISM: Artificial Sequence
<220> FEATURE:
<223> OTHER INFORMATION: Primer

<400> SEQUENCE: 101
atatatcata tgtgcggtat cgttggtgct atcgc                              35

<210> SEQ ID NO 102
<211> LENGTH: 36
<212> TYPE: DNA
<213> ORGANISM: Artificial Sequence
<220> FEATURE:
<223> OTHER INFORMATION: Primer

<400> SEQUENCE: 102
atatatgacg tcttattcca cggtcacgga tttcgc                             36
```